(12) United States Patent
Calos

(10) Patent No.: US 8,420,395 B2
(45) Date of Patent: *Apr. 16, 2013

(54) METHODS OF UNIDIRECTIONAL, SITE-SPECIFIC INTEGRATION INTO A GENOME, COMPOSITIONS AND KITS FOR PRACTICING THE SAME

(75) Inventor: Michele Calos, Stanford, CA (US)

(73) Assignees: Poetic Genetics, Inc., Burlingame, CA (US); The Board of Trustees of the Leland Stanford Junior University, Palo Alto, CA (US)

(*) Notice: Subject to any disclaimer, the term of this patent is extended or adjusted under 35 U.S.C. 154(b) by 546 days.

This patent is subject to a terminal disclaimer.

(21) Appl. No.: 11/003,941

(22) Filed: Dec. 3, 2004

(65) Prior Publication Data

US 2005/0208021 A1 Sep. 22, 2005

Related U.S. Application Data

(63) Continuation of application No. PCT/US03/17702, filed on Jun. 3, 2003.

(60) Provisional application No. 60/416,989, filed on Oct. 7, 2002, provisional application No. 60/385,954, filed on Jun. 4, 2002, provisional application No. 60/385,933, filed on Jun. 4, 2002, provisional application No. 60/386,325, filed on Jun. 4, 2002, provisional application No. 60/385,934, filed on Jun. 4, 2002, provisional application No. 60/385,929, filed on Jun. 4, 2002, provisional application No. 60/386,597, filed on Jun. 4, 2002, provisional application No. 60/385,944, filed on Jun. 4, 2002.

(51) Int. Cl.
*C12N 15/63* (2006.01)
*C12N 15/11* (2006.01)
*C12N 15/52* (2006.01)
*C12N 9/00* (2006.01)

(52) U.S. Cl.
USPC ........ 435/440; 435/320.1; 435/183; 435/325; 536/23.1

(58) Field of Classification Search ................. None
See application file for complete search history.

(56) References Cited

U.S. PATENT DOCUMENTS

| 6,808,925 B2 * | 10/2004 | Calos | 435/462 |
| 2003/0186291 A1 * | 10/2003 | Faust et al. | 435/6 |
| 2004/0003420 A1 * | 1/2004 | Kuhn et al. | 800/14 |
| 2006/0024820 A1 * | 2/2006 | Perkins et al. | 435/320.1 |

FOREIGN PATENT DOCUMENTS

| WO | WO 00/11155 | 3/2000 |
| WO | WO 01/61049 | 8/2001 |

OTHER PUBLICATIONS

Dupont et al, Characterization of genetic elements required for site-specific integration of *Lactobacillus delbrueckii* subsp. *bulgaricus* bacteriophage mv4 and construction of an integration-proficient vector for *Lactobacillus plantarum*, J. Bacteriol. 1995 177: 586-595.*
Thorpe et al, In vitro site-specific integration of bacteriophage DNA catalyzed by a recombinase of the resolvase invertase family, PNAS, 1998, vol. 95 pp. 5505-5510.*
Sclimenti et al, Directed evolution of a recombinase for improved genomic integration at a native human sequence, NAR, 2001, pp. 5044-5051.*
Tseng and Liang, Evolutionary model for predicting protein function by matching local surfaces: a Bayesian Monte Carlo approach, poster abstract downloaded Jun. 9, 2005.*
Protein structure prediction—Wikipedia, downloaded Oct. 14, 2005.*
Tertiary structures—Biology Pages, downloaded Oct. 14, 2005.*
Smith et al, Surface point mutations that significantly alter the structure and stability of a protein's denatured state, Protein Science, 1996, vol. 5, pp. 2009-2019.*
Thyagarajan et al, Site-Specific Genomic Integration in Mammalian Cells Mediated by Phage fC31 Integrase, MCB, Jun. 2001, p. 3926-3934.*
Groth et al, A phage integrase directs efficient site-specific integration in human cells, PNAS, 2000, vol. 11, pp. 5995-6000.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Thyagarajan et al. "Site-Specific Integration in Mammalian Cells Mediated by Phage φC31 Integrase," (2001) *Molecular and Cellular Biology*, 21(12):3926-3934.
Thorpe et al. "Control of Directionality in the Site-Specific Recombination System of the *Streptomyces* phage φC31," (2000) *Molecular Microbiology*, 38(2):232-241.
Christ and Droge "Alterations in the Directionality of λ Site-Specific Recombination Catalyzed by Mutant Integrases In Vivo," (1998) *J. Mol. Biol.*, 288:825-836.
Sclimenti et al. "Directed Evolution of a Recombinase for Improved Genomic Integration at a Native Human Sequence," (2001) *Nucleic Acids Research*, 29(24):5044-5051.

* cited by examiner

*Primary Examiner* — Maria Marvich
(74) *Attorney, Agent, or Firm* — Edward J. Baba; Bozicevic, Field & Francis LLP

(57) ABSTRACT

The subject invention provides a unidirectional site-specific integration system for integrating a nucleic acid into the genome of a target cell. The provided systems include a (1) a mutant, unidirectional site specific integrase, which can be provided by an integrase vector encoding the mutant integrase and (2) a targeting vector that includes: (a) a nucleic acid to be integrated; and (b) a vector attachment site, where the targeting vector attachment site serves as a substrate for the mutant, unidirectional site-specific integrase. In using the subject systems for site-specific integration, the targeting vector and integrase are introduced into the target cell and the cell is maintained under conditions sufficient to provide for site-specific integration of the nucleic acid into the target cell genome via a recombination event mediated by the site-specific integrase. Also provided are kits that include the subject systems. The subjects systems, methods and kits find use in a variety of different applications, several representative ones of which are described in detail as well.

10 Claims, 22 Drawing Sheets

```
             1                                                              50
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    MTQGVVTGVD TYAGAYDRQS RERENSSAAS PATQRSANED KAADLQREVE 51                                                             100
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    RDGGRFRFVG HFSEAPGTSA FGTAERPEFE RILNECRAGR LNMIIVYDVS 101                                                            150
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    RFSRLKVMDA IPIVSELLAL GVTIVSTQEG VFRQGNVMDL IHLIMRLDAS 151                                                            200
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    HKESSLKSAK ILDTKNLQRE LGGYVGGKAP YGFELVSETK EITRNGRMVN 201                                                            250
7C1 Mutant   ---------- ---------- ---------- ---------- -----a----
WT PhiC31 Int ---------- ---------- ---------- ---------- -----a----
5C1 Mutant   ---------- ---------- ---------- ---------- -----t----
1C1 Mutant   ---------- ---------- ---------- ---------- -----a----
Consensus    VVINKLAHST TPLTGPFEFE PDVIRWWWRE IKTHKHLPFK PGSQA-IHPG 251                                                            300
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    SITGLCKRMD ADAVPTRGET IGKKTASSAW DPATVMRILR DPRIAGFAAE 301                                                            350
7C1 Mutant   ---------- ---------- ---------- ---------- ----------
WT PhiC31 Int ---------- ---------- ---------- ---------- ----------
5C1 Mutant   ---------- ---------- ---------- ---------- ----------
1C1 Mutant   ---------- ---------- ---------- ---------- ----------
Consensus    VIYKKKPDGT PTTKIEGYRI QRDPITLRPV ELDCGPIIEP AEWYELQAWL
```

FIG. 5A

```
                351                                                                                          400
7C1 Mutant      ----------  ---------d   --------v-   ----------   ----------
WT PhiC31 Int   ----------  ---------d   --------v-   ----------   ----------
5C1 Mutant      ----------  ---------g   --------v-   ----------   ----------
1C1 Mutant      ----------  ---------d   --------i-   ----------   ----------
Consensus       DGRGRGKGLS  RGQAILSAM-   KLYCECGA-M   TSKRGEESIK   DSYRCRRRKV 401                                                                                          450
7C1 Mutant      ----------  ----------   ----------   ----------   ----------
WT PhiC31 Int   ----------  ----------   ----------   ----------   ----------
5C1 Mutant      ----------  ----------   ----------   ----------   ----------
1C1 Mutant      ----------  ----------   ----------   ----------   ----------
Consensus       VDPSAPGQHE  GTCNVSMAAL   DKFVAERIFN   KIRHAEGDEE   TLALLWEAAR 451                                                                                          500
7C1 Mutant      ----------  ----------   ----------   ----------   ----------
WT PhiC31 Int   ----------  ----------   ----------   ----------   ----------
5C1 Mutant      ----------  ----------   ----------   ----------   ----------
1C1 Mutant      ----------  ----------   ----------   ----------   ----------
Consensus       RFGKLTEAPE  KSGERANLVA   ERADALNALE   ELYEDRAAGA   YDGPVGRKHF 501                                                                                          550
7C1 Mutant      ----------  ----------   ----------   ----------   ----------
WT PhiC31 Int   ----------  ----------   ----------   ----------   ----------
5C1 Mutant      ----------  ----------   ----------   ----------   ----------
1C1 Mutant      ----------  ----------   ----------   ----------   ----------
Consensus       RKQQAALTLR  QQGAEERLAE   LEAAEAPKLP   LDQWFPEDAD   ADPTGPKSWW 551                          600
7C1 Mutant      ---------m  ----------   ----------   ----------   ----------
WT PhiC31 Int   ---------v  ----------   ----------   ----------   ----------
5C1 Mutant      ---------v  ----------   ----------   ----------   ----------
1C1 Mutant      ---------v  ----------   ----------   ----------   ----------
Consensus       GRASVDDKR-  FVGLFVDKIV   VTKSTTGRGQ   GTPIEKRASI   TWAKPPTDDD 601        614
7C1 Mutant      ----qdgtqd  vaa*    (SEQ ID NO: 129)
WT PhiC31 Int   ----qdgted  vaa*    (SEQ ID NO: 128)
5C1 Mutant      ----qdgted  vaa*    (SEQ ID NO: 130)
1C1 Mutant      ----rtarkt  *---    (SEQ ID NO: 131)
Consensus       EDDA------  ----    (SEQ ID NO: 132)
```

FIG. 5B

DNA Sequence of ΦC31 Integrase
(SEQ ID NO: 125)

ATGacacaagggggttgtgaccggggtggacacgtacgcgggtgcttacgaccgtcagtcgcgc
agcgcgaaaattcgagcgcagcaagcccagcgacacagcgtagcgccaacgaagacaaggcgg
cgaccttcagcgcgaagtcgagcgcgacgggggccggttcaggttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggaccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggaccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcagggggcgcggcaagggctttcccggggggca
agccattctgtccgccatggacaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagtcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaacaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtgggggcgcgcgtcagt
agacgacaagcgcgtgttcgtcgggctcttcgtagacaagatcgttgtcacgaagtcgactacg
ggcaggggcagggaacgcccatcgagaagcgcgcttcgatcacgtgggcgaagccgccgaccg
acgacgacgaagacgacgcccaggacggcacggaagacgtagcggcgtag

FIG. 6

Peptide sequence of the ΦC31 mutant integrase 7C1
(SEQ ID NO: 129)

```
  1  MTQGVVTGVD TYAGAYDRQS RERENSSAAS PATQRSANED KAADLQREVE
 51  RDGGRFRFVG HFSEAPGTSA FGTAERPEFE RILNECRAGR LNMIIVYDVS
101  RFSRLKVMDA IPIVSELLAL GVTIVSTQEG VFRQGNVMDL IHLIMRLDAS
151  HKESSLKSAK ILDTKNLQRE LGGYVGGKAP YGFELVSETK EITRNGRMVN
201  VVINKLAHST TPLTGPFEFE PDVIRWWWRE IKTHKHLPFK PGSQAAIHPG
251  SITGLCKRMD ADAVPTRGET IGKKTASSAW DPATVMRILR DPRIAGFAAE
301  VIYKKKPDGT PTTKIEGYRI QRDPITLRPV ELDCGPIIEP AEWYELQAWL
351  DGRGRGKGLS RGQAILSAMD KLYCECGAVM TSKRGEESIK DSYRCRRRKV
401  VDPSAPGQHE GTCNVSMAAL DKFVAERIFN KIRHAEGDEE TLALLWEAAR
451  RFGKLTEAPE KSGERANLVA ERADALNALE ELYEDRAAGA YDGPVGRKHF
501  RKQQAALTLR QQGAEERLAE LEAAEAPKLP LDQWFPEDAD ADPTGPKSWW
551  GRASVDDKRM FVGLFVDKIV VTKSTTGRGQ GTPIEKRASI TWAKPPTDDD
601  EDDAQDGTQD VAA*
```

FIG. 7

DNA Sequence of Integrase mutant 7C1
(SEQ ID NO: 133)

```
ATGacacaagggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacggggccggttcaggttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtatCgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcagggggcgcggcaaggggctttcccggggggca
agccattctgtccgccatggacaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaacaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtggggcgcgcgtcagt
agacgacaagcgcAtgttcgtcgggctcttcgtagacaagatcgttgtcacgaagtcgactacg
ggcagggggcagggaacgcccatcgagaagcgcgcttcgatcacgtgggcgaagccgccgaccg
acgacgacgaagacgacgcccaggacggcacgCaagacgtagcggcgtag
```

FIG. 8

Peptide sequence of the ΦC31 mutant integrase 5C1
(SEQ ID NO: 130)

```
  1  MTQGVVTGVD  TYAGAYDRQS  RERENSSAAS  PATQRSANED  KAADLQREVE
 51  RDGGRFRFVG  HFSEAPGTSA  FGTAERPEFE  RILNECRAGR  LNMIIVYDVS
101  RFSRLKVMDA  IPIVSELLAL  GVTIVSTQEG  VFRQGNVMDL  IHLIMRLDAS
151  HKESSLKSAK  ILDTKNLQRE  LGGYVGGKAP  YGFELVSETK  EITRNGRMVN
201  VVINKLAHST  TPLTGPFEFE  PDVIRWWWRE  IKTHKHLPFK  PGSQATIHPG
251  SITGLCKRMD  ADAVPTRGET  IGKKTASSAW  DPATVMRILR  DPRIAGFAAE
301  VIYKKKPDGT  PTTKIEGYRI  QRDPITLRPV  ELDCGPIIEP  AEWYELQAWL
351  DGRGRGKGLS  RGQAILSAMG  KLYCECGAVM  TSKRGEESIK  DSYRCRRRKV
401  VDPSAPGQHE  GTCNVSMAAL  DKFVAERIFN  KIRHAEGDEE  TLALLWEAAR
451  RFGKLTEAPE  KSGERANLVA  ERADALNALE  ELYEDRAAGA  YDGPVGRKHF
501  RKQQAALTLR  QQGAEERLAE  LEAAEAPKLP  LDQWFPEDAD  ADPTGPKSWW
551  GRASVDDKRV  FVGLFVDKIV  VTKSTTGRGQ  GTPIEKRASI  TWAKPPTDDD
601  EDDAQDGTED  VAA*
```

FIG. 9

DNA Sequence of Integrase mutant 5C1
(SEQ ID NO: 134)

```
ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacggggccggttcagAttcgtcgggcatttcagcgaa
gcgccgggcacgtcggcgttcgggacggcggagcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaatt
gggcgggtacgtcggcgggaaggcgccttacggcttcgagcttgtttcggagacgaaggagatc
acgcgcaacggccgaatggtcaatgtcgtcatcaacaagcttgcgcactcgaccactccccta
ccggaccttcgagttcgagcccgacgtaatccggtggtggtggcgtgagatcaagacgcacaa
acaccttcccttcaagccgggcagtcaagccAccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcaggggcgcggcaaggggctttcccgggggca
agccattctgtccgccatgGcaagctgtactgcgagtgtggcgccgtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggaccgttggcaggaagcacttccggaagcaacaggcagcgctgacgctccggcagcaa
ggggcggaagagcggcttgccgaacttgaagccgccgaagcccgaagcttcccttgaccaat
ggttccccgaagacgccgacgctgacccgaccggccctaagtcgtggtggggcgcgcgtcagt
agacgacaagcgcgtgttcgtcgggctcttcgtagacaagatcgttgtcacgaagtcgactacg
ggcaggggcagggaacgcccatcgagaagcgcgcttcgatcacgtgggcgaagccgccAaccg
acgacgacgaagacgacgcccaggacggcacggaagacgtagcggcg
```

FIG. 10

Peptide sequence of the ΦC31 mutant integrase 1C1
(SEQ ID NO: 131)

```
  1  MTQGVVTGVD  TYAGAYDRQS  RERENSSAAS  PATQRSANED  KAADLQREVE
 51  RDGGRFRFVG  HFSEAPGTSA  FGTAERPEFE  RILNECRAGR  LNMIIVYDVS
101  RFSRLKVMDA  IPIVSELLAL  GVTIVSTQEG  VFRQGNVMDL  IHLIMRLDAS
151  HKESSLKSAK  ILDTKNLQRE  LGGYVGGKAP  YGFELVSETK  EITRNGRMVN
201  VVINKLAHST  TPLTGPFEFE  PDVIRWWWRE  IKTHKHLPFK  PGSQAAIHPG
251  SITGLCKRMD  ADAVPTRGET  IGKKTASSAW  DPATVMRILR  DPRIAGFAAE
301  VIYKKKPDGT  PTTKIEGYRI  QRDPITLRPV  ELDCGPIIEP  AEWYELQAWL
351  DGRGRGKGLS  RGQAILSAMD  KLYCECGAIM  TSKRGEESIK  DSYRCRRRKV
401  VDPSAPGQHE  GTCNVSMAAL  DKFVAERIFN  KIRHAEGDEE  TLALLWEAAR
451  RFGKLTEAPE  KSGERANLVA  ERADALNALE  ELYEDRAAGA  YDGPVGRKHF
501  RKQQAALTLR  QQGAEERLAE  LEAAEAPKLP  LDQWFPEDAD  ADPTGPKSWW
551  GRASVDDKRV  FVGLFVDKIV  VTKSTTGRGQ  GTPIEKRASI  TWAKPPTDDD
601  EDDARTARKT  *
```

FIG. 11

DNA Sequence of Integrase mutant 1C1
(SEQ ID NO: 135)

ATGacacaaggggttgtgaccggggtggacacgtacgcgggtgcttacgaccgtcagtcgcgcg
agcgcgaaaattcgagcgcagcaagcccagcgacacagcgtagcgccaacgaagacaaggcggc
cgaccttcagcgcgaagtcgagcgcgacgggggccggttcaggttcgtcgggcatttcagcgaa
gcgccgggcacgtcggcgttcgggacggcggaAcgcccggagttcgaacgcatcctgaacgaat
gccgcgccgggcggctcaacatgatcattgtctatgacgtgtcgcgcttctcgcgcctgaaggt
catggacgcgattccgattgtctcggaattgctcgccctgggcgtgacgattgtttccactcag
gaaggcgtcttccggcagggaaacgtcatggacctgattcacctgattatgcggctcgacgcgt
cgcacaaagaatcttcgctgaagtcggcgaagattctcgacacgaagaaccttcagcgcgaaCt
gggcgggtacgtcggcgggaaggcgccttacggcttcgagcttgtttcggagacgaaggagatc
acgcgcaacggccgaatggtcaatgtcgtcatcaacaagcttgcgcactcgaccactcccctta
ccggacccttcgagttcgagcccgacgtaatccggtggtggtggcgtgagatcaagacgcacaa
acaccttcccttcaagccgggcagtcaagccgccattcacccgggcagcatcacggggctttgt
aagcgcatggacgctgacgccgtgccgacccggggcgagacgattgggaagaagaccgcttcaa
gcgcctgggacccggcaaccgttatgcgaatccttcgggacccgcgtattgcgggcttcgccgc
tgaggtgatctacaagaagaagccggacggcacgccgaccacgaagattgagggttaccgcatt
cagcgcgacccgatcacgctccggccggtcgagcttgattgcggaccgatcatcgagcccgctg
agtggtatgagcttcaggcgtggttggacggcaggggggcgcggcaaggggcttt cccgggggca
agccattctgtccgccatggacaagctgtactgcgagtgtggcgccAtcatgacttcgaagcgc
ggggaagaatcgatcaaggactcttaccgctgccgtcgccggaaggtggtcgacccgtccgcac
ctgggcagcacgaaggcacgtgcaacgtcagcatggcggcactcgacaagttcgttgcggaacg
catcttcaacaagatcaggcacgccgaaggcgacgaagagacgttggcgcttctgtgggaagcc
gcccgacgcttcggcaagctcactgaggcgcctgagaagagcggcgaacgggcgaaccttgttg
cggagcgcgccgacgccctgaacgcccttgaagagctgtacgaagaccgcgcggcaggcgcgta
cgacggacccgttggcaggaagcacttccggaagcaGcaggcagcgctgacgctccggcagcaa
ggggcggaagagcggcttgccgaacttgaagccgccgaagccccgaagcttccccttgaccaat
ggttccccgaagacgccgacgctgacccgaccggccctaagtcgtggtgggggcgcgcgtcagt
agacgacaagcgcgtgttcgtcgggctcttcgtagacaagatTgttgtcacgaagtcgactacg
ggcaggggggcagggaacgcccatcgagaagcgcgcttcgatcacgtgggcgaagccgccaccg
acgacgacgaagacgacg:ccaggacggcacggaagacgtag

FIG. 12

Peptide sequence of integrase mutant 1C2 (SEQ ID NO: 210)

```
  1  MIQGVVTGVD TYAGAYDRQS RERENSSAAS PATQRSANED KAADLQREVE
 51  RDGGRFRFVG HFSEAPGTSA FGTAERPEFE RILNECRAGR LNMIIVYDVS
101  RFSRLKVMDA IPIVSELLAL GVTIVSTQEG VFRPGNVMDL IHLIMRLDAS
151  HKESSLKSAK ILDTKNLQRE LGGYVGGKAP YGFELVSETK EITRNGRMVN
201  VVINKLAHST TPLTGPFEFE PDVIRWWWRE IKTHKHLPFK PGSQAAIHPG
251  SITGLCKRMD ADAVPTRGET IGKKTASSAW DPATVMRILR DPRIAGFAAE
301  VIYKKKPDGT STTKIEGYRI QRDPITLRPV ELDCGPIIEP AEWYELQAWL
351  DGRRRGKGLS RGQAILSAMD KLYCECGAVM TSKRGEESIK DSYRCRRRKV
401  VDPSAPGQHE GTCNVSMAAL DKFVVERIFN KIRHAEGDEE TLALLWEAAR
451  RFGKLTEAPE KSGERANLVA ERANALNALE EPYEDRAAGA YDGPVGRKHF
501  RKQQAALTLR QQGAEERLAE LEAAEAPKLP LDQWFPEDAD ADPTGPKSWW
551  GRASVDDKRV FVGLFVDKIV VTKSTTGRGQ GTPIEKRASI TWAKPPTDDD
601  EDDARTARKT *RR
```

FIG. 13

Nucleotide sequence for integrase mutant 1C2 (SEQ ID NO: 211)

```
ATGATACAAGGGGTTGTGACCGGGGTGGACACGTACGCGGGTGCTTACGACCGTCAGTC
GCGCGAGCGCGAAAATTCGAGCGCAGCAAGCCCAGCGACACAGCGTAGCGCCAACGAAG
ACAAGGCGGCCGACCTTCAGCGCGAAGTCGAGCGCGACGGGGCCGGTTCAGGTTCGTC
GGGCATTTCAGCGAAGCGCCGGGCACGTCGGCGTTCGGGACGGCGGAGCGCCCGGAGTT
CGAACGCATCCTGAACGAATGCCGCGCCGGGCGGCTCAACATGATCATTGTCTATGACG
TGTCGCGCTTCTCGCGCCTGAAGGTCATGGACGCGATTCCGATTGTCTCGGAATTGCTC
GCCCTGGGCGTGACGATTGTTTCCACTCAGGAAGGCGTCTTCCGGCCGGGAAACGTCAT
GGACCTGATTCACCTGATTATGCGGCTCGACGCGTCGCACAAAGAATCTTCGCTGAAGT
CGGCGAAGATTCTCGACACGAAGAACCTTCAGCGCGAATTGGGCGGGTACGTCGGCGGG
AAGGCGCCTTACGGCTTCGAGCTTGTTTCGGAGACGAAGGAGATCACGCGCAACGGCCG
AATGGTCAATGTCGTCATCAACAAGCTTGCGCACTCGACCACTCCCCTTACCGGACCCT
TCGAGTTCGAGCCCGACGTAATCCGGTGGTGGTGGCGTGAGATCAAGACGCACAAACAC
CTTCCCTTCAAGCCGGGCAGTCAAGCCGCCATTCACCCGGGCAGCATCACGGGGCTTTG
TAAGCGCATGGACGCTGACGCCGTGCCGACCCGGGCGAGACGATTGGGAAGAAGACCG
CTTCAAGCGCCTGGGACCCGGCAACCGTTATGCGAATCCTTCGGGACCCGCGTATTGCG
GGCTTCGCCGCTGAGGTGATCTACAAGAAGAAGCCGGACGGCACGTCGACCACGAAGAT
TGAGGGTTACCGCATTCAGCGCGACCCGATCACGCTCCGGCCGGTCGAGCTTGATTGCG
GACCGATCATCGAGCCCGCTGAGTGGTATGAGCTTCAGGCGTGGTTGGACGGCAGGAGG
CGCGGCAAGGGGCTTTCCCGGGGGCAAGCCATTCTGTCCGCCATGGACAAGCTGTACTG
CGAGTGTGGCGCCGTCATGACTTCGAAGCGCGGGGAAGAATCGATCAAGGACTCTTACC
GCTGCCGTCGCCGGAAGGTGGTCGACCCGTCCGCACCTGGGCAGCACGAAGGCACGTGC
AACGTCAGCATGGCGGCACTCGACAAGTTCGTTGTGGAACGCATCTTCAACAAGATCAG
GCACGCCGAAGGCGACGAAGAGACGTTGGCGCTTCTGTGGGAAGCCGCCCGACGCTTCG
GCAAGCTCACTGAGGCGCCTGAGAAGAGCGGCGAACGGGCGAACCTTGTTGCGGAGCGC
GCCAACGCCCTGAACGCCCTTGAAGAGCCGTACGAAGACCGCGCGGCAGGCGCGTACGA
CGGACCCGTTGGCAGGAAGCACTTCCGGAAGCAACAGGCAGCGCTGACGCTCCGGCAGC
AAGGGGCAGAAGAGCGGCTTGCCGAACTTGAAGCCGCCGAAGCCCCGAAGCTTCCCCTT
GACCAATGGTTCCCCGAAGACGCCGACGCTGACCCGACCGGCCCTAAGTCGTGGTGGGG
GCGCGCGTCAGTAGACGACAAGCGCGTGTTCGTCGGGCTCTTCGTAGACAAGATTGTTG
TCACGAAGTCGACTACGGGCAGGGGCAGGGAACGCCCATCGAGAAGCGCGCTTCGATC
ACGTGGGCGAAGCCGCCAACCGACGACGACGAAGACGACGCCAGGACGGCACGGAAGAC
GTAGCGGCGCAG
```

FIG. 14

Peptide sequence of integrase mutant 11C2 (SEQ ID NO: 212)

```
  1  MTQGVVTGVD  TYAGAYDRQS  RERENSSAAS  PATQRSANED  KAADLQREVE
 51  RDGGRFRFVG  HFSEAPGTSA  FGTAERPEFE  RILNECRARR  LNMIIVYDVS
101  RFSRLKVMDA  IPIVSELLAL  GVTIVSTQEG  VFRPGNVMDL  IHLIMRLDAS
151  HKESSLKSAR  ILDTKNLQRE  LGGYVGGKAP  YGFELVSETK  EITRNGRMVN
201  VVINKLAHST  TPLTGPFEFE  PDVIRWWWRE  IKTHKHLPFK  PGSQAAIHPG
251  SITGLCKRMD  ADAVPTRGET  IGKKTASSAW  DPATVMRILR  DPRIAGFAAE
301  VIYKKKPDGT  PTTKVEGYRI  QRDPITLRPV  ELDCGPIIEP  AEWYELQAWL
351  DGRRRGKGLS  RGQAILSAMD  KLYCECGAVM  TSKRGEESIK  DSYRCRRRKV
401  VDPSAPGQHE  GTCNVSMAAL  DKFVAERIFN  KIRHAEGDEE  TLALLWEAAR
451  RFGKLTEAPE  KSGERANLVA  ERADALNALE  ELYEDRAAGA  YDGPVGRKHF
501  RKQQAALTLR  QQGAVERLAE  LEAAEAPKLP  LDQWFPEDAD  ADPTGPKSWW
551  GRASVDDKRV  FVGLFVDKIV  VTKSTTGRGQ  GTPIEKRASI  TWRSRQPTTT
601  KTTPRTARKT
```

FIG. 15

Nucleotide sequence of mutant integrase 11C2 (SEQ ID NO: 213)

ATGACACAAGGGGTTGTGACCGGGGTGGACACGTACGCGGGTGCTTACGACCGTCAGTC
GCGCGAGCGCGAAAATTCGAGCGCAGCAAGCCCAGCGACACAGCGTAGCGCCAACGAAG
ACAAGGCGGCCGACCTTCAGCGCGAAGTCGAGCGCGACGGGGGCCGGTTCAGGTTCGTC
GGGCATTTCAGCGAAGCACCGGGCACGTCGGCGTTCGGGACGGCGGAGCGCCCGGAGTT
CGAACGCATCCTGAACGAATGCCGCGCCAGGCGGCTCAACATGATCATTGTCTATGACG
TGTCGCGCTTCTCGCGCCTGAAGGTCATGGACGCGATTCCGATTGTCTCGGAATTGCTC
GCCCTGGGCGTGACGATTGTTTCCACTCAGGAAGGCGTCTTCCGGCCGGGAAACGTCAT
GGACCTGATTCACCTGATTATGCGGCTCGACGCGTCGCACAAAGAATCTTCGCTGAAGT
CGGCGAGGATTCTCGACACGAAGAACCTTCAGCGCGAATTGGGCGGGTACGTCGGCGGG
AAGGCGCCTTACGGCTTCGAGCTTGTTTCGGAGACGAAGGAGATCACGCGCAACGGCCG
AATGGTCAATGTCGTCATCAACAAGCTTGCGCACTCGACCACTCCCCTTACCGGACCCT
TCGAGTTCGAGCCCGACGTAATCCGGTGGTGGTGGCGTGAGATCAAGACGCACAAACAC
CTTCCCTTCAAGCCGGGCAGTCAAGCCGCCATTCACCCGGGCAGCATCACGGGGCTTTG
TAAGCGCATGGACGCTGACGCCGTGCCGACCCGGGGCGAGACGATTGGGAAGAAGACCG
CTTCAAGCGCCTGGGACCCGGCAACCGTTATGCGAATCCTTCGGGACCCGCGTATTGCG
GGCTTCGCCGCTGAGGTGATCTACAAGAAGAAGCCGGACGGCACGCCGACCACGAAGGT
TGAGGGTTACCGCATTCAGCGCGACCCGATCACGCTCCGGCCGGTCGAGCTTGATTGCG
GACCGATCATCGAGCCCGCTGAGTGGTATGAGCTTCAGGCGTGGTTGGACGGCAGGAGG
CGCGGCAAGGGGCTTTCCCGGGGGCAAGCCATTCTGTCCGCCATGGACAAGCTGTACTG
CGAGTGTGGCGCCGTCATGACTTCGAAGCGCGGGGAGGAATCGATCAAGGACTCTTACC
GCTGCCGTCGCCGGAAGGTGGTCGACCCGTCCGCACCTGGGCAGCACGAAGGCACGTGC
AACGTCAGCATGGCGGCACTCGACAAGTTCGTTGCGGAACGCATCTTCAACAAGATCAG
GCACGCCGAAGGCGACGAAGAGACGTTGGCGCTTCTGTGGGAAGCCGCCCGACGCTTCG
GCAAGCTCACTGAGGCGCCTGAGAAGAGCGGCGAACGGGCGAACCTTGTTGCGGAGCGC
GCCGACGCCCTGAACGCCCTTGAAGAGCTGTACGAAGACCGCGCGGCAGGCGCGTACGA
CGGACCCGTTGGCAGGAAGCACTTCCGGAAGCAACAGGCAGCGCTGACGCTCCGGCAGC
AAGGGGCGGTAGAGCGGCTTGCCGAACTTGAAGCCGCCGAAGCCCCGAAGCTTCCCCTT
GACCAATGGTTCCCCGAAGACGCCGACGCTGACCCGACCGGCCCTAAGTCGTGGTGGGG
GCGCGCGTCAGTAGACGACAAGCGCGTGTTCGTCGGGCTCTTCGTAGACAAGATCGTTG
TCACGAAGTCGACTACGGGCAGGGGGCAGGGAACGCCCATCGAGAAGCGCGCTTCGATC
ACGTGGCGAAGCCGCCAACCGACGACGACGAAGACGACGCCCAGGACGGCACGGAAGAC
GTAGCGGCGTAG

FIG. 16

Full Length ΦC31 attP Site
(SEQ ID NO: 214)

ccggtactgacggacacaccgaagccccggcggcaaccctcagcggatgccccggggcttcacg
ttttcccaggtcagaagcggttttcgggagtagtgccccaactggggtaaccTTGagttctct
cagttgggggcgtagggtcgccgacatgacacaaggggttgtgaccggggtggacacgtacgcg
ggtgcttacgaccgtcagtcgcggcc

FIG. 17A

Full length ΦC31 attB Site
(SEQ ID NO: 136)

cgatgtaggtcacggtctcgaagccgcggtgcgggtgccagggcgtgcccTTGggctccccggg
cgcgtactccacctcacccatctggtccatcatgatgaacgggtcgaggtggcggtagttgatc
ccggcgaacgcgcggcgcaccgggaagccctcgccctcgaaaccgctgggcgcggtggtcacgg
tgagcacgggacgtgcgacggcgtcggcgggtgcggatacgcggggcagcgtcagcgggttctc
gacggtcacggcgggcatgtcga

FIG. 17B

A 59 bp wild-type φC31 attP site
(SEQ ID NO: 115)

ggagtagtgccccaactggggtaacctTTGagttctctcagttgggggcgtagggtcgc

FIG. 17C

R4 attB295 with core underlined  (SEQ ID NO: 215)

CGTGGGGACGCCGTACAGGGACGTGCACCTCTCCCGCTGCACCGCCTCCAGCGTCGC
CGCCGGCTCGAAGGACGGGGCCGGGATGACGATGCAGGCGGCGTGGGAGGTGGCG
CCCAAGTTGCCCATGACCATGCC<u>GAAGCAGTGGTA</u>GAAGGGCACCGGCAGACACAC
CCGGTCCTGCTCCGTGTAGCCGACCGTGCGGCCCACCCAGTAGCCGTTGTTGAGGAT
GTTGTGGTGGGAGAGCGTGGCGCCCTTGGGGAAGCCGGTGGTGCCGGAGGTGTACT
GGATGTTGACCGGG

FIG. 18A

R4 attP64 with core underlined (SEQ ID NO: 216)

GCATGTTCCCCAAAGCGATACCACTT<u>GAAGCAGTGGTA</u>CTGCTTGTGGGTACACTCT
GCGGGTG

FIG. 18B

DNA Sequence of ΨA (SEQ ID NO: 20)

atttgtagaactattatgggacttaaaggggatatgggaggccacagttgagatg
ccttccaatcagaggcttggtgagattccaagaggtggtttcaaatacagcaata
agtacttgggtttcccTTGgtgtccccatggagattttaagccatgacgcaatgt
ttaaatcagagtggtattttatgacttaagcgggtaaatatgcaattggaaaat
attcagggaagggtgatttggtccagaagagtgggggcatccagagtacagtggg
tgaaatggatcggacttttggaagagagccttgtgctggacaggatggtccagt
attgtcaacacaagtttctcatgcttcactctccttcctagcaacaggaagacgg
aaatgaggccatgcaaaaataaaagaccctgaaagactccagacaatacctgatc
caccctaccattcaccctgtatagccagaagactt

FIG. 19

METHODS OF UNIDIRECTIONAL, SITE-SPECIFIC INTEGRATION INTO A GENOME, COMPOSITIONS AND KITS FOR PRACTICING THE SAME

CROSS-REFERENCE TO RELATED APPLICATIONS

This application is a continuation of application serial no. PCT/US03/17702 filed on Jun. 3, 2003, the disclosure of which is herein incorporated by reference; which application claims priority (pursuant to 35 U.S.C. §119 (e)) to the filing date of the U.S. Provisional Patent Application Ser. Nos. 60/385,954; 60/385,933; 60/386,325; 60/385,934; 60/385,929; 60/386,597; 60/385,944; all filed on Jun. 4, 2002; the disclosures of which are herein incorporated by reference; as well as U.S. Provisional Patent Application Ser. No. 60/416,989 filed on Oct. 7, 2002; the disclosure of which is herein incorporated by reference.

GOVERNMENT RIGHTS

This invention was made with government support under federal grant nos. DK58187, HL68112 and HG02571 awarded by the National Institute of Health. The United States Government may have certain rights in this invention.

INTRODUCTION

1. Field of the Invention

The field of this invention is molecular biology, particularly genetic modification and specifically vectors employed in such genetic modification.

2. Background of the Invention

Permanent genomic modification has been a long sought after goal since the discovery that many human disorders are the result of genetic mutations that could, in theory, be corrected by providing the patient with a non-mutated gene. Permanent alterations of the genomes of cells and tissues is also valuable for research applications, commercial products, protein production, and medical applications. Furthermore, genomic modification in the form of transgenic animals and plants has become an important approach for the analysis of gene function, protein production, the development of disease models, and the design of economically important animals and crops.

A major problem with many genomic modification methods associated with gene therapy is their lack of permanence. Life-long expression of the introduced gene is required for correction of genetic diseases. Indeed, sustained gene expression is required in most applications, yet current methods often rely on vectors that provide only a limited duration of gene expression. For example, gene expression is often curtailed by shut-off of integrated retroviruses, destruction of adenovirus-infected cells by the immune system, and degradation of introduced plasmid DNA (Anderson, W F, Nature 329:25-30, 1998; Kay, et al, Proc. Natl. Acad. Sci. USA 94:12744-12746, 1997; Verma and Somia, Nature 389:239-242, 1997; Stoll et al, Mol. Ther. 4:122-129). Even in shorter-term applications, such as therapy designed to kill tumor cells or discourage regrowth of endothelial tissue after restenosis surgery, the short lifetime of gene expression of current methods often limits the usefulness of the technique.

One method for creating permanent genomic modification is to employ a strategy whereby the introduced DNA becomes part of (i.e., integrated into) the existing chromosomes. Of existing methods, only retroviruses provide for efficient integration. Retroviral integration is random, however, thus the added gene sequences can integrate in an undesired manner, e.g., in the middle of another gene where a knock-out is not desired, or into a region in which the introduced gene sequence is inactive. In addition, a different insertion is created in each target cell. This situation creates safety concerns and produces an undesirable loss of control over the procedure.

Adeno-associated virus (AAV) often integrates at a specific region in the human genome. However, vectors derived from AAV do not integrate site-specifically due to deletion of the toxic rep gene (Flotte and Carter, Gene Therapy 2:357-362, 1995; Muzyczk, Curr. Topics Microbiol. Immunol. 158:97-129, 1992). The small percentage of the AAV vector population that eventually integrates does so randomly. Other methods for genomic modification include transfection of DNA using calcium phosphate co-precipitation, electroporation, lipofection, microinjection, protoplast fusion, particle bombardment, or the Ti plasmid (for plants). All of these methods produce random integration at low frequency. Homologous recombination produces site-specific integration, but the frequency of such integration is very low.

Another method that has been considered for the integration of heterologous nucleic acid segments into a chromosome is the use of a site-specific recombinase. Site-specific recombinases catalyze the insertion or excision of nucleic acid segments. These enzymes recognize relatively short, unique nucleic acid sequences that serve for both recognition and recombination. Examples include Cre (Sternberg and Hamilton, J Mol Biol 150:467-486, 1981), Flp (Broach, et al, cell-29:227-234, 1982; U.S. Pat. Nos. 5,654,182; 5,885,386; 6,140,129; and 6,175,058) and R (Matsuzaki, et al, J Bacteriology 172:610-618, 1990). Examples of use of site-specific recombinases for manipulation of nucleic acids are described in U.S. Pat. Nos. 5,527,695; 5,654,182; 5,677,177; 5,801,030; 5,919,676; 6,091,001; 6,110,736; 6,143,557; 6,156,497; 6,171,861; 6,187,994; and 6,262,341.

One of the most widely studied site-specific recombinases is the enzyme Cre from the bacteriophage P1. Cre recombines DNA at a 34-basepair sequence called loxP, which consists of two 13-basepair palindromic sequences flanking an 8-basepair core sequence. Cre can direct site-specific integration of a loxP-containing targeting vector to a chromosomally placed loxP target in both yeast and mammalian cells (Sauer and Henderson, New Biol 2:441-449, 1990; see also U.S. Pat. Nos. 4,959,317; 5,658,772). Use of this strategy for genomic modification, however, requires that a chromosome first be modified to contain a loxP site (because this sequence is not known to occur naturally in any organism but P1 bacteriophage), a procedure that suffers from low frequency and unpredictability as discussed above. Furthermore, the net integration frequency is low due to the competing excision reaction also mediated by Cre. Similar difficulties arise in the conventional use of other, well-known, site-specific recombinases.

A need still exists, therefore, for a convenient means by which chromosomes can be permanently modified in a site-specific manner. The present invention addresses that need.

RELEVANT LITERATURE

References of interest include: WO 00/11155 and WO 01/61049.

SUMMARY OF THE INVENTION

The subject invention provides a unidirectional site-specific integration system for integrating a nucleic acid into the genome of a target cell. The provided systems include a (1) a mutant, unidirectional site specific integrase, which can be provided by an integrase vector encoding the mutant integrase and (2) a targeting vector that includes: (a) a nucleic acid to be integrated; and (b) a vector attachment site, where the targeting vector attachment site serves as a substrate for the mutant, unidirectional site-specific integrase. In certain embodiments, the system components are provided as a single vector, which includes an integrase coding sequence, a nucleic acid to be integrated and a vector attachment site. In using the subject systems for site-specific integration, the targeting vector and integrase are introduced into the target cell and the cell is maintained under conditions sufficient to provide for site-specific integration of the nucleic acid into the target cell genome via a recombination event mediated by the site-specific integrase. Also provided are kits that include the subject systems. The subjects systems, methods and kits find use in a variety of different applications, several representative ones of which are described in detail as well.

One advantage of the invention is that the methods provide a system for site-specific recombination at a desired site without the need for manipulation of that sequence at the desired integration site. Instead, an integrase is selected that can facilitate site-specific recombination at an endogenous nucleic acid sequence.

Another advantage of the invention is that once a suitable integrase is selected, site-specific recombination can be accomplished in a single step.

Still another advantage is that recombination is unidirectional, thus reducing or avoiding secondary recombination events that can lead to excision of the inserted nucleic acid or deletion of adjacent nucleic acid.

These and other advantages and features of the invention will become apparent to those persons skilled in the art upon reading the details of the invention as more fully described below.

BRIEF DESCRIPTION OF THE DRAWINGS

FIG. 3 illustrates an exemplary "resident plasmid" which is established in *E. coli* and bears a lacZ gene separated from its promoter by a stuffer region containing transcriptional termination signals. The stuffer is flanked by two att test sites, i.e., the att sequences between which recombination is to be directed. For example, the human psi-A pseudo attP site and the wild-type attB site. After recombination, lacZ is transcribed, resulting in blue color on X-gal indicator plates. FIG. 4 illustrates an exemplary "cloning plasmid" which can carry a sequence encoding a modified integrase gene. A library of cloning plasmids can be provided, where each of the cloning plasmids contains a sequence encoding a different modified integrase. The cloning plasmid is transformed into the recipient strain carrying the resident plasmid. Increasing the growth temperature inactivates the temperature sensitive lacI lac repressor gene on the resident plasmid, allowing for transcription of the integrase gene on the cloning plasmid, which is under the control of the lac promoter. Mutant integrases that increase recombination between the att test sites on the resident plasmid will give rise to blue colonies.

FIGS. 5A and 5B illustrates the amino acid changes found in five altered integrases detected by increased blueness of colonies on Xgal plates in the assay using the plasmids depicted in FIGS. 3 and 4 and described in Example 1. These mutant integrases are referred to as 1C1, 5C1, 7C1, 1C2 and 11C2. In FIGS. 5A and 5B, the protein sequence for altered recombinase $7C_1$, wild-type recombinase ΦC31, altered recombinase $5C_1$, and altered recombinase 1C1, are presented relative to a consensus sequence. The asterisks at the ends of the sequences in FIGS. 5A and 5B represent stop codons.

FIG. 6 presents the DNA sequence of the wild-type ΦC31 recombinase.

FIG. 7 presents the peptide sequence of altered recombinase 7C1.

FIG. 8 presents the DNA sequence of altered recombinase 7C1.

FIG. 9 presents the peptide sequence of altered recombinase 5C1.

FIG. 10 presents DNA sequence of altered recombinase 5C1.

FIG. 11 presents the peptide sequence of altered recombinase 1C1.

FIG. 12 presents the DNA sequence of altered recombinase 1C1.

FIG. 13 presents the peptide sequence of altered recombinase 1C2.

FIG. 14 presents the polynucleotide sequence of altered recombinase 1C2.

FIG. 15 presents the peptide sequence of altered recombinase 11C2.

FIG. 16 presents the polynucleotide sequence of altered recombinase 11C2.

FIGS. 17A and 17B present the DNA sequences of the full length ΦC31 attP and attB sites, respectively. FIG. 17C presents a 59 bp wild-type ΦC31 attP site. In the figures the TTG core is indicated in upper case.

FIGS. 18A and 18B present, respectively, attB and attP sequences for the R4 recombinase.

FIG. 19 shows approximately 475 bp of DNA sequence from human chromosome 8 that encompasses the ΦC31 integrase pseudo-attP site ΨA. The core TTG sequence of the pseudo site is shown in bold. Approximately 40 bp surrounding the core represent the minimal attP pseudo site.

DEFINITIONS

Figure 1:
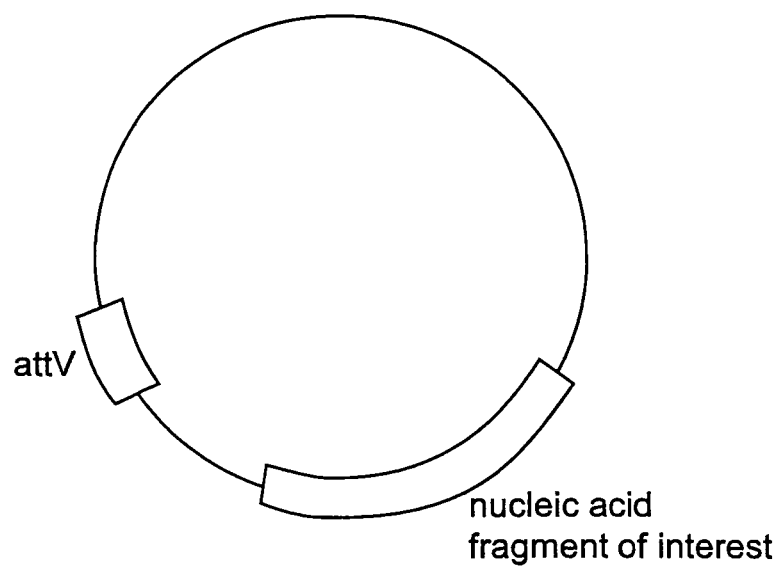
FIG. 1 is a schematic of a targeting vector useful in the invention, which targeting vector includes a nucleic acid of interest for introduction at a target site in a host cell genome and a vector attachment site (attV).

"Recombinases" are a family of enzymes that mediate site-specific recombination between specific DNA sequences recognized by the recombinase (Esposito, D., and Scocca, J. J., Nucleic Acids Research 25, 3605-3614 (1997); Nunes-Duby, S. E., et al., Nucleic Acids Research 26, 391-406 (1998); Stark, W. M., et al., Trends in Genetics 8, 432-439 (1992)).

"Altered recombinases" and "mutant recombinases" are used interchangeably herein to refer to recombinase enzymes in which the native, wild-type recombinase gene found in the organism of origin has been mutated in one or more positions relative to a parent recombinase (e.g., in one or more nucleotides, which may result in alterations of one or more amino acids in the altered recombinase relative to a parent recombinase). "Parent recombinase" is used to refer to the nucleotide and/or amino acid sequence of the recombinase from which the altered recombinase is generated. The parent recombinase can be a naturally occurring enzyme (i.e., a native or wild-type enzyme) or a non-naturally occurring enzyme (e.g., a genetically engineered enzyme). Altered recombinases of interest in the invention exhibit a DNA binding specificity and/or level of activity that differs from that of the wild-type enzyme or other parent enzyme. Such altered binding specificity permits the recombinase to react with a given DNA sequence differently than would the parent enzyme, while an altered level of activity permits the recombinase to carry out the reaction at greater or lesser efficiency. A recombinase reaction typically includes binding to the recognition sequence and performing concerted cutting and ligation, resulting in strand exchanges between two recombining recognition sites.

In particular, altered recombinases that recognize endogenous sequences in a genome of interest are one subject of the present invention. The mutations present in an altered recombinase may comprise base substitutions, deletions, additions, and/or other rearrangements in the DNA sequence encoding the recombinase, and/or any combination of such mutations, either singly or in groups. The altered recombinase may possess broader or narrower DNA recognition specificity compared to the parent enzyme and/or greater or lesser catalytic activity toward a particular DNA sequence, including a wild-type or non wild-type recombinase recognition site. A "recognition site" is a DNA sequence that serves a substrate for a wild-type or altered recombinase so as to provide for unidirectional site-specific recombination. In general, the recombinases used in the invention involve two recognition sites, one that is positioned in the integration site (the site into which a nucleic acid is to be integrated) and another adjacent a nucleic acid of interest to be introduced into the integration site. For example, the recognition sites for phage integrases are generically referred to as attB, which is present in the bacterial genome (into which nucleic acid is to be inserted) and attP (which is present in the phage nucleic acid adjacent the nucleic acid for insertion into the bacterial genome). Recognition sites can be native (endogenous to a target sequence or a phage) or altered relative to a native sequence. Use of the term "recognize" in the context of a recombinase "recognizes" a recognition sequence, is meant to refer to the ability of the recombinase to interact with the recognition site and facilitate site-specific recombination.

A "unidirectional recombinase" is a naturally-occurring recombinase, such as the ΦC31 integrase, a mutated recombinase, such as a mutated ΦC31 integrase that retains unidirectional, site-specific recombination activity, or a bi-directional recombinase modified so as to be unidirectional, such as a cre recombinase that has been modified to become unidirectional.

The native attB and attP recognition sites of phage ΦC31 (i.e. bacteriophage phiC31) are generally about 34 to 40 nucleotides in length (Groth et al. Proc Natl Acad Sci USA 97:5995-6000 (2000)). These sites are typically arranged as follows: AttB comprises a first DNA sequence attB5', a core region, and a second DNA sequence attB3', in the relative order from 5' to 3' attB5'-core region-attB3'. AttP comprises a first DNA sequence attP5', a core region, and a second DNA sequence attP3', in the relative order from 5' to 3' attP5'-core region-attP3'. The core region of attP and attB of ΦC31 has the sequence 5'-TTG-3'. The full-length, native attP and attB sequences for ΦDC31 integrase are provided in FIGS. 17A and 17B, respectively. Other phage integrases (such as the R4 phage integrase) and their recognition sequences can be adapted for use in the invention. The full-length, native attB and attP sequences for the R4 phage integrase are provided in FIGS. 18A and 18B.

Action of the integrase upon these recognitions sites is unidirectional in that the enzymatic reaction produces nucleic acid recombination products that are not effective substrates of the integrase. This results in stable integration with little or no detectable recombinase-mediated excision, i.e., recombination that is "unidirectional". The recombination product of integrase action upon the recognition site pair comprises, for example, in order from 5' to 3': attB5'-recombination product site sequence-attP3', and attP5'-recombination product site sequence-attB3'. Thus, where the targeting vector comprises an attB site and the target genome comprises an attP sequence, a typical recombination product comprises the sequence (from 5' to 3'): attP5'-TTG-attB3{targeting vector sequence} attB5'-TTG-attP3'.

A recognition site "native" to the genome, as used herein, means a recognition site that occurs naturally in the genome of a cell (i.e., the sites are not introduced into the genome, for example, by recombinant means).

A "pseudo-site" is a DNA sequence comprising a recognition site that is bound by a recombinase enzyme where the recognition site differs in one or more nucleotides from a wild-type recombinase recognition sequence and/or is present as an endogenous sequence in a genome that differs from the sequence of a genome where the wild-type recognition sequence for the recombinase resides. In some embodiments a "pseudo attP site" or "pseudo attB site" refer to pseudo sites that are similar to the recognitions site for wild-type phage (attP) or bacterial (attB) attachment site sequences, respectively, for phage integrase enzymes, such as the phage ΦC31. In many embodiments of the invention the pseudo attP site is present in the genome of a host cell, while the pseudo attB site is present on a targeting vector in the system of the invention "Pseudo att site" is a more general term that can refer to either a pseudo attP site or a pseudo attB site. It is understood that att sites or pseudo att sites may be present on linear or circular nucleic acid molecules.

By "nucleic acid fragment of interest" it is meant any nucleic acid fragment adapted for insertion into a genome. Suitable examples of nucleic acid fragments of interest include promoter elements, therapeutic genes, marker genes, control regions, trait-producing fragments, nucleic acid elements to accomplish gene disruption, and the like.

"Therapeutic genes" are those nucleic acid sequences which encode molecules that provide some therapeutic benefit to the host, including proteins (e.g., secreted proteins, membrane-associated proteins (e.g., receptors), structural proteins, and the like) functional RNAs (antisense, hammerhead ribozymes), and the like. One well known example is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease or effect a cure if the gene transfer was permanent.

Other disorders resulting from mutations in a single gene (known as monogenic disorders) include alpha-1-antitrypsin deficiency, chronic granulomatous disease, familial hypercholesterolemia, Fanconi anemia, Gaucher disease, Hunter syndrome, Hurler's syndrome, ornithine transcarbamylase deficiency, purine nucleoside phosphorylase deficiency, severe combined immunodeficiency disease (SCID)-ADA, X-linked SCID, hemophilia, and the like.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer.

A nucleic acid fragment of interest may additionally be a "marker nucleic acid" or "marker polypeptide". Marker genes encode proteins which can be easily detected in transformed cells and are, therefore, useful in the study of those cells. Marker genes are being used in bone marrow transplantation studies, for example, to investigate the biology of marrow reconstitution and the mechanism of relapse in patients. Examples of suitable marker genes include beta-galactosidase, green or yellow fluorescent proteins, chloramphenicol acetyl transferase, luciferase, and the like.

A nucleic acid fragment of interest may additionally be a control region. The term "control region" or "control element" includes all nucleic acid components which are operably linked to a nucleic acid fragment (e.g., DNA) and involved in the expression of a protein or RNA therefrom. The precise nature of the control (or regulatory) regions needed for coding sequence expression may vary from organism to organism. Such regions typically include those 5' noncoding sequences involved with initiation of transcription and translation, such as the enhancer, TATA box, capping sequence, CAAT sequence, and the like. Further exemplary control sequences include, but are not limited to, any sequence that functions to modulate replication, transcriptional or translational regulation, splicing, RNA stability, and the like. Examples include promoters, signal sequences, propeptide sequences, transcription terminators, polyadenylation sequences, enhancer sequences, transcription initiation sequences, intron sequences, ribosome binding sequences, attenuatory sequences, intron splice site sequences, and the like.

A nucleic acid fragment of interest may additionally be a trait-producing sequence, by which it is meant a sequence conferring some non-native trait upon the organism or cell in which the protein encoded by the trait-producing sequence is expressed. The term "non-native" when used in the context of a trait-producing sequence means that the trait produced is different than one would find in an unmodified organism which can mean that the organism produces high amounts of a natural substance in comparison to an unmodified organism, or produces a non-natural substance. For example, the genome of a crop plant, such as corn, can be modified to produce higher amounts of an essential amino acid, thus creating a plant of higher nutritional quality, or could be modified to produce proteins not normally produced in plants, such as antibodies. (See U.S. Pat. No. 5,202,422 (issued Apr. 13, 1993); U.S. Pat. No. 5,639,947 (Jun. 17, 1997).) Likewise, the genomes of industrially important microorganisms can be modified to make them more useful such as by inserting new metabolic pathways with the aim of producing novel metabolites or improving both new and existing processes such as the production of antibiotics and industrial enzymes. Other useful traits include herbicide resistance, antibiotic resistance, disease resistance, resistance to adverse environmental conditions (e.g., temperature, pH, salt, drought), and the like.

Methods of transforming cells are well known in the art. By "transformed" it is meant an alteration in a cell resulting from the uptake of foreign nucleic acid, usually DNA. Use of the term "transformation" is not intended to limit introduction of the foreign nucleic acid to any particular method. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "genomic domain" is meant a genomic region that includes one or more, typically a plurality of, exons, where the exons are typically spliced together during transcription to produce an mRNA, where the mRNA often encodes a protein product, e.g., a therapeutic protein, etc. In many embodiments, the genomic domain includes the exons of a given gene, and may also be referred to herein as a "gene." Modulation of transcription of the genomic domain pursuant to the subject methods results in at least about 2-fold, sometimes at least about 5-fold and sometimes at least about 10-fold modulation, e.g., increase or decrease, of the transcription of the targeted genomic domain as compared to a control, for those instances where at least some transcription of the targeted genomic domain occurs in the control. For example, in situations where a given genomic domain is expressed at only low levels in a non-modified target cell (used as a control), the subject methods may be employed to obtain an at least 2-fold increase in transcription as compared to a control. Transcription level can be determined using any convenient protocol, where representative protocols for determining transcription levels include, but are not limited to: RNA blot hybridization, RT PCR, ELISA and the like.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as integrating vectors.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure, M. O. Dayhoff ed.*, 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.). An example of stringent hybridization conditions is hybridization at 50° C. or higher and 0.1XSSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

A first polynucleotide is "derived from" a second polynucleotide if it has the same or substantially the same nucleotide sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

In the present invention, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

The term "exogenous" is defined herein as DNA which is introduced into a cell by the method of the present invention, such as with the DNA constructs defined herein. Exogenous DNA can possess sequences identical to or different from the endogenous DNA present in the cell prior to transfection.

By "transgene" or "transgenic element" is meant an artificially introduced, chromosomally integrated nucleic acid sequence present in the genome of a host organism.

The term "transgenic animal" means a non-human animal having a transgenic element integrated in the genome of one or more cells of the animal. "Transgenic animals" as used herein thus encompasses animals having all or nearly all cells containing a genetic modification (e.g., fully transgenic animals, particularly transgenic animals having a heritable transgene) as well as chimeric, transgenic animals, in which a subset of cells of the animal are modified to contain the genomically integrated transgene.

A "knock-out" of a target gene means an alteration in the sequence of the gene that results in a decrease of function of the target gene. "Knock-outs" of particular interest are those in which target gene expression is undetectable or insignificant. For example, a knock-out of a receptor gene means that function of the receptor has been substantially decreased so that receptor activity in binding its normal ligand is not detectable or at insignificant levels. Decrease in function can be due to decreases production of a full-length gene product as a result of the genetic alteration, or production of an altered gene product that is deficient in function relative to the native gene product. "Knock-out" transgenics of the invention can be transgenic animals having a heterozygous or homozygous knock-out of the target gene. "Knock-outs" also include conditional knock-outs, where alteration of the target gene can occur upon, for example, exposure of the animal to a substance that promotes target gene alteration. A "knock-in" of a target gene means an alteration in the sequence of the target gene that results in altered expression (e.g., increased (including ectopic) expression) of the target gene, e.g., by introduction of an additional copy of the target gene, or by operatively inserting a regulatory sequence that provides for enhanced expression of an endogenous copy of the target gene (e.g., gene activation). "Knock-in" transgenics can be heterozygous or homozygous for the genetic alteration. "Knock-ins" also encompass conditional knock-ins.

By "phenotypic trait" is meant a physical or biochemical characteristic of an animal that is conferred by a genetic element. Exemplary phenotypic traits that may be conferred by a transgenic element include, but are not necessarily limited to, increase or reduction in a biometric measure (e.g., length/height, weight, and the like), increase or decrease in a level of gene product in a tissue or biological fluid, increase or decrease in a level of a surface molecule (e.g., receptor, cell surface antigen, and the like), increased or decreased susceptibility to a condition or disease, and the like, relative to a non-transgenic animal.

By "genotypic trait" is meant a genetic modification that results from the present of a transgenic element in the genome of an animal. Exemplary genotypic traits that may be conferred by a transgenic element include, but are not necessarily limited to, disruption or introduction of one or more coding sequences, disruption or introduction of one or more promoter elements, or other modifications that can result from a change in the sequence of genomic nucleotide sequence.

By "beneficial gene product" is meant a gene product, usually a protein, which provides some desirable activity or phenotype to a host, which effect may be associated with treatment of a condition of disease. "Beneficial effect" as used herein may include a therapeutic effect or a life-enhancing effect (e.g., enhancement of physical appearance, weight reduction (where such is not necessarily of therapeutic importance), increase or decrease in hair growth, reduction of cellulite or fat, and the like).

"Therapeutic genes" are those nucleic acid sequences which encode molecules that provide some therapeutic benefit to the host, including proteins (e.g., secreted proteins, membrane-associated proteins (e.g., receptors), structural proteins, and the like) functional RNAs (antisense, hammerhead ribozymes), and the like. Therapeutic benefit may also be provided by production of a gene product that prevents or reduces the risk of onset of a disease or condition, e.g., microbial infection, e.g., bacterial, viral, parasitic, or fungal infection.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also mean to encompass delivery of an agent in order to provide for a pharmacologic effect, even in the absence of a disease or condition. For example, "treatment" encompasses delivery of growth factors that can provide for enhanced or desirable effects in the subject (e.g., enhanced milk production in cattle, enhanced weight gain in livestock, etc.).

"Target call" as used herein refers to a cell that in which a genetic modification is desired. Target cells can be isolated (e.g., in culture) or in a multicellular organism (e.g., in a blastocyst, in a fetus, in a postnatal animal, and the like). Target cells of particular interest in the present application are stem cells (e.g., embryonic stem cells (e.g., cells having an embryonic stem cell phenotype), adult stem cells, pluripotent stem cells, hematopoietic stem cells, mesenchymal stem cells, and the like).

The term "embryonic germ cell" refers to a cell found in the gonadal ridge of an embryo/fetus. Cells of the gonadal ridge normally develop into mature gametes.

A "germ cell" is a sperm or egg, or a cell that can become a sperm or egg. Cells that are not germ cells are somatic cells.

The term "primordial germ cells" is used to describe undifferentiated cells isolated from the gonadal ridges of an embryo (e.g. day-25 porcine embryo or a 34-40 day bovine embryo.

The term "stem cell" refers to a cell that has the ability to divide for indefinite periods and to give rise to specialized cells.

The term "adult stem cell" refers to a type of stem cell that gives rise to mature cell types that have characteristic morphologies (e.g., shapes) and specialized functions. The term "progenitor cell" (or "precursor cell") generally refers to an intermediate cell type or types derived from stem cells that are in a state prior to full differentiation. The term "embryonic stem cell" is used to mean an undifferentiated cell present in or isolated from the inner cell mass of a blastocyst-stage embryos, e.g., blastocyst-stage embryos at eight days or less after fertilization. Embryonic stem cells are pluripotent (have the potential to become a wide variety of specialized cell types) and have a noticeably larger nucleus, prominent nucleolus and smaller cytoplasm than adult cells of the same animal.

The terms "embryonic stem cell phenotype" and "embryonic stem-like cell" are used interchangeably herein to describe cells which are undifferentiated and thus are pluripotent which cells are visually distinguished from other differentiated adult cells of the same animal e.g., by a noticeably larger nucleus, (25% or more larger), noticeably larger and prominent nucleolus and smaller (25% or smaller) cytoplasm as compared to differentiated adult cells of the same animal.

The term "chimeric" is used to describe an organism which includes genetic material from two different organisms. Specifically, a chimeric is produced by genetically modifying cells having an embryonic stem cell phenotype, which cells were extracted from a first organism. The genetically modified cells are injected into early stage embryos (preimplantation embryos such as the blastocyst stage) of a second, different organism. The animal resulting from such methodology will include genetic material from the first and second organisms and thus be a "chimeric" organism. Provided that the cell expressing embryonic stem cell phenotype is genetically manipulated to include exogenous material the resulting chimeric will include that exogenous material within some, but not all of its cells.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a vector" includes a plurality of such vectors and reference to "the target cell" includes reference to one or more target cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF PREFERRED EMBODIMENTS

The subject invention provides a unidirectional site-specific integration system for integrating a nucleic acid into the genome of a target cell. The provided systems include a (1) a mutant, unidirectional site specific integrase, which can be provided by an integrase vector encoding the mutant integrase and (2) a targeting vector that includes: (a) a nucleic acid to be integrated; and (b) a vector attachment site, where the targeting vector attachment site serves as a substrate for the mutant, unidirectional site-specific integrase. In using the subject systems for site-specific integration, the targeting vector and integrase are introduced into the target cell and the cell is maintained under conditions sufficient to provide for site-specific integration of the nucleic acid into the target cell genome via a recombination event mediated by the site-specific integrase. Also provided are kits that include the subject systems. The subjects systems, methods and kits find use in a variety of different applications, several representative ones of which are described in detail as well.

In further describing the subject inventions, methods of producing the subject systems and the systems themselves, as well as components thereof, are described first, followed by a review of the methods and representative applications in which the subject systems find use and kits that include the subject systems.

Methods of Producing Unidirectional Site-Specific Integrating Vector Systems

As summarized above, the subject invention provides methods of producing vector systems that find use in unidirectional site-specific integration of nucleic acids into target cell genomes, such as target cell genomes of higher organisms, e.g., multicellular organisms. The subject methods of vector system production are "rational" methods, in that each component of the system is specifically designed and tailored for use in the particular method in which the system is to be employed. The subject methods of rational vector system design include the following steps: (a) identification of the system elements, including: (i) a target genome attachment site; (ii) a vector attachment site; and (iii) a mutant unidirectional site-specific recombinase for recognition of the target and vector attachment sites; and (b) construction of a vector system that incorporates the identified system elements. As such, the subject methods include: (a) a system element identification step; and (b) a system component production step; where the components incorporate the elements identified in the identification step.

In the system element identification step, the vector and genome attachments sites, as well as the mutant integrase that recognizes the identified vector and genome attachment sites, are identified. The order in which the subject elements are identified may vary. For example, the genome and vector attachment sites may be identified first, followed by identification of a mutant integrase that works with the previously identified attachment sites. Alternatively, the mutant site-specific integrase may be identified first, followed by identification of the vector and genome attachment sites to be employed with the integrase. In further describing the subject methods, the various elements are described first followed by a more in depth review of the different approaches that can be employed to identify the various elements.

Overview of System Elements

The systems employed in the subject methods include the following basic system elements: 1) an integrase recognition site pair, which pair includes a) a genome attachment site, and b) a vector attachment site; and 2) a mutant integrase. These basic elements are selected so that the mutant integrase recognizes the genome and vector attachment sites as substrates so as to facilitate site-specific recombination, resulting in introduction of nucleic acid in the vector having the vector attachment site (and the modifying nucleic acid) into the target genome having the genome attachment site (i.e., desired genomic integration site). In addition, integrase interaction with the recognition site substrates produces a recombination product which does not contain a sequence that acts as an effective substrate for the integrase. Thus, the integration event employed in the subject methods is unidirectional—with little or no detectable excision of the introduced nucleic acid by action of the integrase.

In one embodiment, the integrase recognition site pair includes genome and vector attachment sites based on recognition sites that serve as substrates for a mutant phage integrase, such as a mutant ΦC31 integrase. The native genome attachment site of wild-type ΦC31 is attB, while the native vector attachment site of wild-type ΦC31 is attP, each of which sequences are well known in the art. We note here that in the native "ΦC31" system, attB is present in the target bacterial genome and attP is normally present in the phage genome to facilitate integration of the phage genome into the bacterial host cell. However, the present invention provides a "ΦC31" system in which an "attP" sequence (attP or attP pseudo-sequence or engineered sequence based upon attP) is present in the target genome and the "attB" sequence (attB or attb pseudo-sequence or engineered sequence based upon attB) is present on the targeting vector. In certain embodiments of the system, however, the "attP" sequence is present in the targeting vector and the "attB" sequence is present in the target genome. The system of the invention only requires that the genome and vector attachment sites of the recognition site pair serve as substrates for the mutant integrase to accomplish the desired site-specific recombination event. Each of the elements of the system are now described in more detail.

Vector Attachment Site

The vector attachment site (attV) is a stretch, domain or region of nucleotides that, when the system is employed, is present on the vector to be integrated and is recognized by the integrase of the system in which the vector attachment site is a member. In other words, the vector attachment site is a domain of nucleotides that serves as a substrate for the integrase of the system with which it is employed, i.e., it recombines with a genome attachment site in an integrase mediated recombination event. The vector attachment site may vary in length, but typically ranges from about 20 to about 300 nt, usually from about 25 to about 200 nt, and more usually from about 30 to 40 nt. In certain embodiments, however, the vector attachment site may be about 250 nt in length. The vector attachment site has a sequence that is different from the genome attachment site, such that a recombination event mediated by the integrase is a unidirectional or "one-way" recombination event.

Exemplary vector attachment sites, referred to herein for convenience as "attV", generally comprise a first DNA sequence attV5', a core region, and a second DNA sequence attV3', in the relative order from 5' to 3' attV5'-core region-attV3'.

In one embodiment, the vector attachment site is an attachment site for recognition by a mutant phage integrase, sometimes a ΦC31 phage integrase mutant, e.g., an attB site, or a pseudo-site sequence based on the attB site that contains at least one nucleotide difference from a wild-type attB site. Identification of vector attachment sites for use in the invention is described below in more detail.

A system vector attachment site is a substrate for a system unidirectional integrase. Where the vector attachment site is an attB recognition site, the sequence of the vector attachment may be different from the wild-type attB recognition site by at least one base pair alteration (a substitution, deletion or insertion). Sequence alterations may be at any position within the vector attachment site, and in many cases a modified attachment site will have multiple sequence alterations as compared to a wild type attB recognition site. As such, many different attB recognition sites may be successfully used as a vector attachment site. Exemplary vector attachment site sequences, based on the ΦC31 phage attB recognition site, are shown in Table 1.

TABLE 1 exemplary vector attachment site sequences

| attB | B arm sequence | | Core seq. | B' arm sequence | |
|---|---|---|---|---|---|
| wild type | GTGCCAGGGCGTGCCC | (SEQ ID NO: 02) | TTG | GGCTCCCCGGGCGCG | (SEQ ID NO: 03) |
| BmB2 | GTGCCACGGCGTCCCC | (SEQ ID NO: 04) | TTG | GGCTCACCGTCGACG | (SEQ ID NO: 05) |
| BmB3 | GTGCCACGTCAAGCCC | (SEQ ID NO: 06) | TTG | TGCTCACCGGGCGCG | (SEQ ID NO: 07) |
| BmB4 | GTGCCACGTCAAGCCC | (SEQ ID NO: 08) | TTG | TGCTCACCGGGCGCG | (SEQ ID NO: 09) |
| BmB5 | GTGCCAGGGCGTGGCC | (SEQ ID NO: 10) | TTG | GGCTGCCCGAGATCG | (SEQ ID NO: 11) |
| BmB6 | GTGCCAGGGCGTGCCC | (SEQ ID NO: 12) | TTG | TCCCCCCGGGAGCGA | (SEQ ID NO: 13) |
| BmB7 | ATGCCAGGGCGTGCCG | (SEQ ID NO: 14) | TTA | GCCCCCCTAGCGACA | (SEQ ID NO: 15) |
| BmB8 | GTTCCAGGGCGATGCC | (SEQ ID NO: 16) | TTG | AGCTCCCCGTCCGCG | (SEQ ID NO: 17) |
| BmB9 | GAGCCAGTGCGTCCCC | (SEQ ID NO: 18) | TTG | GGCTCCCCGGACGCA | (SEQ ID NO: 19) |
| BmB10 | GTGCCAGGGCGTGCCG | (SEQ ID NO: 20) | TTG | GGCCCCCGGGCGCT | (SEQ ID NO: 21) |
| BmB11 | GTGCCAGGGCGTGCCC | (SEQ ID NO: 22) | TTA | GGATCCCCGGGCCCC | (SEQ ID NO: 23) |
| BmB12 | CTGCCAGGGCGTGCACC | (SEQ ID NO: 24) | TTG | GGCTCCCCGGGTACT | (SEQ ID NO: 25) |
| BmB13 | GGGACAGGGGGTGCCC | (SEQ ID NO: 26) | TTG | GGATCCCCGAGCGCG | (SEQ ID NO: 27) |
| BmB14 | GTGCGAGGGCGTGCCC | (SEQ ID NO: 28) | TTG | GGTACGCCCTACCAT | (SEQ ID NO: 29) |
| BmB15 | GAGTCAGGGCCTGCCC | (SEQ ID NO: 30) | TAG | GGCTCTCCGGGCGTG | (SEQ ID NO: 31) |
| BmB16 | GTGCCAGGGCGTGCCC | (SEQ ID NO: 32) | TTG | GGCTCCCCCCGCCTC | (SEQ ID NO: 33) |
| BmB17 | GAGCCAGGGCGTGCCC | (SEQ ID NO: 34) | TTG | GGCTCCCCGAGCGCC | (SEQ ID NO: 35) |
| BmB19 | GTACCTGGGCGTGCCC | (SEQ ID NO: 36) | TTG | GACTCACCGGGCGTG | (SEQ ID NO: 37) |
| BmB20 | GTGCCAGGGCGATCCC | (SEQ ID NO: 39) | TTG | GGCTCCCCGGCCGTG | (SEQ ID NO: 40) |

TABLE 1-continued exemplary vector attachment site sequences

| attB | B arm sequence | | Core seq. | B' arm sequence | |
|---|---|---|---|---|---|
| BmB21 | GTGCCAAGGCGTGACC | (SEQ ID NO: 41) | TTT | GGCTCCCCGGGCGCT | (SEQ ID NO: 42) |
| BmB22 | ATGCCAGGGCGTGCCA | (SEQ ID NO: 43) | TTG | GGATCCCCAGGCGCC | (SEQ ID NO: 44) |
| BmB23 | GTGCCAGGGCGTGCCC | (SEQ ID NO: 45) | TTG | GGCTCCCCAGCAGCG | (SEQ ID NO: 46) |
| BmB24 | GTGCCACGGCGTGCCC | (SEQ ID NO: 47) | TTG | GGCCCCCAGGCCCA | (SEQ ID NO: 48) |
| BmB25 | GTGCCAGGGTGTGTCC | (SEQ ID NO: 49) | TTG | GGCCCGCCGGGATCG | (SEQ ID NO: 50) |
| BmB26 | GAGCCAGGGCGTGCCA | (SEQ ID NO: 51) | TTG | GGCTCCCCGAGCGCC | (SEQ ID NO: 52) |
| BmB27 | GTGCCAGGGCGTGCAC | (SEQ ID NO: 53) | TTG | GGCTCCCCGGAAACC | (SEQ ID NO: 54) |
| BmB28 | ATGCCAGGGCGTGCCC | (SEQ ID NO: 55) | TTG | GGCTGCCCGGGTGCG | (SEQ ID NO: 56) |
| BmB29 | GTCCCAGGGGATGCCT | (SEQ ID NO:57) | TCG | GGCTCCCTGGGCGCG | (SEQ ID NO: 58) |
| BmB30 | GTGCCGGGCGTGCCC | (SEQ ID NO: 59) | TTG | GGCTCCCCATGATCG | (SEQ ID NO: 60) |
| BmB31 | GTGCCAGGCAGTGCCC | (SEQ ID NO: 61) | TTA | GGCTCCCCAGGCGCG | (SEQ ID NO: 62) |
| BmB32 | GTGACAAGGCGGGCGC | (SEQ ID NO: 63) | TAG | GGCTACCCTCGCGCG | (SEQ ID NO: 64) |
| BmB34 | GTGCCAGGGCAAGCCC | (SEQ ID NO: 65) | TTG | GTCTCTCCGGGCGCT | (SEQ ID NO: 66) |
| BmB35 | GTGGCAGGGCGTGCCC | (SEQ ID NO: 67) | TTG | GGTTCCCCGGGCGAG | (SEQ ID NO: 68) |
| BmB36 | GTGCCAGGGCCACCCC | (SEQ ID NO: 69) | TTG | GGCTCCCCGGGCGCG | (SEQ ID NO: 70) |
| BmB37 | GTGCCAGGGCGTACCA | (SEQ ID NO: 71) | TTG | GGCTCCCTGGGCGCA | (SEQ ID NO: 72) |
| BmB38 | TTGCCAGGGCGTGCAC | (SEQ ID NO: 73) | TTG | TCTTCGGCGTGTGAG | (SEQ ID NO: 74) |
| BmB39 | ATGCCAGGGCGTCTCC | (SEQ ID NO: 75) | TTG | GGCTCACCCCGCTCC | (SEQ ID NO: 76) |
| BmB40 | GTGCCAGGGCGTGCCC | (SEQ ID NO: 77) | TTG | GGCTTCCCGGGGGGG | (SEQ ID NO: 78) |
| BmB42 | GTGCCAGGGTGTGCCC | (SEQ ID NO: 79) | TTG | GGCTCCCCGAGGGAG | (SEQ ID NO: 80) |
| BmB44 | ATGCCAGAGCCAGCCC | (SEQ ID NO: 81) | TTG | GGATCCCCGGGCGCG | (SEQ ID NO: 82) |
| BmB45 | GTGCCAAGGCGTGCCC | (SEQ ID NO: 83) | TTA | GGCTCCCAAGGCGTG | (SEQ ID NO: 84) |
| BmB46 | ATGCCATGGAGAGACC | (SEQ ID NO: 85) | TTA | GGCACCCCGGGCGCC | (SEQ ID NO: 86) |
| BmB48 | ATGCCAGGGTGTGCCC | (SEQ ID NO: 87) | TTC | GGCTCCCCCGTCGCT | (SEQ ID NO: 88) |

Further exemplary vector attachment sequence based on the ΦC31 phage attB recognition site are described by the nucleic acid sequence DKGCSAVGKYGWGCM-STTSKSHYSVCSRNVNNHB (SEQ ID NO:01), where the nucleotide names are standard IUPAC ambiguity codes. The particular sequence of a vector attachment site may be optimized to increase the efficiency of an integration system. FIG. 1 shows an exemplary plasmid of the invention, containing an attV site, which is useful in the methods of the invention.

Mutant Integrases

The mutant integrase of the subject systems is a recombinase that is a mutant of a naturally occurring recombinase, i.e., it differs by at least one amino acid residue from a naturally occurring or wild type recombinase. In many embodiments, the mutant integrase is a mutant of a phage integrase, where specific representative integrases of interest include, but are not limited to: the integrases of ΦC31, R4, TP901-1, A118, ΦFC1 and the like.

Action of the mutant integrase upon the recognition site pair of the vector attachment site and the genome attachment site yields a recombination product that is not generally susceptible to recombination, e.g., recombination of the integrase recombination product by the integrase is insignificant or undetectable.

Genome Attachment Site

The genome attachment site (i.e. attG) is a stretch, domain or region of nucleotides that, when the system is employed, is present in the target cell genome and is recognized by the integrase of the system in which the genome attachment site is a member. The genome attachment site is the desired integration site and is a region, site or domain of the target cell genome that serves as the integration point. "System members" as used herein refers to elements of the systems of the invention (a pair of recognition sites and an integrase) that can interact to accomplish site-specific recombination according to the invention. In other words, the genome attachment site is a domain of nucleotides that serves as a substrate for the integrase of the system with which it is employed, i.e., it recombines with a vector attachment site in an integrase-mediated recombination event. The genome attachment site may vary in length, but typically ranges from about 20 to about 300 nt, usually from about 23 to about 100 nt, more usually from about 28 to about 50 nt, and generally about 40 nt. In certain embodiments, however, the genome attachment site may be about 250 nt in length.

Figure 2:
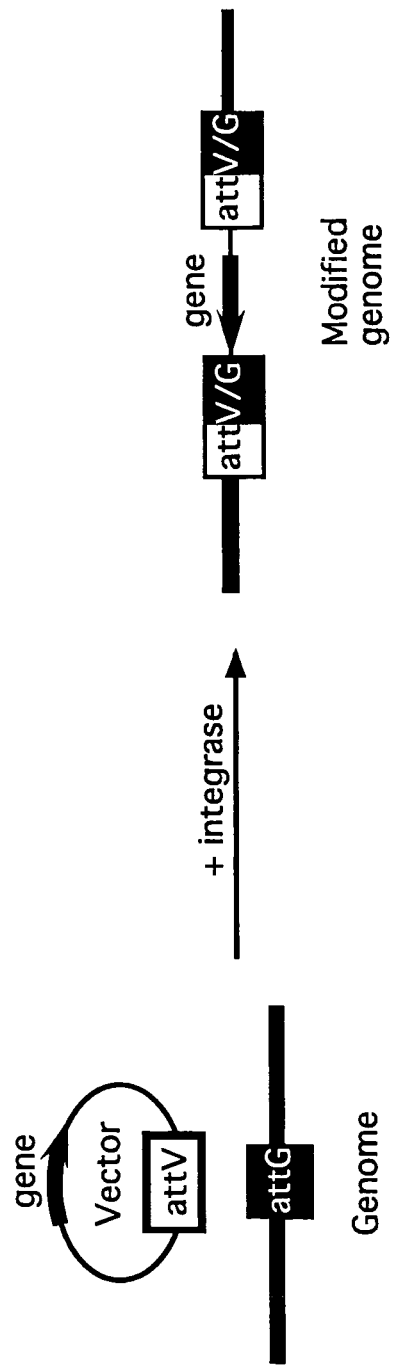
FIG. 2 is a schematic showing introduction of a nucleic acid of interest into a host genome using the system of the invention.

Exemplary genome attachment sites, referred to herein for convenience as "attG", generally comprise a first DNA sequence attG5', a core region, and a second DNA sequence attG3', in the relative order from 5' to 3' attG5'-core region-attG3'. The recombination product of integrase action upon the recognition site pair comprises, for example, in order from 5' to 3': attG5'-recombination product site sequence-attV3', and attV5'-recombination product site sequence-attG3'. Thus, where the targeting vector comprises an attV site and the target genome comprises an attG sequence, a typical recombination product comprises the sequence (from 5' to 3'): attG5'-"core region"-attV3'{targeting vector sequence}attV5'-"core region"-attG3'. Where the targeting vector comprises a modifying sequence, the recombination product comprises the formula: attG5'-"core region"-attV3'-modifying sequence—attV5'-"core region"-attG3'. A schematic integration event is shown in FIG. 2.

In many embodiments, the genome attachment site is an attachment site for recognition by a mutant phage integrase, preferably a ΦC31 phage integrase mutant, e.g. preferably an attP site (or a pseudo-site sequence based on the attP site). Identification of genome attachment sites is described below in more detail.

Integrating Vector System Production

The integrating vector system employed in the subject methods is one that integrates the modifying nucleic acid that it carries into the target cell genome in a manner such that the genomic domain of interest becomes modulated in a desired manner. As such, the integrating vector system is one that integrates its modifying nucleic acid "payload" in a highly site-specific manner that provides for the desired targeted genomic modification.

To obtain an integrating vector system that provides for this requisite site-specific integration, a "rational" protocol is typically employed, in that each component of the system is specifically designed and tailored for use in the particular method in which the system is to be employed, i.e., the particular transcriptional modulation application to be performed. The subject methods of rational vector system design include the following steps: (a) identification of the system elements, including: (i) a target genome attachment site, i.e., a site that, upon integration, provides for the desired genomic modification; (ii) a vector attachment site; and (iii) a mutant unidirectional site-specific recombinase for recognition of the target and vector attachment sites; and (b) construction of a vector system that incorporates the identified system elements. As such, the subject methods include: (a) a system element identification step; and (b) a system component production step, where the components incorporate the elements identified in the identification step. The system component production step allows the system genome attachment site and system vector attachment site to become a substrate for the system integrase.

System vectors may contain more than one vector attachment site, and may contain additional recombination sites (e.g. lox sites, att sites, etc) other than the vector attachment site.

Identification Strategy

Although any convenient identification strategy may be employed, of interest is a variable integrase strategy, in which at least one (i.e. the genome attachment site) or sometimes both of the attachment sites are identified first and an integrase, usually a mutant integrase, is generated, e.g., using high throughput mutant generation protocols, to recognize the first identified attachment sites. Also of interest is a variable attachment site strategy, in which the integrase is identified first and at least one of, and sometimes both of, the genome attachment site and the vector attachment site suitable for use with the identified integrase are then selected. One may also employ an iterative process, in which the variable integrase strategy is employed first to identify a first candidate set of integrases and their corresponding genome and vector attachment sites; followed by a variable attachment site round, in which variants of the initially selected genome and vector attachment sites are screened against the identified integrase to identify an optimal collection of genome and vector attachment sites for the identified integrases. One may also employ the reverse of the above strategy. In this way, an optimal set of attachment sites and integrase can be developed for a given system/application.

The Variable Integrase Approach

As mentioned above, one approach that may be employed involves identification of at least one of the vector and genome attachment sites of the recognition site pair, typically at least the genome attachment site, and then identification or generation of a mutant integrase that can facilitate site-specific recombination with the desired recognition site pair. This approach is referred to herein as the variable integrase approach.

The recognition site pair may be identified using a variety of different approaches, where the particular protocol employed depends, at least in part, on the particular purpose or application for which the system is being designed. For example, where the system is being designed for use in a method where the genome of the target cell is not altered prior to integration, the protocol that is employed is one that screens the sequence of the genome of the target cell in the region of desired integration for an appropriate genome attachment site, i.e., region or domain having a nucleotide sequence that is desirable to serve a substrate for an integrase to facilitate site-specific recombination at the desired site in the genome.

Although any sequence can be used as a genome attachment site providing it can serve as a recombination substrate for a system recombinase in a integrating vector system, in certain embodiments, identification of a suitable target genome attachment site can be accomplished by using sequence alignment and analysis, where the query sequence is a reference sequence which is designed to identify sequences of nucleic acids that will be recognized as substrates of the type of integrase that is to be employed, or for which a mutant integrase can be generated for recognition of the genome attachment site. Examples of reference sequences include sequences known to be recognized by wild type integrases, e.g., att sites, such as attP and attB sites, pseudo att sites, etc.

In certain embodiments, the genome of a target cell, at least in the desired region or location of integration, is searched for sequences having sequence identity to the selected reference sequence for a given integrase, for example, the attP or attB of the phage integrases of ΦC31, R4, and the like. The reference sequence may be a sequence known to be recognized by a given integrase, e.g., a known attB or attP site, or may be a non-naturally occurring sequence which is nonetheless recognized as a substrate by a given integrase, e.g., a consensus sequence for a given integrase, a pseudo-site, and the like. In many other embodiments, a suitable genome attachment site is identified without using a reference sequence, and solely relies on identifying a particular genomic region as an integration site.

Of particular interest in certain embodiments are reference sequences that identify sequences which are recognized by the ΦC31 integrase or mutants thereof. As such, reference sequences of particular interest include the sequences of the ΦC31 attP recognition sites.

Where the genome attachment site is an attP recognition site, the sequence of the genome attachment site may be different from the wild-type attP recognition site by at least one base pair alteration (a substitution, deletion or insertion). Sequence alterations may be at any position within the genome attachment site, and in many cases a modified genome attachment site will have multiple sequence alterations as compared to a wild type attP recognition site. As such, because an integrase is actually modified to recognize particular genome attachment sites, any sequence may be successfully used as a vector attachment site.

Screening a genomic region for suitable genome attachment sites can be aided by identifying sites that are similar to known pseudo-attP sites, such as those described in Table 2, a "consensus" att sequence, or a "framework" att sequence.

Exemplary genome attachment site sequences, based on the ΦC31 attP recognition site, are shown in Table 2, below.

TABLE 2

| SITE | CORE MOTIF | |
|---|---|---|
| wt attP | ACTGGGGTAACCTTTGAGTTCTCTCAGT | (SEQ ID NO: 89) |
| psA | ACTTGGGTTTCCCTTGGTGTCCCCATGG | (SEQ ID NO: 90) |
| psC | CCCTCGGAACCTCTAGGGAAACCCCAGG | (SEQ ID NO: 91) |
| psD | CACAGGATATTTGTAGGACTCCCACTGG | (SEQ ID NO: 92) |
| 1-11 | GACGGGAGAGCTGGAGACAGCACCCTGG | (SEQ ID NO: 93) |
| 1-14 | CCAAAGGAAGTCTTTCCCTAAACCCAGG | (SEQ ID NO: 94) |
| 1-15 | CCAGGGTTAGGCTTAAAGTGAACCCAAT | (SEQ ID NO: 95) |
| 1-9 | CCATAGTAAACTATACGCCTATTCAGGG | (SEQ ID NO: 96) |
| 2-12 | ACAGTGAAAACCTTCTAGTTAACCATGG | (SEQ ID NO: 97) |
| 2-23 | CCTCATTTAATCTATAGGTTCTCCTTGT | (SEQ ID NO: 98) |
| 2-3847 | CCATGGTGAAGCTAAAGCTGAATCTTGG | (SEQ ID NO: 99) |
| 2-7 | CCCTGGAGCTTCTAAAAGATCACCCTGA | (SEQ ID NO: 100) |
| 2-8 | CCAGGGAAAAGCTTCAGTCTCTCCCTGG | (SEQ ID NO: 101) |

Comparisons of multiple attP-based genome attachment site sequences allows the construction of a "consensus" sequence, where a consensus sequences displays the nucleotides that are most likely to be at each position of an integrase substrate attP site. A consensus sequence may be used to search for suitable genome attachment sites in a genome.

ΦC31 attP recognition sites have the following "consensus" sequence:

$AN_1CGAN_2TTN_3TTTN4ATGACAGATN_5N6AAN_7T$ (SEQ ID NO:102) where each of $N_1$, $N_2$, $N_3$, $N_4$, $N_5$, $N_6$, and $N_7$ are any of adenine (A), cytosine (C), guanine (G), or thymine (T). In one embodiment, $N_1$, $N_4$, $N_5$, and $N_6$ are pyrimidine (Y) (either C or T) and $N_2$, $N_3$, and $N_7$ are purines (R) (either A or G).

Genome attachment site selection can also be aided by searching for a "framework" sequence, where the framework sequence may be present in a genome attachment site, but its position within the genome attachment site may not be at any particular fixed position. Examples of two framework sequences are: CNNNGNNNNNCNTTNNNNNCNNNG and CNNGGNTNNCCNNTNNNNNCNCNNNG, where N is any nucleotide. (SEQ ID NOS: 103 & 104).

Nucleic acid sequence databases that include the genome of interest, and particularly the region of the genome into which integration is desired, are searched with the reference sequence using any convenient protocol. In many embodiments, computers in conjunction with appropriate software are employed to search the sequence of the genome of interest. The find patterns algorithm of the Wisconsin Software Package Version 9.0 developed by the Genetics Computer Group (GCG; Madison, Wis.), is an example of a program used to screen all sequences in the GenBank database (Benson et al., 1998, Nucleic Acids Res. 26, 1-7). For example, when selecting genome attachment sites in a target cell, the genomic sequences of the target cell can be searched for suitable genome attachment sites using either the attP or attB sequences associated with a particular recombinase or altered recombinase. Functional sizes and the amount of heterogeneity that can be tolerated in these recombination sequences can be empirically evaluated, for example, by evaluating integration efficiency of a targeting construct using an altered recombinase of the present invention (for exemplary methods of evaluating integration events, see, WO 00/11155, published 2 Mar. 2000). Where such an algorithm is employed, of interest in many embodiments are the identification of attachment sites that share at least about 20%, usually at least about 30% and more usually at least about 40% sequence identity with a wild type attP reference recognition sequence.

In a similar manner, a vector attachment site can be selected based on the knowledge of the genome attachment site. For example, where one scans a desired integration domain for the presence of a suitable attachment site, one can then select a vector attachment site from a collection of known sites that will be suitable for use with the identified genome attachment site. Where the identified genome attachment site is a variant of the wild type ΦC31 attP site, e.g., as may be identified by searching with the above-described consensus reference sequence, one may select as the vector attachment site a site known to recombine with the identified genome attachment site, e.g., the ΦC31 attB site as described in WO 01/61409, or the pseudo sites thereof as provided in Table 1, above.

Turning now to the integrase, in this variable integrase approach, a mutant integrase is then selected from a collection of candidate mutant integrases, e.g., using a screening strategy as described below. The mutant integrases of the initial collection of candidate integrases may be known integrases, where representative integrases include those described in WO 01/61049; the disclosure of the priority document of which is herein incorporated by reference. Alternatively, a candidate mutant integrase may be first synthesized and then screened, e.g., using a screening protocol as described below, for its ability to recognize the previously identified attachment sites as substrates.

To generate a mutant integrase, the coding sequence of a wild type integrase may be mutated so as to encode a mutant integrase. The integrase coding sequences may be mutated in various ways known in the art to generate targeted changes in the sequence of the encoded integrase, properties of the encoded integrase, including attachment site recognition properties of the encoded integrase, etc. The DNA sequence or protein product of such a mutation will usually be substantially similar to the wild type or mutant integrase parental coding sequence from which it is derived, e.g., where the coding sequence of the mutant integrase will differ by at least one nucleotide or amino acid, respectively, and may differ by at least two or more nucleotides or amino acids. The sequence changes may be substitutions, insertions, deletions, or a combination thereof. Deletions may further include larger changes, such as deletions of a domain or coding sequence, e.g., of stretches of 10, 20, 50, 75, 100, 150 or more aa residues. Techniques for in vitro mutagenesis of cloned genes are known. Examples of protocols for site specific mutagenesis may be found in Gustin et al. (1993), Biotechniques 14:22; Barany (1985), Gene 37:111-23; Colicelli et al. (1985), Mol. Gen. Genet. 199:537-9; and Prentki et al. (1984), Gene 29:303-13. Methods for site specific mutagenesis can be found in Sambrook et al., Molecular Cloning: A Laboratory Manual, CSH Press 1989, pp. 15.3-15.108; Weiner et al. (1993), Gene 126:35-41; Sayers et al. (1992), Biotechniques 13:592-6; Jones and Winistorfer (1992), Biotechniques 12:528-30; Barton et al. (1990), Nucleic Acids Res 18:7349-55; Marotti and Tomich (1989), Gene Anal. Tech. 6:67-70; and Zhu (1989), Anal Biochem 177:120-4.

In many embodiments, it is desirable to screen a large number of candidate integrases in order to rapidly identify a mutant integrase that can recognize the preselected attachment sites. In such embodiments, the first step is to generate a plurality, e.g., 2 or more, usually 10 or more, more usually 20 or more, such as 50 or more, 100 or more, 200 or more, 500 or more, etc., candidate integrases. Any convenient protocol for generating large numbers of mutant proteins from an initial wild type protein may be employed, where representative protocols are well known to those of skill in the art and of interest include, but are not limited to: (1) error prone PCR, as described in U.S. Pat. No. 6,358,709 (the disclosure of which are herein incorporated by reference); (2) DNA shuffling, as described in U.S. Pat. Nos. 6,355,484; 6,365,408 (the disclosure of which are herein incorporated by reference); (3) in vivo mutagenesis in mutator cells (e.g., mutator bacterial strains deficient in mismatch repair enzymes) or using mutational vectors, as described in U.S. Pat. Nos. 6,004,804; 6,146,894; 6,165,718; 6,211,351; (the disclosures of which are herein incorporated by reference); (4) directed evolution protocols, as described in U.S. Pat. Nos. 6,358,709, 5,723,323 and 6,171,820 (the disclosures of which are herein incorporated by reference); (4) directed mutation, as described in U.S. Pat. Nos. 5,702,931; 5,932,419; 5,935,830; (the disclosures of which are herein incorporated by reference); and the like. Such protocols result in the production of a population of candidate mutant integrases. The generated population of candidate integrases is then screened in order to identify an integrase that is suitable for use with the pre-identified attachment sites, where representative screening protocols are provided below.

The Variable Attachment Site Approach

As summarized above, one may also employ a variable attachment site approach in order to identify the various elements of the subject system to be produced. In this approach, the integrase employed in the subject methods is first selected from a known set of integrases, and then one or both of the attachment sites of the recognition site pair are selected based on the preselected integrase, e.g., from a candidate collection of attachment sites in order to complete the identification of the system element members.

In these methods, the first step is to identify an integrase. The mutant integrase may be identified in a number of different ways. In certain embodiments, the mutant integrase is identified by selecting an integrase from a known collection of integrases, where representative integrases are known and include those described in WO 01/61049; the disclosure of the priority document of which is herein incorporated by reference.

In this variable attachment site approach, functional attachment sites can be found empirically. For example, a protocol in which plasmids carrying the integrase of interest and a vector with an attachment site therefore and carrying a marker sequence, e.g., a marker expression cassette, can be co-transfected into cells and those cells in which integration has occurred can be identified. The integration sites can then be recovered, for example, by plasmid rescue and analyzed at the DNA sequence level, producing, for example, the DNA sequence of an attachment site from the human genome.

Alternatively, a candidate attachment site may be synthesized and then screened in an assay for suitability for use with the preselected integrase. In many such embodiments, collections of candidate attachment sequences are screened for their compatibility with a preselected integrase. These embodiments are typically embodiments in which the vector and/or genome attachment site is selected to work with the known integrase, e.g., by screening a plurality of candidate attachment sites for their suitability as substrates for the integrase, e.g., by employing a representative screening assay as described below.

For example candidate attachment sites can be generated based upon one or more recognition sites of the selected integrase. For example, where the selected integrase is ΦC31 integrase or a ΦC31 mutant integrase, the candidate attachment sites can be derived from an attB or attP site. In one embodiment, the candidate attachment site is generated so as to have a consensus sequence of an attB site or of an attP site, which consensus sequences are described above.

As summarized above, in this approach, either one or both of the attachment sites may be varied with respect to the preselected integrase.

Sequential Combination of Variable Attachment Site and Variable Integrase Approach A further method for identifying the various system components uses a sequential combination of a variable attachment site and variable integrase approaches. One embodiment of this combinatorial method employs performing a screening assay where an integration vector is firstly integrated into a genome without pre-selecting the genome attachment site. In this method, the non-preselected integration sites are rescued and characterized by DNA sequencing, and a particular site is then selected as a genome attachment site. A system integrase can then be modified to recognize the selected genome attachment site as a system genome attachment site.

Screening Assays

Regardless of the approach employed, many of the approaches will employ a screening assay to test a candidate element with a preselected element, e.g., a candidate attachment site with a preselected integrase, or vice versa. Any convenient screening protocol may be employed.

One convenient screening protocol that may be employed is the "*E. coli* genetic screening" protocol as described in WO 01/61049; the disclosure of the priority document of which is incorporated herein by reference. By way of providing full description, this screening protocol is now reviewed. In this assay, the two selected attachment sites to be tested for recombination are cloned on a plasmid that is resident in *E. coli*. The two attachment sites are separated by a stuffer region containing transcription termination signals. Adjacent to the attachment sites is the coding region of lacZ, without a promoter. An intramolecular integration reaction restores the lac promoter to lacZ, resulting in the production of blue color on Xgal plates. The resident plasmid carries a temperature-sensitive version of lacI and a temperature-sensitive origin of replication. Both of these elements are relatively inactive during growth at 37° C.

In a method of the present invention, a population of cells may be provided where each cell of the population comprises a resident plasmid. As described, the resident plasmid typically comprises a promoter, functional in the cell used for screening, adjacent a first recombination site which is adjacent a transcription terminator, which is adjacent a second recombination site, which is adjacent a coding sequence of interest. Accordingly, the typical order of these components of the resident plasmid is promoter-first recombination site (e.g., genome attachment site)-transcription terminator (one or more transcription termination sequence effective to block read-through transcription)-second recombination site (e.g., vector attachment site)-coding sequence of interest (e.g., a marker or selection coding sequence). The coding sequence of interest may encode a number of different products (e.g., a functional RNA and/or a polypeptide, see below). The product produced from the coding sequence of interest is used for screening and/or selection.

To perform the assay, a vector carrying the integrase, e.g., a preselected integrase or a candidate integrase, is transformed into bacteria containing the resident plasmid, and the transformed cells maintained under appropriate conditions, for example, spread on plates containing kanamycin, tetracyline, and Xgal, and grown at 30° C. Under these conditions, the integrase gene is not expressed, because lac repressor is active and will repress the lac promoter controlling the integrase gene by binding to the lac operator. Transformed cells are grown for approximately 24 hours until moderately sized colonies are obtained.

The plates are then placed at 37° C. for various periods of time. Under these conditions, the resident plasmid does not replicate and integrase is expressed, due to the temperature lability of the lacI gene product (lac repressor) and the plasmid repA replication protein. Under these static conditions, progress of the intramolecular integration reaction is monitored by following expression of lacZ, as manifested by blue color on the Xgal plates.

Different levels of integration produce different patterns of coloration in the resulting colonies, depending on the timing and frequency of integration events. These patterns give a measure of the ability of the selected integrase enzymes to recognize the selected attachment sites, i.e. to determine how the selected elements work together.

Other screening methods may also be employed, e.g., those of Santoro et al. Proc. Nat'l Acad. Sci. USA (2002) 99: 4185-4190 and Bucholz & Stewart, Nat. Biotech. (2001) 19, 1047-1052. Screening also can be directed by using information from the three-dimensional structure and/or hydroxy-radical footprint that indicates which amino acids contact the DNA binding site. Screening may also be performed using yeast cells and human cells, as described in the Examples.

Following identification of the elements of the employed vector system, as described above, the next step is producing vector systems that are employed to site-specifically integrate the modifying nucleic acid. As such, the above identification step provides a set of identified attachment site and integrase elements, which elements are then employed in the construction of a unidirectional site-specific integration system, as described below.

System Construction

The next step in the subject methods is the construction of the various system components, which components employ the various elements as identified above. This step at least includes construction of the targeting vector and integrase delivery elements, and in certain embodiments further includes a step of constructing a vector for introducing a genome attachment site into a target cell, e.g., in those embodiments where the genome attachment site is not already present in the target cell.

The targeting construct or vector includes the vector attachment site as identified above. A targeting vector may further include a polynucleotide of interest. Polynucleotides of interest can include, but are not limited to, expression cassettes encoding polypeptide products, stuffer regions for disruption of target cell coding sequences, which regions may include stop codons, etc., where the nature of the polynucleotide of interest depends on the particular application in which the system is to be employed. The targeting constructs are typically circular and may also contain selectable markers, an origin of replication, and other elements.

A variety of targeting vectors are suitable for use in the practice of the present invention, both for prokaryotic expression and eukaryotic expression. In general, the targeting construct will have one or more of the following features: a promoter, promoter-enhancer sequences, a selection marker sequence, an origin of replication, an inducible element sequence, an epitope-tag sequence, and the like. One or more of the above components may be presented on the vector as an expression cassette, which includes a nucleic acid encoding a product of interest operably linked to a promoter (as well as any other required sequences to provide for a functional expression cassette), which is also referred to herein as a "gene of interest." Specific products of interest and their corresponding encoding sequences are described in greater detail infra.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters are sometimes preferred as they are often particularly strong promoters.

Promoters may be, furthermore, either constitutive or regulatable. Inducible elements are DNA sequence elements which act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, AraC and gal promoters of *E. coli*, the α-amylase (Ulmanen, et al., J. Bacteriol. 162:176-182, 1985) and the sigma-28-specific promoters of *B. subtilis* (Gilman et al., Gene 32:11-20(1984)), the promoters of the bacteriophages of *Bacillus* (Gryczan, In: The Molecular Biology of the Bacilli, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Preferred eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, the actin promoter, the phosphoglycerate kinase promoter, the ubiquitin promoter and the thymidine kinase promoter, the ecdysone-responsive promoter(s), tetracycline-responsive promoter, and the like.

Exemplary promoters for use in the present invention are selected such that they are functional in the cell type (and/or animal or plant) into which they are being introduced.

Selection markers are valuable elements in expression vectors as they provide a means to select for growth of only those cells that contain a vector. Such markers are typically of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media that lacks that essential component.

Common selectable marker genes include those for resistance to antibiotics such as ampicillin, tetracycline, kanamycin, bleomycin, streptomycin, hygromycin, neomycin, Zeocin™, G418, and the like. Selectable auxotrophic genes include, for example, hisD, that allows growth in histidine free media in the presence of histidinol.

A further element useful in an expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in expression vectors employed herein include *E. coli* oriC, colE1 plasmid origin, 2μ and ARS (both useful in yeast systems), SV40, and EBV oriP (useful in mammalian systems), and the like.

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr, chitin binding domain, and the like.

A further useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The foregoing elements can be combined to produce targeting vectors suitable for use in the methods of the invention. Those of skill in the art would be able to select and combine the elements suitable for use in their particular system in view of the teachings of the present specification. Suitable prokaryotic vectors include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)) and many such vectors are commercially available. *Bacillus* plasmids include pC194, pC221, pT127, and the like, and are disclosed by Gryczan (In: The Molecular Biology of the *Bacilli*, Academic Press, NY (1982), pp. 307-329). Suitable *Streptomyces* plasmids include pli101 (Kendall et al., J. Bacteriol. 169:4177-4183, 1987), and *streptomyces* bacteriophages such as ΦC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suitable eukaryotic plasmids include, for example, BPV, EBV, vaccinia, SV40, 2-micron circle, pcDNA3.1, pcDNA3.1/GS, pYES2/GS, pMT, p IND, pIND(Sp1), pVgRXR (Invitrogen), and the like, or their derivatives. Such plasmids are well known in the art (Botstein et al., Miami Wntr. SyTnp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et at., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

The targeting vectors described herein can be constructed utilizing methodologies known in the art of molecular biology (see, for example, Ausubel or Maniatis) in view of the teachings of the specification. As described above, the targeting constructs are assembled by inserting, into a suitable vector backbone, a recombination site, polynucleotides encoding sequences of interest operably linked to a promoter of interest; and, optionally a sequence encoding a positive selection marker.

In addition to the target vector which includes the identified vector attachment site, an integrase introduction element for introducing the identified integrase into the target cell is also constructed. Depending on the particular method by which the integrase is to be introduced into the cell upon use of the system, the integrase introduction element may be a purified preparation of the integrase or a nucleic acid encoding the integrase. The integrase-encoding nucleic acid may be an RNA or a DNA, where the integrase-encoding nucleic acid is introduced into a target cell and the encoded integrase protein is expressed using cellular translational machinery.

Where the integrase component of the system is a purified preparation of the integrase, sequences encoding the integrase may be employed to recombinantly produce the integrase. Integrases having the desired activity can be purified to a desired degree of purity by methods known in the art of protein purification, including, but not limited to, ammonium sulfate precipitation, size fractionation, affinity chromatography, HPLC, ion exchange chromatography, heparin agarose affinity chromatography (e.g., Thorpe & Smith, Proc. Nat. Acad. Sci. 95:5505-5510, 1998).

Where the integrase component is an integrase coding nucleic acid, typically a vector that includes the integrase in a suitable expression cassette is constructed, e.g., by the vector construction methods described above. Expression of the integrase is typically desired to be transient. Accordingly, vectors providing transient expression of the integrase are preferred in the practice of the present invention. However, expression of the altered recombinase may be regulated in other ways, for example, by placing the expression of the recombinase under the control of a regulatable promoter (i.e., a promoter whose expression can be selectively induced or repressed).

In certain embodiments, the system includes two disparate or separate nucleic acid vectors, i.e., an integrase coding vector and targeting vector. The integrase coding vector is a vector that includes a coding sequence for the integrase of the system, as described above. The targeting vector is as described above.

In yet other embodiments, the system includes a single nucleic acid vector that includes both the an integrase coding domain and the components of the targeting vector as described above, e.g., a vector attachment site and nucleic acid to be integrated. In other words, the system is made up of a single nucleic acid vector that at least includes an integrase coding domain, a vector attachment site and a nucleic acid to be integrated, where the single nucleic acid vector may include one or more of the additional components described above.

In certain embodiments, the system components of the vectors described above are present in viral vector delivery vehicles. A variety of viral vector delivery vehicles are known to those of skill in the art and include, but are not limited to: adenovirus, herpesvirus, lentivirus, vaccinia virus and adeno-associated virus (AAV). In certain embodiments, adenoviral vectors is of particular interest. Adenovirus, a double-stranded DNA virus, is currently the best studied gene transfer vector for delivery of heterologous nucleic acid (for a review, see T. C. Becker et al., Meth. Cell Biol. 43:161-89, 1994; and J. T. Douglas and D. T. Curiel, Science & Medicine 4:44-53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

Where viral vectors are employed, in certain embodiments as indicated above the integrase coding sequence is present on a viral vector which is separate from the viral vector containing the targeting vector elements. In yet other embodiments, a single viral vector that includes not only the integrase coding sequence but also the targeting vector elements is employed. In certain embodiments, the construction step further includes preparing a construct for introducing an identified genomic attachment site into a target cell genome. For such embodiments, the identified genomic attachment site is placed into a vector that is suitable for use in integrating the genomic attachment site into the target cell genome, where representative vectors include, but are not limited to: plasmid DNA vectors, retroviral vectors; adeno-associated vectors, adenoviral vectors, double stranded DNA vectors, Ti vectors etc., as further described in the introduction section, above. In these embodiments, the vector construction methods described above and/or known in the art may be employed.

The above-described two-step identification and construction method results in the production of a unidirectional, site-specific vector integration system for use in integrating nucleic acids in a site-specific manner into a target cell genome, i.e., into a chromosome of a target cell, where the target cell is, in many embodiments, a non-bacterial cell, and in many embodiments is a eukaryotic cell, where the eukaryotic cell may be from a single cell or multicellular organism, e.g., animal or plant.

Systems

Also provided by the subject invention are the above produced site-specific integration systems. The subject systems typically include at least a targeting vector, which includes a vector attachment site, and an integrase component, where these components are described above. Also present in certain embodiments of the subject systems is a vector that includes a genomic attachment site for integrating the genomic attachment site into a target cell.

Methods

The above-described unidirectional site-specific integration systems can be used as vectors to stably integrate a wide variety of endogenous and/or exogenous nucleic acids into a target cell genome (exogenous means a nucleic acid having a sequence that is not present in the target cell while endogenous means a nucleic acid that pre-exists in the target cell, prior to insertion, e.g., where one wishes to insert extra copies of the nucleic acid and/or expressable copies of the nucleic acid into the target cell genome). In many embodiments, the sequence of nucleotides present in the exogenous nucleic acid will be one that is not found in the genome of the target cell, i.e., it will be heterologous to the target cell.

As indicated above, the subject systems can be used with a variety of target cells, where target cells in many embodiments are non-bacterial target cells, and often eukaryotic target cells, including, but not limited to, plant and animal target cells, e.g., insect cells, vertebrate cells, particularly avian cells, e.g., chicken cells, fish, amphibian and reptile cells, mammalian cells, including murine, porcine, ovine, equine, rat, ungulates, dog, cat, monkey, and human cells, and the like.

In the methods of the subject invention, the targeting vector and integrase components of the subject systems are introduced into the target cell under conditions sufficient for the integrase to mediate integration of the targeting vector into the target cell. Any convenient protocol may be employed, where the protocol may provide for in vitro or in vivo introduction of the targeting vector into the target cell, depending on the location of the target cell, for production of a transgenic animal according to the invention. For example, where the target cell is an isolated cell, the targeting vector may be introduced directly into the cell under cell culture conditions permissive of viability of the target cell, e.g., by using standard transformation techniques. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the targeting vector may be administered to the organism or host in a manner such that the targeting construct is able to enter the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995,), using viral vectors (Monahan, et al, Gene Therapy 4:40-49, 1997; Onodera, et al, Blood 91:30-36, 1998,), by uptake of "naked DNA", and the like. Techniques well known in the art for the transfection of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

In practicing the subject methods, in addition to the targeting construct, the integrase component (e.g., protein or nucleic acid encoding the same) of the subject systems is also introduced into the target cell, such that the integrase is present to mediate integration of the targeting construct into the target genome. Methods of introducing functional proteins into cells are well known in the art. Introduction of purified altered integrase protein or integrase-encoding RNA ensures a transient presence of the protein and its function, which is often a preferred embodiment. Alternatively, a gene encoding the integrase can be included in an expression vector used to transform the cell. It is generally preferred that the integrase be present for only such time as is necessary for insertion of the targeting construct into the genome being modified. Thus, the lack of permanence associated with most expression vectors, RNA, or protein is not expected to be detrimental. As described above, the integrase can also be introduced into a cell in the form of an RNA, which may be an mRNA. Introduction of integrase-encoding RNA ensures transient expression and removes the possibility that an integrase-encoding nucleic acid will become permanently incorporated into a target genome.

The integrases used in the practice of the present invention can be introduced into a target cell before, concurrently with, or after the introduction of a targeting vector. The integrase proteins can be directly introduced into a cell as a protein, for example, using liposomes, coated particles, or microinjection. Alternately, a polynucleotide encoding the integrase can be introduced into the cell using a suitable expression vector.

As indicated above, in certain embodiments the various integrase and targeting vector components are present in a single nucleic acid vector, which vector may be introduced into the cell using any convenient nucleic acid delivery means, including those described above, e.g., via the viral vector delivery vehicles known and summarized above.

Utility

The subject methods of unidirectional site-specific integration of an exogenous nucleic acid into the genome of a target cell using the subject systems find use in a variety of applications in which the site specific integration of an exogenous nucleic acid into a target cell is desired. Applications in which the subject vectors and methods find use include: research applications, polypeptide synthesis applications and therapeutic applications. Each of these representative categories of applications is described separately below in greater detail.

Research Applications

Examples of research applications in which the subject methods find use include applications designed to characterize a particular gene. In such applications, the vector is employed to insert a gene or coding sequence of interest into a target cell and the resultant effect of the inserted gene on the cell's phenotype is observed. In this manner, information about the gene's activity and the nature of the product encoded thereby can be deduced.

One can also employ the subject vectors to produce models, e.g., cellular and multicellular models, such as transgenic cellular and multicelleular models (e.g., transgenic plants and animals, including but not limited to: rodents, including mice, rats; rabbits; goats; pigs; cows; zebrafish; etc.) in which overexpression and/or misexpression of a gene of interest is produced in a cell and the effects of this mutant expression pattern are observed. One can also use the subject vectors to readily clone genes introduced into a host cell via insertional mutagenesis that yields phenotypes and/or expression patterns of interest. In such applications, the subject vectors are employed to generate insertional mutants through integration of DNA. The phenotype and/or expression pattern of the resultant mutant is then assayed using any convenient protocol.

Polypeptide Synthesis Applications

In addition to the above research applications, the subject methods and vectors also find use in the synthesis of polypeptides, e.g. proteins of interest. In such applications, a vector that includes a gene encoding the polypeptide of interest in combination with requisite and/or desired expression regulatory sequences, e.g. promoters, etc., (i.e. an expression module) is introduced into the target cell that is to serve as an expression host for expression of the polypeptide. Following introduction and subsequent stable integration into the target cell genome, the targeted host cell is then maintained under conditions sufficient for expression of the integrated gene. Once the transformed host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Therapeutic Applications

The subject vectors also find use in therapeutic applications, in which the methods and vectors are employed to stably integrate a therapeutic nucleic acid, e.g., gene or protein/factor coding sequence thereof, into the genome of a target cell, i.e., gene therapy applications. The subject vectors may be used to deliver a wide variety of therapeutic nucleic acids. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like.

The above list of proteins refers to mammalian proteins, and in many embodiments human proteins, where the nucleotide and amino acid sequences of the above proteins are generally known to those of skill in the art. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

Additional applications in which the subject methods and systems find use include those applications described in WO 01/61049, which applications include: the production of genome modified cells; the production of transgenic plants and animals; gene therapy applications; and the like.

Additional specific applications of interest include, but are not limited to: (a) gene transcription modulation applications, as described in pending U.S. application Ser. No. 60/385,933, filed on Jun. 4, 2002, the disclosure of which is herein incorporated by reference; (b) in vitro "knock-in" and "knock-out" applications, as described in pending U.S. application Ser. No. 60/386,325 filed on Jun. 4, 2002, the disclosure of which is herein incorporated by reference; (c) transgenic animal production applications, as described in pending U.S. application Ser. No. 60/385,934 filed on Jun. 4, 2002, the disclosure of which is herein incorporated by reference; (d) transgenic plant production applications, as described in pending U.S. application Ser. No. 60/385,929 filed on Jun. 4, 2002, the disclosure of which is herein incorporated by reference; (e) stem cell modification applications, as described in pending U.S. application Ser. No. 60/386,597 filed on Jun. 4, 2002, the disclosure of which is herein incorporated by reference; (f) gene therapy applications, as described in pending U.S. application Ser. No. 60/385,944 filed on Jun. 4, 2002, the disclosure of which is herein incorporated by reference; etc. Each of these representative applications is now described separately in greater detail.

Methods of Transcription Modulation

The subject invention provides methods of modulating transcription of a genomic domain of a target cell. By modulating is meant changing or altering, including increasing and decreasing, the transcription level or rate of the genomic domain of interest. As such, altered transcription encompasses activating (or causing to be expressed) a genomic domain which is normally silent (untranscribed) in the cell as obtained, increasing transcription of a genomic domain which is not transcribed at physiologically significant levels in the cell as obtained, changing the pattern of regulation or induction such that it is different than occurs in the cell as obtained, increasing levels sufficient for use in protein production as obtained, and reducing (including eliminating) transcription of a genomic domain which is transcribed in the cell as obtained.

By genomic domain is meant a genomic region that includes one or more, typically a plurality of, exons, where the exons are typically spliced together during transcription to produce an mRNA, where the mRNA often encodes a protein product, e.g., a therapeutic protein, etc. In many embodiments, the genomic domain includes the exons of a given gene, and may also be referred to herein as a "gene." Modulation of transcription of the genomic domain pursuant to the subject methods results in at least about 2-fold, sometimes at least about 5-fold and sometimes at least about 10-fold modulation, e.g., increase or decrease, of the transcription of the targeted genomic domain as compared to a control, for those instances where at least some transcription of the targeted genomic domain occurs in the control. For example, in situations where a given genomic domain is expressed at only low levels in a non-modified target cell (used as a control), the subject methods may be employed to obtain an at least 2-fold increase in transcription as compared to a control. Transcription level can be determined using any convenient protocol, where representative protocols for determining transcription levels include, but are not limited to: RNA blot hybridization, reverse transcriptase PCR, ELISA and the like.

Transcription modulation, as described above, is achieved by integrating into the target cell genome a transcription modulation unit that, when integrated into the genome of the target cell according to the subject invention, becomes operatively linked to the targeted genomic domain in a manner that results in the desired transcription modulation of transcription. For example, where transcription is to be enhanced, the subject methods integrate a transcriptional modulation unit that becomes operably linked upon integration to the targeted genomic domain in manner that results in an increase in transcription of the targeted genomic domain. Likewise, where transcription is to be decreased, the subject methods integrate a transcriptional modulation unit that becomes operably linked upon integration to the targeted genomic domain in manner that results in a decrease in transcription of the targeted genomic domain.

As indicated above, the subject methods rely on site-specific integration of a transcriptional modulation unit into the genome of the target cell in a manner that results in transcriptional modulation unit mediated transcriptional modulation of the targeted genomic domain. Depending on the particular application in which the method is employed, the transcriptional modulation unit may be a transcriptional activation unit, e.g., for at least enhancing transcription, including turning on transcription when it is normally not present and increasing the level of transcription when already present. Alternatively, the transcription modulation unit may be a transcriptional inhibition unit, e.g., for at least decreasing transcription, including turning off transcription when it is normally present and decreasing the level of transcription when already present.

Where the transcriptional modulation unit is a transcriptional activation unit, the transcriptional activation unit is made up of a sequence of nucleotides that, when integrated into the genomic DNA of the target cell in the site-specific manner of the subject invention, becomes operably linked to the genomic domain of interest and results in an increase in transcription of the genomic domain of interest. Any sequence of nucleotides that provides for the desired transcription enhancement may be employed.

The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 100 kb, usually from about 5 kb to about 10 kb. In some embodiments, however, the inserted nucleic acid may be as small as about 500 bp or about 100 bp.

In many embodiments, the transcriptional activation unit at least includes a regulatory sequence. The regulatory sequence of the transcriptional activation unit can include one or more promoters (such as a constitutive or inducible promoters), enhancers, scaffold-attachment regions or matrix attachment sites, transcription factor binding sites, or combinations of elements, etc. As such, the regulatory sequence can contain an inducible promoter, with the result that cells resulting from the subject methods do not immediately transcribe the genomic domain but can be induced to do so. Alternatively, constitutive promoters that result in immediate transcription upon introduction may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, thymidine kinase genes, PGK genes, ubiquitin genes, immunoglobulin genes or the HMG-CoA reductase gene). The regulatory sequence may include transcription factor binding sites, where representative sites include, but are not limited to: the TATA Box, the CCAAT Box, AP1, Sp1 or NF-κ B binding sites.

In certain embodiments, the transcriptional activation unit further includes one or more exons. An exon is defined herein as a DNA sequence that is copied into RNA and is present in a mature mRNA molecule. The exons can, optionally, contain DNA that encodes one or more amino acids and/or partially encodes an amino acid (i.e., one or two bases of a codon). Alternatively, the exon may contain DNA which corresponds to a 5' non-coding region. Where the exogenous exon or exons encode one or more amino acids and/or a portion of an amino acid, the DNA construct is designed such that, upon transcription and splicing, the reading frame is in-frame with the second exon or coding region of the targeted genomic domain or gene. As used herein, in-frame means that the encoding sequences of a first exon and a second exon, when fused, join together nucleotides in a manner that does not change the appropriate reading frame of the portion of the mRNA derived from the second exon.

Where the first exon of the targeted genomic domain or gene contains the sequence ATG to initiate translation, the exogenous exon of the construct may contain an ATG and, if required, one or more nucleotides such that the resulting coding region of the mRNA including the second and subsequent exons of the targeted gene is in-frame. Examples of such targeted genes in which the first exon contains an ATG include the genes encoding hEPO, hGH, human colony stimulating factor-granulocyte/macrophage (hGM-CSF), and human colony stimulating factor-granulocyte (hG-CSF).

In addition, in many embodiments the transcriptional activation unit also includes a splice-donor site, specifically an unpaired splice-donor site. A splice-donor site is a sequence that directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AG GURAGU (where R denotes a purine nucleotide) with the GU in the fourth and fifth positions, being required (Jackson, I. J., Nucleic Acids Research 19: 3715-3798 (1991)). The first three bases of the splice-donor consensus site are the last three bases of the exon. Splice-donor sites are functionally defined by their ability to effect the appropriate reaction within the mRNA splicing pathway. An unpaired splice-donor site is defined herein as a splice-donor site that is present in a targeting construct and is not accompanied in the construct by a splice-acceptor site positioned 3' to the unpaired splice-donor site. The unpaired splice-donor site results in splicing to an endogenous splice-acceptor site. A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as:

YYYYYYYYYYNYAG    (SEQ ID NO. 105)

where Y denotes any pyrimidine and N denotes any nucleotide (Jackson, I. J., Nucleic Acids Research 19:3715-3798 (1991)). An intron is defined as a sequence of one or more nucleotides lying between two exons and which is removed, by splicing, from a precursor RNA molecule in the formation of an mRNA molecule.

When present, the encoding DNA (e.g., in exon 1 of the transcriptional activation unit) employed can optionally encode one or more amino acids, and/or a portion of an amino acid, which are the same as those of the endogenous protein. The encoding DNA sequence employed herein can, for example, correspond to the first exon of the gene of interest. The encoding DNA can alternatively encode one or more amino acids or a portion of an amino acid different from the first exon of the protein of interest. Such an embodiment is of particular interest where the amino acids of the first exon of the protein of interest are not critical to the activity or activities of the protein. For example, any exon of human or non-human origin in which the encoded amino acids do not prevent the function of the hybrid signal peptide can be used. In a related embodiment, this technique can also be employed to correct a mutation found in a target gene. Where the desired product is a fusion protein of the endogenous protein and encoding sequences in the transcriptional activation unit, the exogenous encoding DNA incorporated into the cells by the present method includes DNA which encodes one or more exons or a sequence of cDNA corresponding to a translation or transcription product which is to be fused to the product of the endogenous targeted gene. In this embodiment, targeting is used to prepare chimeric or multifunctional proteins which combine structural, enzymatic, or ligand or receptor binding properties from two or more proteins into one polypeptide. For example, the exogenous DNA can encode an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopa-decarboxylase, transcriptional regulatory proteins, α-galactosidase and tyrosine hydroxylase.

While the above description has been primarily limited to elements found in transcriptional activation units, those elements that may be present in transcriptional inhibition units are readily to known to those of skill in the art, and typically include expression inhibition elements, negative regulatory elements, stuffer fragments that disrupt transcription, termination codons, and the like.

The DNA of the transcriptional modification unit employed in the subject methods can be obtained from sources in which it occurs in nature or can be produced, using genetic engineering techniques or synthetic processes.

In the subject methods, the above described transcriptional modulation unit "payload" is integrated into the target cell genome using the subject integration system to obtain the desired transcriptional modification of the target genomic domain.

The subject methods can be used to modulate transcription of genomic domains, e.g., genes, in a variety of target cells, where target cells in certain embodiments are non-bacterial target cells, and often eukaryotic target cells, including plant and animal target cells, e.g., insect cells, vertebrate cells, particularly avian cells, e.g., chicken cells; mammalian cells, including murine, porcine, ovine, equine, rat, dog, cat, monkey, and human cells; and the like.

In the methods of the subject invention, the targeting vector and integrase components of the subject systems are introduced into the target cell under conditions sufficient for the integrase to mediate integration of the targeting vector into the target cell, as described above.

The above described targeting/integration event results in the insertion of the transcriptional modulatory unit into the genome of the target cell in a manner that places the endogenous gene under the control of the transcriptional modulatory unit (for example, by insertion of either a promoter or an enhancer, or both, upstream of the endogenous gene or regulatory region). Optionally, the targeting event can simultaneously result in the deletion or inactivation of the endogenous regulatory element, such as the deletion or inactivation of a tissue-specific negative regulatory element. The targeting event can displace an existing element; for example, a tissue-specific enhancer can be displaced by an enhancer that has broader or different cell-type specificity than the naturally-occurring elements, or displays a pattern of regulation or induction that is different from the corresponding nontransfected cell. In this embodiment the naturally occurring sequences are taken out of operational linkage with the genomic domain of interest and new sequences are added. Alternatively, the endogenous regulatory elements are disrupted or disabled by the targeting event, such as by targeting the exogenous sequences within the endogenous regulatory elements.

After the vector system components are introduced into the cell, the cell is maintained under conditions appropriate for site-specific integration to occur, as is known in the art, where representative conditions are provided in the experimental section, below.

The above described integration event results in the production of a recombinant cell, such as a fungal, plant, or animal cell, and particularly, primary, secondary, or immortalized human or other mammalian cell, in which sequences which alter the transcription of an endogenous gene, e.g., as found in a target genomic domain, are operatively linked to an endogenous gene encoding a product, producing a new transcription unit with expression and/or coding potential that is different from that of the endogenous gene in the target cell prior to practice of the subject method. Particularly, the invention includes a recombinant cell that includes a transcriptional modulation unit which is introduced at a predetermined site by the above described vectors and is operatively linked to an exon, e.g., the second exon, of an endogenous gene. Optionally, there may be multiple exogenous exons (coding or non-coding) and introns operatively linked to any exon of the endogenous gene. The resulting recombinant cells are cultured under conditions that select for amplification, if appropriate, of the DNA encoding the amplifiable marker and the novel transcriptional unit. With or without amplification, cells produced by this method can be cultured under conditions, as are known in the art, suitable for the expression of the protein, thereby producing the protein in vitro, or the cells can be used for in vivo delivery of a therapeutic protein (i.e., gene therapy).

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells that have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized.

Immortalized cells are cell lines (as opposed to cell strains with the designation "strain" reserved for primary and secondary cells), a critical feature of which is that they exhibit an apparently unlimited lifespan in culture.

Cells selected for the subject method can fall into four types or categories: 1) cells which do not, as obtained, make or contain the protein or product (such as a protein that is not normally expressed by the cell or a fusion protein not normally found in nature), 2) cells which make or contain the protein or product but in quantities other than that desired (such as, in quantities less than the physiologically normal lower level for the cell as it is obtained), 3) cells which make the protein or product at physiologically normal levels for the cell as it is obtained, but are to be augmented or enhanced in their content or production, and 4) cells in which it is desirable to change the pattern of regulation or induction of a gene encoding a protein.

Primary, secondary and immortalized cells to be transfected by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Where the recombinant cells are to be used in gene therapy, primary cells are preferably obtained from the individual to whom the transfected primary or secondary cells are administered. However, primary cells can be obtained from a donor (other than the recipient) of the same species.

Recombinant immortalized cells can also be produced by the present method and used for either protein production or gene therapy. Examples of immortalized human cell lines useful for protein production or gene therapy by the present method include, but are not limited to, human embryonic kidney cells (Graham et al J Gen Virol. 1977 36:59-74), 293T cells, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., Cancer Res, 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) may be used. In addition, primary, secondary, or immortalized human cells, as well as primary, secondary, or immortalized cells from other species which display the properties of gene amplification in vitro can be used for in vitro protein production or gene therapy.

Methods of Targeted Genomic Modification

The subject invention provides methods of making a targeted genomic modification in a cell. By "genomic modification" is meant a stable alteration of a cell's genomic DNA, e.g., a permanent change in a cell's chromosome. The term "genomic modification" encompasses changes in a target cell genome of varying size. A feature of the subject invention is that the modification or change results from an integrative event, as described in greater detail below, where a nucleic acid is inserted into the genome to provide for the desired modification or change. As such, the subject methods are properly characterized being integrative targeted genomic modification methods. The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 100 kb, usually from about 5 kb to about 10 kb. In some embodiments, however, the inserted nucleic acid may be as small as about 500 bp or about 100 bp.

As indicated above, the subject methods rely on site-specific integration of a modifying nucleic acid into the genome of the target cell to achieve targeted genomic modification. Depending on the particular application in which the method is employed, the modifying nucleic acid may be an expression disruptive nucleic acid, e.g., as is employed in "knockout" applications reviewed in greater detail below; and/or an expression providing nucleic acid, e.g., as is employed in "knock-in" applications reviewed in greater detail below.

Where the modifying nucleic acid is an expression disruptive nucleic acid, it includes a sequence of nucleotides that, upon integration, disrupts expression of a particular gene or genes, i.e., in interferes or stops transcription of a genomic domain. The modifying nucleic acid may include any convenient sequence of nucleotides that provides for the desired expression disruption, where such sequences may include random "stuffer" sequences, negative regulatory elements, termination codons, and the like.

Where the modifying nucleic acid is an expression providing nucleic acid, the modifying nucleic acid typically includes one or more of the following features: a promoter, promoter-enhancer sequences, one or more coding sequences, and the like. One or more of the above components may be presented on the vector as an expression cassette, which includes a nucleic acid encoding a product of interest operably linked to a promoter (as well as any other required sequences to provide for a functional expression cassette), which is also referred to herein as a "gene of interest." Specific products of interest and their corresponding encoding sequences are described in greater detail infra.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable. Inducible elements are DNA sequence elements which act in conjunction with promoters and may bind either repressors (e.g. lacO/LAC Iq repressor system in E. coli) or inducers (e.g. gall/GAL4 inducer system in yeast). In such cases, transcription is virtually "shut off" until the promoter is derepressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, AraC and gal promoters of E. coli, the—amylase (Ulmanen, et al., J. Bacteriol. 162:176-182, 1985) and the sigma-28-specific promoters of B. subtilis (Gilman et al., Gene 32:11-20(1984)), the promoters of the bacteriophages of Bacillus (Gryczan, In: The Molecular Biology of the Bacilli, Academic Press, Inc., NY (1982)), Streptomyces promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Preferred eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Exemplary promoters for use in the present invention are selected such that they are functional in the cell type (and/or animal or plant) into which they are being introduced.

The DNA of the modifying nucleic acid employed in the subject methods can be obtained from sources in which it occurs in nature or can be produced, using genetic engineering techniques or synthetic processes.

The subject methods can be used to modulate transcription of genomic domains, e.g., genes, in a variety of target cells, where target cells in certain embodiments are non-bacterial target cells, and often eukaryotic target cells, including plant and animal target cells, e.g., insect cells, vertebrate cells, particularly avian cells, e.g., chicken cells; mammalian cells, including murine, porcine, ovine, equine, rat, dog, cat, monkey, and human cells; and the like.

A feature of this embodiment is that the subject systems, described above, are employed to achieve the desired integration. In the methods of the subject invention, the targeting vector and integrase components of the subject systems are introduced into the target cell under conditions sufficient for the integrase to mediate integration of the targeting vector into the target cell, as described above.

The above described targeting/integration event results in the insertion of the modifying nucleic acid into the genome of the target cell in a manner that results in stable targeted genomic modification.

After the vector system components are introduced into the cell, the cell is maintained under conditions appropriate for site-specific integration to occur, as is known in the art, where representative conditions are provided in the experimental section, below.

The above described integration event results in the production of a recombinant cell, such as a fungal, plant, or animal cell, and particularly, primary, secondary, or immortalized human or other mammalian cell, in which sequences which a stabled genomic modification is present. Particularly, the invention includes a recombinant cell that includes a modifying nucleic acid which is introduced at a predetermined site by the above described vectors, such that the modifying nucleic acid is adjacent to the product sequence of the recombination of the targeting vector and genomic attachment sites.

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells that have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. Immortalized cells are cell lines (as opposed to cell strains with the designation "strain" reserved for primary and secondary cells), a critical feature of which is that they exhibit an apparently unlimited lifespan in culture.

Primary, secondary and immortalized cells to be genomically modified by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Where the recombinant cells are to be used in gene therapy, primary cells are preferably obtained from the individual to whom the transfected primary or secondary cells are administered. However, primary cells can be obtained from a donor (other than the recipient) of the same species.

Recombinant immortalized cells can also be produced by the present method. Examples of immortalized human cell lines useful for protein production or gene therapy by the present method include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., Cancer Res, 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) may be used.

The subject methods and systems, as described above, find use in a variety of applications. Applications of interest in which the subject methods and compositions find use include both "knock-out" and "knock-in" applications. In "knock-out" applications, expression of one or both alleles of one or more genes is disrupted by integration of the modifying nucleic acids, such that expression is "knocked out." In contrast, "knock-in" applications are those applications in which at least a coding sequence, and usually an expression cassette, is integrated into the genome of a cell to provide for expression of the coding sequence in the cell.

The subject methods of unidirectional site-specific integration of modifying nucleic acid into the genome of a target cell using the subject systems find use in a variety of applications in which the site specific integration of an exogenous nucleic acid into a target cell is desired. Applications in which the subject vectors and methods find use include: research applications, polypeptide synthesis applications and therapeutic applications, as described above.

Methods of Targeted Genomic Modification in the Production of Transgenic Animals The subject invention provides methods of making a targeted genomic modification in a cell for production of a non-human transgenic animal. By "genomic modification" is meant a stable alteration of a cell's genomic DNA, e.g., a permanent change in a cell's chromosome. The term "genomic modification" encompasses changes in a target cell genome of varying size. A feature of the subject invention is that the modification or change results from an integrative event, as described in greater detail below, where a nucleic acid is inserted into the genome to provide for the desired modification or change.

As such, the subject methods are properly characterized being integrative targeted genomic modification methods. The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 5 kb, usually from about 2 kb to about 10 kb. In some embodiments, however, the inserted nucleic acid may be as small as about 500 bp or about 100 bp.

As indicated above, the subject methods rely on site-specific integration of a modifying nucleic acid into the genome of the target cell to achieve targeted genomic modification. Depending on the particular application in which the method is employed, the modifying nucleic acid may be an expression disruptive nucleic acid, e.g., as is employed in "knockout" applications reviewed in greater detail below; and/or an expression providing nucleic acid, e.g., as is employed in "knock-in" applications reviewed in greater detail below.

Where the modifying nucleic acid is an expression disruptive nucleic acid (e.g., disruption element), it includes a sequence of nucleotides that, upon integration, disrupts expression of a particular gene or genes, i.e., in interferes or stops transcription of a genomic domain or of a functional gene product. The modifying nucleic acid may include any convenient sequence of nucleotides that provides for the desired expression disruption, where such sequences may include random "stuffer" sequences, negative regulatory elements, termination codons and the like.

Where the modifying nucleic acid is an expression providing nucleic acid, the modifying nucleic acid typically includes one or more of the following features: a promoter, promoter-enhancer sequences, one or more coding sequences, and the like. One or more of the above components may be presented on the vector as an expression cassette, which includes a nucleic acid encoding a product of interest operably linked to a promoter (as well as any other required sequences to provide for a functional expression cassette), which is also referred to herein as a "gene of interest." Alternatively, a nucleic acid of interest having a coding sequence can be inserted into the genome so as to provide for operably linking the coding sequence to a promoter endogenous to the host cell. Specific products of interest and their corresponding encoding sequences are described in greater detail infra.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable. Inducible elements are DNA sequence elements which act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, recA, lacZ, AraC and gal promoters of *E. coli*, the β-amylase (Ulmanen, et al., J. Bacteriol. 162:176-182, 1985) and the sigma-28-specific promoters of *B. subtilis* (Gilman et al., Gene 32:11-20(1984)), the promoters of the bacteriophages of *Bacillus* (Gryczan, In: The Molecular Biology of the Bacilli, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Exemplary promoters for use in the present invention are selected such that they are functional in the cell type (and/or animal) into which they are being introduced.

The DNA of the modifying nucleic acid employed in the subject methods can be obtained from sources in which it occurs in nature or can be produced, using genetic engineering techniques or synthetic processes.

The subject methods can be used to modulate transcription of genomic domains, e.g., genes, in a variety of target cells, where target cells in certain embodiments are, for example, invertebrate cells, particularly insect cells, nematode cells, and the like; or vertebrate cells, e.g., avian cells (e.g., chicken cells) or mammalian cells, including murine, porcine, ovine, equine, rat, dog, cat, monkey, and the like.

In the methods of the subject invention, the targeting vector and integrase components of the subject systems are introduced into the target cell using the subject systems, as described above. The above described targeting/integration event results in the insertion of the modifying nucleic acid into the genome of the target cell in a manner that results in stable targeted genomic modification.

After the vector system components are introduced into the cell, the cell is maintained under conditions appropriate for site-specific integration to occur, as is known in the art, where representative conditions are provided in the experimental section, below.

The above described integration event results in the production of a recombinant cell in which a stable genomic modification is present. Particularly, the invention includes a recombinant cell that includes a modifying nucleic acid which is introduced at a predetermined site by the above described vectors, such that the modifying nucleic acid is adjacent to the sequence of the nucleic acid product of the recombination of the targeting vector and genomic attachment sites.

Target Cells

The target cell can be any cell amenable to genetic modification using the systems and methods of the invention, and which is suitable to produce a transgenic animal of the invention. Target cells can be isolated (e.g., in culture) or in a multicellular organism (e.g., in a blastocyst, in a fetus, in a postnatal animal, and the like). Exemplary target cells include, but are not necessarily limited to, primary cells, secondary cells, transformed cells, egg cells, fertilized egg cells, single cell embryos, somatic cells (e.g., muscle, bone, cartilage, ligament, tendon, skin (dermis, epidermis, and the like), cells of the viscera (e.g., lung, liver, pancreas, gastrointestinal tract (mouth, stomach, intestine), and the like), stem cells (e.g., embryonic stem cells (e.g., cells having an embryonic stem cell phenotype), adult stem cells, pluripotent stem cells, hematopoietic stem cells, mesenchymal stem cells, and the like), and germ cells (e.g., primordial germ cells, embryonic germ cells, and the like).

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells that have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. Immortalized cells are cell lines (as opposed to cell strains with the designation "strain" reserved for primary and secondary cells), a critical feature of which is that they exhibit an apparently unlimited lifespan in culture.

Primary, secondary and immortalized cells to be genomically modified by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Where the recombinant cells are to be used in gene therapy, primary cells are preferably obtained from the individual to whom the transfected primary or secondary cells are administered. However, primary cells can be obtained from a donor (other than the recipient) of the same species.

Recombinant immortalized cells can also be produced and introduced into a host, non-human animal to produce a chimeric, transgenic animal of the invention. Numerous examples of immortalized cell lines are known in the art, and many such cell lines are available from the ATCC (Manassas, Va.). Examples of immortalized cell lines include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., Cancer Res, 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of cells of different species. Secondary human fibroblast strains, such as WI-38 (ATCC CCL 75) and MRC-5 (ATCC CCL 171) may be used.

Any animal having a genome susceptible to modification can be genetically modified using the methods and systems of the invention to produce a transgenic animal. The animal can be a vertebrate or an invertebrate, and may be mammalian or non-mammalian (e.g., avian species (e.g., chickens), reptiles, insects, and the like). Exemplary mammalian subjects include, but are not necessarily limited to, non-human primates (monkeys, apes, chimpanzees), rodents (rats, mice, gerbils, hamsters, and the like), ungulates (e.g., cattle, sheep, goats, pigs), horses, dogs, and cats. Exemplary non-mammalian animals include, but are not necessarily limited to, members of nematoda, and members of the phylum arthropoda (particularly members of the class insecta), birds and fish. Of particular interest in many embodiments are worms (e.g., *Caenorhabitis*, particularly *C. elegans*) and flies (e.g., *Drosophilidae*, particularly *D. melanogaster*). The term "ungulate" is used to mean any species or subspecies *of* porcine (pig), bovine (cattle), ovine (sheep) and caprine (goats). In general the term encompasses hooved farm animals.

Transgenic animals of the invention includes animals in which a genetic modification is present in all or a subset of the host animal's cells. The invention thus encompasses transgenic animals produced by application of the systems of the invention to stem cells or germ cells, which are subsequently used to produce transgenic animals. The invention also encompasses application of the systems of the invention to genetically modify adult stem cells or mature cells of a host animal, so as to produce a chimeric, transgenic animal.

The systems of the invention can be readily adapted for use in conventional methods for modification of a target cell in the course of production of a transgenic animal. Exemplary such methods and compositions for use in such methods are described below.

Production of Transgenic Vertebrates

Methods for introduction of nucleic acid into a target cell, and generation of transgenic vertebrates, particularly transgenic mammalian animals, from genetically modified cells are well known in the art. Procedures for making transgenic, non-human animals have also been described and can be adapted for use with the system of the present invention. Production of transgenic non-human animals has been described (see, e.g., U.S. Pat. No. 4,736,866 (mammals, such as rodents, particularly mice); U.S. Pat. No. 5,942,435 (transgenic swine)). Exemplary methods are described generally below.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci., USA, 78:5016; Brinster et al., 1985, Proc. Natl. Acad. Sci., USA, 82:4438). Alternatively, the transgene can be introduced into the pronucleus by viral infection. A detailed procedure for producing transgenic mice has been described (see e.g., Hogan et al., Manipulating the Mouse Embryo, Cold Spring Harbour Laboratory, Cold Spring Harbour, N.Y. (1986); U.S. Pat. No. 5,175,383 (1992)). This procedure has also been adapted for other animal species (e.g., Hammer et al., Nature 315:680 (1985); Murray et al., Reprod. Fert. Devl. 1:147 (1989); Pursel et al., Vet. Immunol. Histopath. 17:303 (1987); Rexroad et al., J. Reprod. Fert. 41 (suppl):119 (1990); Rexroad et al., Molec. Reprod. Devl. 1:164 (1989); Simons et al., BioTechnology 6:179 (1988); Vize et al., J. Cell. Sci. 90:295 (1988); and Wagner, J. Cell. Biochem. 13B (suppl): 164 (1989)).

In brief, the procedure as adapted for use in the present invention generally involves introducing the system elements into an animal by microinjecting the construct(s) into the pronuclei of fertilized mammalian egg(s) to cause one or more copies of the system elements to be retained in the cells of the developing mammal(s). Following introduction of the construct(s) into the fertilized egg, the egg may be incubated in vitro for varying amounts of time, or reimplanted a surrogate host, or both. One common method is to incubate the embryos in vitro for about 1-7 days, depending on the species, and then reimplant them into the surrogate host. The system elements facilitate unidirectional, site-specific recombination to insert the transgene into the genome. The presence of the transgene in the progeny of the transgenically manipulated embryos can be tested by conventional methods, e.g., by Southern blot analysis of a segment of tissue.

Another method for producing germ-line transgenic animals is through the use of embryonic stem (ES) cells. The construct(s) of the system of the invention can be introduced into embryonic stem cells using any suitable method, such as by electroporation (Ausubel et al., Current Protocols in Molecular Biology, John Wiley & Sons (1987)). Detailed procedures for culturing embryonic stem cells (e.g., ES-D3, ATCC# CCL-1934, ES-E14TG2a, ATCC# CCL-1821, American Type Culture Collection, Rockville, Md.) and methods of making transgenic animals from embryonic stem cells can be found in Teratocarcinomas and Embryonic Stem Cells, A Practical Approach, ed. E. J. Robertson (IRL Press, 1987).

In brief, ES cells are obtained from pre-implantation embryos cultured in vitro (Evans, M. J., et al., 1981, Nature, 292:154-156). Transgenes can be efficiently introduced into ES cells, and the resulting transformed ES cells can thereafter be combined with blastocysts from a non-human animal. The ES cells colonize the embryo and contribute to the germ line of the resulting chimeric animal.

ES cells of a variety of animals have been described. For example, murine and other mammalian ES cells are described in U.S. Pat. Nos. 6,190,910; 5,985,659; 5,453,357. Exemplary primate ES cells (e.g., from marmoset and monkey) are described in U.S. Pat. Nos. 6,200,806; and 5,843,780. Exemplary avian cells expressing an ES cell phenotype cells have been described in, for example, U.S. Pat. Nos. 6,333,192; 5,830,510; 5,656,479; and 5,340,749. Exemplary porcine ES cells and methods of obtaining ES cells from other ungulates is described in U.S. Pat. No. 6,194,635 and well as in U.S. Pat. No. 5,942,435.

The transgenic, non-human animals can also be obtained by infecting new cells either in vivo (e.g., direct injection), ex vivo (e.g., infecting the cells outside the host and later reimplanting), or in vitro.

Clones of the non-human transgenic animals described herein can be produced according to the methods described in Wilmut et al. ((1997) Nature, 385:810-813) and PCT publication Nos. WO 97/07668 and WO 97/07669. In brief, a cell, e.g., a somatic cell from the transgenic animal, can be isolated and induced to exit the growth cycle and enter the Go phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Also of interest are the production of transgenic animals that provide for production of a transgenic gene product in body fluids, such as milk (see, e.g., U.S. Pat. Nos. 5,994,616; 6,111,165; 6,118,045; 6,204,431; 6,211,427; 6,222,094; 5,366,894, describing production of transgenic mammals, particular bovine and ovine, in which the transgene is expressed in mammary gland and the protein secreted into the milk, e.g., where expression of the transgene is under control of a casein promoter or milk whey gene promoter) or urine (see, e.g., U.S. Pat. No. 6,339,183, describing transgenic mammals expressing heterologous DNA in urothelium and isolation of biologically active molecules from urine).

Once the transgenic animal is produced, cells of the transgenic animal and cells from a control animal can be screened to determine for the presence of the transgene, e.g., using polymerase chain reaction (PCR). Where the transgene encodes a gene product, the cells can be screened to detect the corresponding mRNA (e.g., by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)) or, where the gene product is a protein, if the protein is produced (e.g., using Western blot analysis; Sambrook et al., Molecular Cloning—A Laboratory Manual, (Cold Spring Harbor Laboratory, 1989)).

Production of Transgenic Invertebrates

Methods for production of transgenic invertebrates are well known in the art (see, e.g., Link, Mech Ageing Dev 2001 Sep. 30; 122(14):1639-49, reviewing transgenic invertebrate models of age-associated neurodegenerative diseases in *D. melanogaster* and *C. elegans*; Candido et al. Trends Biotechnol. 1996 April; 14(4): 125-9, reviewing transgenic *Caenorhabditis elegans* strains as biosensors; Johnson et al. Genetica. 1993; 91(1-3):65-77, reviewing mutants, selective breeding, and transgenics in the dissection of aging processes of *Caenorhabditis elegans*). For example, methods of producing transgenic flies involves introduction of the system elements of the invention into a cell or cells of the fly, e.g. a fly embryo. Introduction of the system elements may be accomplished using any convenient protocol, where suitable protocols include: electroporation, microinjection, vesicle delivery, e.g. liposome delivery vehicles, and the like. Following introduction of the system elements into the cell(s), the transgene is stably integrated into the genome of the cell by unidirectional, site-specific recombination according to the invention. Methods for production of transgenic flies, particularly methods for introduction of nucleic acid into a cell of a fly, and production of transgenic flies from genetically modified cells, are known in the art. See e.g. Brand & Perrimon, Development (1993) 118: 401-415; and Phelps & Brand, Methods (April 1998) 14:367-379.

The methods and systems of the invention can be used to generate fertilized eggs that comprise the transgene stably integrated into the genome in site-specific manner. The fertilized eggs can then be allowed to mature under conditions that give rise to transgenic flies, which can be screened for a desired genotypic or phenotypic trait.

Methods for production of transgenic worms are also well in the art.

Exemplary Transgenic Animals Produced

Any of a variety of genetic modifications can be generated in a transgenic animal produced according to the invention. In general, such animals include those having a "knock-out" in a selected gene, or are "knock-ins" for a selected gene. All genetic modifications described herein can be either heterozygous or homozygous, and may be present in all cells or a subset of cells of the transgenic animal. Transgenic animals that are genetically modified in a subset of cells can be referred to as "chimeric" animals, and may be produced through either in vivo or ex vivo application of the system elements of the invention.

Knock-Out Transgenic Animals

"Knock-out" transgenic animals encompass transgenic animals that are deficient in an endogenous gene product due to a genetic modification produced using the system elements described herein. "Knock-outs" of particular interest are those in which target gene expression is undetectable or insignificant, and those in which a gene product of a target gene is decreased in function relative to the unmodified endogenous gene. Decrease in function can be due to decreased production of a full-length gene product as a result of the genetic alteration, or production of an altered gene product that is deficient in function relative to the native gene product. "Knock-out" transgenics of the invention can be transgenic animals having a heterozygous or homozygous knock-out of the target gene.

The knock-out can be a conditional knock-out, where alteration of the target gene occurs upon exposure of the modified cell to a condition, e.g., exposure to a substance that promotes target gene alteration. For example, a conditional knock-out can be produced by introducing the targeting vector and the integrase as stable chromosomal or extrachromosomal elements (e.g., episomal element), and then providing for the expression of the integrase upon a selected condition (e.g., in the presence of an inducer of a conditional promoter operably linked to the integrase-encoding DNA). Production of the integrase then results in site-specific recombination between the targeting vector attachment site and a genomic attachment site to result in a knock-out of a target gene.

Knock-out transgenic animals can also be generated through alteration of a promoter element(s) operably linked to an endogenous gene, e.g., through insertion of a transcriptional modulation unit. Transcription modulation of a target gene can be achieved by integrating into a target cell genome a transcription modulation unit that, when integrated into the genome of the target cell according to the subject invention, becomes operatively linked to a targeted genomic domain in a manner that results in the desired transcription. Where transcription is to be decreased, the subject methods integrate a transcriptional modulation unit that becomes operably linked upon integration to the targeted genomic domain in manner that results in a decrease in transcription of the targeted genomic domain the transcription modulation unit may be a transcriptional inhibition unit, e.g., for at least decreasing transcription, including turning off transcription when it is normally present and decreasing the level of transcription when already present.

Knock-out transgenic animals can also be produced by introducing an expression disrupting nucleic acid to disrupt an endogenous gene. The introduced nucleic acid need not encoded for any gene product, but rather need only provide for a decrease in production of an endogenous gene product. In this context the introduced nucleic acid is referred to herein as a "disruption element".

A disruption element can comprise, for example a sequence providing one or more termination signals that, when inserted into the endogenous gene, prevent transcription of a full-length gene product. This can be accomplished by, for example, site-specific insertion of the disruption element into a region within a coding sequence of an endogenous gene.

The disruption element can be inserted using the system of the invention so as to decrease efficiency of an endogenous promoter element driving expression of a gene product to which it is normally operably linked. For example, the disruption element can act as a "spacer" that increases the distance between the transcriptional start site of a gene and one or more promoter elements required for efficient transcription. Increasing the distance between these endogenous genetic elements can result in a decrease in transcription of the gene, and thus a decrease in production of the encoded gene product. The disruption element can also be used to modify promoter elements essential to transcription, rendering them ineffective or decreasing their efficiency in promoting expression of the gene to which they are normally operably linked.

The disruption element can also be positioned within the endogenous gene so as to prevent production of splice variants of a gene. This can result in a decrease in production of one or more splice variants, and/or a concomitant increase in production of a particular splice variant, the production of which is not significantly affected by the presence of the disruption element.

Knock-In Transgenic Animals

A "knock-in" transgenic animal is an animal having a cell genetically modified so as to result in altered expression (e.g., increased (including ectopic) expression) of selected gene, which gene may be either present on nucleic acid that was introduced into the cell (e.g., by introduction of an additional copy of an endogenous or exogenous gene which expresses an endogenous or exogenous gene product), or by operatively inserting a regulatory sequence that provides for enhanced expression of an endogenous copy of the target gene (e.g., gene activation, e.g., through introduction of a transcriptional modulation unit).

In one embodiment, the knock-in transgenic animal is generated using a transcriptional modulation unit that provides for enhanced expression of an endogenous gene. In this embodiment, the subject methods integrate a transcriptional modulation unit that becomes operably linked upon integration to the targeted genomic domain in manner that results in an increase in transcription of the targeted genomic domain. Such transcriptional modulation units are also referred to in this context as a transcriptional activation unit.

Transcriptional activation units are generally comprised of a sequence of nucleotides that, when integrated into the genomic DNA of the target cell in the site-specific manner of the subject invention, becomes operably linked to the genomic domain of interest and results in an increase in transcription of the genomic domain of interest. Any sequence of nucleotides that provides for the desired transcription enhancement may be employed.

In many embodiments, the transcriptional activation unit at least includes a regulatory sequence. The regulatory sequence of the transcriptional activation unit can include one or more promoters (such as a constitutive or inducible promoters), enhancers, scaffold-attachment regions or matrix attachment sites, transcription factor binding sites, or combinations of elements, etc. As such, the regulatory sequence can contain an inducible promoter, with the result that cells resulting from the subject methods do not immediately transcribe the genomic domain but can be induced to do so. Alternatively, constitutive promoters that result in immediate transcription upon introduction may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene). The regulatory sequence may include transcription factor binding sites, where representative sites include, but are not limited to: the TATA Box, the CCAAT Box, AP1, Sp1 or NF-κB binding sites.

In certain embodiments, the transcriptional activation unit further includes one or more exons. An exon is defined herein as a DNA sequence that is copied into RNA and is present in a mature mRNA molecule. The exons can, optionally, contain DNA that encodes one or more amino acids and/or partially encodes an amino acid (i.e., one or two bases of a codon). Alternatively, the exon may contain DNA which corresponds to a 5' non-coding region. Where the exogenous exon or exons encode one or more amino acids and/or a portion of an amino acid, the DNA construct is designed such that, upon transcription and splicing, the reading frame is in-frame with the second exon or coding region of the targeted genomic domain or gene. As used herein, in-frame means that the encoding sequences of a first exon and a second exon, when fused, join together nucleotides in a manner that does not change the appropriate reading frame of the portion of the mRNA derived from the second exon.

Where the first exon of the targeted genomic domain or gene contains the sequence ATG to initiate translation, the exogenous exon of the construct may contain an ATG and, if required, one or more nucleotides such that the resulting coding region of the mRNA including the second and subsequent exons of the targeted gene is in-frame. Examples of such targeted genes in which the first exon contains an ATG include the genes encoding HEPO, hGH, human colony stimulating factor-granulocyte/macrophage (hGM-CSF), and human colony stimulating factor-granulocyte (hG-CSF).

In addition, in many embodiments the transcriptional activation unit also includes a splice-donor site, specifically an unpaired splice-donor site. A splice-donor site is a sequence that directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AG GURAGU (where R denotes a purine nucleotide) with the GU in the fourth and fifth positions, being required (Jackson, I. J., Nucleic Acids Research 19: 3715-3798 (1991)). The first three bases of the splice-donor consensus site are the last three bases of the exon. Splice-donor sites are functionally defined by their ability to effect the appropriate reaction within the mRNA splicing pathway. An unpaired splice-donor site is defined herein as a splice-donor site that is present in a targeting construct and is not accompanied in the construct by a splice-acceptor site positioned 3' to the unpaired splice-donor site. The unpaired splice-donor site results in splicing to an endogenous splice-acceptor site. A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as:

YYYYYYYYYYNYAG, (SEQ ID NO: 209)

where Y denotes any pyrimidine and N denotes any nucleotide (Jackson, I. J., Nucleic Acids Research 19:3715-3798 (1991)). An intron is defined as a sequence of one or more nucleotides lying between two exons and which is removed, by splicing, from a precursor RNA molecule in the formation of an mRNA molecule.

When present, the encoding DNA (e.g., in exon 1 of the transcriptional activation unit) employed can optionally encode one or more amino acids, and/or a portion of an amino acid, which are the same as those of the endogenous protein. The encoding DNA sequence employed herein can, for example, correspond to the first exon of the gene of interest. The encoding DNA can alternatively encode one or more amino acids or a portion of an amino acid different from the first exon of the protein of interest. Such an embodiment is of particular interest where the amino acids of the first exon of the protein of interest are not critical to the activity or activities of the protein. For example, any exon of human or non-human origin in which the encoded amino acids do not prevent the function of the hybrid signal peptide can be used. In a related embodiment, this technique can also be employed to correct a mutation found in a target gene. Where the desired product is a fusion protein of the endogenous protein and encoding sequences in the transcriptional activation unit, the exogenous encoding DNA incorporated into the cells by the present method includes DNA which encodes one or more exons or a sequence of cDNA corresponding to a translation or transcription product which is to be fused to the product of the endogenous targeted gene. In this embodiment, targeting is used to prepare chimeric or multifunctional proteins which combine structural, enzymatic, or ligand or receptor binding properties from two or more proteins into one polypeptide. For example, the exogenous DNA can encode an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopadecarboxylase, transcriptional regulatory proteins, α-galactosidase and tyrosine hydroxylase.

While the above description has been primarily limited to elements found in transcriptional activation units, those elements that may be present in transcriptional inhibition units are readily to known to those of skill in the art, and typically include expression inhibition elements, negative regulatory elements, stuffer fragments that disrupt transcription, termination codons and the like.

"Knock-ins" can be conditional knock-ins. For example, a conditional knock-out can be produced by introducing the targeting vector and the integrase as stable chromosomal or extrachromosomal elements (e.g., episomal element), and then providing for the expression of the integrase upon a selected condition (e.g., in the presence of an inducer of a conditional promoter operably linked to the integrase-encoding DNA). Production of the integrase then results in site-specific recombination between the targeting vector attachment site and a genomic attachment site to result in introduction of a coding sequence for expression in the target cell or introduction of a transcription modulation unit so as to be operably linked to an endogenous gene to provide for increased expression of the endogenous gene.

The transgenic animals produced using the systems of the invention find use in a variety of different applications, several representative ones of which are described in detail below.

The subject methods and systems, as described above, find use in a variety of applications. Applications of interest in which the subject methods and compositions find use include both "knock-out" and "knock-in" applications. In "knock-out" applications, expression of one (heterozygous) or both (homozygous) alleles of one or more genes is disrupted by integration of the modifying nucleic acids, such that expression is "knocked out." In contrast, "knock-in" applications are those applications in which at least a coding sequence, and preferably an expression cassette, is integrated into the genome of a cell to provide for expression the coding sequence in the cell.

The subject methods of unidirectional site-specific integration of modifying nucleic acid into the genome of a target cell using the subject systems find use in a variety of applications in which the site specific integration of an exogenous nucleic acid into a target cell is desired. Applications in which the subject vectors and methods find use include: research applications, polypeptide synthesis applications and therapeutic applications. Each of these representative categories of applications is described separately below in greater detail.

Research Applications

Examples of research applications in which transgenic animals produced using the methods find use include applications designed to characterize a particular gene. In such applications, the targeting vector is employed to insert a gene or coding sequence of interest into a target cell, which in turn is the basis for production of a transgenic, non-human animal. The resultant effect of the inserted gene on the transgenic animal's phenotype is observed. In this manner, information about the gene's activity and the nature of the product encoded thereby can be deduced. The vector may also be used to remove or reduce the activity of an endogenous gene.

The vectors can also be employed to identify and define DNA sequences that control gene expression, e.g. in a temporal (e.g. certain developmental stage) or spatial (e.g. particular cell or tissue type) manner. In such applications, the targeting vector includes a candidate gene or candidate promoter element, which is then stably integrated into the genome of a target cell in a site-specific manner, e.g., to provide for expression of the candidate gene in the target cell or to provide for control of expression of a known gene under the candidate promoter. The transgenic animal is then produced using such a genetically modified cell, and the effect upon one or more phenotypic traits analyzed (e.g., effect upon expression of known genes, effect upon resistance or susceptibility to a disease or condition (e.g., tumor growth promotion or inhibition), and the like). From this analysis the candidate gene or candidate promoter can be characterized.

Yet another research application in which the subject transgenic animals find use is in the identification and characterization of the results of gene expression studies. For example, a plurality of animals produced from distinct vector-targeted, and genetically modified cells are prepared in which the gene of interest is inserted into distinct locations in the genome of various targeted cells, where expression of the gene of interest is dependent on endogenous promoter mediation, i.e. where the gene of interest lacks a promoter or is coupled to only a weak promoter. By plurality is meant at least two, where the number usually ranges from about 2 to 5000, usually from about 2 to 200. This plurality of vector targeted cells may be produced by introducing the vector in a plurality of cells or taking a collection of pretargeted cells that are homogenous with respect to the insertion site of the gene, i.e. progeny of a single targeted cell, and then introducing transposase into one or more of, but not all of, the constituent members of the collection. This approach is more readily adapted to production of less expensive, less labor-intensive transgenic animals, such as, for example, *Drosophila* or *Caenorhabditis*.

Polypeptide Synthesis Applications

In addition to the above research applications, the subject methods and vectors also find use of transgenic animals in the synthesis of gene products of interest, such as polypeptides, e.g. proteins of interest. In such applications, a vector that includes a gene encoding a polypeptide of interest, optionally in combination with requisite and/or desired expression regulatory sequences, e.g. promoters, etc., (i.e. an expression module) is introduced into the target cell, which is then used to produce a transgenic animal. The DNA encoding the polypeptide of interest can optionally be provided in an expression cassette, which provides for a promoter operably linked to the coding sequence of the DNA. The promoter can be, for example, a constitutive promoter, an inducible promoter, or a tissue- or cell-specific promoter. In one embodiment of interest, where the transgenic animal is a mammal from which milk can be readily obtained (e.g., a cow, goat, and the like), the promoter is one that provides for expression in a mammary gland, and for production of the polypeptide of interest in milk.

Once the transgenic animal expressing the protein of interest is prepared, the protein can then be isolated and purified from appropriate tissues or bodily fluids (e.g., blood, serum, milk, and the like) to produce a desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Veterinarian Applications—Therapeutic and Agricultural Applications

The subject invention also contemplates the use of the unidirectional, site-specific recombination system to generate transgenic animals that, as a result of having genetically modified cells, exhibit a phenotypic trait that is desirable, e.g., due to a therapeutic effect of the encoded gene product (including prophylactic effect), due to an enhanced growth rate or weight gain, due to increased production of milk or other food product obtained from livestock, and the like.

In this application, the system elements are employed to stably integrate a nucleic acid encoding a gene product (e.g., hormone, antimicrobial gene product, and the like) into the genome of a target cell, which is in turn is used to produce a transgenic animal. The subject vectors may be used to deliver a wide variety of therapeutic nucleic acids or nucleic acids encoding a gene product that provides commercial advantage in agricultural livestock. Specific genes of interest include, but are not limited to, genes encoding growth hormone (e.g, bovine growth hormone), antigenic polypeptides (e.g., as in polypeptide-based vaccines for prevention or reduction of risk of disease from microbial infection, e.g., bacterial, viral, fungal, or parasitic pathogens), interleukins, cytokines, small peptides, genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. Other exemplary utilities for the system include: knocking out, for example, genes in pig that cause transplant rejection in humans, so that a pig can be used as an organ donor; manipulating the genomes of insect pests and disease vectors to interfere with their reproduction or ability to transmit disease; manipulating the genomes of fish and chickens to improve their quality in growth as a food source and reduce disease in them; and making milk and other food products less immunogenic and more nutritious.

Methods of Targeted Genomic Modification in the Production of Stem Cells

The subject invention provides methods for making a targeted genomic modification in a stem celsl, which may be an adult stem cell or an embryonic stem cell or a progenitor cell. Any stem cell having a genome susceptible to modification can be genetically modified using the methods and systems of the invention to produce a recombinant stem cell having a targeted genomic modification. The stem cell can be obtained from a vertebrate or an invertebrate, and may be mammalian or non-mammalian (e.g., avian species (e.g., chickens), reptiles, insects, and the like). Exemplary mammalian subjects include, but are not necessarily limited to, non-human primates (monkeys, apes, chimpanzees), rodents (rats, mice, gerbils, hamsters, and the like), lagomorphs (e.g., rabbits), ungulates (e.g., cattle, sheep, goats, pigs), horses, dogs, and cats. Exemplary non-mammalian animals include, but are not necessarily limited to, members of nematoda, and members of the phylum arthropoda (particularly members of the class insecta). Of particular interest in many embodiments are worms (e.g., *Caenorhabitis*, particularly *C. elegans*) and flies (e.g., *Drosophilidae*, particularly *D. melanogaster*). The term "ungulate" is used to mean any species or subspecies *of* porcine (pig), bovine (cattle), ovine (sheep) and caprine (goats). In general the term encompasses hooved farm animals.

The subject invention provides methods of making a targeted genomic modification in a target stem cell for production of a recombinant stem cell. By "genomic modification" is meant a stable alteration of a cell's genomic DNA, e.g., a permanent change in a cell's chromosome. The term "genomic modification" encompasses changes in a target cell genome of varying size. A feature of the subject invention is that the modification or change results from an integrative event, as described in greater detail below, where a nucleic acid is inserted into the genome to provide for the desired modification or change.

As such, the subject methods are properly characterized being integrative targeted genomic modification methods. The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 5 kb, usually from about 2 kb to about 10 kb. In some embodiments, however, the inserted nucleic acid may be as small as about 500 bp or about 100 bp.

As indicated above, the subject methods rely on site-specific integration of a modifying nucleic acid into the genome of the target cell to achieve targeted genomic modification. Depending on the particular application in which the method is employed, the modifying nucleic acid may be an expression disruptive nucleic acid, e.g., as is employed in "knock-out" applications reviewed in greater detail below; and/or an expression providing nucleic acid, e.g., as is employed in "knock-in" applications reviewed in greater detail below.

Where the modifying nucleic acid is an expression disruptive nucleic acid (e.g., disruption element), it includes a sequence of nucleotides that, upon integration, disrupts expression of a particular gene or genes, i.e., in interferes or stops transcription of a genomic domain or of a functional gene product. The modifying nucleic acid may include any convenient sequence of nucleotides that provides for the desired expression disruption, where such sequences may include random "stuffer" sequences, negative regulatory elements, termination codons and the like.

Where the modifying nucleic acid is an expression providing nucleic acid, the modifying nucleic acid typically includes one or more of the following features: a promoter, promoter-enhancer sequences, one or more coding sequences, and the like. One or more of the above components may be presented on the vector as an expression cassette, which includes a nucleic acid encoding a product of interest operably linked to a promoter (as well as any other required sequences to provide for a functional expression cassette), which is also referred to herein as a "gene of interest." Alternatively, a nucleic acid of interest having a coding sequence can be inserted into the genome so as to provide for operably linking the coding sequence to a promoter endogenous to the host cell. Specific products of interest and their corresponding encoding sequences are described in greater detail infra.

The expression providing nucleic acid may provide for expression of the encoded gene product in the target stem cell, or may provide for expression of the encoded gene product in a mature cell that is derived from the modified target stem cell. For example, the expression providing nucleic acid may be expressed at low or undetectable levels in a modified hematopoietic stem cell produced according to the invention. The modified hematopoietic stem cells may then differentiate to produce, for example, mature modified lymphocytes that express the introduced, encoded gene product at a desired level. Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters. Promoters may be, furthermore, either constitutive or regulatable. Inducible elements are DNA sequence elements which act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on." Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, recA, lacZ, AraC and gal promoters of *E. coli*, the β-amylase (Ulmanen, et al., J. Bacteriol. 162:176-182, 1985) and the sigma-28-specific promoters of *B. subtilis* (Gilman et al., Gene 32:11-20 (1984)), the promoters of the bacteriophages of *Bacillus* (Gryczan, In: The Molecular Biology of the *Bacilli*, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters can also provide for expression of an operably linked nucleic acid preferentially or specifically in a particular type of stem cell (e.g., a hematopoietic, mesenchymal, neuronal stem cell, or other stem cell) or in a cell or particular cell type derived from (e.g., that differentiates from) a genetically modified stem cell produced according to the invention. For example, U.S. Pat. No. 5,556,954 describes a hematopoietic stem cell specific promoter and a hematopoietic stem cell specific enhancer.

Exemplary promoters for use in the present invention are selected such that they are functional in the cell type (and/or animal) into which they are being introduced.

The DNA of the modifying nucleic acid employed in the subject methods can be obtained from sources in which it occurs in nature or can be produced, using genetic engineering techniques or synthetic processes.

The target stem cell can be any cell amenable to genetic modification using the systems and methods of the invention, and which is suitable to produce a transgenic animal of the invention. Stem cells suitable for use in the methods of the invention can be isolated from an animal, or can be derived from cell lines. Genetic modification of stem cells according to the invention can be performed on isolated stem cells (e.g., in culture) or in a multicellular organism (e.g., in a blastocyst, in a fetus, in a postnatal animal, and the like). Exemplary target stem cells include, primary stem cells, secondary stem cells, and transformed stem cells. Further exemplary stem cells include, but are not limited to, embryonic stem cells (e.g., cells having an embryonic stem cell phenotype), adult stem cells, pluripotent stem cells, progenitor cells, hematopoietic stem cells, mesenchymal stem cells, and the like), and germ cells (e.g., primordial germ cells, embryonic germ cells, and the like).

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells that have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. Immortalized cells are cell lines (as opposed to cell strains with the designation "strain" reserved for primary and secondary cells), a critical feature of which is that they exhibit an apparently unlimited lifespan in culture.

Primary, secondary and immortalized cells to be genomically modified by the present method can be obtained from a variety of tissues and include all stem cell types which can be maintained in culture. For example, primary and secondary cells which can be transfected by the present method include stem cells that can differentiate to provide fibroblasts, keratinocytes, epithelial cells (e.g., mammary epithelial cells, intestinal epithelial cells), endothelial cells, glial cells, neural cells, formed elements of the blood (e.g., myeloid cells, lymphocytes, bone marrow cells), muscle cells and precursors of these somatic cell types. Where the recombinant stem cells are to be used in gene therapy, primary cells are preferably obtained from the individual to whom the transfected primary or secondary cells are administered. However, primary cells can be obtained from a donor (other than the recipient) of the same species.

As noted above, stem cells can be isolated from any animal, with mammalian stem cells, especially human stem cells being of particular interest. Stem cells can be obtained from any of a variety of sources, including bone marrow, cord blood or peripheral blood, or other tissue (skin, liver, pancreas, intestine, lung, eye (e.g., cornea), and the like), and other sources that will be readily apparent to the ordinarily skilled artisan.

Stem cells useful in the methods of the invention include ES cells, adult stem cells, as well as tissue-specific stem cells such as hematopoietic stem cells, epidermal stem cells, epidermal progenitor cells, neural crest stem cells, corneal epithelial stem cells, and the like.

Stem cells and germ cells are described in detail in "Stem Cells: Scientific Progress and Future Research Directions", June 2001, prepared by the National Institutes of Health, Dept. of Health and Human Services, U.S.A. (available on the internet on the National Institutes of Health web site), which document is incorporated herein by reference in its entirety. Stem cells of particular interest are those approved for use by President George W. Bush and are published at the world wide website of the NIH.

Human Stem Cells and Germ Cells

A variety of human stem cells, as well as human germ cells, have been described. Human germ cells isolated from the gonadal ridge are described in the art at, for example, Shamblott et al. 2001 Proc. Natl. Acad. Sci. U.S.A. 98, 13-118; and Shamblott et al. 1998 Proc. Natl. Acad. Sci. U.S.A. 95, 13726-13731. Also see, U.S. Pat. No. 6,245,566.

Human ES cells can give rise to a variety of cell types including, but not limited to, for example, ectoderm, endoderm, mesoderm, progenitor cells (e.g., epithelial, neuronal, hepatic, etc.) cardiomyoctyes, hematopoietic cells, neurons, ganglia, brain cells, skin, adrenal cells, liver (e.g., hepatocytes), pancreatic cells, muscle cells (striated muscle or smooth muscle), bone, kidney, cells of the urogential tract, epithelium, stratified squamous epithelium, cartilage, and the like.

Non-limiting examples of human stem cells, as well as methods of their isolation and maintenance, are as follows: human hematopoietic stem cells (U.S. Pat. Nos. 5,061,620; 5,643,741; 5,716,827; 5,750,397; 5,763,197; 5,914,108; 6,280,718); primate ES cells (including human, marmoset, and monkey) (U.S. Pat. No. 6,200,806); liver stem cells (U.S. Pat. No. 6,129,911) breast epithelial cells with stem cell characteristics (U.S. Pat. No. 5,814,511); pluripotent stem cells (U.S. Pat. Nos. 5,807,686; 5,672,346); and mesenchymal stem cells (U.S. Pat. No. 5,486,359); and pluripotent ES cells (U.S. Pat. No. 5,453,357).

Further exemplary human ES cells are described in Reubinoff et al., 2000 Nat. Biotechnol. 18, 399-404; Thomson et al., 1998 Science. 282, 1145-1147; Itskovitz-Eldor et al., 2000 Mol. Med. 6, 88-95; Assady et al., 2001. Diabetes, 50:1691-7.; Kehat et al., 2001 J Clin Invest. 108(3):407-14; Schuldiner et al., 2000 Proc. Natl. Acad. Sci. U.S.A. 97, 11307-11312; Roach et al., 1994 Exp. Cell. Res. 215, 189-198; Pera and Herszfeld, 1998 Reprod. Fertil. Dev. 10, 551-555; Trojanowski et al., 1993 Exp. Neurol. 122, 283-294.

Exemplary human embryonic carcinoma stem cells are described in Roach et al., 1994 Exp. Cell. Res. 215, 189-198; Pera and Herszfeld, 1998 Reprod. Fertil. Dev. 10, 551-555; Trojanowski et al., 1993 Exp. Neurol. 122, 283-294; Reynolds et al., 1994 Neurosci. Lett. 165, 129-132; McBurney et al., 1988 J. Neurosci. 8, 1063-10731; Andrews, 1984. Lab. Invest. 50, 147-162; Thompson et al., 1984 J. Cell. Sci. 72, 37-64; and Pera, 1989 Differentiation. 42, 10-23.

Exemplary human adult stem cells are described in Kuznetsov, 2001 J. Cell Biol. 153, 1133-40; Kocher et al., 2001 Nat. Med. 7, 430-436; Alison et al., 2000 Nature. 406, 257; Theise et al., 2000 Hepatology. 32, 11-16.; Azizi et al., 1998 Proc. Natl. Acad. Sci. U. S. A. 95, 3908-3913; Pittenger et al., 1999 Science. 284, 143-147; Woodbury et al., 2000 J. Neurosci. Res. 61, 364-370; Sanchez-Ramos et al., 2000 Exp. Neurol. 164, 247-256; Liechty et al., 2000 Nat. Med. 6, 1282-1286; Baum et al., 1992 Proc. Natl. Acad. Sci. U. S. A. 89, 2804-2808; Galli et al., 2000 Nat. Neurosci. 3, 986-991; Palmer et al. 2001 Nature. 411, 42-43; Uchida et al. 2000 Proc. Natl. Acad. Sci. U.S.A. 97, 14720-14725; Zuk et al., 2001 Tissue Eng. 7, 211-228; McCune et al. 1988 Science. 241, 1632-1639; Namikawa et al. 1990 J. Exp. Med. 172, 1055-1063; Zulewski et al., 2000 Diabetes. 50, 521-533; Brozmeyer et al. 1989 Proc. Natl. Acad. Sci. U.S.A. 86, 3828-3832; and Erices et al., 1999. Br. J. Haematol. 109, 235-242. Adult stem cells can give rise to, for example, adipocytes, osetocytes, mature endothelia, blood vessels, hepatocytes cholangiocytes, stromal-derived cells, chondrocytes, neurons, bone marrow stromal cells, cardiomyocytes, myocytes, thymic stromal cells, red blood cell lineages, white blood cell lineages, astrocytes, oligodendrocytes, precursor cells (e.g., of adiptocyte, osteocytes, chondrocytes, myocytes, hematopoietic cells, etc.), pancreatic cells, osteoblasts, etc.

Specific examples of human stem cells include, but are not limited to, the following stem cells provided in the Table below. The NIH code refers to the code assigned by the United States' National Institutes of Health, Dept. of Health and Human Welfare.

| NIH Code | Provider's Code | Provider | NIH Code | Provider's Code | Provider |
|---|---|---|---|---|---|
| BG01 | hESBGN.01 | BresaGen, Inc (Athens, GA) | KA42 | hICM42 | Karolinksa |
| BG02 | hESBGN.02 | BresaGen | KA43 | hICM43 | Karolinksa |
| BG03 | hESBGN.0 | BresaGen | MB01 | MB01 | Maria Biotech Co. Ltd. (Seoul, KR) |
| BG04 | hESBGN.04 | BresaGen | MB02 | MB02 | Maria Biotech |
| Cy12 | hES-1-2 | CyThera, Inc. (San Diego, CA) | MB03 | MB03 | Maria Biotech |
| CY30 | hES-3-0 | CyThera, Inc. | MI01 | Miz-hES1 | MizMedi Hospital - Seoul Universtiy (Seoul, KR) |
| CY40 | hES-4-0 | CyThera, Inc. | NC01 | FCNCBS1 | National Centre for Biological Sciences/Tata Institute of Fundamental Research (NCBS/TIFR) (Bangalore, India) |
| CY51 | hES-5-1 | CyThera, Inc. | NC02 | FCNCBS2 | NCBS/TIFR |
| CY81 | hES-8-1 | CyThera, Inc. | NC03 | FCNCBS3 | NCBS/TIFR |
| CY82 | hES-8-2 | CyThera, Inc. | CH01 | CHA-hES-1 | Pochon CHA University (Seoul, KR) |
| CY91 | hES-9-1 | CyThera, Inc. | CH02 | CHA-hES-2 | Pochon |
| CY92 | hES-9-2 | CyThera, Inc. | RL05 | RLS ES 05 | Reliance Life Sciences (Mumbia, India) |
| CY10 | hES-10 | CyThera, Inc. | RL07 | RLS ES 07 | Reliance |
| ES01 | HES-1 | ES Cell International (ESCI) (Melbourne, AU) | RL10 | RLS ES 10 | Reliance |

-continued

| NIH Code | Provider's Code | Provider | NIH Code | Provider's Code | Provider |
|---|---|---|---|---|---|
| ES02 | HES-2 | ESCI | RL13 | RLS ES 13 | Reliance |
| ES03 | HES-3 | ESCI | RL15 | RLS ES 15 | Reliance |
| ES04 | HES-4 | ESCI | RL20 | RLS ES 20 | Reliance |
| ES05 | HES-5 | ESCI | RL21 | RLS ES 21 | Reliance |
| ES06 | HES-6 | ESCI | TE03 | I 3 | Technion University (Haifa, Israel) |
| GE01 | H1 | Geron Corporation (Menlo Park, CA) | TE32 | I 3.2 | Technion |
| GE07 | H7 | Geron | TE33 | I 3.3 | Technion |
| GE09 | H9 | Geron | TE04 | I 4 | Technion |
| GE13 | H13 | Geron | TE06 | I 6 | Technion |
| GE14 | H14 | Geron | TE62 | I 6.2 | Technion |
| GE91 | H9.1 | Geron | TE07 | J 3 | Technion |
| GE92 | H9.2 | Geron | TE72 | J 3.2 | Technion |
| SA01 | Salgrenska 1 | Goteburg University (Goteburg, SE) | UC01 | HSF-1 | Univ. Calif. San Francisco (UCSF) (San Franciso, CA) |
| SA02 | Salgrenska 2 | Goteburg | UC06 | HSF-6 | UCSF |
| SA03 | Salgrenska 3 | Goteburg | WA01 | H1 | Wisconsin Alumni Research Foundation (WiCell Research Institute, Inc.) (WARF) (Madison, WI) |
| KA08 | hICM8 | Karolinska Institute (Stockholm, SE) | WA07 | H7 | WARF |
| KA09 | hICM9 | Karolinksa | WA09 | H9 | WARF |
| KA40 | hICM40 | Karolinksa | WA13 | H13 | WARF |
| KA41 | hICM41 | Karolinksa | WA14 | H14 | WARF |

Non-Human Stem Cells and Germ Cells

ES cells of a variety of non-human animals have been described. For example, murine and other mammalian ES cells are described in U.S. Pat. Nos. 6,190,910; 5,985,659; 5,453,357; and 5,670,372. Exemplary primate ES cells (e.g., from marmoset and monkey) are described in U.S. Pat. Nos. 6,200,806; and 5,843,780. Exemplary avian cells expressing an ES cell phenotype cells have been described in, for example, U.S. Pat. Nos. 6,333,192; 5,830,510; 5,656,479; and 5,340,749. Exemplary porcine ES cells and methods of obtaining ES cells from other ungulates is described in U.S. Pat. No. 6,194,635 and well as in U.S. Pat. No. 5,942,435. Mouse stem cells are also described in "Stem Cells: Scientific Progress and Future Research Directions", June 2001, prepared by the National Institutes of Health, Dept. of Health and Human Services, U.S.A. (available on the internet on the National Institutes of Health web site), and various publications cited therein, each of which is incorporated herein by reference in its entirety.

Further exemplary stem cells have been described, including, but not limited to multipotent neuroepithelial stem cells and lineage-restrcited olgiodendrocyte-astrocyte precursors (U.S. Pat. No. 6,361,996); and liver stem cells (U.S. Pat. No. 6,129,911); neural crest stem cells (U.S. Pat. Nos. 5,824, 4890; 5,589,376).

Exemplary non-human germ cells have been described, including, but not limited to primordial germ cells (U.S. Pat. No. 6,271,436); insect germ cells (U.S. Pat. No. 6,027,937). Stem and germ cells of *Drosophila* are reviewed in Jones Curr Biol. 2001 Jun. 26; 11(12):R484.6, and discussed in Bhat et al., Establishment of stem cell identity in the *Drosophila* germline. Dev Dyn. 1997 December; 210(4):371-82;

The unidirectional, site-specific system, its related compositions, and methods of use can be used to generate genetically modified stem cells and germ cells, which genetically modified cells can be used to accomplish a variety of desirable beneficial effects in a host into which the modified cells are transplanted or are present. For example, the system can be used to effect insertion of a coding sequence of interest (e.g., in an expression cassette) into the genome of a stem cell to provide for production of a beneficial gene product of interest. The unidirectional, site-specific system can also be used to provide modulation of expression of a gene endogenous to the stem cell, e.g., to activate expression of an endogenous gene. The unidirectional, site-specific system can also be used to disrupt expression of an endogenous gene, so as to reduce production of a functional, endogenous gene product. Other modifications, as well as uses of genetically modified stem and germ cells having such genetic modifications, will be readily apparent to the ordinarily skilled artisan upon reading the present specification.

Of particular interest is the modification of the genome of a stem cell (e.g., ES or adult stem cell) or germ cell for implantation in a subject (e.g., ex vivo therapy) where the subject is a human, a domesticated animal (including pets and livestock) or other animal in which it is desirable to provide for an improved trait (e.g., increased milk production in cows, immunoresistance to infection) or veterinary aid (e.g., treatment of an acute or chronic infection). Delivery of proteins to a human subject using the systems and methods described herein are of particular interest.

Exemplary applications in modification of a host genome are described below in more detail.

Production and Delivery of a Gene Product of Interest

In one embodiment, the invention features stem cells and/or germ cells modified using the unidirectional, site-specific systems described herein, where the targeting vector comprises a nucleic acid of interest, which has a coding sequence encoding a gene product of interest. This nucleic acid of interest is the "payload" for introduction at target site in the genome. The nucleic acid of interest may be either genomic or may lack one or more introns normally present in a gene encoding the gene product of interest. Often, the nucleic acid of interest is a cDNA.

In one embodiment, the genome attachment site is positioned so that introduction of the "payload" nucleic acid provides for expression of the encoded gene product from a promoter endogenous to the host genome.

In another embodiment, the nucleic acid of interest is provided in the form of an expression cassette. The expression cassette comprises a nucleic acid of interest and a promoter operably linked to a coding sequence of the nucleic acid of interest. In this embodiment, the expression cassette is inserted into the host genome by unidirectional, site-specific recombination, and the gene product encoded by the nucleic acid of interest can be expressed from the promoter of the expression cassette.

The expression cassette can comprise one or more promoters (such as a constitutive or inducible promoters), and other elements that promote transcription of a coding sequence to which they are operably linked in the expression cassette, such as enhancers, scaffold-attachment regions or matrix attachment sites, transcription factor binding sites, or combinations of such elements, etc. As such, the regulatory sequence can contain an inducible promoter, so that transcription occurs at higher levels under conditions in which the promoter is active, i.e., the induction conditions. Alternatively, constitutive promoters that result in transcription upon operable introduction into the genome may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene). The regulatory sequence may include transcription factor binding sites, where representative sites include, but are not limited to: the TATA Box, the CCAAT Box, AP1, Sp1 or NF-κ B binding sites. It may also be desirable to include one or more exons in the expression cassette to facilitate efficient transcription of the coding sequence of interest.

The gene product of interest can be selected so as to supplement an endogenous gene product, e.g., to provide for increased levels of a gene product in the host where the gene product is present at some level in the host prior to application of the methods and compositions of the invention. For example, while human growth hormone (hGH) may be produced at some level in the host, an expression cassette having a coding sequence for hGH can provide for elevated levels of the protein by supplementing the endogenous hGH, and provide a desired effect.

In another related embodiment, the introduced nucleic acid provides for delivery of a gene product that is deficient in the host (e.g., is undetectable in the subject), but which would be endogenous to a normal host. The deficiency may be due to a disease or condition that is associated with a defective gene product, a defective gene which does not provide for expression of the gene product, or a defective cell or tissue type that does not provide for production of the gene product.

In another embodiment, the nucleic acid of interest is inserted into the genome so as to effectively replace and/or disrupt an endogenous gene. In this embodiment, the target gene may be defective, e.g., may not provide for expression of a functional gene product or for any gene product. This approach is useful where the defective endogenous gene product is dominant to the desired gene product or when the defective gene can be repaired by insertion of a connected segment of the gene.

Nucleic Acid of Interest for Introduction Using the Systems of the Invention and Expression in a Host Any number of gene products can be delivered to a subject according to the methods of the invention. Delivery of nucleic acid encoding a therapeutic gene is of particular interest. "Therapeutic genes" are those nucleic acid sequences which encode molecules that provide some therapeutic benefit to the host, including proteins (e.g., secreted proteins, membrane-associated proteins (e.g., receptors), structural proteins, cytoplasmic proteins, and the like) functional RNAs (antisense, hammerhead ribozymes), and the like. Secreted proteins include those that may be found in a bodily fluid of a subject (e.g., in blood, lymph, saliva, gastrointestinal secretions, and the like). In one embodiment of particular interest, the mammalian subject is a human subject and the introduced nucleic acid encodes a human protein or other human gene product.

In general, therapeutic gene products encompass a wide variety of gene products, such as: 1) a secreted protein with predominantly systemic effects; 2). a secreted protein with predominantly local effects; 3) a membrane protein imparting new or enhanced cellular responsiveness; 4) a membrane protein facilitating removal of a toxic product; 5) an intracellular protein; 7) an intracellular protein directly affecting gene expression and 8) antisense-engineered RNA to inhibit gene expression.

Therapeutic gene products can also encompass gene products that are deleterious to a specific cell type. Specific examples of cancer therapeutic genes that may be delivered include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

One well known example of a therapeutic gene encoding a membrane-associated protein is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease, or effect a cure if the gene transfer was permanent. For example, autologous stem cells, particular those that can give rise to lung epithelia, can be modified to include a functional CFTR, and implanted in the subject to provide for replacement lung tissue.

Other disorders resulting from mutations in a single gene (known as monogenic disorders) include alpha-1-antitrypsin deficiency, chronic granulomatous disease, familial hypercholesterolemia, Fanconi anemia, Gaucher disease, Hunter syndrome, Hurler's syndrome, ornithine transcarbamylase deficiency, purine nucleoside phosphorylase deficiency, severe combined immunodeficiency disease (SCID)-ADA, X-linked SCID, hemophilia, and the like. In these cases, replacement or disruption of the defective gene with, for example, an expression cassette, encoding a functional form of the gene may be desirable.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer.

Proteins of interest for delivery using the methods of the invention fall into many different classes. For example, secreted proteins can be enzymes (e.g., proteases, phospholipases, and the like), protease inhibitors, hormones (e.g., pituitary hormones), growth factors, cytokines, chemokines, chemotactins, gonadotrophins, lipid-binding proteins, somatamedians, gonadotrophins, and immunoglobulins. Other secreted proteins of interest include antimicrobial polypeptides (e.g., antibacterial, antifungal, antiviral, and/or antiparasitic polypeptides), and antibodies or antigen-binding antibody fragments (e.g, FAbs) thereof (e.g., orthoclone OKT-e (anti-CD3), GPIIb/IIa monoclonal antibody).

Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like.

Examples of secreted proteins of interest include, but are not necessarily limited to insulin, erythropoietin, tissue plasminogen activator (tPA), urokinase, streptokinase, neutropoesis stimulating protein (also known as filgastim or granulocyte colony stimulating factor (G-CSF)), thrombopoietin (TPO), growth hormone (including human and bovine growth hormone), alpha-L-iduronidase, α1'-antitrypsin, glucose 6-phosphatase, α-L-fucosidase, β-glucuronidase, galactose 1-phosphate uridyltransferase, adenosine deaminase, β-globin, purine nucleoside phosphorylase, sphingomyelinase, glucocerebrosidase, ornithine transcarbamylase, argininosuccinate synthetase, phenylalanine hydroxylase, branched-chain α-ketoacid dehydrogenase, fumarylacetoacetate hydrolaseinterleukins, small peptides, emoglobin, insulinotropin, imiglucerase, sarbramostim, endothelian, soluble CD4, and antibodies and/or antigen-binding fragments (e.g, FAbs) thereof (e.g., orthoclone OKT-e (anti-CD3), GPIIb/IIa monoclonal antibody), liary neurite transforming factor (CNTF), granulocyte macrophage colony stimulating factor (GM-CSF), brain-derived neurite factor (BDNF), parathyroid hormone(PTH)-like hormone, insulinotrophic hormone, insulin-like growth factor-1 (IGF-I), platelet-derived growth factor (PDGF), epidermal growth factor (EGF), acidic fibroblast growth factor, basic fibroblast growth factor, transforming growth factor β, neurite growth factor (NGF)interferons (IFN) (e.g., IFN-α2b, IFN-α2a, IFN-αN1, IFN-β1b, IFN-γ), interleukins (e.g, IL-1, IL-2, IL-8), tumor necrosis factor (TNF) (e.g, TNF-α, TNF-β)), transforming growth factor-alpha and -beta, clotting factors (e.g., clotting factors VIII, IX, and the like), catalase, calcitonin, arginase, phenylalanine ammonia lyase, L-asparaginase, pepsin, uricase, trypsin, chymotrypsin, elastase, carboxypeptidase, lactase, sucrase, intrinsic factor, vasoactive intestinal peptide (VIP), calcitonin, Ob gene product, cholecystokinin (CCK), serotonin, and glucagon. Heterologous secreted proteins of interest can include antimicrobial polypeptides (e.g., antibacterial, antifungal, antiviral, and/or antiparasitic polypeptides) and antigens (e.g., as may be used in a vaccine), each of which may find particular use in veterinarian applications.

Specific membrane proteins of interest include, but are not necessarily limited to adrenergic receptors, serotonin receptors, low-density lipoprotein receptor, CD-18, sarcoglycans (which are deficient in muscular dystrophy), etc. Intracellular proteins (e.g., proteins that are primarily located within the intracellular compartment or which exhibit a desired biological activity within a cell) also may be delivered according to the invention. Such intracellular proteins can include fumarylacetoacetate hydrolase (FAH), deficient in Hereditary Tyrosinemia Type 1. Specific examples of intracellular proteins include antiviral proteins (e.g., proteins that can provide for inhibition of viral replication or selective killing of infected cells), structural protein such as collagens, i.e. the type VII collagen COL7A1 gene, defective in Recessive Dystrophic Epidermolysis Bullosa (RDEB) and dystrophin, defective in muscular dystrophy.

Specific examples of intracellular proteins include antiviral proteins (e.g., proteins that can provide for inhibition of viral replication or selective killing of infected cells), Numerous proteins that are desirable for delivery according to the invention are well known in the art and the DNA encoding these proteins has been isolated. For example, the sequence of the DNAs encoding insulin, human growth hormone, intrinsic factor, clotting factor VIII, and erythropoietin are available from Genbank and/or have been described in the scientific literature (e.g., human clotting factor VIII gene: Gitschier et al., Nature 312:326-330, 1984; Wood et al., Nature 312:330-337, 1984; human intrinsic factor: Hewitt et al., Genomics 10:432-440, 1991). Moreover, proteins commonly used in treatments can be used in the procedures of the present invention. Such proteins are disclosed in, for example, the Physicians' Desk Reference (2002 Physicians' Desk Reference, 56th Ed., Medical Economics Data Production Co., Montvale, N.J.; incorporated by reference) and can be dosed using methods described in, for example, Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., supra; Suggs et al., Proc. Natl. Acad. Sci. USA 78:6613-6617, 1981; U.S. Pat. No. 4,394,443; each of which are incorporated herein by reference with respect to identification and isolation of DNA encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (USPNs 4,683,195 and 4,683,202). The clones may be expressed or the DNA of interest can be excised or synthesized for use in other constructs. If desired, the DNA of interest can be sequenced using methods well known in the art.

It may also be desirable to produce altered forms of the therapeutic proteins that are, for example, protease resistant or have enhanced activity relative to the wild-type protein. For example, where the therapeutic protein is a hormone, it may be desirable to alter the protein's ability to form dimers or multimeric complexes. For example, insulin may be modified so as to prevent its dimerization has a more rapid onset of action relative to wild-type, dimerized insulin.

Transcription Modulation of a Gene Endogenous to the Host Cell Genome

The invention also provides methods of modulating transcription of a genomic domain of a target stem cell or germ cell. By modulating is meant changing or altering, including increasing and decreasing, the transcription level or rate of the genomic domain of interest. As such, altered transcription encompasses activating (or causing to be expressed) a genomic domain which is normally silent (untranscribed) in the cell as obtained, increasing transcription of a genomic domain which is not transcribed at physiologically significant levels in the cell as obtained, changing the pattern of regulation or induction such that it is different than occurs in the cell as obtained, and reducing (including eliminating) transcription of a genomic domain which is transcribed in the cell as obtained. Such transcription modulation may be useful in directing the cell toward a particular pathway of differentiation, or in providing for expression of a gene at a particular developmental stage.

By genomic domain is meant a genomic region that includes one or more, typically a plurality of, exons, where the exons are typically spliced together during transcription to produce an mRNA, where the mRNA often encodes a protein product, e.g., a therapeutic protein, etc. In many embodiments, the genomic domain includes the exons of a given gene, and may also be referred to herein as a "gene." Modulation of transcription of the genomic domain pursuant to the subject methods results in at least about 2-fold, sometimes at least about 5-fold and sometimes at least about 10-fold modulation, e.g., increase or decrease, of the transcription of the targeted genomic domain as compared to a control, for those instances where at least some transcription of the targeted genomic domain occurs in the control. For example, in situations where a given genomic domain is expressed at only low levels in a non-modified target cell (used as a control), the subject methods may be employed to obtain an at least 2-fold increase in transcription as compared to a control. Transcription level can be determined using any convenient protocol, where representative protocols for determining transcription levels include, but are not limited to: RT PCR, RNA blotting, ELISA and the like.

Transcription modulation, as described above, is achieved by integrating into the target cell genome a transcription modulation unit that, when integrated into the genome of the target cell according to the subject invention, becomes operatively linked to the targeted genomic domain in a manner that results in the desired transcription modulation if transcription. For example, where transcription is to be enhanced, the subject methods integrate a transcriptional modulation unit that becomes operably linked upon integration to the targeted genomic domain in manner that results in an increase in transcription of the targeted genomic domain. Likewise, where transcription is to be decreased, the subject methods integrate a transcriptional modulation unit that becomes operably linked upon integration to the targeted genomic domain in manner that results in a decrease in transcription of the targeted genomic domain.

As indicated above, the subject methods rely on site-specific integration of a transcriptional modulation unit into the genome of the target cell in a manner that results in transcriptional modulation unit mediated transcriptional modulation of the targeted genomic domain. Depending on the particular application in which the method is employed, the transcriptional modulation unit may be a transcriptional activation unit, e.g., for at least enhancing transcription, including turning on transcription when it is normally not present and increasing the level of transcription when already present. Alternatively, the transcription modulation unit may be a transcriptional inhibition unit, e.g., for at least decreasing transcription, including turning off transcription when it is normally present and decreasing the level of transcription when already present.

Where the transcriptional modulation unit is a transcriptional activation unit, the transcriptional activation unit is made up of a sequence of nucleotides that, when integrated into the genomic DNA of the target cell in the site-specific manner of the subject invention, becomes operably linked to the genomic domain of interest and results in an increase in transcription of the genomic domain of interest. Any sequence of nucleotides that provides for the desired transcription enhancement may be employed.

In many embodiments, the transcriptional activation unit at least includes a regulatory sequence. The regulatory sequence of the transcriptional activation unit can include one or more promoters (such as a constitutive or inducible promoters), enhancers, scaffold-attachment regions or matrix attachment sites, transcription factor binding sites, or combinations of elements, etc. As such, the regulatory sequence can contain an inducible promoter, with the result that cells resulting from the subject methods do not immediately transcribe the genomic domain but can be induced to do so. Alternatively, constitutive promoters that result in immediate transcription upon introduction may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene). The regulatory sequence may include transcription factor binding sites, where representative sites include, but are not limited to: the TATA Box, the CCAAT Box, AP1, Sp1 or NF-κB binding sites.

In certain embodiments, the transcriptional activation unit further includes one or more exons. An exon is defined herein as a DNA sequence that is copied into RNA and is present in a mature mRNA molecule. The exons can, optionally, contain DNA that encodes one or more amino acids and/or partially encodes an amino acid (i.e., one or two bases of a codon). Alternatively, the exon may contain DNA which corresponds to a 5' non-coding region. Where the exogenous exon or exons encode one or more amino acids and/or a portion of an amino acid, the DNA construct is designed such that, upon transcription and splicing, the reading frame is in-frame with the second exon or coding region of the targeted genomic domain or gene. As used herein, in-frame means that the encoding sequences of a first exon and a second exon, when fused, join together nucleotides in a manner that does not change the appropriate reading frame of the portion of the mRNA derived from the second exon.

Where the first exon of the targeted genomic domain or gene contains the sequence ATG to initiate translation, the exogenous exon of the construct may contain an ATG and, if required, one or more nucleotides such that the resulting coding region of the mRNA including the second and subsequent exons of the targeted gene is in-frame. Examples of such targeted genes in which the first exon contains an ATG include the genes encoding HEPO, hGH, human colony stimulating factor-granulocyte/macrophage (hGM-CSF), and human colony stimulating factor-granulocyte (hG-CSF).

In addition, in many embodiments the transcriptional activation unit also includes a splice-donor site, specifically an unpaired splice-donor site. A splice-donor site is a sequence that directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AG GURAGU (where R denotes a purine nucleotide) with the GU in the fourth and fifth positions, being required (Jackson, I. J., Nucleic Acids Research 19: 3715-3798 (1991)). The first three bases of the splice-donor consensus site are the last three bases of the exon. Splice-donor sites are functionally defined by their ability to effect the appropriate reaction within the mRNA splicing pathway. An unpaired splice-donor site is defined herein as a splice-donor site that is present in a targeting construct and is not accompanied in the construct by a splice-acceptor site positioned 3' to the unpaired splice-donor site. The unpaired splice-donor site results in splicing to an endogenous splice-acceptor site. A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as:

YYYYYYYYYYNYAG, (SEQ ID NO: 209)

where Y denotes any pyrimidine and N denotes any nucleotide (Jackson, I. J., Nucleic Acids Research 19:3715-3798 (1991)). An intron is defined as a sequence of one or more nucleotides lying between two exons and which is removed, by splicing, from a precursor RNA molecule in the formation of an mRNA molecule.

When present, the encoding DNA (e.g., in exon 1 of the transcriptional activation unit) employed can optionally encode one or more amino acids, and/or a portion of an amino acid, which are the same as those of the endogenous protein. The encoding DNA sequence employed herein can, for example, correspond to the first exon of the gene of interest. The encoding DNA can alternatively encode one or more amino acids or a portion of an amino acid different from the first exon of the protein of interest. Such an embodiment is of particular interest where the amino acids of the first exon of the protein of interest are not critical to the activity or activities of the protein. For example, any exon of human or non-human origin in which the encoded amino acids do not prevent the function of the hybrid signal peptide can be used. In a related embodiment, this technique can also be employed to correct a mutation found in a target gene. Where the desired product is a fusion protein of the endogenous protein and encoding sequences in the transcriptional activation unit, the exogenous encoding DNA incorporated into the cells by the present method includes DNA which encodes one or more exons or a sequence of cDNA corresponding to a translation or transcription product which is to be fused to the product of the endogenous targeted gene. In this embodiment, targeting is used to prepare chimeric or multifunctional proteins which combine structural, enzymatic, or ligand or receptor binding properties from two or more proteins into one polypeptide. For example, the exogenous DNA can encode an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopa-decarboxylase, transcriptional regulatory proteins, α-galactosidase and tyrosine hydroxylase.

While the above description has been primarily limited to elements found in transcriptional activation units, those elements that may be present in transcriptional inhibition units are readily to known to those of skill in the art, and typically include expression inhibition elements, negative regulatory elements, stuffer fragments that disrupt transcription, termination codons, and the like.

The DNA of the transcriptional modification unit employed in the subject methods can be obtained from sources in which it occurs in nature or can be produced, using genetic engineering techniques or synthetic processes.

Operatively linked or functionally placed is defined as a configuration in which the elements of the transcriptional modulation unit are appropriately targeted at a position relative to an endogenous gene such that the regulatory element present in the transcriptional modulation unit influences the production of a primary RNA transcript which initiates at a CAP site (optionally included in the transcriptional modulation unit) and includes sequences corresponding to the exon and splice-donor site of the transcriptional modulation unit (when present), DNA lying upstream of the endogenous gene's regulatory region (if present), the endogenous gene's regulatory region (if present), the endogenous gene's 5' non-transcribed region (if present), and exons and introns (if present) of the endogenous gene. In an operatively linked configuration the splice-donor site of the targeting construct directs a splicing event to a splice-acceptor site flanking one of the exons of the endogenous gene, such that a desired protein can be produced from the fully spliced mature transcript. In one embodiment, the splice-acceptor site is endogenous, such that the splicing event is directed to an endogenous exon, for example, of the endogenous gene. In another embodiment where the splice-acceptor site is included in the targeting construct, the splicing event removes the intron introduced by the transcriptional activation unit.

The above described targeting/integration event results in the insertion of the transcriptional modulatory unit into the genome of the target cell in a manner that places the endogenous gene under the control of the transcriptional modulatory unit (for example, by insertion of either a promoter or an enhancer, or both, upstream of the endogenous gene or regulatory region). Optionally, the targeting event can simultaneously result in the deletion of the endogenous regulatory element, such as the deletion of a tissue-specific negative regulatory element. The targeting event can displace an existing element; for example, a tissue-specific enhancer can be displaced by an enhancer that has broader or different cell-type specificity than the naturally-occurring elements, or displays a pattern of regulation or induction that is different from the corresponding nontransfected cell. In this embodiment the naturally occurring sequences are taken out of operational linkage with the genomic domain of interest and new sequences are added. Alternatively, the endogenous regulatory elements are disrupted or disabled by the targeting event, such as by targeting the exogenous sequences within the endogenous regulatory elements.

The endogenous gene modulated can be any of a variety of genes of interest, including those therapeutic genes described above that are endogenous to the subject.

Disruption Element

In another embodiment, a nucleic acid of interest is inserted into the genome of a stem cell or germ cell so as to disrupt one or more endogenous genes. The introduced nucleic acid need not encoded for any gene product, but rather need only provide for a decrease in production of an endogenous gene product. In this context the introduced nucleic acid is referred to herein as a "disruption element".

A disruption element can comprise, for example a sequence providing one or more termination signals that, when inserted into the endogenous gene, prevent transcription of a full-length gene product. This can be accomplished by, for example, site-specific insertion of the disruption element into a region within a coding sequence of an endogenous gene.

The disruption element can be inserted using the system of the invention so as to decrease efficiency of an endogenous promoter element driving expression of a gene product to which it is normally operably linked. For example, the disruption element can act as a "spacer" that increases the distance between the transcriptional start site of a gene and one or more promoter elements required for efficient transcription. Increasing the distance between these endogenous genetic elements can result in a decrease in transcription of the gene, and thus a decrease in production of the encoded gene product. The disruption element can also be used to modify promoter elements essential to transcription, rendering them ineffective or decreasing their efficiency in promoting expression of the gene to which they are normally operably linked. The disruption element can also be positioned within the endogenous gene so as to prevent production of splice variants of a gene. This can result in a decrease in production of one or more splice variants, and/or a concomitant increase in production of a particular splice variant, the production of which is not significantly affected by the presence of the disruption element.

Disruption elements can be used to generate, for example, genetically modified stem cells for a variety of purposes. For example, the methods and systems of the invention can be used to insert a disruption element to decrease expression levels or render cells null for a receptor of a microbial pathogen ("pathogen receptor null cells"). These cells can then be introduced into the patient to provide for cells resistant to infection. For example, U.S. Pat. No. 6,365,404 describes production of modified hematopoietic cells which give rise to T-lymphocytes that serve as target cells for HIV infection, and which can "mop up" infectious HIV due to increased cell surface membrane density of viral receptors on the T-lymphocyte cell surface, but which T cells are incapable of hosting viral replication. In addition, modified stem cells that are deficient or decreased in expression of the CKR-5 receptor are described. The host's CD4 T-cell lymphocytes are replaced with lymphocytes derived from autologous or homologous stem cells that are genetically modified in this manner, thus providing a T cell population that is resistant to HIV infection. The methods of the invention can be readily applied to make the genetic modifications described in this specific example.

In another example, described in U.S. Pat. No. 6,361,997, genetically modified CD34-negative adherently growing stem cells, and their uses in gene therapy, are described. Genetically modified, very early haematopoietic and mesenchymal stem cells (negative for the expression of the surface molecule CD34) are used in gene therapy of mono- or oligogenetic diseases or in cell therapy. Autologous CD34-negative adherently growing stem cell cultures from the peripheral blood of the patient are applied and are genetically modified with a nucleic acid encoding a gene product of interest efficiently transfected or infected with genetic constructs. The gene products of these genes should can substitute defective or absent proteins or factors in the patient organism in the long term. After expansion, the autologous stem cells can also be used for cell therapy (organ replacement therapy). The methods of the invention can be readily applied to make the genetic modifications described in this specific example. In another example, U.S. Pat. No. 5,830,760 describes hematopoietic cell lines having altered retinoic acid receptors, and their methods of use. The methods of the invention can be readily applied to make the genetic modifications described in this specific example.

In another example, the method of the present invention can be applied to generate a "universal stem cell", which cell is sufficiently decreased in cell surface markers to render the cell amenable to transplantation in two or more subjects, even where the subjects differ in their major histocompatibility complexes (MHC) such that transplantation of tissues between the two hosts would otherwise result in rejection of the transplant. In short, the universal stem cell provides a "null" cell with respect to graft-vs-host rejection, so that the cell can be engrafted in many hosts. Such null cells can be generated by disrupting expression of functional or cell surface-exposed MHC antigens, e.g., Class I MHC antigens, Class II MHC antigens, or both Class I and II MHC antigens. The cells may be further modified by introduction or inactivation of a gene of interest. Existence of such stem cell lines would make it unnecessary to obtain, modify and propagate stem cells from each individual patient. Thus universal stem cells are a valuable therapeutic resource.

MHC antigen lacking cells can be applied to a variety of purposes. For example, the modified cells may used to generate transgenic animals, which lack MHC antigens in all tissues and organs. Such animals, particularly mice and other small mammals, may be used experimentally to determine the effect of an agent, particularly to screen drugs. They may be used as a model system for various transplantation therapies, including transplants of skin, kidney, liver, etc.

The Class I and Class II MHC antigens are heterodimers, each consisting of an alpha and a beta subunit. In Class I MHC antigens, the beta subunit is $\beta_2$-Microglobulin. Of particular interest is the inactivation of at least one, preferably both, copies of a subunit of an MHC antigen, more particularly, $\beta_2$-microglobulin gene, the $\alpha$ subunit(s) of the Class I or II MHC antigens, or the beta-subunit(s) of the Class II MHC antigens, or any combination thereof. The human Class II MHC antigens are HLA-DR, DP AND DQ, where DR is of primary interest. Exemplary universal donor cells, including stem cells, are described in U.S. Pat. Nos. 5,413,923; 5,416,260; 5,574,205; 5,705,732; and 6,139,835. The site-specific, unidirectional genomic modification methods of the invention can be readily applied to make the genetic modifications described in this specific example.

Other uses of stem and germ cells modified using the site-specific, unidirectional integration systems of the invention will be readily apparent upon reading the present specification.

Genetically modified stem cells or germ cells can be used to produce a transgenic, non-human animal. The animal can be a vertebrate or an invertebrate, and may be mammalian or non-mammalian (e.g., avian species (e.g., chickens), reptiles, insects, and the like). Exemplary mammalian subjects include, but are not necessarily limited to, non-human primates (monkeys, apes, chimpanzees), rodents (rats, mice, gerbils, hamsters, and the like), ungulates (e.g., cattle, sheep, goats, pigs), horses, dogs, and cats. Exemplary non-mammalian animals include, but are not necessarily limited to, members of nematoda, and members of the phylum arthropoda (particularly members of the class insecta). Of particular interest in many embodiments are worms (e.g., *Caenorhabitis*, particularly *C. elegans*) and flies (e.g., *Drosophilidae*, particularly *D. melanogaster*). The term "ungulate" is used to mean any species or subspecies *of* porcine (pig), bovine (cattle), ovine (sheep) and caprine (goats). In general the term encompasses hooved farm animals.

Transgenic animals of the invention includes animals in which a genetic modification is present in all or a subset of the host animal's cells. The invention thus encompasses transgenic animals produced by application of the systems of the invention to stem cells or germ cells, which are subsequently used to produce transgenic animals. The invention also encompasses application of the systems of the invention to genetically modify adult stem cells or mature cells of a host animal, so as to produce a chimeric, transgenic animal. The systems of the invention can be readily adapted for use in conventional methods for modification of a target cell in the course of production of a transgenic animal. Exemplary such methods and compositions for use in such methods are described below.

Production of Transgenic Vertebrates

Methods for introduction of nucleic acid into a target cell, and generation of transgenic vertebrates, particularly transgenic mammalian animals, from genetically modified cells are well known in the art. Procedures for making transgenic, non-human animals have also been described and can be adapted for use with the system of the present invention. Production of transgenic non-human animals has been described (see, e.g., U.S. Pat. No. 4,736,866 (mammals, such as rodents, particularly mice); U.S. Pat. No. 5,942,435 (transgenic swine)). Exemplary methods are described generally below. Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci., USA, 78:5016; Brinster et al., 1985, Proc. Natl. Acad. Sci., USA, 82:4438). Alternatively, the transgene can be introduced into the pronucleus by viral infection. A detailed procedure for producing transgenic mice has been described (see e.g., Hogan et al., Manipulating the Mouse Embryo, Cold Spring Harbour Laboratory, Cold Spring Harbour, N.Y. (1986); U.S. Pat. No. 5,175,383 (1992)). This procedure has also been adapted for other animal species (e.g., Hammer et al., Nature 315:680 (1985); Murray et al., Reprod. Fert. Devl. 1:147 (1989); Pursel et al., Vet. Immunol. Histopath. 17:303 (1987); Rexroad et al., J. Reprod. Fert. 41 (suppl):119 (1990); Rexroad et al., Molec. Reprod. Devl. 1:164 (1989); Simons et al., BioTechnology 6:179 (1988); Vize et al., J. Cell. Sci. 90:295 (1988); and Wagner, J. Cell. Biochem. 13B (suppl): 164 (1989)). In brief, the procedure as adapted for use in the present invention generally involves introducing the system elements into an animal by microinjecting the construct(s) into the pronuclei of fertilized mammalian egg(s) to cause one or more copies of the system elements to be retained in the cells of the developing mammal(s). Following introduction of the construct(s) into the fertilized egg, the egg may be incubated in vitro for varying amounts of time, or reimplanted a surrogate host, or both. One common method is to incubate the embryos in vitro for about 1-7 days, depending on the species, and then reimplant them into the surrogate host. The system elements facilitate unidirectional, site-specific recombination to insert the transgene into the genome. The presence of the transgene in the progeny of the transgenically manipulated embryos can be tested by conventional methods, e.g., by Southern blot analysis of a segment of tissue. Another method for producing germ-line transgenic animals is through the use of embryonic stem (ES) cells. The construct(s) of the system of the invention can be introduced into embryonic stem cells using any suitable method, such as by electroporation (Ausubel et al., Current Protocols in Molecular Biology, John Wiley & Sons (1987)). Detailed procedures for culturing embryonic stem cells (e.g., ES-D3, ATCC# CCL-1934, ES-E14TG2a, ATCC# CCL-1821, American Type Culture Collection, Rockville, Md.) and methods of making transgenic animals from embryonic stem cells can be found in Teratocarcinomas and Embryonic Stem Cells, A Practical Approach, ed. E. J. Robertson (IRL Press, 1987). In brief, ES cells are obtained from pre-implantation embryos cultured in vitro (Evans, M. J., et al., 1981, Nature, 292:154-156). Transgenes can be efficiently introduced into ES cells, and the resulting transformed ES cells can thereafter be combined with blastocysts from a non-human animal. The ES cells colonize the embryo and contribute to the germ line of the resulting chimeric animal.

The transgenic, non-human animals can also be obtained by modifying cells either in vivo (e.g., direct injection), ex vivo (e.g., modifying the cells outside the host and later reimplanting), or in vitro (e.g., modifying cells in a blastocyst or embryo, which then develops into a transgenic animal).

Clones of the non-human transgenic animals described herein can be produced according to the methods described in Wilmut et al. ((1997) Nature, 385:810-813) and PCT publication Nos. WO 97/07668 and WO 97/07669. In brief, a cell, e.g., a somatic cell from the transgenic animal, can be isolated and induced to exit the growth cycle and enter the Go phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated. Also of interest are the production of transgenic animals that provide for production of a transgenic gene product in body fluids, such as milk (see, e.g., U.S. Pat. Nos. 5,994,616; 6,111,165; 6,118,045; 6,204,431; 6,211,427; 6,222,094; 5,366,894, describing production of transgenic mammals, particular bovine and ovine, in which the transgene is expressed in mammary gland and the protein secreted into the milk, e.g., where expression of the transgene is under control of a casein promoter or milk whey gene promoter) or urine (see, e.g., U.S. Pat. No. 6,339,183, describing transgenic mammals expressing heterologous DNA in urothelium and isolation of biologically active molecules from urine).

Once the transgenic animal is produced, cells of the transgenic animal and cells from a control animal can be screened to determine for the presence of the transgene, e.g., using polymerase chain reaction (PCR). Where the transgene encodes a gene product, the cells can be screened to detect the corresponding mRNA (e.g., by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)) or, where the gene product is a protein, if the protein is produced (e.g., using Western blot analysis; Sambrook et al., Molecular Cloning—A Laboratory Manual, (Cold Spring Harbor Laboratory, 1989)).

Production of Transgenic Invertebrates

Transgenic invertebrates and methods of production of same are well known in the art (see, e.g., Link, Mech Ageing Dev 2001 Sep. 30; 122(14):1639-49, reviewing transgenic invertebrate models of age-associated neurodegenerative diseases in *D. melanogaster* and *C. elegans*; Candido et al. Trends Biotechnol. 1996 April; 14(4):125-9, reviewing transgenic *Caenorhabditis elegans* strains as biosensors; Johnson et al. Genetica. 1993; 91(1-3):65-77, reviewing mutants, selective breeding, and transgenics in the dissection of aging processes of *Caenorhabditis elegans*).

Introduction of the system elements into an invertebrate stem or germ cell may be accomplished using any convenient protocol, where suitable protocols include: electroporation, microinjection, vesicle delivery, e.g. liposome delivery vehicles, and the like. Following introduction of the system elements into the cell(s), the transgene is stably integrated into the genome of the cell by unidirectional, site-specific recombination according to the invention. Methods for production of transgenic flies, particularly methods for introduction of nucleic acid into a cell of a fly, and production of transgenic flies from genetically modified cells, are known in the art. See e.g. Brand & Perrimon, Development (1993) 118: 401-415; and Phelps & Brand, Methods (April 1998) 14:367-379. The methods and systems of the invention can be used to generate fertilized eggs that comprise the transgene stably integrated into the genome in site-specific manner. The fertilized eggs can then be allowed to mature under conditions that give rise to transgenic flies, which can be screened for a desired genotypic or phenotypic trait.

Insect stem and germ cells are known in the art. For example, U.S. Pat. No. 6,027,937 describes insect germ cells and methods for the propagation. These germ cells can be modified using the systems of the invention, and then cultured, e.g., in a medium supplemented with soluble cytokines and mitogenic agents and independent of feeder-cells, to induce proliferation. The resulting modified cells can then be used to generate modified, transgenic insects.

Methods for production of transgenic worms are also well in the art.

Exemplary Transgenic Animals Produced

Any of a variety of genetic modifications can be generated in a transgenic animal produced according to the invention. In general, such animals include those having a "knock-out" in a selected gene, or are "knock-ins" for a selected gene. All genetic modifications described herein can be either heterozygous or homozygous, and may be present in all cells or a subset of cells of the transgenic animal. Transgenic animals that are genetically modified in a subset of cells (e.g., having modified adult stem cells and progeny thereof present in a tissue) can be referred to as "chimeric" animals, and may be produced through either in vivo or ex vivo application of the system elements of the invention.

Knock-Out Transgenic Animals

"Knock-out" transgenic animals encompass transgenic animals that are deficient in an endogenous gene product due to a genetic modification produced using the system elements described herein. "Knock-outs" of particular interest are those in which target gene expression is undetectable or insignificant, and those in which a gene product of a target gene is decreased in function relative to the unmodified endogenous gene. Decrease in function can be due to decreased production of a full-length gene product as a result of the genetic alteration, or production of an altered gene product that is deficient in function relative to the native gene product. "Knock-out" transgenics of the invention can be transgenic animals having a heterozygous or homozygous knock-out of the target gene.

The knock-out can be a conditional knock-out, where alteration of the target gene occurs upon exposure of the modified cell to a condition, e.g., exposure to a substance that promotes target gene alteration. For example, a conditional knock-out can be produced by introducing the targeting vector and the integrase as stable chromosomal or extrachromosomal elements (e.g., episomal element), and then providing for the expression of the integrase upon a selected condition (e.g., in the presence of an inducer of a conditional promoter operably linked to the integrase-encoding DNA). Production of the integrase then results in site-specific recombination between the targeting vector attachment site and a genomic attachment site to result in a knock-out of a target gene.

Knock-out transgenic animals can also be generated through alteration of a promoter element(s) operably linked to an endogenous gene, e.g., through insertion of a transcriptional modulation unit. Transcription modulation of a target gene can be achieved by integrating into a target cell genome a transcription modulation unit that, when integrated into the genome of the target cell according to the subject invention, becomes operatively linked to a targeted genomic domain in a manner that results in the desired transcription. Where transcription is to be decreased, the subject methods integrate a transcriptional modulation unit that becomes operably linked upon integration to the targeted genomic domain in manner that results in a decrease in transcription of the targeted genomic domain. the transcription modulation unit may be a transcriptional inhibition unit, e.g., for at least decreasing transcription, including turning off transcription when it is normally present and decreasing the level of transcription when already present.

Knock-out transgenic animals can also be produced by introducing an expression disrupting nucleic acid to disrupt an endogenous gene using a "disruption element" as described above.

Knock-In Transgenic Animals

A "knock-in" transgenic animal is an animal having a cell genetically modified so as to result in altered expression (e.g., increased (including ectopic) expression) of selected gene, which gene may be either present on nucleic acid that was introduced into the cell (e.g., by introduction of an additional copy of an endogenous or exogenous gene which expresses an endogenous or exogenous gene product), or by operatively inserting a regulatory sequence that provides for enhanced expression of an endogenous copy of the target gene (e.g., gene activation, e.g., through introduction of a transcriptional modulation unit as described above).

"Knock-ins" can be conditional knock-ins. For example, a conditional knock-out can be produced by introducing the targeting vector and the integrase as stable chromosomal or extrachromosomal elements (e.g., episomal element), and then providing for the expression of the integrase upon a selected condition (e.g., in the presence of an inducer of a conditional promoter operably linked to the integrase-encoding DNA). Production of the integrase then results in site-specific recombination between the targeting vector attachment site and a genomic attachment site to result in introduction of a coding sequence for expression in the target cell or introduction of a transcription modulation unit so as to be operably linked to an endogenous gene to provide for increased expression of the endogenous gene.

The transgenic animals produced using the systems of the invention find use in a variety of different applications, several representative ones of which are described in detail below.

The subject genetically modified stem and germ cells, as described above, find use in a variety of applications. Applications of interest in which the subject methods and compositions find use include both therapy and production of transgenic, non-human animals.

Applications using stem cells and germ cells genetically modified using the subject vectors and methods described herein include, but are not limited to: research applications, polypeptide synthesis applications and therapeutic applications. Each of these representative categories of applications is described separately below in greater detail.

Research Applications

Examples of research applications in which transgenic animals produced using genetically modified stem cells or genetically modified germ cells as described herein. Such transgenic, non-human animals can be used to, for example, characterize a particular gene. In such applications, the targeting vector is employed to insert a gene or coding sequence of interest into a target cell, which in turn is the basis for production of a transgenic, non-human animal. The resultant effect of the inserted gene on the transgenic animal's phenotype is observed. In this manner, information about the gene's activity and the nature of the product encoded thereby can be deduced. Similarly the transgenic, non-human animals so produced can be used to identify and define DNA sequences that control gene expression, e.g. in a temporal (e.g. certain developmental stage) or spatial (e.g. particular cell or tissue type) manner.

Yet another research application for use of transgenic animals generated from stem cells or germ cells genetically modified according to the invention is in the identification and characterization of the results of gene expression studies. For example, a plurality of animals produced from distinct vector-targeted, and genetically modified cells are prepared in which the gene of interest is inserted into distinct locations in the genome of various targeted cells, where expression of the gene of interest is dependent on endogenous promoter mediation, i.e. where the gene of interest lacks a promoter or is coupled to only a weak promoter. By plurality is meant at least two, where the number usually ranges from about 2 to 5000, usually from about 2 to 200. This plurality of vector targeted cells may be produced by introducing the vector in a plurality of cells or taking a collection of pretargeted cells that are homogenous with respect to the insertion site of the gene, i.e. progeny of a single targeted cell, and then introducing transposase into one or more of, but not all of, the constituent members of the collection. This approach is more readily adapted to production of less expensive, less labor-intensive transgenic animals, such as, for example, *Drosophila* or *Caenorhabditis*.

Polypeptide Synthesis Applications

In addition to the above research applications, the subject genetically modified stem cells and germ cells also find use in the synthesis of gene products of interest, such as polypeptides, e.g. proteins of interest. In such applications, a vector that includes a gene encoding a polypeptide of interest, optionally in combination with requisite and/or desired expression regulatory sequences, e.g. promoters, etc., (i.e. an expression module) is introduced into the target cell, which is then used to produce a transgenic animal. The DNA encoding the polypeptide of interest can optionally be provided in an expression cassette, which provides for a promoter operably linked to the coding sequence of the DNA. The promoter can be, for example, a constitutive promoter, an inducible promoter, or a tissue- or cell-specific promoter. In one embodiment of interest, where the transgenic animal is a mammal from which milk can be readily obtained (e.g., a cow, goat, and the like), the promoter is one that provides for expression in a mammary gland, and for production of the polypeptide of interest in milk.

Once the transgenic animal expressing the protein of interest is prepared, the protein can then be isolated and purified from appropriate tissues or bodily fluids (e.g., blood, serum, milk, and the like) to produce a desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Veterinarian Applications—Therapeutic and Agricultural Applications

The subject invention also contemplates the use of genetically modified stem and germ cells modified using the unidirectional, site-specific recombination system to generate transgenic animals that, as a result of having genetically modified cells, exhibit a phenotypic trait that is desirable, e.g., due to a therapeutic effect of the encoded gene product (including prophylactic effect), due to an enhanced growth rate or weight gain, due to increased production of milk or other food product obtained from livestock, and the like.

In this application, the system elements are employed to stably integrate a nucleic acid encoding a gene product (e.g., hormone, antimicrobial gene product, and the like) into the genome of a stem cell, which is in turn is used to produce a transgenic animal. The subject vectors may be used to deliver a wide variety of therapeutic nucleic acids or nucleic acids encoding a gene product that provides commercial advantage in agricultural livestock. Specific genes of interest include, but are not limited to, genes encoding growth hormone (e.g., bovine growth hormone), antigenic polypeptides (e.g., as in polypeptide-based vaccines for prevention or reduction of risk of disease from microbial infection, e.g., bacterial, viral, fungal, or parasitic pathogens), interleukins, cytokines, small peptides, genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. Further genes include: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, a 1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase.

Therapeutic Applications

Genetically modified stem cells also find use in therapy of subject, particularly human subject. For example, stem cells—which can be obtained from the subject to be treated (autologous) or from another source—are genetically modified to provide for expression of a desired gene product, which gene product provides for a beneficial effect in the subject. In another embodiment, the stem cells are genetically modified so as to decrease expression of one or more genes. This latter embodiment is of interest in the development of, for example, universal donor cells for use in transplantation, making it possible to have a bank of cells, tissues, and organs available for transplantation in a patient, with little or no regard to the patient's transplantation antigens (e.g., MHC type).

Other uses of the stem cells and germ cells genetically modified according to the invention will be readily apparent to the ordinarily skilled artisan upon reading the present specification.

Site-Specific, Unidirectional Recombination in Modification of a Host Cell Genome to Achieve a Beneficial Effect The unidirectional, site-specific system, its related compositions, and methods of use can be applied to accomplish a variety of desirable modifications in a host cell genome. For example, the system can be used to effect insertion of a coding sequence of interest, which can be provided in an expression cassette, to provide for production of a beneficial gene product of interest. The unidirectional, site-specific system can also be used to provide modulation of expression of an endogenous in the host cell, e.g., to activate expression of an endogenous gene. The unidirectional, site-specific system can also be used to disrupt expression of an endogenous gene, so as to reduce production of a functional gene product that is endogenous to the host cell. The unidirectional, site-specific system can also be used to repair a gene, by inserting a correct segment of the gene in the correct position to replace the defective segment. Other uses of the unidirectional, site-specific systems described herein will be readily apparent to the ordinarily skilled artisan upon reading the present specification.

As such, the subject methods are properly characterized being integrative targeted genomic modification methods. The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 5 kb, usually from about 2 kb to about 10 kb. In some embodiments, however, the inserted nucleic acid may be as small as about 500 bp or about 100 bp.

The genome modified according to the invention can be that of any suitable host, usually a mammalian host. Of particular interest is the modification of the genome of a subject, or the modification of a host cell for implantation in a subject (e.g., ex vivo therapy) where the subject is a human, a domesticated animal (including pets and livestock) or other animal in which it is desirable to provide for an improved trait (e.g., increased milk production in cows, immunoresistance to infection) or veterinary aid (e.g., treatment of an acute or chronic infection). Delivery of proteins to a human subject using the systems and methods described herein are of particular interest.

Exemplary applications in modification of a host genome are described below in more detail.

Production and Delivery of a Gene Product of Interest

In one embodiment, the invention features unidirectional, site-specific systems for introduction of a nucleic acid of interest into the genome of a host cell. In one embodiment, the targeting vector comprises a nucleic acid of interest, which has a coding sequence encoding a gene product of interest. This nucleic acid of interest is the "payload" for introduction at target site in the genome. The nucleic acid of interest may be either genomic or may lack one or more introns normally present in a gene encoding the gene product of interest. Frequently, the nucleic acid of interest is a cDNA.

In one embodiment, the genome attachment site is positioned so that introduction of the "payload" nucleic acid provides for expression of the encoded gene product from a promoter endogenous to the host genome.

In another embodiment, the nucleic acid of interest is provided in the form of an expression cassette. The expression cassette comprises a nucleic acid of interest and a promoter operably linked to a coding sequence of the nucleic acid of interest. In this embodiment, the expression cassette is inserted into the host genome by unidirectional, site-specific recombination, and the gene product encoded by the nucleic acid of interest can be expressed from the promoter of the expression cassette.

The expression cassette can comprise one or more promoters (such as a constitutive or inducible promoters), and other elements that promote transcription of a coding sequence to which they are operably linked in the expression cassette, such as enhancers, scaffold-attachment regions or matrix attachment sites, transcription factor binding sites, or combinations of such elements, etc. As such, the regulatory sequence can contain an inducible promoter, so that transcription occurs at higher levels under conditions in which the promoter is active, i.e., the induction conditions. Alternatively, constitutive promoters that result in transcription upon operable introduction into the genome may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene. The regulatory sequence may include transcription factor binding sites, where representative sites include, but are not limited to: the TATA Box, the CCAAT Box, AP1, Sp1 or NF-κ B binding sites. It may also be desirable to include one or more introns in the expression cassette to facilitate efficient transcription of the coding sequence of interest.

The gene product of interest delivered according to the invention can be selected so as to supplement an endogenous gene product, e.g., to provide for increased levels of a gene product in the host where the gene product is present at some level in the host prior to application of the methods and compositions of the invention. For example, while human growth hormone (hGH) may be produced at some level in the host, an expression cassette having a coding sequence for hGH can provide for elevated levels of the protein by supplementing the endogenous hGH, and provide a desired effect.

In another related embodiment, the introduced nucleic acid provides for delivery of a gene product that is deficient in the host (e.g., is undetectable in the subject), but which would be endogenous to a normal host. The deficiency may be due to a disease or condition that is associated with a defective gene product, a defective gene which does not provide for expression of the gene product, or a defective cell or tissue type that does not provide for production of the gene product.

In another embodiment, the nucleic acid of interest is inserted into the genome so as to effectively replace and/or disrupt an endogenous gene. In this embodiment, the target gene may be defective, e.g., may not provide for expression of a functional gene product or for any gene product. This approach is useful where the defective endogenous gene product is dominant to the desired gene product when the defective portion of the gene can be replaced by a correct version.

Nucleic Acid of Interest for Introduction Using the Systems of the Invention and Expression in a Host Any number of gene products can be delivered to a subject according to the methods of the invention. Delivery of nucleic acid encoding a therapeutic gene is of particular interest. "Therapeutic genes" are those nucleic acid sequences which encode molecules that provide some therapeutic benefit to the host, including proteins (e.g., secreted proteins, membrane-associated proteins (e.g., receptors), structural proteins, cytoplasmic proteins, and the like) functional RNAs (antisense, hammerhead ribozymes), and the like. Secreted proteins include those that may be found in a bodily fluid of a subject (e.g., in blood, lymph, saliva, gastrointestinal secretions, and the like). In one embodiment of particular interest, the mammalian subject is a human subject and the introduced nucleic acid encodes a human protein or other human gene product.

In general, therapeutic gene products encompass a wide variety of gene products, such as: 1) a secreted protein with predominantly systemic effects; 2). a secreted protein with predominantly local effects; 3) a membrane protein imparting new or enhanced cellular responsiveness; 4) a membrane protein facilitating removal of a toxic product; 5) an intracellular protein; 7) an intracellular protein directly affecting gene expression; 8) an intracellular protein with autolytic effects; 9) a gene product-engineered DNA which binds to or sequesters a regulatory protein; 10) a ribozyme; and 11) antisense-engineered RNA to inhibit gene expression.

Examples of indications for which gene products of types 7), 8), 9), and 11) above are relevant include treatment of a tumor, (e.g., a solid tumor, lymphoma, leukemia), treatment of cells infected with an intracellular microbe, and aberrantly proliferative cells (as in aberrant angiogenesis or fibrosis). Thus, therapeutic gene products can also encompass gene products that are deleterious to a specific cell type. Specific examples of cancer therapeutic genes that may be delivered via the subject vectors include: genes that enhance the anti-tumor activity of lymphocytes, genes whose expression product enhances the immunogenicity of tumor cells, tumor suppressor genes, toxin genes, suicide genes, multiple-drug resistance genes, antisense sequences, and the like.

One well known example of a therapeutic gene encoding a membrane-associated protein is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease, or effect a cure if the gene transfer was permanent.

Other disorders resulting from mutations in a single gene (known as monogenic disorders) include alpha-1-antitrypsin deficiency, chronic granulomatous disease, familial hypercholesterolemia, Fanconi anemia, Gaucher disease, Hunter syndrome, Hurler's syndrome, ornithine transcarbamylase deficiency, purine nucleoside phosphorylase deficiency, severe combined immunodeficiency disease (SCID)-ADA, X-linked SCID, hemophilia, and the like. In these cases, replacement or disruption of the defective gene with, for example, an expression cassette, encoding a functional form of the gene may be desirable.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer.

Proteins of interest for delivery using the methods of the invention fall into many different classes. For example, secreted proteins can be enzymes (e.g., proteases, phospholipases, and the like), protease inhibitors, hormones (e.g., pituitary hormones), growth factors, cytokines, chemokines, chemotactins, gonadotrophins, lipid-binding proteins, somatamedians, gonadotrophins, and immunoglobulins. Other secreted proteins of interest include antimicrobial polypeptides (e.g., antibacterial, antifingal, antiviral, and/or antiparasitic polypeptides), and antibodies or antigen-binding antibody fragments (e.g, FAbs) thereof (e.g., orthoclone OKT-e (anti-CD3), GPIIb/IIa monoclonal antibody).

Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, a 1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like.

Examples of secreted proteins of interest include, but are not limited to insulin, erythropoietin, tissue plasminogen activator (tPA), urokinase, streptokinase, neutropoesis stimulating protein (also known as filgastim or granulocyte colony stimulating factor (G-CSF)), thrombopoietin (TPO), growth hormone (including human and bovine growth hormone), alpha-L-iduronidase, α1-antitrypsin, glucose 6-phosphatase, α-L-fucosidase, β-glucuronidase, galactose 1-phosphate uridyltransferase, adenosine deaminase, β-globin, purine nucleoside phosphorylase, sphingomyelinase, glucocerebrosidase, ornithine transcarbamylase, argininosuccinate synthetase, phenylalanine hydroxylase, branched-chain α-ketoacid dehydrogenase, fumarylacetoacetate hydrolaseinterleukins, small peptides, emoglobin, insulinotropin, imiglucerase, sarbramostim, endothelian, soluble CD4, and antibodies and/or antigen-binding fragments (e.g, FAbs) thereof (e.g., orthoclone OKT-e (anti-CD3), GPIIb/IIIa monoclonal antibody), liary neurite transforming factor (CNTF), granulocyte macrophage colony stimulating factor (GM-CSF), brain-derived neurite factor (BDNF), parathyroid hormone (PTH)-like hormone, insulinotrophic hormone, insulin-like growth factor-1 (IGF-I), platelet-derived growth factor (PDGF), epidermal growth factor (EGF), acidic fibroblast growth factor, basic fibroblast growth factor, transforming growth factor β, neurite growth factor (NGF)interferons (IFN) (e.g., IFN-α2b, IFN-α2a, IFN-αN1, IFN-β1b, IFN-γ), interleukins (e.g, IL-1, IL-2, IL-8), tumor necrosis factor (TNF) (e.g, TNF-α, TNF-β)), transforming growth factor-alpha and -beta, clotting factors (e.g., clotting factors VIII, IX, and the like), catalase, calcitonin, arginase, phenylalanine ammonia lyase, L-asparaginase, pepsin, uricase, trypsin, chymotrypsin, elastase, carboxypeptidase, lactase, sucrase, intrinsic factor, vasoactive intestinal peptide (VIP), calcitonin, Ob gene product, cholecystokinin (CCK), serotonin, and glucagon. Heterologous secreted proteins of interest can include antimicrobial polypeptides (e.g., antibacterial, antifingal, antiviral, and/or antiparasitic polypeptides) and antigens (e.g., as may be used in a vaccine), each of which may find particular use in veterinarian applications.

Membrane proteins of interest can include receptors (e.g., transmembrane receptors, such as G-protein coupled receptors (GPCRs) etc.

Specific membrane proteins of interest include, but are not necessarily limited to adrenergic receptors, serotonin receptors, low-density lipoprotein receptor, CD-18, sarcoglycans (which are deficient in muscular dystrophy), etc.

Intracellular proteins (e.g., proteins that are primarily located within the intracellular compartment or which exhibit a desired biological activity within a cell) also may be delivered according to the invention. Such intracellular proteins can include fumarylacetoacetate hydrolase (FAH), deficient in Hereditary Tyrosinemia Type 1.

Specific examples of intracellular proteins include antiviral proteins (e.g., proteins that can provide for inhibition of viral replication or selective killing of infected cells), structural protein such as collagens, i.e. the type VII collagen COL7A1 gene, defective in Recessive Dystrophic Epidermolysis Bullosa (RDEB) and dystrophin, defective in muscular dystrophy.

Numerous proteins that are desirable for delivery according to the invention are well known in the art and the DNA encoding these proteins has been isolated. For example, the sequence of the DNAs encoding insulin, human growth hormone, intrinsic factor, clotting factor VIII, and erythropoietin are available from Genbank and/or have been described in the scientific literature (e.g., human clotting factor VIII gene: Gitschier et al., Nature 312:326-330, 1984; Wood et al., Nature 312:330-337, 1984; human intrinsic factor: Hewitt et al., Genomics 10:432-440, 1991). Moreover, proteins commonly used in treatments can be used in the procedures of the present invention. Such proteins are disclosed in, for example, the Physicians' Desk Reference (2002 Physicians' Desk Reference, 56th Ed., Medical Economics Data Production Co., Montvale, N.J.; incorporated by reference) and can be dosed using methods described in, for example, Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., supra; Suggs et al., Proc. Natl. Acad. Sci. USA 78:6613-6617, 1981; U.S. Pat. No. 4,394,443; each of which are incorporated herein by reference with respect to identification and isolation of DNA encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (USPNs 4,683,195 and 4,683,202). The clones may be expressed or the DNA of interest can be excised or synthesized for use in other constructs. If desired, the DNA of interest can be sequenced using methods well known in the art.

It may also be desirable to produce altered forms of the therapeutic proteins that are, for example, protease resistant or have enhanced activity relative to the wild-type protein. For example, where the therapeutic protein is a hormone, it may be desirable to alter the protein's ability to form dimers or multimeric complexes. For example, insulin may be modified so as to prevent its dimerization has a more rapid onset of action relative to wild-type, dimerized insulin.

Transcription Modulation of a Gene Endogenous to the Host Cell Genome

The invention also provides methods of modulating transcription of a genomic domain of a target cell. By modulating is meant changing or altering, including increasing and decreasing, the transcription level or rate of the genomic domain of interest. As such, altered transcription encompasses activating (or causing to be expressed) a genomic domain which is normally silent (untranscribed) in the cell as obtained, increasing transcription of a genomic domain which is not transcribed at physiologically significant levels in the cell as obtained, changing the pattern of regulation or induction such that it is different than occurs in the cell as obtained, and reducing (including eliminating) transcription of a genomic domain which is transcribed in the cell as obtained.

By genomic domain is meant a genomic region that includes one or more, typically a plurality of, exons, where the exons are typically spliced together during transcription to produce an mRNA, where the mRNA often encodes a protein product, e.g., a therapeutic protein, etc. In many embodiments, the genomic domain includes the exons of a given gene, and may also be referred to herein as a "gene." Modulation of transcription of the genomic domain pursuant to the subject methods results in at least about 2-fold, sometimes at least about 5-fold and sometimes at least about 10-fold modulation, e.g., increase or decrease, of the transcription of the targeted genomic domain as compared to a control, for those instances where at least some transcription of the targeted genomic domain occurs in the control. For example, in situations where a given genomic domain is expressed at only low levels in a non-modified target cell (used as a control), the subject methods may be employed to obtain an at least 2-fold increase in transcription as compared to a control. Transcription level can be determined using any convenient protocol, where representative protocols for determining transcription levels include, but are not limited to: RT PCR, RNA blotting, ELISA, and the like.

Transcription modulation, as described above, is achieved by integrating into the target cell genome a transcription modulation unit that, when integrated into the genome of the target cell according to the subject invention, becomes operatively linked to the targeted genomic domain in a manner that results in the desired transcription modulation if transcription. For example, where transcription is to be enhanced, the subject methods integrate a transcriptional modulation unit that becomes operably linked upon integration to the targeted genomic domain in manner that results in an increase in transcription of the targeted genomic domain. Likewise, where transcription is to be decreased, the subject methods integrate a transcriptional modulation unit that becomes operably linked upon integration to the targeted genomic domain in manner that results in a decrease in transcription of the targeted genomic domain.

As indicated above, the subject methods rely on site-specific integration of a transcriptional modulation unit into the genome of the target cell in a manner that results in transcriptional modulation unit mediated transcriptional modulation of the targeted genomic domain. Depending on the particular application in which the method is employed, the transcriptional modulation unit may be a transcriptional activation unit, e.g., for at least enhancing transcription, including turning on transcription when it is normally not present and increasing the level of transcription when already present. Alternatively, the transcription modulation unit may be a transcriptional inhibition unit, e.g., for at least decreasing transcription, including turning off transcription when it is normally present and decreasing the level of transcription when already present.

Where the transcriptional modulation unit is a transcriptional activation unit, the transcriptional activation unit is made up of a sequence of nucleotides that, when integrated into the genomic DNA of the target cell in the site-specific manner of the subject invention, becomes operably linked to the genomic domain of interest and results in an increase in transcription of the genomic domain of interest. Any sequence of nucleotides that provides for the desired transcription enhancement may be employed.

In many embodiments, the transcriptional activation unit at least includes a regulatory sequence. The regulatory sequence of the transcriptional activation unit can include one or more promoters (such as a constitutive or inducible promoters), enhancers, scaffold-attachment regions or matrix attachment sites, transcription factor binding sites, or combinations of elements, etc. As such, the regulatory sequence can contain an inducible promoter, with the result that cells resulting from the subject methods do not immediately transcribe the genomic domain but can be induced to do so. Alternatively, constitutive promoters that result in immediate transcription upon introduction may be employed. The regulatory sequence can be isolated from cellular or viral genomes, where representative regulatory sequences of interest include, but are not limited to, those that regulate the expression of SV40 early or late genes, adenovirus major late genes, the mouse metallothionein-I gene, the elongation factor-1α gene, cytomegalovirus genes, collagen genes, actin genes, immunoglobulin genes or the HMG-CoA reductase gene). The regulatory sequence may include transcription factor binding sites, where representative sites include, but are not limited to: the TATA Box, the CCAAT Box, AP1, Sp1 or NF-κB binding sites.

In certain embodiments, the transcriptional activation unit further includes one or more exons. An exon is defined herein as a DNA sequence that is copied into RNA and is present in a mature mRNA molecule. The exons can, optionally, contain DNA that encodes one or more amino acids and/or partially encodes an amino acid (i.e., one or two bases of a codon). Alternatively, the exon may contain DNA which corresponds to a 5' non-coding region. Where the exogenous exon or exons encode one or more amino acids and/or a portion of an amino acid, the DNA construct is designed such that, upon transcription and splicing, the reading frame is in-frame with the second exon or coding region of the targeted genomic domain or gene. As used herein, in-frame means that the encoding sequences of a first exon and a second exon, when fused, join together nucleotides in a manner that does not change the appropriate reading frame of the portion of the mRNA derived from the second exon.

Where the first exon of the targeted genomic domain or gene contains the sequence ATG to initiate translation, the exogenous exon of the construct may contain an ATG and, if required, one or more nucleotides such that the resulting coding region of the mRNA including the second and subsequent exons of the targeted gene is in-frame. Examples of such targeted genes in which the first exon contains an ATG include the genes encoding HEPO, hGH, human colony stimulating factor-granulocyte/macrophage (hGM-CSF), and human colony stimulating factor-granulocyte (hG-CSF).

In addition, in many embodiments the transcriptional activation unit also includes a splice-donor site, specifically an unpaired splice-donor site. A splice-donor site is a sequence that directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AG GURAGU (where R denotes a purine nucleotide) with the GU in the fourth and fifth positions, being required (Jackson, I. J., Nucleic Acids Research 19: 3715-3798 (1991)). The first three bases of the splice-donor consensus site are the last three bases of the exon. Splice-donor sites are functionally defined by their ability to effect the appropriate reaction within the mRNA splicing pathway. An unpaired splice-donor site is defined herein as a splice-donor site that is present in a targeting construct and is not accompanied in the construct by a splice-acceptor site positioned 3' to the unpaired splice-donor site. The unpaired splice-donor site results in splicing to an endogenous splice-acceptor site. A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as:

YYYYYYYYYYNYAG, (SEQ ID NO: 209)

where Y denotes any pyrimidine and N denotes any nucleotide (Jackson, I. J., Nucleic Acids Research 19:3715-3798 (1991)). An intron is defined as a sequence of one or more nucleotides lying between two exons and which is removed, by splicing, from a precursor RNA molecule in the formation of an mRNA molecule.

When present, the encoding DNA (e.g., in exon 1 of the transcriptional activation unit) employed can optionally encode one or more amino acids, and/or a portion of an amino acid, which are the same as those of the endogenous protein. The encoding DNA sequence employed herein can, for example, correspond to the first exon of the gene of interest. The encoding DNA can alternatively encode one or more amino acids or a portion of an amino acid different from the first exon of the protein of interest. Such an embodiment is of particular interest where the amino acids of the first exon of the protein of interest are not critical to the activity or activities of the protein. For example, any exon of human or non-human origin in which the encoded amino acids do not prevent the function of the hybrid signal peptide can be used. In a related embodiment, this technique can also be employed to correct a mutation found in a target gene. Where the desired product is a fusion protein of the endogenous protein and encoding sequences in the transcriptional activation unit, the exogenous encoding DNA incorporated into the cells by the present method includes DNA which encodes one or more exons or a sequence of cDNA corresponding to a translation or transcription product which is to be fused to the product of the endogenous targeted gene. In this embodiment, targeting is used to prepare chimeric or multifunctional proteins which combine structural, enzymatic, or ligand or receptor binding properties from two or more proteins into one polypeptide. For example, the exogenous DNA can encode an anchor to the membrane for the targeted protein or a signal peptide to provide or improve cellular secretion, leader sequences, enzymatic regions, transmembrane domain regions, co-factor binding regions or other functional regions. Examples of proteins which are not normally secreted, but which could be fused to a signal protein to provide secretion include dopadecarboxylase, transcriptional regulatory proteins, α-galactosidase and tyrosine hydroxylase.

While the above description has been primarily limited to elements found in transcriptional activation units, those elements that may be present in transcriptional inhibition units are readily to known to those of skill in the art, and typically include expression inhibition elements, negative regulatory elements, stuffer fragments that disrupt transcription, termination codons, and the like.

The DNA of the transcriptional modification unit employed in the subject methods can be obtained from sources in which it occurs in nature or can be produced, using genetic engineering techniques or synthetic processes.

Operatively linked or functionally placed is defined as a configuration in which the elements of the transcriptional modulation unit are appropriately targeted at a position relative to an endogenous gene such that the regulatory element present in the transcriptional modulation unit influences the production of a primary RNA transcript which initiates at a CAP site (optionally included in the transcriptional modulation unit) and includes sequences corresponding to the exon and splice-donor site of the transcriptional modulation unit (when present), DNA lying upstream of the endogenous gene's regulatory region (if present), the endogenous gene's regulatory region (if present), the endogenous gene's 5' non-transcribed region (if present), and exons and introns (if present) of the endogenous gene. In an operatively linked configuration the splice-donor site of the targeting construct directs a splicing event to a splice-acceptor site flanking one of the exons of the endogenous gene, such that a desired protein can be produced from the fully spliced mature transcript. In one embodiment, the splice-acceptor site is endogenous, such that the splicing event is directed to an endogenous exon, for example, of the endogenous gene. In another embodiment where the splice-acceptor site is included in the targeting construct, the splicing event removes the intron introduced by the transcriptional activation unit.

The above described targeting/integration event results in the insertion of the transcriptional modulatory unit into the genome of the target cell in a manner that places the endogenous gene under the control of the transcriptional modulatory unit (for example, by insertion of either a promoter or an enhancer, or both, upstream of the endogenous gene or regulatory region). Optionally, the targeting event can simultaneously result in the deletion of the endogenous regulatory element, such as the deletion of a tissue-specific negative regulatory element. The targeting event can displace an existing element; for example, a tissue-specific enhancer can be displaced by an enhancer that has broader or different cell-type specificity than the naturally-occurring elements, or displays a pattern of regulation or induction that is different from the corresponding nontransfected cell. In this embodiment the naturally occurring sequences are taken out of operational linkage with the genomic domain of interest and new sequences are added. Alternatively, the endogenous regulatory elements are disrupted or disabled by the targeting event, such as by targeting the exogenous sequences within the endogenous regulatory elements.

The endogenous gene modulated can be any of a variety of genes of interest, including those therapeutic genes described above that are endogenous to the subject.

Disruption Element

In another embodiment, a nucleic acid of interest is inserted into the host genome so as to disrupt an endogenous gene. The introduced nucleic acid need not encode for any gene product, but rather need only provide for a decrease in production of an endogenous gene product. In this context the introduced nucleic acid is referred to herein as a "disruption element".

A disruption element can comprise, for example a sequence providing one or more termination signals that, when inserted into the endogenous gene, prevent transcription of a full-length gene product. This can be accomplished by, for example, site-specific insertion of the disruption element into a region within a coding sequence of an endogenous gene.

The disruption element can be inserted using the system of the invention so as to decrease efficiency of an endogenous promoter element driving expression of a gene product to which it is normally operably linked. For example, the disruption element can act as a "spacer" that increases the distance between the transcriptional start site of a gene and one or more promoter elements required for efficient transcription. Increasing the distance between these endogenous genetic elements can result in a decrease in transcription of the gene, and thus a decrease in production of the encoded gene product. The disruption element can also be used to modify promoter elements essential to transcription, rendering them ineffective or decreasing their efficiency in promoting expression of the gene to which they are normally operably linked.

The disruption element can also be positioned within the endogenous gene so as to prevent production of splice variants of a gene. This can result in a decrease in production of one or more splice variants, and/or a concomitant increase in production of a particular splice variant, the production of which is not significantly affected by the presence of the disruption element.

Disruption elements find use where the desired beneficial effect is to decrease a level of a gene product that is aberrantly expressed, e.g., to decrease expression of a gene product that is overexpressed in cancerous cells, e.g., metastatic cells, or to eliminate production of an aberrant product that has a dominant negative effect.

Introduction of the system elements to accomplish administration of a gene product according to the invention can be accomplished in two general ways: 1) by ex vivo genomic modification of a cell, and introduction of the cell into the subject; or 2) in vivo genomic modification of a target cell. Each of these approaches is described below.

In one embodiment, delivery of a gene product of interest is accomplished by modification of the genome of a cell, and subsequent introduction of the modified cell into the subject, e.g., as in ex vivo therapy. By "ex vivo" it is meant that cells or organs are modified outside of the body, and then such cells or organs are typically returned to a living body. For example, where the target cell is a cell of an organism that has been removed from the organism, the targeting vector may be introduced directly into the cell under cell culture conditions permissive of viability of the target cell, e.g., by using standard transformation techniques. Techniques well known in the art for the transfection of cells (see discussion above) can be used for the ex vivo administration of nucleic acid constructs. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The cell modified and subsequently introduced into the subject may be any suitable cell that is compatible for subsequent implantation. The cell is generally selected according to a variety of factors such as the gene product of interest to be delivered, the subject to receive the implant, and desired beneficial effect. The cell can be a primary cell, a secondary cell, or from a suitable cell line.

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells that have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized.

Cells selected for the subject method can fall into four types or categories: 1) cells which do not, as obtained, make or contain the protein or product (such as a protein that is not normally expressed by the cell or a fusion protein not normally found in nature), 2) cells which make or contain the protein or product but in quantities other than that desired (such as, in quantities less than the physiologically normal lower level for the cell as it is obtained), 3) cells which make the protein or product at physiologically normal levels for the cell as it is obtained, but are to be augmented or enhanced in their content or production, and 4) cells in which it is desirable to change the pattern of regulation or induction of a gene encoding a protein.

Primary and secondary cells for modification, and introduction to the host in ex vivo therapy can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types including stem and progenitor cells. Primary cells are usually of interest for ex vivo therapy, and can be obtained from the individual to whom the transfected primary or secondary cells are administered (e.g., to provide for a recombinant, autologous transplant). However, primary cells can be obtained from a donor (other than the recipient) of the same species.

Methods for introduction or implantation of cells modified according to the invention are well known in the art. The modified cell can be introduced by various routes of administration and at various sites (e.g., renal subcapsular, subcutaneous, central nervous system (including intrathecal), intravascular, intrahepatic, intrasplanchnic, intraperitoneal (including intraomental), or intramuscular implantation). Once implanted in the individual, the modified cells produce the gene product of interest encoded by DNA of interest.

In this embodiment, the system elements are administered to the organism or host in a manner such that the targeting construct enters the target cell(s), e.g., via an in vivo protocol.

By "in vivo," it is meant the target construct is administered to a living body of an animal. Methods for the administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995,), using viral vectors (Monahan, et al, Gene Therapy 4:40-49, 1997; Onodera, et al, Blood 91:30-36, 1998,), by uptake of "naked DNA", and the like. The exact formulation, route of administration and dosage can be chosen empirically. (See e.g. Fingl et al., 1975, in "The Pharmacological Basis of Therapeutics", Ch. 1 pl).

Several general strategies for accomplishing nucleic acid-based therapy have been studied and have been reviewed extensively (Yang, N—S., Crit. Rev. Biotechnol. 12:335-356 (1992); Anderson, Science 256:808-813 (1992); Miller, A. S., Nature 357:455-460 (1992); Crystal, R. G., Amer. J. Med. 92(suppl 6A):44S-52S (1992); Zwiebel, J. A. et al., Ann. N.Y. Acad. Sci. 618:394-404 (1991); McLachlin, J. R. et al., Prog. Nucl. Acid Res. Molec. Biol. 38:91-135 (1990); Kohn, D. B. et al., Cancer Invest. 7:179-192 (1989).

DNA transfer can be achieved using a number of approaches described below. As is known in the art an optimal gene delivery system should bind the DNA and make it soluble, effectively transfer the DNA into the cell, protect it from nucleases, release the DNA for efficient activity, and, optionally and where desired, be targetable to specific cells. The optimal system may differ according to the particular gene transfer application, e.g., systemic versus local delivery, target cell type, etc.

The following represent exemplary modes of accomplishing in vivo delivery of nucleic acid. In general, the methods and compositions useful in connection with the invention are non-viral (e.g., do not involve use of a viral nucleic acid that facilitates integration into the host cell). Viral-based delivery can be used with the proviso that the viral nucleic acid does not integrate at a detectable level into the hose genome, but rather only serves to introduce the DNA into the cell.

Retroviral Vectors. Retroviral-mediated human gene therapy utilizes amphotrophic, replication-deficient retrovirus systems in which the retroviral integrase has been inactivated (Temin, H. M., Human Gene Therapy 1:111 (1990); Temin et al., U.S. Pat. No. 4,980,289; Temin et al., U.S. Pat. No. 4,650,764; Temin et al., U.S. Pat. No. 5,124,263; Wills, J. W. U.S. Pat. No. 5,175,099; Miller, A. D., U.S. Pat. No. 4,861,719; Miller, A. D., Curr. Top. Microbiol. Immunol. 158:1-24 (1989); Miller, D. G. et al., Mol. Cell. Biol. 10:4239 (1990)).

For use in the present methods, DNA encoding the system elements of the invention is packaged into retrovirus vectors using one of several known packaging cell line that produce replication-defective retroviruses (see, for example, Cone, R. D. et al., Proc. Natl. Acad. Sci. USA 81:6349-6353 (1984); Mann, R. F. et al., Cell 33:153-159 (1983); Miller, A. D. et al., Molec. Cell. Biol. 5:431-437 (1985),; Sorge, J., et al., Molec. Cell. Biol. 4:1730-1737 (1984); Hock, R. A. et al., Nature 320:257 (1986); Miller, A. D. et al., Molec. Cell. Biol. 6:2895-2902 (1986). Newer packaging cell lines which are efficient an safe for gene transfer have been described more recently (Bank et al., U.S. Pat. No. 5,278,056).

Other Viral Vectors. Other virus vectors may also be used, including recombinant adenovirus vectors (Horowitz, M. S., In: *Virology*, Fields, B. N. et al., eds, Raven Press, New York, 1990, p. 1679; Berkner, K. L., Biotechniques 6:616-629 (1988), Strauss, S. E., In: *The Adenoviruses*, Ginsberg, H. S., ed., Plenum Press, New York, 1984, chapter 11) or adeno-associated virus (AAV) (Ohi, S. et al., Gene 89:279-282 (1990); Dixit, M. et al., Gene 104:253-257 (1991); Samulski, R. J. et al., EMBO J. 10:3941 (1991)). Herpes simplex virus (HSV) is well-adapted for neuron-specific delivery (Geller, A. I. et al., Science 241:1667-1669 (1988)). Advantages of adenovirus vectors for human gene therapy include the fact that no human malignancies are known to be associated with such viruses, the adenovirus genome is double stranded DNA which can be manipulated to accept foreign genes of up to 7.5 kb in size, and live adenovirus is a safe human vaccine organisms.

Another vector useful in the present invention is vaccinia virus, which can be rendered non-replicating (U.S. Pat. Nos. 5,225,336; 5,204,243; 5,155,020; 4,769,330). Descriptions of recombinant vaccinia viruses containing heterologous DNA and its uses in immunization and gene therapy are reviewed in: Moss, B., Curr. Opin. Genet. Dev. (1993) 3:86-90; Moss, B. Biotechnology (1992) 20:345-362; Moss, B., Curr Top Microbiol Immunol (1992) 158:25-38; Moss, B., Science (1991) 252:1662-1667; Piccini, A et al., Adv. Virus Res. (1988) 34:43-64; Moss, B. et al., Gene Amplif Anal (1983) 3:201-213.

A nontoxic and efficient method has recently been reported based on the Sendai virus, also known as hemagglutinating virus of Japan (HVJ). HVJ-liposome-mediated gene transfer is performed Morishita R et al., Hypertension (1993) 21:894-89. Tomita N et al., Biochem Biophys Res Commun (1992) 186:129-34 developed a method in which plasmid DNA and high mobility group 1 protein (a nuclear protein) are co-encapsulated in liposomes and co-introduced into target cells by HVJ-mediated membrane fusion. This is a general method in which foreign genes and nuclear proteins are encapsulated into the same liposomes, which are then treated with inactivated HVJ. In this method, HVJ enables foreign genes to be introduced directly into the cytoplasm by membrane fusion and the nuclear proteins transport the foreign genes rapidly into the nuclei (Tomita N et al., Cancer Detect Prev (1994) 18:485-491; Tomita, N. et al., Circ Res (1993) 73:898-905).

Artificial Viral Envelopes. Based on the concept of viral mimicry, artificial viral envelopes (AVE) are designed based on the structure and composition of a viral membrane, such as HIV-1 or RSV and used to deliver genes into cells in vitro and in vivo. See, for example, U.S. Pat. No. 5,252,348, Schreier H. et al., J. Mol. Recognit., 1995, 8:59-62; Schreier H et al., J. Biol. Chem., 1994, 269:9090-9098; Schreier, H., Pharm. Acta Helv. 1994, 68:145-159; Chander, R et al. Life Sci., 1992, 50:481-489, which references are hereby incorporated by reference in their entirety. The envelope is preferably produced in a two-step dialysis procedure where the "naked" envelope is formed initially, followed by unidirectional insertion of the viral surface glycoprotein of interest. This process and the physical characteristics of the resulting AVE are described in detail by Chander et al., (supra).

Examples of AVE systems are (a) an AVE containing the HIV-1 surface glycoprotein gp160 (Chander et al., supra; Schreier et al., 1995, supra) or glycosyl phosphatidylinositol (GPI)-linked gp120 (Schreier et al., 1994, supra), respectively, and (b) an AVE containing the respiratory syncytial virus (RSV) attachment (G) and fusion (F) glycoproteins (Stecenko, A. A. et al., Pharm. Pharmacol. Lett. 1:127-129 (1992).

In short, vesicles are constructed which mimic the natural membranes of enveloped viruses in their ability to bind to and deliver materials to cells bearing corresponding surface receptors. The AVE systems described herein can be physically and chemically essentially identical to the natural virus yet is entirely "artificial", as it is constructed from phospholipids, choloesterol, and recombinant viral surface glycoproteins. Hence, there is no carry-over of viral genetic information and no danger of inadvertant viral infection. Construction of the AVEs in two independent steps allows for bulk production of the plain lipid envelopes which, in a separate second step, can then be marked with the desired viral glycoprotein, also allowing for the preparation of protein cocktail formulations if desired.

Non-Viral and Liposome Mediated Delivery. In addition to virus-mediated or bacterially-mediated gene transfer in vivo, physical means well-known in the art can be used for direct gene transfer, including administration of plasmid DNA (Wolff et al., 1990, supra) and particle-bombardment mediated gene transfer (Yang, N.-S., et al., Proc. Natl. Acad. Sci. USA 87:9568 (1990); Williams, R. S. et al., Proc. Natl. Acad. Sci. USA 88:2726 (1991); Zelenin, A. V. et al., FEBS Lett. 280:94 (1991); Zelenin, A. V. et al., FEBS Lett. 244:65 (1989); Johnston, S. A. et al., In Vitro Cell. Dev. Biol. 27:11 (1991)). Furthermore, electroporation, a well-known means to transfer genes into cell in vitro, can be used to transfer DNA molecules according to the present invention to tissues in vivo (Titomirov, A. V. et al., Biochim. Biophys. Acta 1088:131 (1991). In order to overcome therapy-limiting toxicity, antigenicity and lack of expression of transgenes in nonreplicating cells, non-viral vectors may be used. Such methods of gene transfer is also known as "carrier mediated gene transfer" (Wu, C. H. et al., J. Biol. Chem. 264:16985 (1989); Wu, G. Y. et al., J. Biol. Chem. 263:14621 (1988); Soriano, P. et al., Proc. Natl. Acad. Sci. USA 80:7128 (1983); Wang, C-Y. et al., Proc. Natl. Acad. Sci. USA 84:7851 (1982); Wilson, J. M. et al., J. Biol. Chem. 267:963 (1992)).

Introduction of naked DNA into secretory gland cells (e.g., liver, salivary gland, pancreas) by intraductal introduction has been described in U.S. Pat. Nos. 6,255,289; 6,225,290; 5,885,971; 5,837,693. Delivery of naked DNA to intestinal epithelial cells by oral administration has been described in U.S. Pat. Nos. 6,258,789; 6,004,944.

Cationic (ammonium derivatized) lipids also provide a means for delivery of DNA into a cell. These positively charged lipids form complexes with negatively charged DNA, resulting in DNA charged neutralization and compaction. The complexes endocytosed upon association with the cell membrane, and the DNA somehow escapes the endosome, gaining access to the cytoplasm. Cationic lipid:DNA complexes appear highly stable under normal conditions. Studies of the cationic lipid DOTAP suggest the complex dissociates when the inner layer of the cell membrane is destabilized and anionic lipids from the inner layer displace DNA from the cationic lipid. Several cationic lipids are available commercially. Two of these, DMRI and DC-cholesterol, have been used in human clinical trials. A synthetic cationic lipid of interest is N-[1-(2,3-dioleyloxy)propyl]-N,N,N-trimethylammonium chloride (DOTMA). A method employing cationic liposomes is useful for direct gene transfer in the therapy of cancer and other diseases as discussed by Farhood, H. et al., Ann N Y Acad Sci (1994) 716:23-35). The use of cationic liposomes may be combined with Adeno-associated (AAV)-based plasmids to introduce the vectors of the invention into cancer cells. (Vieweg, J et al. Cancer Res (1995) 55:2366-2372).

In another embodiment of this invention, nucleic acid is introduced into cells by using targeted liposomes (Nicolau, C. et al., Proc. Natl. Acad. Sci. USA 80:1068 (1983), Soriano et al., supra) such as immunoliposomes, which can incorporate acylated monoclonal antibodies into the lipid bilayer (Wang et al., supra). Polyclonal antibodies and mAbs specific for various types of tumors, viral antigens or cell surface markers of various normal cell types are well-known in the art. Thus, for example, an antibody specific for a class or subclass of lymphocytes, or for a particular T cell receptor variable region, can be used to target the DNA to a particular lymphocyte population in the treatment of autoimmunity. An antibody specific for a tumor associated antigen is used to target the therapeutic composition to cells of a tumor.

Proteoliposome delivery vesicles can be prepared by the protein-cochleate method. Self-assembling lipid-based complexes termed cochleate are used for in vivo DNA transfer (Gould-Fogerite, S. et al., 1985, Anal. Biochem. 148:15-25; Mannino, R. J. et al., 1988, Biotechniques 6:682-690; Papahadjopoulos, D. et al., Biochim. Biophys. Acta, 1975, 394: 483-491). Cochleates are prepared by calcium-induced fusion of phosphatidyl serine-cholesterol liposomes (anionic) resulting in an insoluble "jellyroll-like" structure. The layers of the jellyroll are composed of alternating sheets of negatively charged phospholipid and calcium. Gould-Fogerite, S. et al., Gene, 1989, 84:429-438, discloses a system in which proteins mediating the entry of enveloped viruses into cells are integrated in the lipid bilayer, and materials are encapsulated at high efficiency within the aqueous interior of these vesicles.

Also useful are polycations such as asialoglycoprotein/polylysine (Wu et al., 1989, supra) wherein the conjugate includes (a) a molecule recognizing the target tissue and (b) a DNA binding compound to bind to the DNA being transfected. Polylysine is an example of a DNA binding molecule which binds DNA without damaging it. This conjugate is then complexed with plasmid DNA using known methods for transfer. Polyvinyl-based polymer (PVP) formulations are also useful in transfer of DNA into a cell (Genetic Engineering News, Nov. 15, 1995, pg. 1). Cationic lipid/colipid delivery systems may also be used (see, e.g., Genetic Engineering News, Nov. 15, 1995, pg. 1).

Dendrimers, a macromolecular architecture, are also useful for gene transfection (Haensler, J. et al., Bioconjug. Chem. 4:372-379 (1993); Tomalia, D. A., Sci. Amer. 272:62-66 (1995); Bielinska, A. et al., J. Invest. Med. 43 (Suppl. 2):330A (1995); Kukowska-Latallo, J. et al., FASEB J. 9:A409 (1995); Bielinska, A. et al., FASEB J. 9:A312 (1995)).

In practicing the subject methods, in addition to the targeting construct, the integrase component (e.g., protein or nucleic acid encoding the same) of the subject systems is also introduced into the target cell, such that the integrase is present to mediate integration of the targeting construct into the target genome. Methods of introducing functional proteins into cells are well known in the art. Introduction of purified altered integrase protein or integrase-encoding RNA ensures a transient presence of the protein and its function, which is often a preferred embodiment. Alternatively, a gene encoding the integrase can be included in an expression vector used to transform the cell. It is generally preferred that the integrase be present for only such time as is necessary for insertion of the targeting construct into the genome being modified. Thus, the lack of permanence associated with most expression vectors, RNA, or protein is not expected to be detrimental. As described above, the integrase can also be introduced into a cell in the form of an RNA, which may be an mRNA. Introduction of integrase-encoding RNA ensures transient expression and removes the possibility that an integrase-encoding nucleic acid will become permanently incorporated into a target genome.

The integrase used in the practice of the present invention can be introduced into a target cell before, concurrently with, or after the introduction of a targeting vector. The integrase proteins can be directly introduced into a cell as a protein, for example, using liposomes, coated particles, or microinjection. Alternately, a polynucleotide encoding the integrase can be introduced into the cell using a suitable expression vector.

After the vector system components are introduced into the cell, the cell is maintained under conditions appropriate for site-specific integration to occur, as is known in the art, where representative conditions are provided in the experimental section, below.

Methods of Targeted Genomic Modification in Plants

As summarized above, the subject invention provides methods of making a targeted genomic modification in a plant cell. By "genomic modification" is meant a stable alteration of a plant cell's genomic DNA, e.g., a permanent change in a plant cell's chromosome. The term "genomic modification" encompasses changes in a target plant cell genome of varying size. The genome is, for example, the nuclear genome or the chloroplast genome. A feature of the subject invention is that the modification or change results from an integrative event, as described in greater detail below, where a nucleic acid is inserted into the genome to provide for the desired modification or change. As such, the subject methods are properly characterized being integrative targeted genomic modification methods. The size of the inserted nucleic acid may vary, being at least about 1 kb in length, usually at least about 5 kb in length and more usually at least about 10 kb in length, where the size of the inserted nucleic acid may be as long as 100 kb or longer. In many embodiments, the size of the inserted nucleic acid that results in the genomic modification ranges in length from about 1 kb to about 10 kb, usually from about 5 kb to about 8 kb. In some embodiments, however, an inserted nucleic acid may be as small as about 500 bp or 100 bp.

As indicated above, the subject methods rely on site-specific integration of a modifying nucleic acid into the genome of the target plant cell to achieve targeted genomic modification. Depending on the particular application in which the method is employed, the modifying nucleic acid may be an expression disruptive nucleic acid, e.g., as is employed in methods to reduce endogenous gene expression using "knock-out" strategy reviewed in greater detail below; and/or an expression modulating nucleic acid, e.g., as is employed in "modulating" or "silencing" applications reviewed in greater detail below. The modifying nucleic acid may be used to modulate exogenous or exogenous gene expression.

Where the modifying nucleic acid is an expression disruptive nucleic acid, it includes a sequence of nucleotides that, upon integration, disrupts expression of a particular gene or genes, i.e., it interferes or stops transcription of a genomic domain or translation of an mRNA. The modifying nucleic acid may include any convenient sequence of nucleotides that provides for the desired expression disruption, where such sequences may include random "stuffer" sequences, negative regulatory elements, termination codons, introns, untranslated regions, transcriptional termination regions, promoters and the like.

Where the modifying nucleic acid is an expression modulating nucleic acid, the modifying nucleic acid typically includes one or more of the following features: a promoter, promoter-enhancer sequences, one or more coding sequences, and the like. One or more of the above components may be presented on the vector as an expression cassette, which includes a nucleic acid encoding a product of interest operably linked to a promoter (as well as any other required sequences to provide for a functional expression cassette), which is also referred to herein as a "gene of interest." A "gene of interest" may be provided by the modifying nucleic acid, or may be domain in a genome of the target plant cell. Specific products of interest and their corresponding encoding sequences are described in greater detail infra.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins that regulate the activity of a given promoter. Viral promoters serve the same function as bacterial or eukaryotic promoters and either provide a specific RNA polymerase in trans (bacteriophage T7) or recruit cellular factors and RNA polymerase. Viral promoters may be preferred as they are generally particularly strong promoters.

Promoters may be, furthermore, constitutive, tissue specific, or regulatable. Inducible elements are DNA sequence elements which act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, AraC and gal promoters of *E. coli*, the α-amylase (Ulmanen, et al., J. Bacteriol. 162:176-182, 1985) and the sigma-28-specific promoters of *B. subtilis* (Gilman et al., Gene 32:11-20, 1984), the promoters of the bacteriophages of *Bacillus* (Gryczan, In: The Molecular Biology of the *Bacilli*, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microbiol. 1:277-282, 1987); Cenatiempo (Biochimie 68:505-516, 1986); and Gottesman (Ann. Rev. Genet. 18:415-442, 1984).

Examples of constitutive plant promoters which are useful for expressing exogenous or endogenous nucleic acids include: the cauliflower mosaic virus (CaMV) 35S promoter, which confers constitutive, high level expression in most plant tissues (see, e.g., Odel et al. (1985) Nature 3 13:8 10); the nopaline synthase promoter (An et al. (1988) Plant Physiol 88:547); the octopine synthase promoter (Fromm et al. (1989) Plant Cell 1: 977) and the like. A variety of plant gene promoters that regulate gene expression in response to environmental, hormonal, chemical, developmental signals, and in a tissue-active manner may be used for gene expression in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought light, pathogens, chemicals, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter (described in U.S. Pat. No. 5,773,697), fruit-specific promoters that are active during fruit ripening (such as the drul promoter (U.S. Pat. No. 5,783, 393), or the 2A11 promoter (U.S. Pat. No. 4,943,674) and the tomato polygalacturonase promoter (Bird et al. (1988) Plant Mol Biol 11:65-71), root-specific promoters, such as those disclosed in U.S. Pat. Nos. 5,618,988, 5,837,848 and 5,905, 186, pollen-active promoters such as PTA29, PTA26 and PTA13 (U.S. Pat. No. 5,792,929), promoters active in vascular tissue (Ringli and Keller (1998) Plant Mol Biol 37:977-988), flowers (Kaiser et al, (1995) Plant Mol Biol 28:231-243), pollen (Baerson et al. (1994) Plant Mol Biol 26:1947-1959), carpels (Ohl et al. (1990) Plant Cell 2:83 7-848), pollen and ovules (Baerson et al. (1993) Plant Mol Biol 22:255-267), auxin-inducible promoters (such as that described in van der Kop et al. (1999) Plant Mol Biol 39:979-990 or Baumann et al. (1999) Plant Cell 11:323-334), cytokinin-inducible promoter (Guevara-Garcia (1998) Plant Mol Biol 38:743-753), promoters responsive to gibberellin (Shi et al. (1998) Plant Mol Biol 38:1053-1060, Willmott et al. (1998) 38:817-825) and the like. Inducible promoters include the ecdysone-responsive promoter(s), tetracycline-responsive promoter, and the like. Additional promoters are those that elicit expression in response to heat (Ainley et al. (1993) Plant Mol Biol 22: 13-23), light (e.g., the pea rbcS-3A promoter, Kuhlemeier et al. (1989) Plant Cell 1:471, and the maize rbcS promoter, Schaffner and Sheen (1991) Plant Cell 3: 997); wounding (e.g., wunI, Siebertz et al. (1989) Plant Cell 1: 961); pathogens (such as the PR—I promoter described in Buchel et al. (1999) Plant Mol. Biol. 40:387 3 96, and the PDF 1.2 promoter described in Manners et al. (1998) Plant Mol. Biol. 3 8:1071-80), and chemicals such as methyl jasmonate or salicylic acid (Gatz et al. (1997) Plant Mol Biol 48: 89-108). In addition, the timing of the expression can be controlled by using promoters such as those acting at senescence (An and Amazon (1995) Science 270: 1986-1988); or late seed development (Odell et al. (1994) Plant Physiol 106: 447-458). Exemplary promoters for use in the present invention are selected such that they are functional in the cell type into which they are being introduced.

The DNA of the modifying nucleic acid employed in the subject methods can be obtained from sources in which it occurs in nature or can be produced, using genetic engineering techniques or synthetic processes.

The subject methods can be used to make targeted genomic modifications in a variety of target plant cells, where target cells in certain embodiments include cells from monocots and dicots and in particular cells from agriculturally important plant species, including, but not limited to, crops such as soybean, wheat, corn, potato, cotton, rice, oilseed rape (including canola), sunflower, alfalfa, sugarcane, castor and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose cells may be targetted include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassaya, turnip, radish, yarn, and sweet potato, *Arabidopsis*, beans, mint and other labiates.

Woody species, such as pine, poplar, yew, rubber, palm, eucalyptus etc. and lower plants such as mosses, ferns, and algae may also be targetted. A target cell may also be selected from various plant families including *Brassicaceae, Compositae, Euphorbiaceae, Leguminosae, Linaceae, Malvaceae, Umbilliferae* and *Graminae*.

In the methods of the subject invention, the targeting vector and integrase components of the subject systems are introduced into the target plant cell under conditions sufficient for the integrase to mediate integration of the targeting vector into the plant target cell, as reviewed above.

Methods of introducing exogenous nucleic acids into plant cells are well known in the art. By "transformed" it is meant an alteration in a cell resulting from the uptake of foreign nucleic acid, usually DNA. Use of the term "transformation" is not intended to limit introduction of the foreign nucleic acid to any particular method. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo). A targeting vector may be administered to the plant in a manner such that the targeting construct is able to enter the target cell(s), e.g., via an in vivo or ex vivo protocol. By "in vivo," it is meant in the target construct is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9: 957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). The principle methods for introduction of DNA into chloroplasts are biolistic bombardment, polyethylene glycol transformation of protoplasts and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. In the methods of the invention, any double stranded DNA vector may be used as a transformation vector, especially when the method of introduction does not utilize *Agrobacterium*.

In practicing the subject methods, in addition to the targeting construct, the integrase component (e.g., protein or nucleic acid encoding the same) of the subject systems is also introduced into the target cell, such that the integrase is present to mediate integration of the targeting construct into the target genome. Methods of introducing functional proteins into cells are well known in the art. Introduction of purified altered integrase protein or integrase-encoding RNA ensures a transient presence of the protein and its function, which is often a preferred embodiment. Alternatively, a gene encoding the integrase can be included in an expression vector used to transform the cell. It is generally preferred that the integrase be present for only such time as is necessary for insertion of the targeting construct into the genome being modified. Thus, the lack of permanence associated with most expression vectors, RNA, or protein is not expected to be detrimental. As described above, the integrase can also be introduced into a cell in the form of an RNA, which may be an mRNA. Introduction of integrase-encoding RNA ensures transient expression and removes the possibility that an integrase-encoding nucleic acid will become permanently incorporated into a target genome.

The integrase used in the practice of the present invention can be introduced into a target cell before, concurrently with, or after the introduction of a targeting vector. The integrase proteins can be directly introduced into a cell as a protein, for example, using liposomes, coated particles, whiskers, or microinjection. Alternately, a polynucleotide encoding the integrase can be introduced into the cell using a suitable expression vector. The integrase proteins may already be present in the cell, expressed from, e.g. nucleic acid that has been transferred into the cell through stable transformation.

The above described targeting/integration event results in the insertion of a modifying nucleic acid into the genome (chloroplast or nuclear) of the target plant cell in a manner that places the nucleic acid at a specific, pre-determined site in the genome. The modifying nucleic acid insertion may introduce a an expression modulating nucleic acid such as a promoter to modulate the expression of an endogenous gene. Alternatively the insertion may introduce an expression cassette to effect heterologous protein expression. The insertion may also result in an insertion of a disruptive nucleic acid into an endogenous gene, resulting in at least a decrease in the expression of the protein encoded by the gene. After the vector system components are introduced into the cell, the cell is maintained under conditions appropriate for site-specific integration to occur, as is known in the art, where representative conditions are provided in the experimental section, below.

Plant cells selected for the subject method can fall into four types or categories: 1) cells which do not, as obtained, make or contain the protein or product (such as a protein that is not normally expressed by the cell or a fusion protein not normally found in nature), 2) cells which make or contain the protein or product but in quantities other than that desired (such as, in quantities less than the physiologically normal lower level for the cell as it is obtained), 3) cells which make the protein or product at physiologically normal levels for the cell as it is obtained, but are to be augmented or enhanced in their content or production, and 4) cells in which it is desirable to change the pattern of regulation or induction of a gene encoding a protein.

The subject methods and systems, as described above, find use in a variety of applications. Applications of interest in which the subject methods and compositions find use as a novel method for transforming plants, in particular plants that are inefficient to transform using other methods, and in chloroplast transformation. The methods and compositions find further use in heterologous protein expression, and in controlling the regulation of expression of specific genes of interest in plants, including the production of plants that have "knock-out" mutations of genes of interest. The insertion of nucleic acid sequences at a specific site in a plant genome finds further use in reducing position and silencing effects and in reducing or eliminating unexpected effects caused by random integration of exogenous DNA.

Applications in which the subject vectors and methods find use include: transformation of plant nuclear and chloroplast genomes, heterologous protein expression, modulation of endogenous gene expression, and the production of "knock-out" plants. Each of these representative categories of applications is described separately below in greater detail.

Heterologous Protein Production

For heterologous protein production, the invention provides two strategies. The first strategy provides a modifying nucleic acid molecule comprising an attV site and an expression modulating nucleic acid such as a promoter operably linked to a gene of interest to form an expression cassette (FIG. 2). A selectable marker is usually contained within the modifying nucleic acid. Using the methods of the invention, the modifying nucleic acid is inserted at a specific site in the chloroplast or nuclear genome of a plant and the polypeptide encoded by the gene of interest is expressed in the plant cell. An alternative strategy provides a modifying nucleic acid molecule comprising an attV site and a gene of interest (FIG. 2). A selectable marker is usually contained within the modifying nucleic acid. Using methods of the invention, the expression cassette is inserted at a specific location in the chloroplast or nuclear genome of a plant in such a manner that the gene of interest becomes operably linked to an endogenous expression modulating nucleic acid. Once nucleic acid has been introduced into a plant cell, cells are maintained under conditions, as are known in the art, which result in expression of a polypeptide encoded by the gene of interest. Expression of the gene of interest is driven by sequences that are endogenous to the plant. The subject invention finds particular utility as a method for heterologous protein expression in chloroplasts (a type of plastid). The introduction of genes by engineering the chloroplast genome may reduce transgene dispersal into the wild plant population. As there are no plastids, and hence no plastid DNA in the pollen of most crops, any gene introduced into the chloroplast genome is unlikely to be transferred via pollen to the next generation. Plastid transformation has several additional advantages compared to nuclear transformation. First of all, the high ploidy level of the plastome 5-80 (*Chlamydomonas*) or 500-10,000 (*Nicotiana*) genome copies per cell enables a high degree of expression. Chloroplast genes are also expressed as cistrons, and thus several genes can be stacked in a single transformation event. In addition, gene silencing appears to be absent in plastids and therefore more likely to be stable. Thus, chloroplast may be very effective for heterologous protein expression.

Polypeptides made according to this method include industrial polypeptides such as endoglucanase, nitrile hydratase, peroxidase, xylanase, laccase, amylase, chitinase, glucose isomerase, collagenase, amylase, xylanase, cellulase, lipase, chymosin, rennin, various proteases, protease inhibitors and the like), polypeptides of interest to the cosmetic industry (such as collagen, keratin, various other proteins for use in formulation of cosmetics, and the like), polypeptides of use to the food industry (such as sweetener polypeptides e.g. thaumatin, and other flavor enhancing proteins), polypeptides that have adhesive properties and the like.

Polypeptides made according to this method also include proteins that can otherwise modify a plant's nutritional qualities. These include genes encoding polypeptides high in essential amino acids or amino acids that are limiting in diets, especially arginine, histidine, isoleucine, leucine, lysine, methionine, phenylalanine, threonine, tryptophan and valine. Proteins such as the high lysine 10 KDa zein from *Zea mays*, the 2S high methionine Brazil nut storage protein, polypeptides that alter the amino acid content of seeds such as those described in DeClercq et al., 1990 (Plant Physiol. 94:970-979), enzymes such as lauroyl-ACP thioesterase from *Umbellularia californica* that affect lipid composition (U.S. Pat. No. 5,298,421), synthetic or modified storage polypeptides such as peptides encoding poly-lysine or poly-phenylalanine or fusions of one or more coding regions high in essential amino acids may also be expressed.

Other proteins include phytase to improve the nutritional properties of seed for monogastric animals through the release of phosphate from stored phytate, the addition of chlorophyllase to reduce undesirable chlorophyll contamination of seed oils, especially canola oil and addition of enzymes to reduce anti-metabolites, pigments or toxins from seeds.

Polypeptides made according to this method also include therapeutic proteins, such as hGH, hEPO, insulin, hGM-CSF, hG-CSF, FSHβ, as interleukin-1β, α-interferon, antigens, such as viral coat proteins, microbial cell wall, toxin proteins or various other antigenic peptides, the anticoagulant hirudin, blood clotting factors and bactericidal peptides or antibodies, specifically a single-chain antibody comprising a translational fusion of the VH or VL chains of an immunoglobulin and the like. Other uses include the inclusion of fusion proteins that contain antigens or vaccines against disease. This application may be particularly relevant to improvements in health care of fish or other wildlife that are not readily assessable by conventional means, as modified plants can be converted directly into a convenient food source.

Polypeptides made according to this method can also provide resistance to herbicides (such as CP4 enolpyruvylshikimate-3-phosphate synthase), provide resistance to insects (such as endotoxins of *B. thuringiensis* or cowpea trypsin inhibitor (Hoffman et al., 1992, J. Economic Entomol. 85: 2516-1522)), bacterial or arachnid protein toxins (Gordon and Zlotkin, 1993, FEBS Lett., 315:125-128) and chitinase enzymes for the digestion of fungal cell walls (Broglie et al., 1991, Science 254: 5035, 1194-1197; Benhamou et al., 1993, Plant Journal 2:295-305; Dunsmuir et al., 1993, In Advances in molecular genetics of plant-microbe interactions, Vol 2. pp 567-571, Nester, E. W. and Verma, D. P. S. eds.). Further exemplary polypeptides include peptides such as magainin or secropin or a portion of an immunoglobulin specific for an agronomic pest, such as a fungal cell wall or membrane thus improving seed resistance to pre- and post-harvest spoilage, or any other protein that can improve a plant's traits.

Any polypeptide, such as an enzyme involved in biochemical pathways, a transcription factor, a signal transduction molecule such as a receptors or kinase, or a protein that can modify a plant's trait can be produced using this method.

As such, the subject methods find use in the synthesis of polypeptides, e.g. proteins of interest. In such applications, a vector that includes nucleic acid encoding a polypeptide of interest is introduced into the target cell that is to serve as an expression host for expression of the polypeptide. Following introduction and subsequent stable integration into the target cell genome, the targeted host cell is then maintained under conditions sufficient for expression of the gene that is operably linked to a expression modulating nucleic acid.

Modulation of Endogenous Gene Expression

The subject invention provides methods of modulating expression of a gene of interest in a genomic domain of a target plant cell. In the subject methods, a unidirectional site-specific integration system is employed to site-specifically integrate a an expression modulating nucleic acid, such as a promoter, into the genome of a target cell such that the expression modulating nucleic acid becomes operably linked to the gene of interest. The expression of a gene of interest is modulated by the introduced expression modulating nucleic acid. Using this method, transgenic plant cells can ectopically express, over-express, express at a desirable time, or otherwise alter the expression of a polypeptide encoded by an endogenous nucleic acid. Such cells may be used to improve a plant's trait, or express or repress a gene of interest. The transcriptional modulation element will preferably contain a constitutive, tissue specific, or inducible promoter.

Proteins made according to this method include any protein of a plant. Proteins of interest include transcription factors, which are identified by the presence of a region or domain of structural similarity or identity to a specific consensus sequence or the presence of a specific consensus DNA-binding site (see, for example, Riechmann et al., Science 290: 2105-2110 (2000; WO0215675). Plant transcription factors belong to a transcription factor family, such as the AP2 (APETALA2) domain transcription factor family (Riechmann and Meyerowitz (1998) Biol. Chem. 379:633-646); the MYB transcription factor family (Martin and Paz-Ares, (1997) Trends Genet. 13:67-73); the MADS domain transcription factor family (Riechmann and Meyerowitz (1997) Biol. Chem. 378:1079-1101); the WRKY protein family (Ishiguro and Nakamura (1994) Mol. Gen. Genet. 244:5 63-5 7 1); the zinc finger protein family (Klug and Schwabe (1995) FASEB J 9: 597-604); the homeobox (HB) protein family (Duboule (1994) Guidebook to the Homeobox Genes, Oxford University Press); the CAAT element binding proteins (Forsburg and Guarente (1989) Genes Dev. 3:1166-1178); the NAM protein family (Souer et al. (1996) Cell 85:159-170); the IAA/AUX proteins (Rouse et al. (1998) Science 279:13 71-13 73); the HLH/MYC protein family (Littlewood et al. (1994) Prot. Profile 1:639-709); the bZIP family of transcription factors (Foster et al. (1994) FASEB J 8:192 200); the scarecrow (SCR) family (Di Laurenzio et al. (1996) Cell 86:423-433); the polycomb (PCOMB) family (Kennison (1995) Annu. Rev. Genet. 29:289-3 03); the teosinte branched (TEO) family (Luo et al. (1996) Nature 3 83:794-799; the AB13 family (Giraudat et al. (1992) Plant Cell 4:1251-1261); the triple helix (TH) family (Dehesh et al. (1990) Science 250:1397-1399); the EIL family (Chao et al. (1997) Cell 89:1133-44); the YABBY family (Bowman et al. (1999) Development 126:23 87-96); the PAZ family (Bohmert et al. (1998) E J 17:170-80); the golden (GLD) family (Hall et al. (1998) Plant Cell 10:925-936), the TUBBY family (Boggin et al, (1999) Science 286:2119-2125); the ARF (auxin response factor) family (Ulmasov, et al. (1999) Proc. Nad. Acad. Sci. USA 96: 5844-5849); the Jumonji family, Balciunas et al (Trends Biochem Sci. (2000) 25: 274-276); the bZIP-NIN family (Schauser et al Nature. (1999) 402: 191-195) and the like.

As indicated by any part of the list above and as known in the art, transcription factors have been sometimes categorized by class, family, and sub-family according to their structural content and consensus DNA-binding site, for example. Many of the classes and many of the families and sub-families are listed here. However, the inclusion of one sub-family and not another, or the inclusion of one family and not another, does not mean that the invention does not encompass polynucleotides or polypeptides of a certain family or sub-family. The list provided here is merely an example of the types of transcription factors and the knowledge available concerning the consensus sequences and DNA-binding site motifs that help define them (each of the references noted above are specifically incorporated herein by reference).

Proteins made according to this method also include cytochrome P450s, kinases, leucine-rich repeat proteins, receptors, and enzymes involved or implicated in the biosynthesis of the following compounds: taxol, tocopherol, tocotrienol, sterols, phytosterols, vitamins, wax monomers, anti-oxidants (such as vitamins C and E), amino acids, lignins, cellulose, tannins, prenyl-lipids (such as chlorophylls and carotenoids), glucosinolates, terpenoids, phospholipids, amino acids, sugar, carbohydrates, hormones etc. Proteins made by the methods of the invention also include storage proteins, proteins involved in responses to biotic and abiotic stresses, including cold temperatures, freezing and disease, and the like. Any protein that causes a trait modification can be expressed using this method.

As such, the subject methods find use in the synthesis of polypeptides, e.g. proteins of interest. In such applications, a vector (FIG. 2) that includes an expression modulating nucleic acid is introduced into the target cell that is to serve as an expression host for expression of the polypeptide. Following introduction and subsequent stable integration into the target cell genome, the targeted host cell is then maintained under conditions sufficient for expression of the gene that is now operably linked to the newly integrated transcriptional modulatory unit.

Reduction of Endogenous Gene Expression

It is often desirable to reduce the expression of an endogenous gene for functional studies, or because the encoded protein is undesirable. A reduction of expression of an endogenous gene is particularly desirable in the manipulation of biochemical pathways, where one may wish to "turn off" an enzyme to force biochemical intermediates into different parts of a pathway to make alterative end-products. Methods for reducing gene expression can also be used in combination with methods for increasing gene expression or for heterologous protein expression. The subject invention provides several methods for reducing expression of a genomic domain in a target plant cell. The methods for reducing expression of a genomic domain are sub-divided into gene "silencing" and "knock-out" strategies.

Gene Silencing Strategies

Methods for gene silencing, including antisense, RNAi, ribozyme and cosuppression technologies are based in hybridization of an expressed exogenous nucleic acid with an RNA transcribed from an endogenous gene of interest in a plant cell. Because the methods are based on hybridization, the methods are particularly applicable to silencing of gene families that share a level of sequence identity, for example for families of genes that contain 60% or more, 70% or more, 80% or more, 90% or more or 95% or more sequence identity over 100, 200, or 500 or more nucleotides. RNA-induced silencing strategies for plants are reviewed in Matzke et al (Curr Opin Genet Dev. 2001 11:221-7). Such cells may be used to improve a plant's trait. The transcriptional modulation element will preferably contain a constitutive, tissue specific, or inducible promoter.

Antisense molecules are complementary to that of an RNA molecule normally transcribed by the cell. Binding of the antisense molecule to the endogenous target RNA can inhibit expression of the target in any of several ways, e.g., by preventing ribosome binding and thus interfering with translation. Antisense silencing of plant gene expression is a technology that well known in the art (van der Kroll Gene. 1988 72:45-50).

RNAi, otherwise known as double-stranded RNA interference (dsRNAi), has been extensively documented in the nematode *C. elegans* (Fire, A., et al, Nature, 391, 806-811, 1998) and an identical phenomenon occurs in plants, in which it is usually referred to as post-transcriptional gene silencing (PTGS) (Van Blokland, R., et al., Plant J., 6: 861-877, 1994; deCarvalho-Niebel, F., et al., Plant Cell, 7: 347-358, 1995; Jacobs, J. J. M. R. et al., Plant J., 12: 885-893, 1997; reviewed in Vaucheret, H., et al., Plant J., 16: 651-659, 1998). The phenomenon also occurs in fungi (Romano, N. and Masino, G., Mol. Microbiol., 6: 3343-3353, 1992, Cogoni, C., et al., EMBO J., 15: 3153-3163; Cogoni, C. and Masino, G., Nature, 399: 166-169, 1999), in which it is often referred to as "quelling". RNAi silencing can be induced many ways in plants, but preferably a nucleic acid encoding an RNA that forms a "hairpin" structure is most preferable. Alternative strategies include expressing RNA from each end of the encoding nucleic acid, making two RNA molecules that will hybridize. Current strategies for RNAi induced silencing in plants are reviewed by Carthew et al (Curr Opin Cell Biol. 2001 13:244-8).

Cosupression is induced by expression of an RNA molecule in the "sense" orientation and is well known in the art. The mechanisms of cosupression are not understood. The method is known to the skilled person and has been described, for example, in Jorgensen (Trends Biotechnol. 8 (1990), 340-344), Niebel et al. (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al. (Mol. Gen. Genet. 248 (1995), 311-317), de Borne et al. (Mol. Gen. Genet. 243 (1994), 613-621) and other sources.

Ribozymes are an RNA molecule that hybridizes to a complementary sequence in a substrate RNA and cleaves the substrate RNA in a sequence specific manner at a substrate cleavage site. Typically, a ribozyme contains a catalytic region flanked by two binding regions. The ribozyme binding regions hybridize to the substrate RNA, while the catalytic region cleaves the substrate RNA at a substrate cleavage site to yield a cleaved RNA product. The nucleotide sequence of the ribozyme binding regions may be completely complementary or partially complementary to the substrate RNA sequence with which the ribozyme binding regions hybridize. Complete complementarity is preferred in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. Ribozymes are further defined in U.S. Pat. Nos. 6,355,414 and 5,616,459.

For gene silencing, the invention provides three strategies. The first strategy provides an modifying nucleic acid containing an attV site and an expression modulating nucleic acid operably linked to an antisense RNA, a sense RNA, an RNAi molecule, or a ribozyme for a gene of interest (FIG. 2). Using the methods of the invention, the expression cassette is inserted at a specific site in the chloroplast or nuclear genome of a plant. Expression of the antisense RNA, sense RNA, RNAi molecule, or ribozyme is driven by the expression modulating nucleic acid, and the gene or genes whose products the expressed molecules bind to will be silenced. An alternative strategy provides an modifying nucleic acid containing an attV site and an antisense RNA, a sense RNA, an RNAi molecule, or a ribozyme for a gene of interest (FIG. 2). Using methods of the invention, the modifying nucleic acid is inserted at a specific location in the chloroplast or nuclear genome of a plant. Expression of the antisense RNA, a sense RNA, an RNAi molecule, or ribozyme is driven by sequences that are endogenous to the plant and the gene or genes whose products the expressed molecules bind to will be silenced. In an alternative strategy, an modifying nucleic acid is provided that contains a transcriptional modulation element that is designed for insertion downstream of a gene of interest in such a way that an antisense RNA molecule is expressed for the gene of interest, and the antisense RNA molecule interferes with the expression of the gene of interest (FIG. 2).

Any endogenous gene of a plant, as described above, can be silenced.

Gene Knock-Out Strategies

In the subject methods for reducing exogenous gene expression, a unidirectional site-specific integration system is employed to site-specifically integrate a modifying nucleic acid containing a disruptive nucleic acid (FIG. 2) into a gene of interest in the nuclear or chloroplast genome of a plant cell in a manner sufficient reduce the expression or activity of the polypeptide encoded by the gene of interest. Insertion can be into any part of the target gene, including an exon, intron, promoter or terminator in such a manner as to affect the rates of transcription, splicing, translation, RNA turnover of the gene. Plants that are homozygous or heterozygous for a gene knock-out may be tested for a particular phenotype, or used for other utilities.

A particular need for efficient gene knock-out strategies exists in many plant species for functional studies of a gene and for plant improvement. For example, in the genome of a model species, *Arabidopsis thaliana*, it is known that there are approximately 25,000 genes. The functions of the vast majority of the 25,000 genes is, as yet, unknown. One method for investigating the functions of a gene of interest is to reduce the expression of the gene of interest, either by gene silencing or gene knock-out strategies. Plants containing a gene with a reduced expression may be screened for a biological or molecular phenotype, and the function of the gene of interest may be obtained. A further need exists in crop species for methods of performing functional studies. In many cases, functional information is known for a particular gene of interest in a model species such as *Arabidopsis* but functional information for an orthologous gene of interest in a crop species is unavailable. Methods of the invention facilitate the functional studies of the orthologous crop species genes of interest. These methods are applicable for determining whether a gene of interest is a suitable target for an herbicide: if reduction of the expression of the gene of interest causes cell death, then a herbicide can be designed to inhibit the protein encoded by the gene of interest.

Gene knock-out strategies are likely to be more effective in reducing gene expression because the insertion point of an exogenous nucleic acid into a target endogenous gene can be pre-chosen, thus increasing the chances of having very little or no gene expression.

The expression of any gene encoding e.g. a transcription factor, cytochrome P450, kinase, enzyme etc, as described above or as is known in the art can be reduced. Of particular interest are genes encoding allergens such as pollen allergens: Lol p5 from rye grass, other pollen proteins from birch pollen, ragweed pollen, Parol (the major allergen of *Parietaria* oficinalis) and the cross-reactive allergen Paijl (from *Parietaria judaica*) and other atmospheric pollens from *Olea europaea, Artemisia* sp., *gramineae*, etc. Genes that encode other allergens are also of interest, including those of latex and nuts, in particular peanut. A further class of gene that is of particular interest the class that encode toxic molecules, such as ricin from castor bean, red kidney bean agglutinin and jack bean concanavalin A.

Biochemical pathways of a plant may also be manipulated by reducing expression of particular genes, for example desaturation of fatty acids (Miquel et al J Biol Chem 1992 267:1502-9; Arondel et al Science. 1992 258:1353-5), ethylene biosynthesis (Grierson Biochem Soc Symp. 1994 60:165-72), and carotenoid biosynthesis (Plant J. 2000 24:413-9). Modification of wood quality may be accomplished by reducing expression of genes involved in lignin biosynthesis or in the synthesis of cell wall polysaccharides. Of particular interest are genes involved in plant taste, for example genes involved in glucosinolate biosynthesis (Kroymann et al Plant Physiol. 2001 127:1077-88). Useful changes in plant growth and development may also be accomplished by reducing expression of genes encoding plant hormones or other growth regulating substances. For example, dwarf plants can be obtained by reducing synthesis of gibberellin or the ability of the plant to respond to giberellin. Alterations in fruit ripening or flower senescence may be obtained by reducing expression of genes involved in ethylene synthesis or the ability of the plant to respond to ethylene.

Transgenic Cells and Non-Human Transgenic Animals

Also provided by the subject invention are transgenic cells and non-human transgenic animals and plants. A feature of the subject cells, animals and plants that include the same is the presence of the subject targeting vector nucleic acid integrated into the cell's genome. Similarly, the transgenic animals and plants of the subject invention are characterized by including at least one transgenic cell, as described supra.

Plant Cells, Tissues, Plants and Products

Also provided by the subject invention are transformed plant cells, tissues, plants and products that contain the transformed plant cells. A feature of the subject transformed cells, and tissues and products that include the same is the presence of the subject targeting vector nucleic acid that includes a modifying nucleic acid integrated into its genome. Recombinant plant cells of the present invention are useful as populations of recombinant cells, or as a tissue, seed, whole plant, stem, fruit, leaf, root, flower, stem, tuber, grain, animal feed, a field of plants the like.

Kits

Also provided by the subject invention are kits for practicing the subject methods, as described above. The subject kits at least include one or more of, usually all of: a targeting vector and integrase component, as described above, where the integrase component can be provided in any suitable form (e.g., as a protein formulated for introduction into a target cell or in an integrase vector which provides for expression of the desired integrase following introduction into the target cell). In certain embodiments, the kits further include a vector that includes a genomic attachment site. Other optional components of the kit include: restriction enzymes, control plasmids; buffers; etc. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 4:
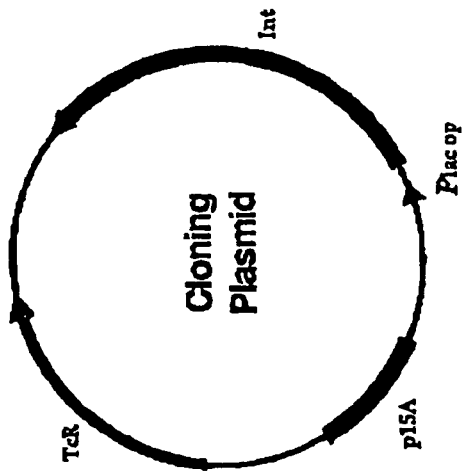
FIGS. 3 and 4 depict plasmids useful in screening for candidate mutant integrases useful in the invention.
Figure 3:
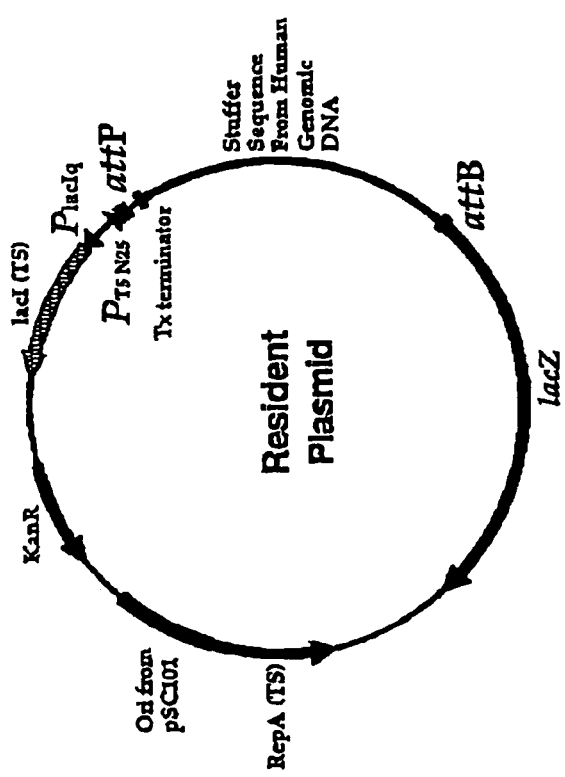

Production of Mutant Integrases and Thermally-Induced Screening Assay for Identifying Mutant Integrases That Faciltiate Site-Specific Recombination with a Desired Recognition Site Pair This assay uses two plasmids, called the resident plasmid (FIG. 3) and the cloning plasmid (FIG. 4). Construction of these plasmids was carried out as follows.

Resident plasmid. The temperature sensitive (TS) plasmid pTSK30 was used as the backbone for the final resident plasmid. pTSK30 (Phillips, G. J., Plasmid 41:78-81 (1999)) was cut with DrdI and SmaI to remove the lacZ alpha gene. The DrdI end was made blunt with T4 polymerase, gel isolated, and re-ligated to a compatible SmaI blunt end resulting in the plasmid pTSK1st. A special linker that provided unique recognition sites was placed into this vector. This linker sequence was CGCGtggtgc ttgcttagcg ctagcgcatg c (Linker 1; SEQ ID NO:106). The CGCG sequence shown in capitals (i.e., the first four nucleotides) is a M1uI overhang, whereas all other sequence represents double stranded DNA generated by complementary oligonucleotides. The pTSK1st plasmid was cut with Eco01091 and the ends made blunt with T4 polymerase so that it would be compatible with the blunt end of the linker. Once the Eco01091 end was made blunt, the plasmid was cut with M1uI. The linker was ligated into the vector to make pTSK2nd.

An additional linker (Linker 2) was then added to the pTSK2nd plasmid to make pTSK3rd. The pTSK2nd plasmid was cut with M1uI and B1pI to accept a customized linker in this position. The following complementary oligonucleotides were used to create Linker 2: CGCGtgacgtc aaaaccggtg cggccgcgaa ttccggtccg aaacctagga aactgcaggg cgcgccaaag c (SEQ ID NO:107), and TAAgctttgg cgcgccctgc agtttcctag gtttcggacc ggaattcgcg gccgcaccgg ttttgacgtc a (SEQ ID NO:108). This linker introduced further unique restriction enzyme recognition sites. Bases shown in uppercase (SEQ ID NO:107, first four nucleotides and SEQ ID NO:108 first three nucleotides) represent the overhangs of the linker duplex. pTSK4th was created by placing a PmeI recognition site into pTSK3rd. pTSK3rd was cut with FspI to provide a position for the following blunt-ended PmeI linker (Linker 3). Linker 3 was generated by annealing the oligonucleotides ggggtttaaacggg (SEQ ID NO:109) and cccgtttaaacccc (SEQ ID NO:110).

pTSK5th was made by introducing the phage T5 promoter into pTSK4th. The T5 promoter was created from oligonucleotides ctcataaaaa atttatttgc tttcaggaaa atttttctgt ataatagatt catαaatttg agagaggagt ta (SEQ ID NO:111; T5 oligo 1) and CCGGtaactc ctctctcaaa tttatgaatc tattatacag aaaaattttc ctgaaagcaa ataaattttt tatgagACGT (SEQ ID NO:112; T5 oligo 2). pTSK4th was cut with the restriction enzymes AatII and AgeI, providing sites for directional ligation of the T5 promoter. A "stuffer sequence" was then added to pTSK5th. The stuffer acted as a spacer between the two attachment sites and to help prevent transcription read-through. The stuffer sequence was taken from a modified Promega (Madison, Wis.) plasmid called pGL3-CMV. pGL3-CMV was made by placing a CMV promoter in the SmaI site within the pGL3-Basic Promega plasmid. A 1.4 kb ApoI fragment from pGL3-CMV was placed in the compatible EcoRI site of pTSK5th to make pTSK6th.

A transcription terminator sequence was added to pTSK6th in the RsrII and AvrII sites, resulting in pTSK7th. The transcription terminator was made by annealing the complimentary oligonucleotides GTCcgtggat ttgttcagaa cgctcggttg ccgccgggcg tttttattg gc (SEQ ID NO:113; transcription terminator oligo 1) and CTAGgccaat aaaaaacgcc cggcggcaac cgagcgttct gaacaaatcc acg (SEQ ID NO:114; transcription terminator oligo 2), resulting in the terminator duplex with RsrII and AvrII overhangs. The pTSK8th plasmid received the GFPuv reporter gene in the SphI and NheI sites, which was later replaced with the full-length lacZ gene to provide greater sensitivity.

A temperature-sensitive mutant of the lac repressor gene (lacI TS) was introduced into pTSK8th at the PmeI site. The lacI TS promoter and gene sequence was removed from the plasmid pNH40lacIqTS (Hasan, N., Szybalski, W., Gene 163: 35-40 (1995)) with EcoRI and made blunt to accommodate the PmeI ends on the pTSK8th vector which resulted in the plasmid pTSK9th. A 59 bp wild-type ΦC31 attP site (ggagtagtgc cccaactggg gtaacctTTG agttctctca gttgggggcg tagggtcgc, FIG. 17C, SEQ ID NO:115, the TTG core is in upper case) was placed into pTSK9th's unique NotI restriction site resulting in the plasmid pTSK9th(attP-NotI). The GFPuv gene in this plasmid was replaced by the full-length lacZ gene to give p10th(attP-NotI).

To enhance the expression of lacZ, a Shine-Delgarno and Kozac sequence were introduced by PCR upstream of the ATG translation starting position. The lacZ PCR primers also introduced restriction enzyme sites NheI and SphI so that the lacZ fragment could conveniently replace the GFPuv gene found in the previous generation plasmid. The ΦC31 attB site was added into the unique AscI site of p10th(attP-NotI) to give the plasmid p11th-PB. An attB site was made from the following oligonucleotides CGCGcctgcg ggtgccaggg cgtgcccttg ggctcccgg gcgcgtactc cgg (SEQ ID NO:116; attB oligo 1) and CGCGccggag tacgcgcccg gggagcccaa gggcacgccc tggcacccgc agg (SEQ ID NO:117; attB oligo 2).

The stuffer sequence in this plasmid was then replaced with a sequence that would better reduce the amount of lacZ background. In order to perform the sequence replacement, the original stuffer sequence was removed. FseI and RsrII were used to remove most of this sequence, while making the remaining PstI site unique to this vector. The ends were made blunt by T4 polymerase and religated to give the plasmid pAPB. The primers CGTTGGGACC CGTTTCCGTG (SEQ ID NO:118; primer 1) and AGAGACGAGG AGAGGGGAGC (SEQ ID NO:119; primer 2) were used to perform PCR from human genomic DNA. A PCR using this primer set produced a 2.3 kb GC-rich fragment from an intron of the human FGFR3 gene. Immediately internal to these primers are PstI sites. The PCR product was cut with PstI and ligated into the unique PstI site present in pΔPB, resulting in the plasmid pPB(+)stuffer(+). Only one orientation of this stuffer sequence was able to prevent background expression.

A similar version of this plasmid was made by replacing the wild-type attP with the pseudo-site A (ΨA) sequence from the human genome (FIG. 19; SEQ ID NO:120). The ΨA was isolated from the human genome by PCR using the primers ATTTGTAGAA CTATTATGGG (SEQ ID NO:121; psiA primer 1) and AAGTCTTCTG GCTATACAGG (SEQ ID NO:122; psiA primer 2). The approximately 470-bp ΨA was then cloned into pCR2.1 topo (Invitrogen). The ΨA site was removed with XbaI and SpeI and cloned into the SpeI site of pBC-PB (Groth, et al., Proc. Natl. Acad. Sci. 97:5995-6000 (2000)), resulting in the plasmid pBC-psEco1-B (+). The EcoRI fragment containing ΨA from this plasmid was removed and made blunt with T4 polymerase. To remove the wild-type attP site from the pPB(+)stuffer(+) plasmid so that it could be replaced with ΨA, the plasmid was cut with SacII and AvrII and made blunt. The blunted ΨA-EcoRI fragment was ligated into this position resulting in the plasmid pRES-psA.

Cloning plasmid. The pINT plasmid (Groth, et al., Proc. Natl. Acad. Sci. 97:5995-6000 (2000)) was modified for use in this assay. To first make the vector tetracycline resistant (TcR), pINT was cut with DraIII and PflMI and made blunt with T4 polymerase. This step provided a position for the TcR gene and also removed the kanamycin resistance (KanR) gene from the pINT vector. From pBR322, the TcR gene was removed with EcoRI and PflMI, made blunt, and used to replace the KanR gene, resulting in the plasmid pINT-Tc 2nd(+). A plasmid called pREC was created from pINT-Tc 2nd(+) by placing in a linker in place of the integrase gene. The pINT-Tc 2nd(+) plasmid was cut with BstEII and SpeI, which removed the integrase gene. A linker (Linker 4) created with the oligonucleotides GTCACgctcgagagatctga (SEQ ID NO:123; linker 4, first oligo) and CTAGtcagatctctcgagc (SEQ ID NO:124; liner 4, second oligo) was placed into these sites, which introduced unique restriction enzyme sites to the plasmid (BglII and XhoI).

A mutant integrase library could now be moved in and out of the vector without disrupting the plasmid, because unique sites flank the integrase gene. The wild-type ΦC31 integrase gene was re-introduced into the pREC plasmid to generate the pINT-CRS plasmid. This step was done by removing integrase from the pINT-Tc 2nd(+) plasmid with BamHI and SpeI. The pREC plasmid was cut with BglII and SpeI to accept the integrase gene in this position. The ligation reaction was possible because BglII and BamHI ends are compatible with each other. XhoI and SpeI sites are unique to the pINT-CRS vector and can be used to shuttle an integrase library to and from the vector.

Performing the Assay.

The resident and cloning plasmids described above were used in an assay system developed for identifying evolved, improved integrases. The screen allows the isolation of altered recombinases (e.g., integrases) that now show improved recombination efficiency towards wild-type or pseudo-att site sequences. The efficiency of an improved integrase for recombining any pair of att sites can be determined in this assay and is measured by screening for colonies that produce more lacZ gene product, the enzyme β-galactosidase. The resident plasmid only expresses β-galactosidase after an integrase-mediated intramolecular integration event has occurred. Without this recombination event, the resident plasmid is configured with a "stuffer sequence" containing transcription termination signals separating the att sites. Directly upstream of the attachment site sequences resides a strong bacterial promoter. Downstream of the att sites and stuffer sequence is the lacZ gene. In the event of recombination, the stuffer sequence is removed and the promoter mediates the transcription of lacZ, producing β-galactosidase. β-galactosidase production can be conveniently detected by growing bacteria on plates containing the indicator dye X-gal (Miller, J. H., Experiments in Molecular Genetics, 1972).

To perform the assay, bacteria carrying the resident plasmid were made competent for transformation. The resident plasmid was kanamycin resistant (KanR) and used a variant of the pSC101 backbone for replication. In this variant, the pSC101 backbone had a mutation in the RepA gene rendering it temperature sensitive. The resident plasmid also carried the att sites of choice (in this example, attB, FIG. 17B, and ΨA FIG. 19), lacZ, and a temperature sensitive lacI gene. Bacteria carrying this plasmid grew normally at 30° C., but did not grow at 42° C. because of the TS mutant RepA. Similarly, the TS lacI produced lac repressor that was fully functional at 30° C., but inactive at 42° C. Both of the TS components act in an intermediate temperature sensitive manner at intermediate temperatures. For example, bacteria carrying the TS plasmid did not cease to grow at 37° C., but the amount of growth was significantly reduced. In the same manner, the TS lac repressor was not completely inactive at 37° C., but it was not stable enough to cause complete repression of the lac promoter/operator. Because the ΦC31 integrase loses stability at higher temperatures, 37° C. was used as the induction temperature; however, it is possible to screen for integrase mutants that perform well at 42° C.

The second plasmid (the cloning plasmid) used in this system carried the modified candidate integrase library. This cloning plasmid was tetracycline resistant (TcR) and contained the p15A origin of replication. Both plasmids of the system had compatible origins and therefore can be propagated together in the same bacterial cell. To complete the cloning plasmid, a modified integrase library was ligated into the unique XhoI and SpeI restriction sites that were positioned immediately downstream of the lac promoter/operator. The cloning plasmid carrying the modified integrase library was then transformed into bacteria carrying the resident plasmid.

The modification of the integrase gene was performed using an exemplary applicable method for generating modified integrases, in this case the "shuffling" technique, which was performed in manner similar to published protocols (Stemmer, W. P. C., Proc. Natl. Acad. Sci. USA 91, 10747-10751 (1994); Stemmer, W. P. C., Nature 370, 389-391 (1994)). Briefly, the ΦC31 integrase gene (the coding region DNA sequence is presented as SEQ ID NO:125, FIG. 6) was copied from the pINT-CRS vector by PCR with the primers CTAAAGGGAA CAAAAGCTGGA G (SEQ ID NO:126; phiC31 primer 1) and TGATATGGGG CAAATGGTGGT C (SEQ ID NO:127; phiC31 primer 2). These primers lie directly adjacent to the unique XhoI and SpeI restriction sites, which were used to clone the modified integrase library back into the vector. Five micrograms of integrase gene were treated with 2.4 U of DNAse for 25 minutes at room temperature. Fragments of the integrase gene were run out on a 1.6% NuSieve gel in 1×TAE. Fragments in the range of approximately 50 bp-250 bp long were cut out of the gel. DNA fragments were removed from the low-melt gel with beta-agarase. Forty-five cycles of primer-less extensions were performed as described (Stemmer, W. P. C., Proc. Natl. Acad. Sci. USA 91, 10747-10751 (1994); Stemmer, W. P. C., Nature 370, 389-391 (1994)).

To amplify the modified integrase library, a portion of the primer-less reaction was added to the primers shown above, and further PCR was performed. A portion of the resulting PCR product was analyzed by gel electrophoresis. The expected size of 1.9 kb was obtained, although minor additional bands were observed. To increase the likelihood of creating a library carrying only the full-length modified integrase gene and not truncated products from inefficient PCR, gel isolation of the final product was performed. The integrase gene library was cut with the restriction enzymes XhoI and SpeI and ligated into the source cloning vector devoid of the integrase gene. Ligation reactions used to produce the plasmid library were cleaned with MinElute Qiagen columms (Qiagen, Valencia, Calif.) and transformed into electro-competent DH10B bacteria (Life Technologies) carrying the resident plasmid pRES-ΨA described above, which bears the wild type attB site and the ΨA pseudo attP site derived from the human genome (FIG. 19).

After transformation, cells were allowed to recover in medium for 1 hour and 20 minutes at 30° C. Expression of the integrase was repressed upon transformation because of the high levels of the lac repressor expressed from the resident plasmid. Because the integrase gene was under the control of the lac promoter/operator, it was under continuous repression unless activated by an elevated temperature. As long as the cells were maintained at 30° C., integrase expression remained turned off, both cloning and resident plasmids replicated, and the bacteria grew normally. Transformants were grown on agar plates containing tetracycline, kanamycin, and X-gal. The transformation was plated to give ≦150 colonies per 100-mm plate to allow for optimal growth and screening.

Colonies were permitted to grow at 30° C. for 26-33 hours to produce large colonies. Plates were then moved to 37° C. for an induction period. During this time, the TS lac repressor became less active, allowing the expression of integrase. In addition, colony growth was slowed due to the TS replication mutant on the resident plasmid. Since the bacteria were under double antibiotic selection, only those cells carrying both plasmids survived. Depending on the activity of the integrase towards the att sites on the resident plasmid, different amounts of time at 37° C. were required to assay for an improved integrase.

Exemplary Results of the Assay

The screening assay and vectors described above were used to find evolved ΦC31 integrase genes that mediated more efficient recombination between attB and the ΨA pseudo attP sequence derived from the human genome. The ΦC31 integrase gene was subjected to one round of DNA modification as described above, and the resulting "shuffled" set of fragments was ligated into the cloning plasmid. The plasmid library of the resulting modified integrases was transformed into DH10B bacteria carrying pRES-psA (the resident plasmid, described above) and the screening assay was performed.

Transformant colonies were grown on plates at 30° C. until moderately large colonies were obtained. The plates were then moved to 37° C. for 24 hours to inactivate the TS lacI, allowing expression of the integrase gene encoded by the cloning plasmid. Mutant integrases capable of efficiently recombining the test att sites excise the stuffer sequence and allow transcription of lacZ on the resident plasmid. Plates were then moved to room temperature overnight. This period allowed time for β-galactosidase to cleave the X-gal substrate in the plates, necessary to generate blue color in the colonies. Colonies were then scored by eye for increased blueness. Several bluer colonies were obtained from screening approximately 1,000 colonies. Plasmid DNAs from three such colonies, designated mutants 1C1, 5C1, and 7C1, were purified and used for DNA sequence and functional analysis. The mutants were assigned numbers followed by "C1," indicating that the mutants were obtained from a library that underwent one cycle of "shuffling."

Following the above procedures using the ΦC31 recombinase (parent, wild-type DNA sequence presented as SEQ ID NO:125, FIG. 6; parent, wild-type protein sequence presented as SEQ ID NO:128, FIGS. 5A and 5B) three altered recombinases were identified 1C1, 5C1, and 7C1. An alignment of the protein sequences of the wild-type and altered recombinases is presented in FIGS. 5A and 5B. In FIGS. 5A and 5B, the protein sequence for altered recombinase 7C1 (SEQ ID NO:129), wild-type recombinase ΦC31 (SEQ ID NO:128), altered recombinase 5C1 (SEQ ID NO:130), and altered recombinase 1C1 (SEQ ID NO:131), are presented relative to a consensus sequence (SEQ ID NO:132). The asterisk at the ends of the sequences in FIGS. 5A and 5B represents a stop codon. FIG. 7 (SEQ ID NO:129) and FIG. 8 (SEQ ID NO:133) present, respectively, the peptide and DNA sequences of altered recombinase $7C_1$. FIG. 9 (SEQ ID NO:130) and FIG. 10 (SEQ ID NO:134) present, respectively, the peptide and DNA sequences of altered recombinase $5C_1$. FIG. 11 (SEQ ID NO:131) and FIG. 12 (SEQ ID NO:135) present, respectively, the peptide and DNA sequences of altered recombinase 1C1.

As discussed above, these altered recombinases may be used in further rounds of screening using the methods of the present invention.

The following provides a summary of the DNA sequence changes present in each of the mutant integrases (i.e., altered recombinases) relative to the wild-type sequence:

| 1C1 mutant: | |
|---|---|
| 225 bp (G->A) | silent |
| 511 bp (T->C) | silent |
| 1135 bp (G->A) | (aa379) Valine[V] -> Isoleucine[I] |
| 1509 bp (A->G) | silent |
| 1707 bp (C->T) | silent |
| 1810 bp (C deletion) | Created the new reading frame: (605)Arg-(606)Thr-(607)Ala-(608)Arg-(609)Lys-(610)Thr-* {Versus the wild-type sequence: (605)Gln-(606)Asp-(607)Gly-(608)Thr-(609)Gln-(610)Asp-(611)Val-(612)Ala-(613)Ala-*} |

| 5C1 mutant: | |
|---|---|
| 171 bp (G->A) | silent |
| 736 bp (G->A) | (aa246) Alanine[A] ->Threonine[T] |
| 1109 bp (A->G) | (aa370) Aspartic acid[D]-> Glycine[G] |
| 1788 bp (G->A) | silent |

| 7C1 mutant: | |
|---|---|
| 882 bp (T->C) | silent |
| 1678 bp (G->A) | (aa560) Valine[V] ->Methionine[M] |
| 1825 bp (G->C) | (aa609) Glutamic acid[E]-> Glutamine[Q] |

To roughly quantify the relative improvements in substrate recognition for the mutant integrases, they were individually tested in a time course assay. The plasmids pREC, pINT-CRS, p1C1, p5C1, and p7C1 were transformed into the DH10b strain carrying the resident plasmid pRES-psA and grown for 33 hours at 30° C. Plasmids pREC and pINT-CRS were controls, constituting the cloning plasmid either not carrying an integrase gene or carrying the wild-type phiC31 integrase gene, respectively. The three mutants, 1C1, 5C1, and 7C1, were also carried in the cloning plasmid. After the colonies were fully grown, plates were placed 37° C. to reduce the activity of the temperature sensitive proteins. As a non-induced control, one plate per group was not subjected to the higher temperature and was incubated at room temperature throughout the course of the experiment. Colonies were scored for blueness without temperature induction of integrase expression at 37° C. and again after periods of 37° C. incubation ranging between 16 and 39 hours. At the time of analysis, colonies were scored as being blue if they contained at least small areas of blue color.

The results of this time course analysis were as follows. The pREC control failed to give blue colonies at any of the time points, as expected, because this plasmid does not contain an integrase gene. pINT-CRS, carrying the wild-type integrase, produced low levels of recombination, reflected by the presence of blue in some of the colonies. With 16-39 hours of induction at 37° C., 10-30% of the pINT-CRS colonies contained some blue areas. Although longer induction times resulted in a higher percentage of colonies with blue areas, the amount of blue per colony was small and was relatively similar between the time points. By comparison, the 1C1 mutant generated blue areas in nearly 100% of the colonies with a 16 hour incubation at 37° C. For this mutant, increasing the amount of time at 37° C. did not increase the number of blue colonies, but did increase the amount of blue present within the colonies. The areas of blue present within colonies steadily increased with increased induction time at 37° C. The 5C1 mutant integrase performed slightly less efficiently compared to the 1C1 mutant. With 16 hours at 37° C., approximately 70% of the colonies contained areas of blue, reaching 100% with 24 hours of induction. Ratios of blue to white colonies increased with induction times, as did the amount of blue within a colony. The 7C1 mutant performed similarly to the wild-type integrase. This mutant was apparently not significantly improved over the wild type, but was a variant that looked bluer on the original screening plate. This result is possible, because the wild-type integrase has a residual level of activity towards ΨA. Picking mutants like 7C1 can be avoided by reducing the induction time, thereby creating a more stringent screen for improved genes.

These results demonstrate the ability of the method of the present invention to produce evolved recombinases starting with parent recombinase (e.g., ΦC31 integrase). Such altered recombinases can be selected that mediated more efficient recombination between, for example, attB and a genomic site in a target organism (e.g., the ΨA pseudo attP sequence derived from the human genome). The nucleic acid coding sequences of such altered recombinases typically differ from the coding sequences of their parent recombinase(s) by at least one base pair, typically giving rise to at least one amino acid difference in the polypeptide coding sequences of the altered recombinases relative to the parent. Further, coding sequence variations identified in different altered recombinases may be combined into a coding sequence for a single altered recombinase. Candidate plasmids from the shuffling procedure described above may be subjected to a second round of shuffling. Although it is an optional procedure, two rounds of shuffling were performed. Plasmid pINT-T plasmid DNAs were purified from the best 12 candidates from cycle 1 and mixed together in equal proportion and subjected to DNA shuffling to produce cycle 2. In this way, the distinct mutations present in the cycle 1 mutants could be mixed in a combinatorial way to produce new configurations in which favorable features could be combined to produce integrases with additional benefits. Because the cycle 1 mutants all gave evidence of blue color after 24 hours of induction at 37° C., to increase the stringency of the cycle 2 assay, the induction period was reduced to 6 hours. None of the cycle 1 mutations showed more than a pale degree of blueness at this time point, so appearance of deep blue colonies at 6 hours would indicate a further gain in integration efficiency.

The cycle 2 library was transformed into E. coli, and from a screen of ~10,000 colonies, we obtained 11 candidates that produced blue colonies after 6 hours of integrase induction. Based on the amount of blue color present, 1C2, 2C2, and 11C2 appeared to be the most efficient integrases. The mutant integrases were retested and the DNA of pRES-ψA from blue colonies was examined by restriction mapping and DNA sequencing. Again, the attR recombination junction was found to be perfect to the base in each case, indicating that the mutant integrases mediated a precise recombination reaction, had not become promiscuous, and appeared to have an elevated ability to perform intramolecular integration between attB and ψA.

The complete DNA sequences of two of the best cycle 2 integrases were determined and are reported schematically in FIG. 14 (1C2) and 16 (11C2). We found evidence that efficient DNA shuffling had occurred, because many of the mutations present in the cycle 2 mutants had already been seen in cycle 1 and were now present in new combinations. Since not all of the cycle 1 mutants were sequenced, we could not determine whether new mutations appeared in cycle 2. The Gln to Pro mutation at amino acid 134, derived from 17C1, appeared in all four cycle 2 mutants analyzed at the sequence level. A single base deletion distinct from the one in 1C1 was present in 11C2 and caused a different frameshift that changed the amino acid sequence of the carboxy terminus of the protein. Polypeptide sequence for 1C2 and 11C2 are shown in FIGS. 13 and 15 respectively.

Example 2

Assaying Altered Integrases in Mammalian Cells

The screening assay for improved integrases was performed in E. coli. The altered integrases emerging from this screen can be tested in other species to determine if the desirable properties detected in bacteria are retained. The wild-type ΦC31 integrase and the 1C1 integrase mutants described in Example 1 were compared to each other in mammalian tissue culture cells for their ability to mediate the integration of a plasmid carrying the attB recognition site (FIG. 17B; SEQ ID NO:136) and the neomycin resistance gene into human chromosomes. Efficiencies of the integrases were determined by evaluating the number of neomycin resistant colonies formed after G418 selection.

The 293 human embryonic kidney cell line was used for these experiments (Graham, F. L., et al., J. Gen. Virol. 36, 59-72 (1977)). Cells were grown to 50-80% confluency in 60-mm-diameter dishes and transfected with 50 ng of the donor attB neo plasmid pNC-attB and 5 µg of pCMVInt (Groth, A. C., et al., Proc. Natl. Acad. Sci. USA 97, 5995-6000 (2000)), pCMV-1C1, or pCMVSPORTβGal (Life Technologies, Gaithersburg Md.) by using Lipofectamine (Life Technologies). pNC-attB was a plasmid comprising (in the following order) a CMV promoter, the ΦC31 attB sequence (FIG. 17B, SEQ ID NO:136), sequences coding a neomycin resistance gene, and sequence coding a green florescence protein gene. pCMV-1C1 is identical to pCMVInt, except in place of the wild-type ΦC31 integrase gene, it carries the 1C1 mutant integrase under the control of the CMV promoter. The pCMVSPORTβGal negative control plasmid has no integrase gene. Twenty-four hours after transfection, the cells were transferred onto 100-mm-diameter dishes and grown for an additional 24 hours before medium was replaced with medium containing Geneticin at 350 µg/ml (G418, a neomycin analog; Life Technologies). Typically, 5 µg of DNA was near the upper limit for transfection of 60-mm-diameter dishes of 293 cells without appreciable toxicity.

Selection was continued for 14 days, then individual neomycin resistant colonies were counted. When pCMVSPORT-βGal, which lacks an integrase gene, was co-transfected with pNC-attB, some neomycin resistant colonies were obtained and were considered the background due to random integration. Co-transfections of pNC-attB with pCMVInt and pCMV-1C1 both resulted in increases in colony numbers above background of more than 10-fold. This experiment was repeated twice with similar results.

Human 293 cells were also transfected with plasmids carrying the 1C2 and 11C2 mutant integrases. Quantitative PCR data (Sclimenti et al., 2001 Nucleic Acids Res. 2001 29:5044-51.) showed that the 1C2 and 11C2 integrases directed an 2 to 3-fold increased absolute frequency of integration at the target site, and a 5 to 6-fold increase in the specificity of integration over mutant enzymes produced by a single round of shuffling.

These results demonstrate that the altered 1C1, 1C2 and 11C2 integrases mutant functions well in mammalian cells to facilitate site-specific recombination. The mutant integrase mediates efficient integration into the genome, performing genomic modification at a similar or higher frequency than the wild-type integrase. Integration specific for the ΨA site was demonstrated by analyzing individual neomycin resistant colonies by PCR. For this assay a primer specific for the integration junction between the donor pNC-attB plasmid and the human genomic DNA in the vicinity of ΨA was used.

Example 3

Methods to Identify Genome Attachment Sites and Knock Out the Human LDH-A Gene

Identification of genomic pseudo sites It is often useful to be able to choose a genomic site where integration is desired and to engineer an integrase to mediate integration at that site, even when the enzyme had no prior history of affinity for that location. In many applications, even though site-specific integration is required, integration anywhere within a region of 1 or more kb will produce the desired result.

Two general approaches can be applied to find pseudo att site sequences. The first is to introduce the target segments of DNA into the bacterial assay system for directed evolution (Sclimenti et al., 2001 Nucleic Acids Res. 2001 29:5044-51)

and let the mutated integrase library choose a pseudo site. The other approach focuses on predicting with the computer where a potential pseudo site is located within the region of interest, allowing the screen to focus on a smaller region of DNA. Such a strategy is described in the following example, in which pseudo attP sites were found in a genomic region where integration would result in knock-out of the human gene for lactate dehydrogenase A (LDH-A).

To avoid being restricted to working with pseudo sites that share substantial sequence identity to the 39-bp minimal wild-type attP site (Groth et al., 2000 Proc. Natl. Acad. Sci. USA 97, 5995-6000) or to functional native pseudo attP sites, smaller sequence patterns comprising just 7-10 bps were derived that represent a minimal framework or consensus for functional pseudo attP sites. An analysis of more than a dozen functional pseudo attP sites for the ΦC31 integrase (Thyagarajan et al., 2001 Molecular and Cellular Biology 21, 3926-3934) was carried out by using the Motif Search software (GCG Wisconsin Package, Accelrys).

Although there was a great deal of sequence divergence between the pseudo sites, there were approximately 7 positions that were more conserved relative to other positions. A suggestion that emerged from this finding was that an integrase binds to the framework base pairs more strongly than to the others and recognizes a framework subset of base pairs within the pseudo site. An interesting feature of the alignment was that the regions where the cross-over occurred (the 3-bp core sequences) overlapped in the different pseudo sites. Since the core sequences overlapped, while preserving the framework pattern, such a pattern could represent a template that can be used to search for the minimal sequence requirements needed to engineer an integrase toward a small target sequence.

The framework pattern found, Pattern 5, was CNNNGNNNNNCNTTNNNNNNNCNNNG (SEQ ID NO:137), where N is any nucleotide. Bases were included as part of the framework if at least 70% (9/13) of them were the same for a particular position of the alignment, with two exceptions. The first exception was the core sequence defined in the pattern as a TT. The alignment indicated that the second T of the TT-core was not present in 70% of the pseudo sites. Because the wild-type integrase reaction carries out recombination utilizing the TT as the cross-over sequence in bacteria and in a cell-free system (Thorpe and Smith, 1998 Proc. Natl. Acad. Sci. USA 95, 5505-5510), it was considered to be an important base pair and was included as part of Pattern 5. The other exception involved the exclusion of a base pair based on similar logic. In one position of the consensus, a cytosine was common to 85% of the sites. This position was not included in the framework because it was absent in the wild-type sequence, indicating that it is not necessary and could be excluded for the purpose of understanding a minimal attP site.

A different framework, Pattern F, was derived by comparing three attP sites that are known to function well in mammalian cells: the wild-type attP, human pseudo site A (HpsA), and mouse pseudo-site L1 (MpsL1). The resulting framework (Pattern F) is CNNGGNTNNCCNNTNNNNNCNCNNNG (SEQ ID NO:138), where N is any nucleotide. With the exception of the first "T" in the TT-core, Pattern F partially overlaps with the bases defined in Pattern 5 when superimposed.

In order to find potential pseudo attP sites within the desired gene, sequence searches were performed to look for two general features. The first was overall sequence identity with the wild-type attP site. Programs such as BestFit were used to locate sequences within the region of interest that have the highest degree of overall identity to wild-type attP. Sequences having highest degree of identity were desirable. However, since it was easier to find a sequence containing the minimal elements of the attP site, the framework patterns representing the most important base pairs were used as search tools to locate potential pseudo sites more readily. This approach is especially useful in cases where the chromosomal target region is limited in size.

Evolving integrases for knock-out of hLDH-A We set out to evolve integrases toward sequences that resembled attP within the human LDH-A gene, in order to use the integrases to disrupt the LDH reading frame (i.e. create a knock-out in LDH-A). Lactic acid is an important waste product generated by cells in tissue culture that interferes with the process of overproducing therapeutic proteins. Cell lines generating less of this waste product are desirable for use in protein production. Therefore, LDH-A was chosen as an example to demonstrate integrative disruption. The LDH protein is a tetramer that exists in five different isozyme forms, $LDH_{1-5}$. Each isozyme catalyzes the conversion of pyruvic acid to lactic acid, but performs the conversion at different efficiencies. Each form of the enzyme possesses a unique makeup of M and H subunits. The LDH-A gene produces the M subunit. The more M subunits in the protein, the more efficient it is at carrying out this conversion. Therefore, disrupting expression of the LDH-A gene reduces the amount of M subunits available to complete the tetramer. LDH proteins containing less of the more active M subunit would be less efficient at catalyzing the pyruvate to lactate conversion, which would provide better conditions for protein production.

The coding region of LDH-A was analyzed to determine whether it contained sequences resembling the attP site, either by having a high degree of sequence identity or by matching a framework pattern. First the wild-type attP site was used as a searching parameter to locate any potential pseudo sites with a high percentage of sequence identity. A sequence within exon 6 (E6) was found to have 55% sequence identity (22/40), with a concentration of identity in the core region. The sequence of the E6 site is agcccaggatgtgtagc-ctTTgagtttgatcacctcataa, where the TT-core is indicated in uppercase. When this was compared to the Pattern 5 framework, only 3 of the 7 base pairs matched. A potential pseudo attP site found in exon 2 (E2a) presented a different situation in which the overall percent identity was lower, but the sequence contained more of the framework bases. In this case the predicted site within exon 2 had 6 of 7 framework base pairs, but only 37.5% overall sequence identity with attP.

The E2a sequence is cctttgccagagacaatctTTggtgt-tctaaggaaaaggc (SEQ ID NO:139), where the TT-core is indicated in uppercase. The percent identity was determined by comparing E2a to wild-type attP and designating the TT as the core where the cross-over with attB occurs. If E2a is compared to attP using the PRETTY program, the alignment is slightly different. In a program such as PRETTY, sequences are aligned to generate a consensus with the highest percentage of sequence identity. PRETTY gapped one position on the end of the sequence and obtained a 42.5% identity, resulting in 5 of 7 framework base pairs matching Pattern 5. How an evolved integrase sees the recognition site is unclear. The attR sequence resulting from recombination would be identical in either case.

Exons 2 and 6 were amplifed by PCR, including approximately 30 bp of the flanking intron sequences. The products were verified by sequence analysis, placed into the Resident plasmid of the bacterial screen (Sclimenti et al., 2001 Nucleic Acids Res. 2001 29:5044-51), and used to identify integrases from a library of shuffled integrase genes.

Because we included entire exons as target regions for an integrase to recognize, it was possible that a mutant integrase would choose a site other than those predicted. In the case of the exon 2 sequence, it was anticipated that mutant integrases would recombine using the E2a site. Although this did occur, an additional site that was not predicted was also used by several of the mutants. This site was termed E2b and its sequence is ctgccatgttggagatccaTCatctctcccttcaatttgt (SEQ ID NO:140).

From the first round of screening, 2 mutants were found to carry out the intramolecular integration event at E2a, while 4 others utilized E2b as the pseudo attP site. The TC is in uppercase because these integrases use TC as the cross-over region, which was determined by analyzing the sequence after recombination. Since TC is not compatible with the attB TT core, it is not known how the resulting attR sequence results in a TT core. Assuming that the TC is the functional core region of the site, the percent identity to attP is only 32.5%, and it contains 4 of the 7 framework base pairs in Pattern 5.

To obtain the maximum amount of sequence identity to the wild-type attP site, the E2b sequence was compared using PRETTY. In this case, the highest sequence identity was not obtained when manually aligned with a defined TC core. Instead, a 1 bp gap was inserted on the end of the sequence to generate a maximum overall identity of 37.5%, with 4 of 7 Pattern 5 base pairs present. However, results obtained from the recombinants argued that the integrase does not recognize E2b in this manner. Instead, it appeared to prefer the alignment of E2b in which the percent identity to the wild-type site is 32.5%. Again, this interpretation was indicated by analzying the sequence of attR after recombination. Both overall sequence identity and number of framework base pairs present in the E2b site were lower when compared to the E2a site, yet twice as many mutants were found to prefer the E2b pseudo attP in our bacterial screen (see below). It is clear that using criteria based solely on the highest number of framework base pairs or the most overall attP sequence identity can be misleading for predicting pseudo sites. Another strategy would be a blind approach, using short regions of the chromosome as potential targets. The blind approach offers a viable alternative approach, because sequence analysis by computer in its current form is not always predictive.

Directed evolution results in detail Libraries for the E2 and E6 sites were created from a pool of 24 mutant integrases that were evolved toward human pseudo site A (HpsA) (Sclimenti et al., 2001 Nucleic Acids Res. 2001 29:5044-51). Each of the mutants was tested on both exon sequences for activity. Interestingly, two of these mutants possessed some activity toward exon 6, while none of the mutants had any inherent activity toward exon 2. In the cases where the mutants recognized the pseudo site within exon 6, only 1 of the 2 had significant activity and carried out the reaction specifically. This mutant was used as a benchmark for evolving integrases towards the exon 6 sequence, looking for those that performed more efficiently and could carry out the reaction specifically.

In the case of the exon 2 sequence, any mutant performing an intra-molecular integration reaction within the exon would be an improvement, because none of the starting integrases could carry out the reaction at all. The first criterion in the evolution process is to find mutants that perform recombination precisely between attB and a pseudo attP site within the exon. This analysis can be performed easily in a PCR-based pre-screen in which successful recombination is indicated when an expected size product is amplified. Once this basic criterion is fulfilled, one can demand higher efficiencies from the mutants. After the first library was analyzed with the bacterial screen, colonies producing any detectable blue color on Xgal plates were chosen for colony PCR analysis. An expected size PCR amplified product was an indication that mutant integrases acquired new recombination properties.

Integrases evolved toward the pseudo attP in exon 6 Approximately 100 mutant integrases were examined in a pre-screen for their ability to perform recombination using the exon 6 sequence. Because two of the mutants used to create the library already possessed low levels of activity towards the E6 site and generated small amounts of blue color, only mutants surpassing this level of blueness were included in the pre-screen. Thirteen of the 100 colonies examined indicated proper recombination. All 13 of the PCR amplified junctions migrated identically on a high percentage gel, and 4 of them were sequenced. The 4 were identical, and recombination occurred precisely as predicted, with the mutants recognizing the E6 site as the pseudo attP.

These first cycle mutants were then pooled and mutated for further improvements. The best cycle 1 (C1) integrases were used as a benchmark for the cycle 2 (C2) mutants to surpass. Twenty-three cycle 2 mutants were created. Each of these mutants generated bluer colonies, indicating a more active integrase. PCR over the recombined junction showed a more precise reaction, with only the expected band present and with no detectable spurious amplification. Thus, not only were the efficiencies of these integrases improved, but their specificity was higher as well.

To gain some perspective on the degree of improvement, the top E6C2 mutants were compared to the human 11C2 integrase ($H_{11}C2$) (Sclimenti et al., 2001). A plasmid carrying the H11C2 integrase was tested in the same way as were the top 4 E6C2 integrases, but instead of transforming 11C2 into cells carrying the hLDH-A exon 6 sequence (bacteria strain DH-E6), the H11C2 mutant was transformed into a strain containing the HpsA attP plasmid. The best E6C2 mutants produced colonies with a deeper blue in a shorter period of time compared with colonies carrying Hi 1C2. By this comparison it appeared that the E6C2 evolved integrases were more active toward their E6 site than 11C2 was on its psA site.

Integrases evolved toward pseudo attPs within exon 2 (E2a and E2b) Because none of the precursor mutants used to create the first round library had activity on the exon 2 sequence, colonies were chosen for a pre-screen based on the presence of any amount of blue color. Approximately 180 colonies were analyzed in the PCR-based pre-screen. A total of 6 mutants were found to mediate recombination with exon 2. Unlike those evolved towards the E6 site, the first round screening towards the exon 2 sequence resulted in fewer C1 mutants that were capable of mediating proper recombination. In addition, 2 pseudo sites within the exon were found, E2a and E2b. Two of the mutants recombined using the E2a site while the other 4 mutants preferred the E2b sequence. Because four mutants were generated that seemed to prefer the E2b site over the E2a site, it seemed beneficial to continue the directed evolution using E2b as the target. Four mutants will not produce a library with great diversity, so the objective of the following round was to generate further mutants that simply performed the reaction properly. Once enough mutants are created that carry out the reaction in a precise manner, higher efficiency demands are placed on the enzymes.

The evolved integrases are then tested for their ability to target exon 2 or exon 6 of the LDH-A gene in human 293 cells in culture. Enzymes that perform this reaction efficiently are used to integrate attB plasmids into the LDH-A gene such that the gene is disrupted.

Example 4

A Method to Generate in Bacteria Multiple Integrases with Altered Specificity and Test them en masse in Mammalian Cells Cellular context may affect recognition by integrases of pseudo att sites (Thyagarajan et al., 2001 Molecular and Cellular Biology 21, 3926-3934) present in the chromosomes of animal or plant cells. Therefore, mutant, evolved integrases isolated from a bacterial screen (Sclimenti et al., 2001 Nucleic Acids Research Nucleic Acids Res. 2001 29:5044-51.) alone may not always carry over their improved phenotype in the cellular context where they are intended for use. One solution to this problem is to merge the bacterial assay with a proven method of analyzing mutant integrases in mammalian cells. This strategy takes advantage of the simplicity of screening mutants in the bacterial assay, while directly evaluating whether their improved characteristics are displayed in the mammalian environment where they will be used.

Both of the bacterial plasmids for use in the present assay are the same as those used previously (Thyagarajan et al., 2001 Molecular and Cellular Biology 21, 3926-3934), with the exception of a minor modification to the Library plasmid. So that each mutant integrase-encoding fragement does not have to be moved from the Library plasmid to a mammalian expression vector, a CMV promoter was added upstream of the lacZ promoter. A PvuII site in the Library plasmid is present directly upstream of bacterial promoter/operator and was used for this modification.

Using the bacterial assay for a primary screen produces mutant integrases that are functional and mediate recombination between the desired att sites. The goal of this primary screen is to collect functional mutant integrases that are more efficient at recognizing the desired attP and attB combination for further testing in mammalian cells. Integrases should not be considered specific/efficient until screened in the cells where they will finally be used.

In several examples where integrases have been evolved toward native sequences present in the human and mouse genomes, approximately 20,000-30,000 colonies were screened for improved integrases. Each of these screens produced 10-20 mutants with significant improvements. In these cases, transformed bacterial cells were spread on 10 cm petri plates where approximately 150-175 colonies were formed per plate. Screening this number of colonies per plate would require working with many plates and would become cumbersome if a large number of mutants were desired. To circumvent this problem, in this method, libraries are screened on square plates 23×23 cm (530 cm$^2$). With these larger plates, approximately 13,000-16,000 colonies are present per plate. One plasmid library of mutant integrases prepared identically as before would be enough to screen 1.5-2×10$^6$ mutants. Use of 60-75 23×23 cm plates provides enough surface area to screen >1×10$^6$ mutants with sufficient room for growth and analysis of colonies and as a result would generate 400-800 high-performing mutant integrases.

Plates are poured using an automatic sterilizer and dispenser. Each of the plates contains the appropriate antibiotics and Xgal in 200-250 ml of Luria broth agar. Such a set-up prepares one 23×23 cm plate in ~22 seconds, so making 75 plates is accomplished easily within a day. The protocol for the assay is as follows:

Step 1. Generate mutant integrases from bacterial screen (100-1000 mutants).

a. Screen integrase library (made for example by DNA shuffling (Stemmer, 1994)) on 50-75 23×23 cm plates. Choose those colonies that turn bluest in the shortest period of time.

b. Grow at 42° C. in 1.3 ml of 2× medium (e.g. 2×LB, TB, or YT broth) for 20-24 hrs.

c. Mini-prep DNA to produce ~200 ng of each mutant plasmid. For example, the QIAwell Plasmid Purification System produces this amount of DNA for low-copy number plasmids such as the pACYC vector (P15A origin). The kit is optimized for high throughput production, while purifying DNA suitable for transfection.

Once enough mutants are isolated from the bacterial screen, the mini-prep mutant DNAs are tested in a tissue culture setting without any additional plasmid modifications. Transfections of mammalian cells are performed in a 96-well format and assayed for integration frequency at the intended target site. In addition, toxicity assays are performed on the cellular supernatants to gauge whether the mutants have a negative effect on the cells.

Step 2. Assay for increased integration frequency by quantitative PCR.

d. Perform co-transfections in the 96-well format using reagents such as Fugene. This particular reagent requires low amounts of DNA for transfections while providing a high level of transfection efficiency. Approximately 50 ng of the mutant integrase plasmid is co-transfected with 2.5-10 ng of an attB donor plasmid. About 25-50% of the mini-prep DNA is used for transfections.

e. DNA concentrations are fairly uniform throughout the plate. Therefore, each well receives approximately the same amount of integrase plasmid. A DNA spectrophotometric plate reader could be used if more precise transfection parameters are desired.

f. To address the issue of toxicity, cells are allowed to grow for several more days than usual. Forty-eight to 96 hours after transfection, genomic DNA is isolated and purified. The QIAamp 96 DNA Blood Kit isolates sufficient amounts of genomic DNA (approximately 200-400 ng) for quantitative PCR.

g. Multiple probes are used in the Q-PCRs, a probe/primer set for recombinant sequences and a probe/primer set for a standard control. The latter is not only useful for knowing how much DNA is loaded per reaction, but can also be an indicator of any integrase toxicity.

As the mutant integrases are screened in tissue culture, those that successfully mediate recombination at the native site are chosen and pooled together for additional cycles of mutagenesis and screening. Once mutants have been identified for their site-specific integrative properties, these characteristics often remain, while the integrases accumulate additional beneficial properties.

Mini-prep and genomic preparations are compatible with available robotic systems for higher throughput.

This method allows one to scale-up by 10-100-fold the numbers of evolved integrase mutants easily obtained in the bacterial screen. The method also provides an easy way to accurately assess the activity of large numbers of mutant integrases in the desired target cell, here a mammalian cell.

Example 5

A Method to Screen in Mammalian Cells for Integrases with Altered Specificity and/or Efficiency A method where altered integrases are developed directly in the cell type where they will be used is presented. If an altered integrase is to be used in mammalian cells, its isolation and testing in a distant species, such as bacteria, may not faithfully predict the properties necessary to be effective in mammalian cells. Therefore, we have developed a screen where integrases can be conveniently evolved directly in the mammalian environment. A phage integrase such as the φC31 integrase (Groth et al., 2000 Proc. Natl. Acad. Sci. USA 97, 5995-6000) and its attB and attP wild-type or pseudo sites (Thyagarajan et al., 2001 Molecular and Cellular Biology 21, 3926-3934) are used in the assay.

The screen can be performed in various mammalian cell lines, such as 293 or CHO cell lines, depending on the attP site being targeted. In this example, the site being targeted is a wild-type attP site placed into human 293 cells. The screen is designed to yield evolved integrases that mediate integration at attP more frequently than does the wild-type integrase. The screen consists of three components, the target plsamid, the donor plasmid, and the mutant integrase library.

The target plasmid has a wild-type attP site placed 5' of the DsRed2 open reading frame, a polyadenylation signal, and an expression cassette encoding the neomycin phosphotransferase resistance marker. This marker provides resistance to kanamycin in *Escherichia coli* and to geneticin (G418) in mammalian cells. The DsRed gene does not have a mammalian promoter to drive its expression. The target plasmid is linearized with either DraIII or ApaLI. The linearized plasmid is transfected into the recipient 293-Ecotropic (293-E) cells via electroporation. 293E cells are cells that can be infected by retroviral particles produced by the *Phoenix*-E cell line (Pear et al., 1997 Generation of high titre, helper-free retroviruses by transient transfection. In *Methods in Molecular Medicine: Gene Therapy Protocols*, P. Robbins, ed. (Totowa, N.J.: Humana Press), pp. 41-57). After electroporation with the linearized target plasmid, the cells are placed under geneticin selection. After 14 days of selection, individual colonies are isolated and expanded to form the recipient cell lines. These cell lines have the DsRed2 gene integrated into the chromosome. Because this gene does not have a mammalian promoter, the protein is not expressed in the target cells, and consequently the cells are not red.

The donor plasmid has a mammalian promoter (either CMV or PGK) and an attB site placed 3' of it. Site-specific integration of this plasmid via recombination with the attP site in the target plasmid inserted in the genome results in activation of the DsRed2 gene and causes the cells to turn red when excited at a wavelength of 558 nm. Random integration of the donor does not result in activation of the DsRed2 marker, and the cells do not fluoresce. The donor plasmid does not have a mammalian selectable marker, although one can be added if required.

The final part of the screening assay is the library of mutated phage integrases. To ensure that each transfected cell has only one copy of an integrase gene, we use a retrovirus-based system to infect the target cells. Under the right conditions for infection, the number of cells receiving only one copy of the integrase expression cassette are maximized. After the retrovirus containing the integrase expression cassette infects the cell, the RNA containing the genetic information will be converted to DNA and this DNA molecule will randomly integrate into the genome of the infected cell using the retroviral integrase. Once integration is complete, the phage integrase will be expressed in the infected cell. Since the probability of a cell receiving multiple integrase genes is minimized, there should only be one integrase gene per cell. The integrase expression cassette also has a GFP gene driven by the same promoter. An Internal Ribosome Entry Site (IRES) enables both polypeptides to be translated from the same mRNA molecule.

DNA shuffling, or another method to produce a diverse library of integrases, is performed as described (Sclimenti et al., 2001 Nucleic Acids Res. 2001 29:5044-51; Stemmer, 1994 Proc. Natl. Acad. Sci. USA 91, 10747-10751.). The shuffled library is cloned into the plasmid pBMN-1-GFP (gift from Garry Nolan, Stanford University). Plasmid DNA prepared from the library clones are transfected into *Phoenix*-ECO cells in order to make retroviral libraries. Infectious retrovirus particles are harvested and used to infect 293-E cells.

Infected cells are sorted by flow cytometry for GFP to separate cells that express the integrase from those that don't express the enzyme, because GFP expression parallels expression of the integrase. Cells that express the integrase are transfected with the donor plasmid described earlier. Now the three components required for site-specific recombination, the attP, the attB, and the integrase are all present in the same cell.

Figure 20:
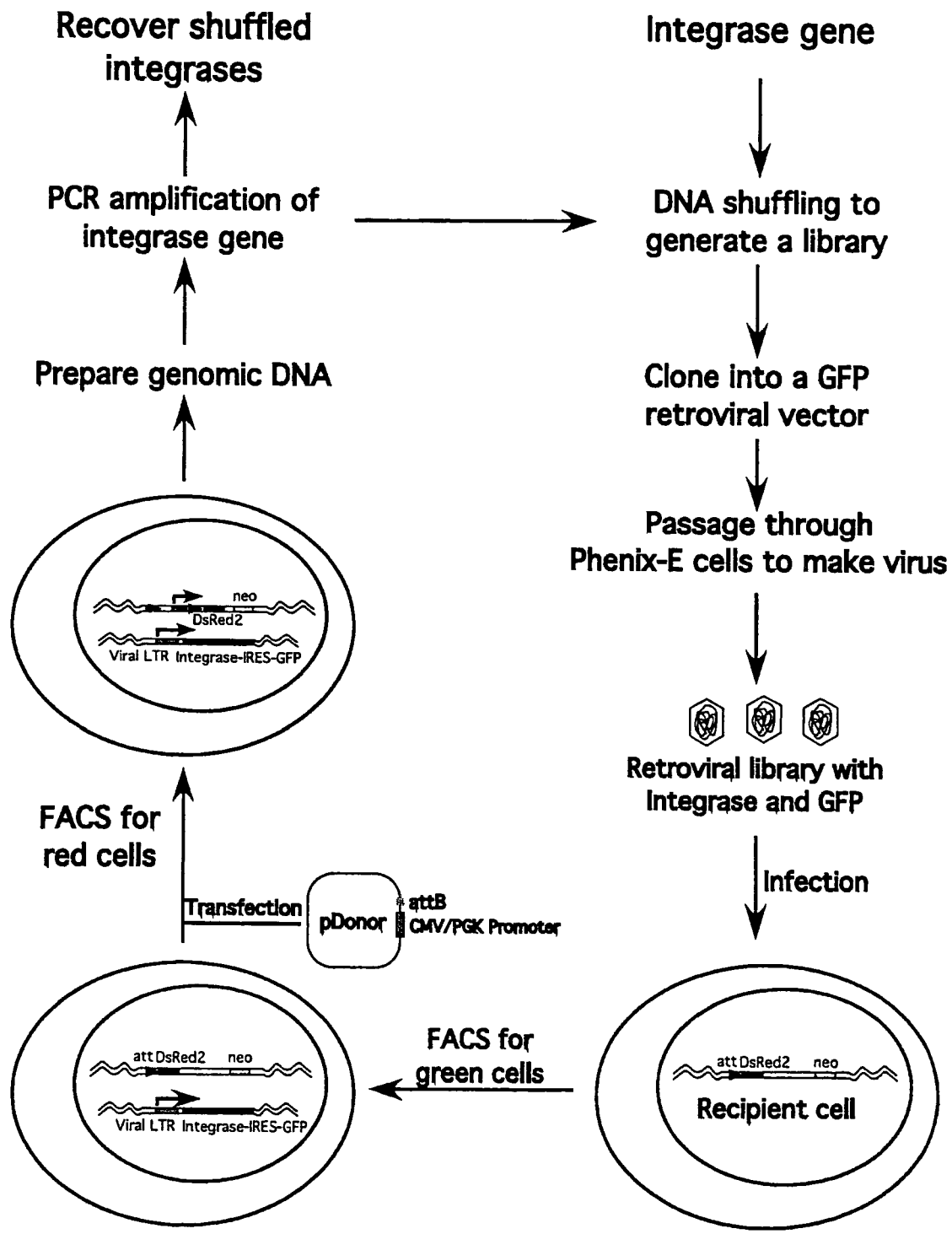
FIG. 20 shows a schematic representation of the mammalian screen for improved integrases. The mutated library of integrases is screened in a recipient cell line containing the desired att site substrate for recombination. Cells positive for recombination are screened by flow cytometry, and the integrase gene is isolated from them. The altered integrases are either cycled through another round of mutation or individual clones are analyzed for improved recombination frequencies.

Screening for improved integrases involves passing the cells through a fluorescence activated cell sorter and looking for activation of DsRed2 expression. Cells positive for DsRed2 expression are cultured further, and genomic DNA is prepared from them. Because retrovirus-mediated infection results in chromosomal integration of the integrase library, DNA encoding functional integrases can be rescued by PCR amplification and used as a substrate for the next round of shuffling. Cycles are continued until a satisfactory integrase is produced. This method is schematically presented in FIG. 20.

Example 6

A Method to Screen in Yeast for Integrases with Altered Specificity and Efficiency We describe a system to perform the directed evolution of integrases and attB/attP sequences in yeast. This system builds upon previously described technology used to evolve bacteriophage integrases (e.g., φC31) in *E. coli* to recognize and recombine with non-wild-type attP/attB sequence combinations (Sclimenti et al., 2001 Nucleic Acids Res. 2001 Dec. 15; 29(24):5044-51).

Our data suggest that phage integrase behavior differs between the mammalian and *E. coli* environments (Sclimenti et al., 2001 Nucleic Acids Res. 2001 Dec. 15; 29(24):5044-51; Thyagarajan et al., 2001 Molecular and Cellular Biology 21, 3926-3934). For this reason, we seek to evolve integrases intended for use in mammalian systems in a genetic background that more closely mimics a mammalian environment than does *E. coli*. Simple eukaryotic organisms such as *Saccharomyces cerevisiae* and *Schizosaccharomyces pombe* share important elements with higher organisms such as features of nuclear structure, chromatin, and DNA repair machinery, while still offering the advantages of microbial-rate growth, ability to culture and screen large populations, and ease of genetic analysis. For these reasons, yeast provides a good vehicle for performing directed evolution of the integrase system.

In its simplest form, applying the integrase technology to a yeast system takes advantage of current technology developed in *E. coli*. Using assay plasmids similar to pINT and pRES (Sclimenti et al., 2001 Nucleic Acids Res. 2001 Dec. 15; 29(24):5044-51), adapted for expression in yeast and introduced into yeast, a colorimetric assay is used to compare unrecombined (white) or integrase-recombined (blue) colonies. A plasmid library bearing mutant integrases is transformed into yeast, and the best candidates are contained in the bluest colonies. These best candidates are used in a second round of DNA shuffling to produce a further improved candidate pool, and this process can be repeated as often as desired.

A second assay takes full advantage of yeast chromosomal structure by selecting for mutant integrases that have recombined the donor plasmid into a yeast chromosome. An example of such an assay is illustrated as follows: A YIp (yeast integrating plasmid) carrying the pseudo attP site and an inducible selectable marker such as the neo resistance gene under the GAL1 promoter is inserted into the yeast genome by homologous recombination. Integrants are then selected. Multicopy tandem insertions of neo are desired and can be specifically selected with G418 as has been described (Parekh et al., 1996 Biotechnol. Prog. 12, 16-21).

Once selected, yeast bearing the pseudo attP site tandem array are co-transformed with two plasmid libraries, one bearing a promoter, an attB, and a selectable marker such as HIS3, the other bearing a promoter, an integrase gene, and a different selectable marker, such as URA3. Using standard genetic techniques, co-transformants are selected. Improved integrase/attB combinations will mediate integration at the pseudo attP site, bringing the selection gene under the control of the integrated promoter and resulting in improved survival under selection. These best candidates are used in a second round of DNA shuffling to produce a further improved candidate pool, and further cycles can be performed. This system can be used as described to co-evolve integrases and attBs. Alternatively, a single attB could be used to evolve integrase alone, or vice versa.

If improved integrase/attB/pseudo attP combinations confer increased survival under selective pressure as in the assay described above, a competitive growth environment may help identify the best combinations. Competitive growth in continuous culture (i.e., growth in a chemostat) is a well-established method of directed evolution, and competitive growth of integrase mutants may prove useful in evolving the integrase system toward a pseudo attP site. We describe here the evolution of integrases and attB sequences toward a pseudo attP site. Similar methods are applied to evolve an integrase and attP toward a genomic pseudo attB site.

Example 7

A Method to Generate and Test Altered Att Site Sequences with Improved Recombination Behavior We have evolved the attB site to optimize the recombination efficiency of an evolved integrase, 11C2 (Sclimenti et al., 2001 Nucleic Acids Res. 2001 29:5044-51.), with the human chromosomal pseudo attP site psA (Thyagarajan et al., 2001 Molecular and Cellular Biology 21, 3926-3934).

A library of mutated 34 bp attB sequences was constructed. Each position in the mutant attB library contained 5% of each of the three other bases. This protocol led to a mutant library in which approximately 20% of the oligonucleotides had 5 mutations, and greater than 50% of the mutant attBs contained between 4 and 6 mutations. The plasmid, ppsASL was constructed by removing the attB from pRESψA (Sclimenti et al., 2001 Nucleic Acids Res. 2001 29:5044-51.) with AscI and replacing it with a linker. The attB library was ligated into SpeI— and SacII-digested ppsASL to give ppsASmBL. The positive control plasmid, ppsASBL was made by cloning attB oligonucleotides into the SpeI site in ppsASL. Intramolecular integration events excise a stuffer sequence located between the mutant attB and the psA attP on this plasmid and permit lacZ transcription, resulting in blue color on Xgal plates, as described (Sclimenti et al., 2001 Nucleic Acids Res. 2001 29:5044-51.).

After overnight ligation of a 10-fold molar excess of the mutant attB oligonucleotide library with SpeI- and SacII-digested ppsASL, ligase was removed with MicropureEZ columns (Millipore), and salt was removed with a YM100 column (Millipore). The plasmid library ppsASmBL was transformed into E. coli DH-11C2, which are E. coli DH10B containing the plasmid p11C2. The plasmid p11C2 contains the gene for improved integrase 11C2 driven by the Lac promoter. The library transformation into E. coli DH-11C2 was plated on LB containing kanamycin, tetracycline, and XGal and incubated at 30° for 20 hours.

After 20 hours, plates were checked every two hours for 6 hours for colonies that had a darker color than colonies resulting from the transformation of ppsASBL into E. coli DH-11C2. To confirm that the blue colonies were the result of a recombination event, they were screened by PCR amplification of the attL junction using the primers, 5'GATACCAGGTTCTGAGCTGCC3' (SEQ ID NO:141) and 5'AAGTCCGATCCATTTCACCCA3' (SEQ ID NO:142). If colonies were positive for the attL, they were also screened by PCR amplification of the attR junction using the primers 5'GTTTTCCCAGTCACGACGTTG3' (SEQ ID NO:143) and 5'CTTCCAATCAGAGGCTTGGTG3' (SEQ ID NO:144) or 5'ATTTGTAGAACTATTATGGG3' (SEQ ID NO:145). Sequence of the improved mutant attBs was obtained from either the attL and attR PCR products or from PCR amplification of the intact attB using the primers 5'GTTTTCCCAGTCACGACGTTG3' (SEQ ID NO:146) and 5'GATACCAGGTTCTGAGCTGCC3' (SEQ ID NO:147). PCR products were cleaned up with S300-HR microspin columns (Amersham) before sequencing.

To provide unselected mutant attB sequences for comparison, the ppsASmBL library was also transformed into E. coli DH10B lacking an integrase gene. These transformations were plated on LB containing kanamycin and X-Gal. The attBs from these colonies were amplified by PCR using the primers 5'GTTTTCCCAGTCACGACGTTG3' (SEQ ID NO:148) and 5'GATACCAGGTTCTGAGCTGCC3' (SEQ ID NO:149), cleaned up with S300-HR microspin columns and sequenced. The mutability of attB with psA and integrase 11C2 was calculated as published (Guo et al., 2000 Science 289:452-457) using the sequence of the improved mutant attBs and the unselected attBs.

Figure 21:
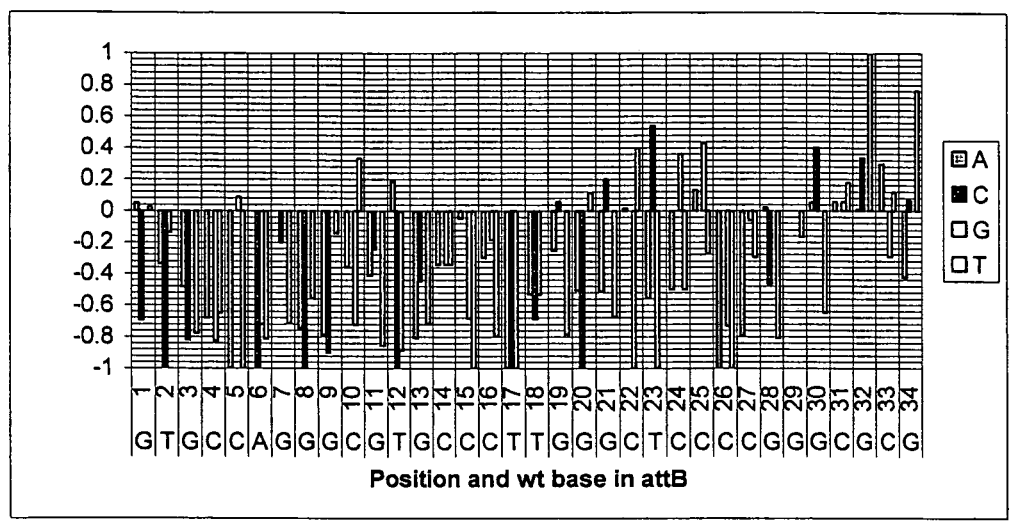
FIG. 21 shows the mutability of attB. The mutability of attB with integrase 11C2 and human pseudo attP site psA was calculated from a pool of 42 improved mutant attB sequences and 102 mutant attB sequences unselected for function. The positive values were normalized to the highest value at position 32. A positive value indicates that the specific mutation occurred more often in the improved pool than the general pool. Values of −1 indicate that the mutation never occurred in the improved mutant attB pool. From the mutability data, a framework for the attB can be developed. Using a mutability cut-off of −0.2, the attB framework using IUPAC base ambiguity codes is DKGCSAVGKYGWGCMSTTSKSHYSVC-SRNVNNHB (SEQ ID NO:01).

We found 42 improved mutant attB sites by using this intramolecular integration assay in E. coli. The sequences of these mutants are listed in Table 1. Using the sequence of these improved attBs, the mutability of attB with human psA and integrase 11C2 was analyzed. The mutability is graphed in FIG. 21. Positive mutability scores are representative of selection for that mutation, while negative mutability scores represent selection against that particular mutation. Any base in attB with a mutability score near positive or negative one is probably important for interaction with the integrase 11C2.

Properties of the improved mutant attBs are confirmed and the improvement quantitated by using a transient transfection assay in human 293 cells. Cells are transfected with 200 ng of the assay plasmid containing the proper mutant attB and 1 µg of pCS11C2, which contains the gene for integrase 11C2 driven by the CMV promoter. The cells are harvested 48 hours after transfection, and episomal DNA is extracted (Hirt, 1967 J. Mol. Biol. 26, 365-369). The DNA is then transformed into E. coli DH10B and plated on LB containing kanamycin and X-Gal. The recombination frequency is calculated as the number of blue colonies over the total number of colonies multiplied by 100.

The best mutant attBs from the transient excision assay are further tested in an integration assay in mammalian cells. Integration frequency at psA is measured by quantitative PCR. The mutant attB with the highest integration frequency is used as the recombination partner for pseudo attP psA in further rounds of improvement of the integrase 11C2 using DNA shuffling (Sclimenti et al., 2001 Nucleic Acids Res. 2001 29:5044-51.).

In addition to evolving the attB with human psA and integrase 11C2, both attB and attP are evolved toward each other with the wild type φC31 integrase. The evolution of attP allows us to derive a framework minimal consensus sequence for attP and use it to search for pseudo attP sites in silico.

Example 8

A Method to Create Specific Deletions in a Chromosome

The serine family of site-specific recombinases contains several integrase enzymes, each with different recognition sequences. We have characterized efficient function of phage integrases φC31, TP901-1, and R4 in mammalian cells (Groth et al., 2000 Proc. Natl. Acad. Sci. USA 97, 5995-6000; Olivares et al., 2001 Gene 278, 167-176; Stoll et al., 2002. J. Bacteriol. 184). Each integrase is able to complete intramolecular and intermolecular integration reactions, including integration into mammalian chromosomes. We focus here on the ability of these enzymes to catalyze a unidirectional intrachromosomal integration reaction between the attB and attP sites, which provides for excision of the material between the attB and attP sites.

In order to determine the frequency of such excision catalyzed by these integrases, we established human cell lines containing integrated copies of each integrase's attB and attP recognition sites. Transfection with integrase-expression plasmids, followed by quantitative PCR analysis, allowed us to calculate the excision frequency for each integrase in a chromosomal context.

Plasmid pBB-B304-P333 has been described (Stoll et al., 2002. J. Bacteriol. 184) and will be referred to as pBB-TP (BP). This plasmid contains the full length TP901-1 attP and attB recognition sites flanking the 3.5 kb lacZ gene. The linker XmaR4attP64, containing a 64-bp R4 integrase attP site, was cloned into the XmaI site of pBB-TP(BP), generating the plasmid pBB-TP(BP)-R4(P). Next, the 224-bp φC31 attP site was cloned, as a SpeI fragment from pBCPB+ (Groth et al., 2000 Proc. Natl. Acad. Sci. USA 97, 5995-6000), into the SacII site of pBB-TP(BP)-R4(P), generating plasmid pBB-TP(BP)-R4(P)-φC31 (P). Into the XhoI site of this plasmid, the 313-bp φC31 attB site was cloned as an XhoI fragment, generating the plasmid pBB-TP(BP)-R4(P)-φC31 (BP). The 416-bp R4 attB was liberated from pBC-R4PB (Olivares et al., 2001 Gene 278, 167-176) as an XhoI fragment and cloned into the BamHI site of pBB-TP(BP)-R4 (P)-+C31(BP), to create plasmid pBB-TP(BP)-R4(BP)-φC31 (BP). Lastly, a 2.0-kb SalI-NruI fragment from pEF (Stoll et al., 2001 Molecular Therapy 4, 122-129), encoding the gene for hygromycin resistance driven by the TK promoter, was cloned into the AgeI site of pBB-TP(BP)-R4(BP)-φC31(BP), generating the assay plasmid pTripleBP-Hyg.

pTripleBP-Hyg was linearized with XmnI, purified by phenol/chloroform extraction, and ethanol precipitated. 5 µg linearized plasmid was electroporated into 293 cells, and the cells were allowed to recover in Dulbecco's modified Eagle medium supplemented with 9% FBS and 1% penicillin-streptomycin. After 24 h, cells were placed under selection in medium containing 200 µg/ml hygromycin B (CalBiochem, La Jolla, Calif.). After 14-21 days under selection, single colonies were picked and expanded. Cell lines were screened for presence of intact Triple-attP and Triple-attB sites by PCR and by Southern analysis.

Each integrase was independently cloned into the expression plasmid pIRES-hrGFP-1a (Stratagene). The TP901-1 integrase was cloned into the EcoRI-XhoI sites of pIRES-hrGFP-1a as a 1.5-kb EcoRI-XhoI fragment, generating the plasmid pTP-1-hrGFP. A 1.4-kb EcoRI fragment from pTA-R4Int, containing the R4 integrase, was cloned into the EcoRI site of pIRES-hrGFP-1a, creating the expression plasmid pR4-I-hrGFP. The ΦC31 integrase was cloned from pCSI as a 1.9-kb blunted SpeI-BamHI fragment and ligated into the SmaI-BamHI sites of pIRES-hrGFP-1a, to generate the vector pI-I-hrGFP. Each of these vectors expresses integrase under the control of the CMV promoter, followed by an Internal Ribosomal Entry Site (IRES) and the humanized Renilla reniformis GFP (hrGFP) open reading frame.

293-pTripleBP cell lines were transfected with 2-5 µg of pInt-1-hrGFP plasmid using Fugene 6 (Roche Applied Scientific, Indianapolis, Ind.), according to the manufacturer's protocol. At 24 h after transfection, cells were FACS sorted, based on hrGFP expression, thus sorting for cells that received integrase expression plasmid. 72 h post-transfection, cells were harvested and genomic DNA was prepared using DNeasy Tissue Kits (Qiagen, Valencia, Calif.). PCR was performed on the genomic DNA, using primers fwdTripleB 5'-GATGGCCCACTACGTGAACC-3' (SEQ ID NO:150) and revTripleP 5'-CACTTTATGCTTCCGGCTCGTA-3' (SEQ ID NO:151), followed by nested PCR using primers attBfwdseq-F 5'-GGCGAGAAAGGAAGGGAAGA-3' (SEQ ID NO:152) and T3 (PAN facility, Stanford, Calif.). Excision products were readily detectable for all three integrase/att combinations.

Quantitative PCR (Gibson et al., 1996 Genome Research 6, 995-1001) on genomic DNA was performed using the following primer/probe combinations: TP901 attR: fwdTPex-qPCR 5'-TGATGTTACTGCTGATAATGTAGATATCATAT-3' (SEQ ID NO:153), revTPex-qPCR 5'-ATTAAAATTCACGGAAGAAAGCTTT-3' (SEQ ID NO:154), TPEx-attR-probe 5'-CGAGTTTTTATTTCGTT-TATTTCAATCAAGGTAAATGC-3'(SEQ ID NO:155); ΦC31 attR: fwdPhiEx-qPCR 5'-GGCTTCACGTTTTC-CCAGGT-3' (SEQ ID NO:156), revPhiEx-qPCR 5'-CCA-GATGGGTGAGGTGGAGT-3' (SEQ ID NO:157), PhiEx-attR-probe 5'-CTGGGGTAACCTTTGGGCTCCCCG-3' (SEQ ID NO:158); R4 attR: fwdR4ex-qPCR 5'-TCTCATG-CATAGAAGGCCCG-3' (SEQ ID NO:159), revR4ex-qPCR 5'-GGCTACACGGAGCAGGACC-3' (SEQ ID NO:160), R4ex-attR-probe 5'-CGATACCACTTGAAGCAGTGGTA-GAAGGGCAC-3' (SEQ ID NO:161). Each of these probes is 5' labeled with the dye 6-FAM, and 3' labeled with the quencher TAMRA. As an internal control for chromosomal copy number, the human RAD52 gene was amplified, using the primer/probe combination: fwdRad52-qPCR 5'-GGGTCGCTGCATAAACTGTTG-3'(SEQ ID NO:162), revRad52-qPCR 5'-AAATTCCACACGTGACCTCGT-3' (SEQ ID NO:163), huRad52-probe 5'-ATGCCTGGT-GCTTTGCGACTTGTCA-3'(SEQ ID NO:164). The hygromycin resistance gene was also amplified as an internal control for integrated pTripleBP-Hyg copy number, using the following primer/probe combination: fwdHyg-qPCR 5'-CTCGGAGGGCGAAGAATCTC-3'(SEQ ID NO:165), revHyg-qPCR 5'-GCAGCTATTTACCCGCAGGA-3'(SEQ ID NO:166), Hyg-probe 5'-TCAGCTTCGATGTAG-GAGGGCGTGG-3' (SEQ ID NO:167). The huRad52 and Hyg probes are 5' labeled with the dye VIC and 3' labeled with the quencher TAMRA.

Comparison of Hyg$^R$ gene amplification and huRad52 genomic reference amplification in the 293-pTripleBP cell lines allows us to determine the copy number of integrated pTripleBP-Hyg vectors in each cell line. If there is only one integrated vector per genome in these cell lines, then each amplified attR junction represents a single chromosomal excision. If there are multiple integrants in these cell lines, an amplified attR junction may represent one excision event or multiple excision events in that particular cell line. However, as experiments are carried out on multiple independent cell lines, we are able to adjust for these copy number differences by comparing excision frequencies among cell lines. This strategy allows us to more accurately determine the frequency of chromosomal excision for each integrase. Quantitative PCR data provides us with the number of amplified attR junctions in transected-cell line genomic DNA and the number of amplified huRad52 genomic references. A relative excision frequency is calculated by taking the ratio of amplified attR to amplified huRad52 genomic reference and adjusting for cell line vector copy number. Analysis of the data allows calculation of the relative chromosomal excision frequency for each integrase and direct comparison of these excision frequencies for all three integrases, acting in the same chromosomal context.

Example 9

Integrative Activation of the Gamma Globin Gene to Treat Sickle Cell Anemia

Sickle cell disease is one of the commonest genetic diseases worldwide but no effective gene therapy has been developed.

Effective treatment of sickle cell anemia could be provided using site-specific integration technology (Thyagarajan et al., 2001 Molecular and Cellular Biology 21, 3926-3934) that can bring about long-term expression through genomic integration of target genes into well-expressed chromosomal locations.

One strategy is to use the φC31 integrase to place a plasmid carrying attB and an expressed γ-globin or a mutant anti-sickling β-globin into a safe site in the genomes of hematopoietic stem cells of the patient, then introduce the corrected cells by bone marrow transplantation, after which they will re-populate the blood.

In another strategy, the native, inactive γ-globin gene, which is naturally anti-sickling, is activated in blood cells by using an altered, site-specific integrase to integrate an active promoter upstream of the γ-globin gene. This integration is carried out by searching the sequence upstream of the γ-globin gene for pseudo attP sites. An integrase is then evolved, for example by using methods that have been described (Sclimenti et al., 2001 Nucleic Acids Research 29, 5044-5051.), that has high specificity for the pseudo attP site upstream of the γ-globin gene.

This integrase is used to integrate a plasmid carrying attB adjacent to a promoter active in red blood cells, such as the β-globin promoter, upstream of the γ-globin gene. Hematopoietic stem cells from the patient are electroporated with the attB-promoter and evolved integrase plasmids, resulting in efficient integration of the γ-globin promoter upstream of the γ-globin gene and its resultant activation. The modified hematopoietic stem cells are reintroduced into the patient by bone marrow transplantation and lead to production of red blood cells in which γ-globin is expressed in concert with β-globin, correcting the sickling defect.

This gene activation strategy can also be employed in other gene therapy strategies in which activation of a native gene leads to correction of the disease phenotype.

Example 10

Integrative Activation of the Human Erythropoietin Gene

A strategy for production of therapeutic proteins involves activation of the native human gene for the desired protein in a human cell environment, to ensure generation of a correctly modified gene product. This goal can be achieved by using integrases that have been evolved to integrate with high specificity at positions that will activate transcription of the desired gene in cultured cells that have been proven to be favorable for large-scale protein production, such as human 293 cells. The insertion system of the invention is used to activate human erythropoietin (EPO) expression.

The 5' region sequence from the human EPO gene was analyzed for the presence of possible pseudo attP sites that could serve as targets for directed evolution of the φC31 integrase. Searches within the 1.5 kb region upstream of EPO were performed to locate prospective pseudo sites inside this region. Such pseudo attP site sequences are then placed into the Resident plasmid (Sclimenti et al., 2001 Nucleic Acids Research 29, 5044-5051) to act as targets for mutant integrases in a screen for improved function.

In this experiment, sequences that have the potential to be used as pseudo attP targets for an evolved integrase are found using three criteria. 1) Maximize overall identity to the wild-type attP site. Programs such as Gap and BestFit (Wisconsin Package, GCG) are used to locate areas with the highest amount of sequence identity compared to wild-type attP. 2) Search with framework patterns that represent minimal consensus or identity within attP. Pattern F (C**GG*TCCT*****C*C*G) (SEQ ID NO:138) and Pattern 5 (C*G*****C*TT******C*G) (SEQ ID NO:137), where * is any nucleotide, derived by the Pretty program and described in Example C, were used to locate sequences that matched these framework patterns. Sequences that match the patterns are directly aligned to the wild-type attP site while preserving the framework alignment. The framework patterns overlap 100% with the wild-type site, enabling this alignment. 3) Obtain the highest degree of sequence identity, while preserving the framework. Programs such as Pretty will align multiple sequences to maximize the percent identity among the sequences compared. When Pretty aligns the prospective pseudo attP site to wild-type attP identically, as do the framework patterns, it indicates that the framework sequences overlap with the prospective site while maintaining the highest level of sequence identity to the wild-type attP.

Seven potential pseudo-sites were located upstream of EPO when the above search criteria were applied. Three of the seven potential sites appeared superior in this comparison. Two of these three were in close proximity and were PCR amplified so that they were both included in the same PCR product.

The primers AGAGACAAGGTCTTGCCATGT (SEQ ID NO:168) and AGGCTGCATTGCTGAGTTCTT (SEQ ID NO:169) were used to amplify a 381 bp region approximately 1.2 kb upstream of transcription initiation of EPO. The sequences of the sites Epo(−1216 bp) and Epo(−1146 bp) are CATTTGACAGATGAGGACATTGAGGGCTCAAGGAC-GAGGC (SEQ ID NO:170) and TCCTGCTCTGGGAATCT-CACTCATCTGGCTCAGGGTTTCC (SEQ ID NO:171), respectively. The Epo(−1216 bp) site is 42.5% identical to the wild-type attP site, while the Epo(−1146 bp) site has 40% identity. Both possess significant overlap with the framework patterns. Another site close to the ATG that is also 42.5% identity.

The 381 bp PCR-amplified sequence is placed into the pRES plasmid, transformed into the *E. coli* strain DH10B, and made electrocompetent. As in other examples, mutant integrases are identified that can mediate the proper recombination event toward the desired pseudo sites, in this case the 381 bp region upstream of EPO. Identification is accomplished by screening a mutated integrase library in a screening assay for evolved integrases, such as the one described by Sclimenti et al. (Sclimenti et al., 2001 Nucleic Acids Research 29, 5044-5051). When approximately ten cycle 1 mutant integrases are produced that facilitate precise recombination within the target sequence, these evolved integrases are then used to generate the next round of mutant integrases. The selection criterion for cycle 2 enzymes is more demanding than for cycle 1 enzymes. Cycle 2 integrases must surpass the efficiencies of those isolated from the cycle 1 screening. The main criterion for cycle 1 mutants is specificity, i.e. carrying out recombination precisely between the tested att sites. Once an increased level of specificity is present in the mutants, higher demands are placed on the screen that call for more efficient enzymes.

Approximately 100-200 cycle 2 mutants are created by screening 50-100 23×23 cm agar plates with the appropriate drug selection. These clones are individually isolated and prepared for transfection into mammalian (eg. 293) cells in a 96-well format. About 48-72 hours after transfection, the cells are harvested for their genomic DNA and analyzed by quantitative PCR (qPCR) for integration events at the pseudo site upstream of EPO. The Taqman probe and primers are specific for a recombinant junction created by recombination between the attB and pseudo attP sites. Only if a specific integration event has occurred will the primers/probe amplify to give a quantitative signal due to the desired site-specific integration event. The subset of mutant integrases performing well in the mammalian cell environment are chosen for further mutagenesis.

An integrase with sufficient specificity and efficiency is used to introduce appropriate gene expression signals upstream of EPO that trigger production of useful levels of the gene product in a human cell line that grows well in mass culture such as 293.

Example 11

Protein Production in Chinese Hamster Ovary (CHO) Cells

We describe a procedure for overexpressing a human protein using CHO cells.

Methods.

Plasmids. The plasmids pCMV-Int and pHZ-attB have been described (Groth et al., 2000 Proc. Natl. Acad. Sci. USA 97, 5995-6000; Thyagarajan et al., 2001 Molecular and Cellular Biology 21, 3926-3934). The plasmid pNBL2 was cloned as follows. A 308 bp EcoRI fragment from pTA-attB (Groth et al., 2000 Proc. Natl. Acad. Sci. USA 97, 5995-6000) containing the attB site was cloned into the blunted M1uI site of pEGFP-C1 (Clontech, Palo Alto, Calif.) to generate pDB2. This plasmid was restricted with AflI and HpaI, treated with Klenow fragment of *E. coli* DNA polymerase, and ligated to generate pNB. A 2.8 kb KpnI fragment from pL-attB (Thyagarajan et al., 2001 Molecular and Cellular Biology 21, 3926-3934) was then cloned into the KpnI site of pNB to generate pNBL2.

Plasmid rescue. Plasmid rescues were performed as described (Thyagarajan et al., 2001 Molecular and Cellular Biology 21, 3926-3934). In short, genomic DNA from hygromycin-resistant pools of cells was restricted with BamHI, ligated at low DNA concentrations, and transformed into electrocompetent DH10B *E. coli*. Transformed bacteria were recovered by plating on LB agar plates containing ampicillin (100 µg/ml) and zeocin (50 µg/ml). Restriction analysis and sequencing were used to detect site-specific integrants. Plasmid DNA from rescued plasmids was sequenced using the primers attBR (5'-GTCGACATGCCCGCCGTGACCG-3') (SEQ ID NO:172) for attR and WTF-2 (5'-TCAACTAC-CGCCACCTCGAC-3') (SEQ ID NO:173) for attL. Once the sequences of the crossover regions were obtained, primers were designed to amplify the genomic DNA containing the pseudo attP site from non-transfected CHO cells via PCR. Amplification products obtained from these reactions were sequenced to determine the genomic pseudo site sequence.

Results.

Integration at pseudo attP sites. The plasmids pHZ and pHZ-attB were transfected into CHO cells with either pCMV-Sport β-Gal carrier or pCMV-Int, and selection was carried using 600 µg/ml of hygromycin. After 12 days of selection, individual colonies were counted. The results of these experiments are presented in Table 3. When an attB-containing donor was transfected in the presence of the integrase, we found a greater than 10-fold increase in integration frequency. No such increase was found in the absence of integrase or with a donor lacking the attB site. These results demonstrated that increased integration frequencies required the presence of both the integrase and an attB site in the donor and provide evidence for the existence of pseudo attP sites in the CHO genome, as we have described for the human and mouse genomes (Thyagarajan et al., 2001 Molecular and Cellular Biology 21, 3926-3934).

TABLE 3

Hygromycin-resistant colonies obtained after transfection of the indicated donors into CHO cells.

| CHO cell line | # Hygromycin colonies | |
|---|---|---|
| | (−) Int | (+) Int |
| No att site (n = 1) | 17 | 6 |
| attB donor (n = 1) | 19 | >200 |

Pseudo site sequences. To determine the DNA sequences of the sites of integration mediated by φC31 integrase in CHO cells, a plasmid rescue strategy was employed. Pseudo attP site sequences purified from the CHO genome are shown in Table 4, along with the wild-type attP sequence. Running the sequences through MEME, a pattern-recognition software in GCG (Genetics Computer Group, Madison, Wis.), identified a conserved motif in wild-type attP and all four pseudo sites (boxed region in Table 4). The boxed region in Table 4 represents the common motif recognized by MEME, a motif-recognizing program in GCG. The letters in upper case represent identity with the wild-type attP sequence (shown in the last row). The bold, underlined letters in attP represent bases that are identical in at least three of the four pseudo attP sequences. Outside this motif, the identity of the pseudo sites to wild-type attP appears minimal. Pseudo site CHO4 shows maximum homology at 52% over the 40-bp minimal attP region. Similar results have been seen with pseudo sites identified in human and mouse cells (Thyagarajan et al., 2001), showing that total sequence identity is not an important factor for the recognition of pseudo attP sites.

TABLE 4

Sequences of pseudo sites targetted by φC31 integrase in CHO cells.

| | | density | Identity |
|---|---|---|---|
| CHO2 | tgaaaaaccCTaaGGTAttCtagGgGagaaactgtcTtcc (SEQ ID NO: 174) | 10/40 | 25% |
| CHO4 | GagtCttAgCTGaGGTcAtCcTTGtGgatTCctAGgaGtt (SEQ ID NO: 175) | 21/40 | 52% |
| CHO6 | tTaCtttccCTGtGGTtACCcTgGgtcagcCatAccacat (SEQ ID NO: 176) | 15/40 | 37% |
| CHO7 | tTGtagggcCccaGcaAAaCcTTGtccaggCggAtTTcct (SEQ ID NO: 177) | 14/40 | 35% |
| AttP | CCCCAACTGGGGTAACCTTTGAGTTCTCTCAGTTGGG (SEQ ID NO: 178) | | |

Screen for high expressing pseudo sites. A strategy was designed to detect pseudo sites that supported high expression of integrated genes. An attB-containing donor plasmid (pNBL2) containing a selection marker (neomycin phosphotransferase) and a marker for expression (luciferase) was constructed as described earlier. This plasmid was transfected into CHO cells along with pCMV-Int. Selection was carried out with 600 μg/ml of geneticin (Invitrogen) for 8 days, and well-isolated individual clones were picked for expansion. Crude protein extracts prepared from these clones were analyzed for luciferase activity as described (Thyagarajan et al., 2001), and the clones were ranked in order of expression.

Clones 4945, 4964, 4944, 4967, 4948, and 4946 were the highest expressors of the 24 clones tested. Luciferase expression in these clones was significantly higher than the average luciferase expression calculated for all 24 clones. These clones were further expanded and genomic DNA was prepared from them. Plasmid rescue was then performed on the genomic DNA to determine the sites of integration of the donor plasmid. The sequence of the integration sites is determined.

Evolution of an integrase towards the high-expressor pseudosite. To evolve an enzyme that carries out site-specific recombination more efficiently and specifically at psCHOE1, our best expressing pseudo site, we use a strategy similar to the one used to develop integrase 11C2, which is evolved toward the human pseudo site (Sclimenti et al., 2001 Nucleic Acids Research 29, 5044-5051). After two to three cycles of directed evolution, we find that the enzyme CHOE1-1 is significantly better at directing integration at psCHOE1. This enzyme is significantly better catalytically and is more specific at directing integration at psCHOE1 in CHO cells. The evolved integrase is used to reproducibly integrate therapeutic genes cloned on plasmids carrying an attB or evolved attB site into this high expressing site in the CHO genome.

Example 12

Integrative Knock-Out of Immunogens in the Pig

The number of organs available for transplantation falls far short of the need. One solution to this problem is xenotransplantation, in which organs from animals such as the pig are used for transplantation into patients.

A barrier to such xenotransplantation is the presence of antigens on the animal cells that are foreign to humans and would lead to a vigorous immune response causing rejection of the transplanted organ.

In particular, the presence of α-1,3-galactose residues on the surface of pig cells is a major obstacle to transplantation. This immunogen could be removed if the pig α-1,3-galactosyltransferase gene were inactivated.

One way to knock out the α-1,3-galactosyltransferase gene is to tailor a site-specific integrase to recognize a site within the coding region of the gene and use the altered integrase to insert a sequence that would effectively disrupt expression of the gene.

This strategy can be enabled by using evolved versions of site-specific integrases, such as the φC31 integrase that has been shown to work well in mammalian cells (Groth et al., 2000 Proc. Natl. Acad. Sci. USA 97, 5995-6000), recognize native mammalian sequences (Thyagarajan et al., 2001 Molecular and Cellular Biology 21, 3926-3934), and is susceptible to directed evolution to change its sequence recognition properties (Sclimenti et al., 2001 Nucleic Acids Research 29, 5044-5051.).

The knockout is carried out by searching the coding sequence of the pig α-1,3-galactosyltransferase gene for pseudo attP sites, for example by using computer programs that search for framework or motif elements involved in recognition of attP by the φC31 integrase. The best candidate pseudo attP sequences are used as targets for directed evolution of integrases, by placing the attP sequences in genetic screens for evolved integrases, such as the screen described (Sclimenti et al., 2001 Nucleic Acids Research 29, 5044-5051.).

When an integrase is obtained that recognizes the pseudo attP site in the α-1,3-galactosyltransferase gene with high efficiency and specificity, the altered integrase is injected into early pig embryos in conjunction with an attB plasmid carrying gene-disrupting sequences such as translational and transcriptional terminators. If the integrase has sufficient activity, it knocks out both copies of the gene in some of the embryos. Transgenic pigs resulting from these embryos lack active α-1,3-galactosyltransferase and organs derived from them are therefore are less immunogenic to human hosts.

The same strategy can be used to knockout other immunogens in animals. The strategy can also be used to knock out immunogens in human stem cells, to enable them to be transplanted to others patients without immune barriers.

Example 13

Site-Specific Genomic Integration Produces Therapeutic Factor IX in Mice

Experimental Methods

Animal Studies: We obtained 6-8 week C57B1/6 mice from the Jackson Laboratory and housed them under specific-pathogen-free conditions. Animals were treated according to the NIH Guidelines for Animal Care and the guidelines of Stanford University. Plasmid DNA in 0.9% saline (1.8 ml) was injected into the tail vein over 5-8 s. Mice were periodically bled by the retro-orbital technique. In some cases, mice were subjected to a surgical two-thirds partial hepatectomy as previously described.

Blood analysis: We analyzed mouse serum for total hAAT or hFIX antigens by an ELISA assay. We assessed liver injury in mice following plasmid injection by analysing serum glutamate pyruvate transaminase (SGPT) levels for up to 9 days as described (Sigma Procedure No. 505) and found no evidence of integrase-dependent liver toxicity.

Plasmid construction: The φC31 integrase expression plasmid pCMV-Int has been described. Carrier plasmid pCS was generated by removing the integrase coding sequence from pCMV-Int using SpeI/NheI followed by religation. A 2.0-kb XhoI fragment from pRSV.hAAT.bpA was cloned into the XhoI site of pBCSK(+) (Stratagene) to form pBC-hAAT. pTA-attB was cut with EcoRI to release a 312 bp fragment encompassing the full length φC31 attB site. The cohesive ends were blunted, and the attB fragment was ligated into the blunted NotI/SalI sites of pBC-hAAT to create pBC-hAAT-B. The human factor IX minigene was removed from vector pBS-ApoEHCR-hAATp-hFIXmg-bpA with SpeI and ligated into the XbaI/SpeI sites in the polylinker of pBCSK(+) to create pBC-hFIX. The pBC-hFIX plasmid was digested and blunted at the BamHI/XhoI sites, and the same blunted attB fragment from pTA-attB was ligated to make the 9.7 kb pBC-hFIX-B.

Pseudo site rescue by nested inverse PCR: Mice that received pBC-hAAT-B and integrase were sacrificed and liver genomic DNA was prepared. 10 μg were digested with pairs of restriction enzymes that have incompatible cohesive ends and that cut at least once in pBC-hAAT-B. The digests were phenol/chloroform extracted, ethanol precipitated, and resuspended in 500 μl of 1× ligation buffer, to which was added 1000 units of T4 DNA ligase (New England Biolabs). Low concentration ligations were incubated at 17 C overnight, phenol:chloroform extracted, ethanol precipitated, and resuspended in 20 μl TE. Primary amplifications with primers attB-F2 (ATGTAGGTCACGGTCTCGAAGC) (SEQ ID NO:179) and attL-iPCR-1 (CCTACTCAGACAATGC-GATGC) (SEQ ID NO:180) were carried out on 0.5 μl of the ligation for 30 cycles of [95 C 30", 60 C 30", 72 C 60"]. Primers were removed from the primary reactions using the QiaQuick PCR purification kit (Qiagen), and a portion of the eluate was reamplified with nested primers attB-F3 (CGAAGCCGCGGTGCG)(SEQ ID NO:181) and attL-iPCR-2 (GGAGGGGCAAACAACAGAT) (SEQ ID NO:182) using an annealing temperature gradient from 55 C-72 C. Approximately 10 bands were excised from the gel, purified, and cloned into pCR2.1-TOPO using the TOPO Cloning Kit (Invitrogen). Insert-containing colonies were sequenced using standard primers. Two of the ten bands represented coherent attL fragments, and the genomic locations they represented were named mpsL1 and mpsL2. By using specific primers designed for mpsl (mpsL1-F: GTGGCA-CATTCCTTAATCCC (SEQ ID NO:183) and mpsL1-R: TGAGGAGGAGCCTTAGCAAC) (SEQ ID NO:184) and mpsL2 (mpsL2-F: TGAGTCTGCCTTGAGCCTTA (SEQ ID NO:185) and mpsL2-R: CAAAGGGCCTGACCTA-GAGT) (SEQ ID NO:185) in combination with vector-specific primers attB-F3 and hAATB-R (CAATACGCAAAC-CGCCTCT)(SEQ ID NO:187), attL and attR recombination junctions were amplified from genomic liver DNA.

Quantitative PCR of in vivo recombination junctions: All quantitative PCR reactions were performed in an ABI Sequence Detector 7700 with ABI Taqman PCR Core Reagents. Reaction conditions were as recommended by ABI.

In combination with primers attB-F4 (CGGTGCGGGT-GCCA) (SEQ ID NO:188) and mpsL1-qPCR2 (AAGCCTT-TAATAAAATGAAGCAAAAGTTC) (SEQ ID NO:189), the probe (6FAM-TGTTTTAGTTTTGCACCTTCCCATTTAT-TCACAG-TAMRA) (SEQ ID NO:190) allows measurement of all integrase-mediated events that took place at mpsL1. Similar quantitation of total mpsL2 attL recombination was performed using primers attB-F4 and mpsL2-qPCR1 (AGAGCACAGCAGAGGTGACCA) (SEQ ID NO:191) and probe (6-FAM-TCTTGTTTTGCTTCCTGTCCAT-CAAGGG-TAMRA) (SEQ ID NO:192).

Quantities of attL junction in each sample were normalized to genome copy number using a probe (VIC-CAACAAC-CAGGACAGCGTCCCACA-TAMRA) (SEQ ID NO:193) and primer set (rad52-F: CAAACTTCTGCCACTC-GAACCT (SEQ ID NO:194), and rad52-R: TGGTTTCT-GATGGCAATGGA (SEQ ID NO:195)) that detect the single copy mouse RAD52 gene. Standard dilution curves for the attL of interest and the RAD52 set were performed on known quantities of standard plasmid, which contained the attL sequence of interest (mpsl or mpsL2) along with the RAD52 region.

To quantitate total plasmids per genome, a probe (6FAM-TGATGCCGCTGGCGATTCAGG-TAMRA) (SEQ ID NO:196) and primer set (F: CGCAAGGCGACAAGGTG, (SEQ ID NO:197) R: CCATCACAAACGGCATGATG) (SEQ ID NO:198) were designed to detect a portion of the chloramphenicol resistance gene included on all attB vectors. Genome copy number was again measured using the RAD52 probe/primers described above.

Analysis of extrachromosomal plasmid DNA: Genomic DNA was prepared (Qiagen Blood and Cell Maxi Kit) from a portion of liver taken during the partial hepatectomy ("pre-PH") and another portion of the liver taken at the terminus of the experiment ("post-PH"). Electrocompetent E. coli were transformed with 2 μg of DNA and spread on chloramphenicol plates to select for the attB vector. After 16-20 hours at 37 C, colonies were counted to determine plasmids/μg genomic DNA.

Results

Integrase-mediated expression of hAAT in mouse liver: Plasmids were constructed that contained a φC31 attB site and either a cDNA expression construct of the human $\alpha_1$-antitrypsin gene (hAAT) or a mini-gene version of HFIX optimized for gene expression. To evaluate the activity of the φC31 integrase in vivo, we injected 25 μg of the hAAT-attB plasmid with either 25 μg of carrier plasmid or the integrase expression vector pCMV-Int in ~1.8 ml saline into the tail vein of mice over 5-8 seconds. This hydrodynamic-based method delivers naked DNA to mouse hepatocytes at efficiencies up to 40%, without delivering significant amounts of DNA to non-liver tissues. Serum levels of hAAT were highest one day after injection, then dropped steadily in the absence of integrase. When pCMV-Int was included, hAAT levels stabilized within 1-2 weeks and remained at levels ~12-fold higher than when the carrier plasmid was used, indicating that the integrase significantly increased and stabilized expression levels. Provision of more integrase did not appreciably increase the stable levels of hAAT beyond that obtained using 25 μg of integrase. Neither an hAAT plasmid lacking attB plus 100 μg pCMV-Int, nor an hAAT attB plasmid plus 100 μg of PCMV-S12F-Int, a mutant substituting the catalytic serine and lacking DNA cleavage activity, raised expression levels. These experiments revealed that the increased hAAT expression levels were dependent on the presence of the attB site on the hAAT plasmid and the catalytic serine of the integrase protein.

High level hFIX expression persists after partial hepatectomy: We constructed a hFIX-attB plasmid by using a cassette optimized for hFIX expression in mouse liver. It is known that the hFIX protein produced by this mini-gene construct is functional, because it ameliorates the clotting disorder in mice with factor IX deficiency. Mice that received the hFIX-attB and integrase plasmids by hydrodynamic tail vein injection produced 3970+/−1040 ng/mL hFIX, ~12-fold more than mice that received the hFIX-attB plasmid alone (327+/−82 ng/mL). To investigate whether or not the DNA responsible for hFIX expression was integrated, two-thirds partial hepatectomies (PH) were performed on subsets of the mice. This procedure stimulates cell division and removes a large fraction of unintegrated DNA. As is evident, the high hFIX levels of the mice that received integrase remained stable after PH, while those of the mice that did not receive integrase dropped significantly. This result suggested that the high level hFIX expression observed was due to integrated hFIX plasmid, rather than to residual extrachromosomal DNA.

Analysis of total and extrachromosomal vector DNA in liver cells: To evaluate the numbers of extrachromosomal hFIX-attB plasmids present in various mouse liver samples, electrocompetent *E. coli* were transformed with equal quantities of DNA prepared from livers before and after PH. Plating on chloramphenicol selection medium and counting colonies allows quantitation of extrachromosomal hFIX-attB vectors present in the liver. The PH caused loss of ~80-90% of the extrachromosomal hFIX-attB plasmids from the liver, independent of integrase. Furthermore, mice that received integrase had significantly lower numbers of extrachromosomal vectors than did mice that received integrase, consistent with integrase-mediated integration of a large portion of delivered vectors.

A primer/probe set for Taqman quantitative PCR that detects the chloramphenicol resistance gene in the hFIX-attB vector was used in to quantitate the amount of vector DNA persisting in the liver after PH. This method measures the total number of vector molecules present, independent of whether they are integrated or extrachromosomal. The pre-PH amounts of total vector are approximately equivalent for all mice. Post-PH levels reveal that inclusion of integrase causes greater persistence of the hFIX-attB vector, suggesting its genomic integration.

Identification of genomic pseudo attP integration sites in vivo: To prove that φC31 integrase-mediated genomic integration had occurred, we sought to demonstrate covalent linkage of the hFIX plasmid with sequences in the genomes of liver cells. The persistence of transfected extrachromosomal plasmid DNA in the liver made standard plasmid rescue methods unfeasible, so a nested inverse PCR approach was employed (see Experimental Protocol) to specifically amplify integration junctions (attL) that would be indicative of genomic integration. By using this approach, two different genomic integration sites were identified and named mpsl and mpsL2, for mouse pseudo site from liver. By using primers in the attB site in combination with primers flanking the mpsL1 and mpsL2 genomic regions, the attL and attR junctions were PCR amplified from the liver genomic DNA of mice that received integrase and the attB donor. The resultant bands were sequenced and aligned with the genomic sites. The switch from attB to genomic sequence at or near the TTG core and the detectable sequence identity between the genomic sequence and attP confirmed integrase-riiediated integration at genomic pseudo attP sites.

The PCR primers that detect mpsl attL were used to screen all of the livers harvested from animals that received the hAAT-attB or hFIX-attB plasmid, with and without integrase. 100% (13/13) of the livers that received integrase were positive for the PCR band indicating integration at mpsL1, whereas 0% (0/7) of the animals that did not receive integrase showed an integration event at mpsL1. This result was statistically significant ($p<0.00001$) and suggested that integration at the mpsL1 pseudo attP site in liver cells was a frequent event specifically mediated by the φC31 integrase.

Quantitation of in vivo site-specific integration events: We employed Taqman quantitative PCR to determine the fraction of genomes in a given liver that contained integration events at mpsl and mpsL2. A primer/probe set that specifically amplified the attL junction resulting from integration of attB at mpsl was used in combination with another probe set that allowed quantitation of haploid genomes using the single copy target gene RAD52. The percent of haploid liver genomes that were positive for an integration at mpsL1 ranged from 0.62 to 3.44, with an average of 1.8%+/−0.89%. If 2% of haploid genomes have an integration event at mpsL1, then up to 4% of diploid genomes may carry such an event. If we obtained the maximal 40% transfection efficiency for the delivery reported for the hydrodynamic injection method, then ~10% of the transfected liver cells may have experienced an integration event at mpsL1. A similar analysis at the mpsL2 site revealed that integrations at this position were close to the lower limit of detection and >100-fold lower than the integration frequency at mpsL1.

This demonstrates that the phage phiC31 integrase is highly effective at site-specifically integrating introduced plasmid DNA bearing an attB site into endogenous positions in the genome of mouse liver cells. The high frequency of integration and the robust level of gene expression resulting from integrated DNA were sufficient to provide normal plasma levels of human factor IX that remained stable long-term. Therefore, introduction of the FIX gene by using this integrase system is expected to provide a permanent cure for hemophilia in mouse models and in patients.

Example 14

Phage φC31 Integrase-Mediated Gene Therapy in a Mouse Model of Hereditary Tyrosinemia Type I In this study, we tested the ability of this system to provide gene therapy in the mouse model of Hereditary Tyrosinemia Type 1 (HT1), deficient in fumarylacetoacetate hydrolase (FAH) (Grompe et al., 1993 Genes Devel. 7, 2298-2307.).

The full-length cDNA human FAH sequence was cloned into two vectors, one with an attB site (PBC-B FAH1) and one without an attB site (pBC-FAH1). Each construct was injected into FAH−/− mice in a 1:1 ratio with the integrase vector (PCSI) or an empty vector control (pCS) (Groth et al., 2000 Proc. Natl. Acad. Sci. USA 97, 5995-6000) by using high-pressure tail vein injection (Zhang et al., 1999 Human Gene Therapy 10, 1735-1737). The mice were removed from the protective drug NTBC to allow for selection of the FAH+ hepatocytes (Grompe et al., 1995 Nature Genetics 10, 453459). After 20 days, the mouse livers were harvested and histologically evaluated for FAH+cells. Most FAH+ nodules of integrase-treated liver consisted of dysplastic cells, which may be related to integrase over-expression in conjunction features of the disease cell background. Nodules produced by lower doses of integrase are not dysplastic.

Mice harvested after longer selection (90 days) had >75% repopulation with FAH+hepatocytes that appeared healthy and of normal size. Therefore, long-term, stable correction of the FAH deficiency was possible with the integrase system. The copy number and structure of integrase-mediated insertion events are under investigation.

By using integrases evolved to target particular sites in the mouse genome, we obtain high-frequency, more specific integration that can correct the FAH deficiency even more efficiently.

Example 15

Construction of Transgenic Mice

Integrase mRNA, as well as integrase DNA were tested. For the injections, either the integrase expression vector pCMVint or φC31 integrase RNA were co-injected with the assay vector pBCPB (Groth et al., 2000 Proc. Natl. Acad. Sci. USA 97, 5995-6000). The assay vector pBCPB contains a lacZ gene flanked by both attB and attP sites. The φC31 integrase protein recognizes the attB and attP sites, catalyzing intramolecular integration, resulting in the removal of the lacZ gene from the pBCPB plasmid backbone. The action of the site-specific integrase leaves precise recombination products that can be assayed by PCR through the use of recombination sequence specific primers.

Single cell embryos from FVB/NacfBR strain (Taconic laboratories) were injected with 3 ng/μl nucleic acid solutions (diluted in miTE) directly into the pronucleus (femto-liter range). Two groups of embryos were studied, one receiving pCMVint (n=31) and the other integrase RNA (n=32). Both groups were co-injected along with the assay vector pBCPB. The embryos were then frozen at the two cell stage and DNA was extracted. Primers were used to specifically amplify the wild type attL junction in integrase reacted assay vector. A product of correct size was observed in the groups of embryos that received integrase RNA or DNA. The group co-injected with integrase RNA produced a band of correct size with ~25% of the template required to detect a band of correct size in the pCMVint/pBCPB DNA injections. This shows that integrase mRNA is more efficacious than DNA in the embryonic environment. A control experiment performed in tissue culture was unable to detect integrase action in cells transfected with pET11φC3 lpolyA, which has a T7 bacteriophage promoter).

Proof of integrase-mediated, site-specific genomic integration in the embryonic environment: The above pilot experiment proved that integrase was active on plasmid DNA injected into mouse embryos. We then confirmed that site-specific genomic integration could also occur. We have previously shown that φC31 integrase can recognize and insert attB containing circular DNA into pseudo attP sites in the murine genome. Pseudo attP sites are sequences in the genome that have partial identity to the wild type attP sequence (Thyagarajan et al., 2000 Gene 244, 47-54; Thyagarajan et al., 2001 Molecular and Cellular Biology 21, 3926-3934). A major location for φC31 integrase mediated integration was identified in vivo in hepatocytes and was named mpsL1 (mouse pseudo site in liver) (E. C. Olivares and M. P. Calos, manuscript submitted). The mpsL1 pseudo attP site is contained on a BAC clone whose GenBank accession number is AC 079573). Following identification of this pseudo site in hepatocytes, mpsL1 integration was also detected in the NIH3T3 cell line, showing that mpsl appears to be a site commonly used by φC31 integrase in the mouse genome and is likely to be a useful site to assay integration in many, if not all, murine tissues.

For this experiment the GFP vector pEGFPB2 carrying an attB site was injected either with (n=35) or without (n=27) φC31 integrase mRNA. GFP expression was used to assay the number of embryos with integrated DNA, because non-integrated DNA would be lost during a 5 day incubation with rapid cellular division in vitro to the multi-cell or blastocyst stage. The two groups had similar numbers of GFP positive clones (6/35 of those receiving integrase and 5/27 without integrase n=5/27). However, the group that received the integrase mRNA contained embryos with a more intense green fluorescence, probably indicating early, stable integration of the GFP gene-containing vector into pseudo sites.

Following fluorescent microscopic analysis, the embryos were harvested for DNA extraction as before. This DNA was then applied as a template in a PCR assay, designed to amplify the attL junction produced when φC31 integrase mediates site-specific integration at mpsL1. The group that received φC31 integrase RNA produced a band of 208 bp that was subsequently cloned and sequenced. The DNA sequence of 70 bp from the embryonic PCR product clearly demonstrated φC31 integrase-mediated site-specific integration at mpsL1. There was one base mismatch located downstream of the crossover event, which may be a polymorphism in the mouse FVB/NacfBR strain. Detection of integration at the mpsL1 site proved that φC31-mediated site-specific integration occurred within the embryonic genome.

Production of integrase-mediated, site-specific genomic integrant animals. In order to obtain animals modified with φC31 site-specific integrase, a larger quantity (>100) of embryos were injected with pFIXB2, with or without φC31 integrase mRNA. The embryos were implanted into surrogate mothers, at 20 embryos per animal. When the pups were about three weeks old, tail clips are taken for genomic DNA isolation and subsequent screening for site-specific integration. Pups are first PCR screened, and then genomic DNA of positive integrants is further investigated through Southern analysis. These data prove that the insertions are site-specific integration events. Therefore transgenic animals are produced though the utilization of the site-specific φC31 integrase system. These resultant animals have a single copy of a transgene efficiently placed site-specifically in their genomes, a accomplishment not feasible with any other existing technology.

Use of an integrase optimized by directed evolution to integrate preferentially at a pre-chosen genomic pseudo site produces efficient integration with a high degree of specificity for the designated integration site.

Materials and methods. Vectors used: The φC31 integrase gene was amplified to include the NdeI restriction site from the pTA-int plasmid (Groth et al., 2000 Proc. Natl. Acad. Sci.

USA 97, 5995-6000) using the primers Native 5' NdeI (+) (CGA CTA GTC ATA TGG ACA CGT ACG CGG GTG CT) (SEQ ID NO:199) and 3' BamHI φC31 (AGC CGG ATC CGG GTG TCT CGC TA) (SEQ ID NO:200). The pET11 vector (Novagen) has the previously amplified φC31 integrase gene directionally inserted into NdeI and BamHI sites so that the T7 promoter drives φC31 integrase RNA production (pET11φC31). The oligonucleotides BamHI-polyA-top (GAT CGC GCC AAA AAA AAA AAA AAA AAA AAA AAA AAA AAA CCG) (SEQ ID NO:201) and BamHI-polyA-bottom (GAT CCG GTT TTT TTT TTT TTT TTT TTT TTT TTT TTT TGG CGC) (SEQ ID NO:202) were annealed, digested with BamHI and inserted into the BamHI site in pET11φC31 to create pET11C31polyA. The φC31 integrase expression vector pCMVInt was described previously (Groth et al., 2000 Proc. Natl. Acad. Sci. USA 97, 5995-6000). The wild type att site assay vector pBCPB was also described (Groth et al., 2000 Proc. Natl. Acad. Sci. USA 97, 5995-6000). The assay construct pEGFPB2 is based on the vector pEGFP—N2 from Clonetech. A lacZ promoter (to drive GFP expression in bacteria) and the first 26 amino acids of α-galactosidase were cloned into the multicloning site of pEGFP—N2 in frame with eGFP to create pCMVlacGFP. The attB fragment was released from pTA-attB (described previously) with EcoRI and the ends of the fragment were blunted. The blunt attB fragment was inserted into pCMV-lacGFP vector, blunted at the DraIII restriction site. This cloning of the attB with the TTG core pointing towards the GFP terminator sequence resulted in creation of the assay vector pEGFPB2. A similar vector was made having the human factor IX mini-gene (Miao et al., 2000 Molecular Therapy 1, 522-532) in place of GFP.

Nucleic acid preparations for microinjection: The φC31 integrase mRNA was transcribed from the vector pET11φC31 polyA using the mMessage mMachine (Ambion). φC31 RNA and DNA were purified and diluted in microinjection TE (miTE) buffer (10 mM Tris and 0.1 mM EDTA, pH 7.4) to reach a final concentration of 3 ng//μl. For the injections 3 ng/μl of each nucleic acid is used. For example embryos injected with integrase RNA and assay vector, the final nucleic acid concentration is 6 ng//μl. All DNA and RNA preparations were tested for functionality in tissue culture prior to injection.

PCR screening for integration: Standard embryo DNA retrieval technique for PCR was employed (Page et al., 1995 Transgenic Res. 4, 12-17). The primers attBF2 (ATG TAG GTC ACG GTC TCG AAG C) (SEQ ID NO:203) and attP1+ (TGG CGG CCG CTC TAG AAC TA) (SEQ ID NO:204) were used to specifically amplify the wild type attL junction in integrase reacted pBCPB, a 175 bp product will be amplified. For detection of mpsl integration in embryos, a primary PCR using the primers attBF3 (CGA AGC CGC GGT GCG) (SEQ ID NO:205) and mpsL1-R2 (GTA AAT GTT ATT GCG GCT CT) (SEQ ID NO:206) was purified and used as a template in a secondary PCR using attBF3 as before and the nested primer mpsL1-R1 (TGA GGA GGA GCC TTA GCA AC) (SEQ ID NO:207). The secondary PCR amplifies a nested product of 208 bp. Pups were PCR screened using attBF3 and mpsL1-R2. Positive integrants at mpsL1 resulted in a 513 bp product.

Example 16

Construction of Transgenic Fish

In this method, the phiC31 integrase is provided as either an mRNA or in the form of a protein extract.

Production of φC31 integrase protein. The integrase enzyme is purified, either from a crude extract of *E. coli* or 293 cells expressing the protein. The protein does not need to be completely pure. Partially purified integrase is produced by expressing the integrase with 6×His tags in *E. coli* and fractionating it over the complementary column. Crude or partially purified integrases are tested for activity in an in vitro assay prior to injection to confirm their efficacy.

Production of φC31 integrase mRNA. Integrase mRNA is produced by in vitro transcription of the integrase gene using either T3, T7, or SP6 RNA polymerase. This RNA is checked for efficacy in 293 cells prior to injection into fish embryos.

Microinjection into embryos. Microinjection of the integrase protein and the plasmid containing an attB site is performed as described (Ivics, Z., et al., 1993 Mol Mar Biol Biotechnol. 2:162-173). Briefly, approximately 106 copies of the attB plasmid are injected into the cytoplasm of early fish embryos at the 1 to 2 cell stage. This DNA is mixed with either purified or crude protein extracts containing the integrase enzyme or with mRNA encoding the integrase. This mixture is incubated at 0° C. for 10 minutes and at room temperature for 20 minutes prior to injection.

Screening for transgenic fish. Initial screening for the presence of transgenic fish is done by using a reporter gene such as GFP. Fish embryos positive for GFP are analyzed further. DNA is prepared from transgenic fish and the integration site is determined by plasmid rescue. This allows us to determine whether the integration was catalyzed by the integrase or was random in nature.

Once active pseudo sites are identified, integrases are evolved to target the preferred pseudo site with higher efficiency and specificity, as described (Sclimenti et al., 2001 Nucleic Acids Research 29, 5044-5051).

Successful application of integrase technology is useful in the effort to generate transgenic fish for research and commercial purposes.

Example 17

Construction of Transgenic Insects with Altered Integrases

We show that the φC31 integrase system provides such a system, as demonstrated in the convenient laboratory insect, *Drosophila melanogaster*.

Materials and Methods Transient intramolecular recombination assay: For expression of φC31 integrase in *Drosophila* cells, a plasmid, DInt, which expresses integrase under the inducible control of the metallothionien promoter, was constructed as follows. The φC31 integrase gene was removed from the plasmid pCMVInt (Groth et al., 2000 Proc. Natl. Acad. Sci. USA 97, 5995-6000) by digestion with BamHI and SpeI, blunted with T4 DNA polymerase, and ligated into the unique EcoRV site of the plasmid pMK33. The plasmid pBCPB+ (Groth et al., 2000 Proc. Natl. Acad. Sci. USA 97, 5995-6000) containing a lacZ gene flanked by wt attB and attP sites was used to assay recombination. *Drosophila* S2 cells were maintained at 25° in Schneider medium supplemented with 9% fetal bovine serum and 1% penicillin/streptomycin. Cells were transfected with Fugene6 as follows. The DNA (2.05 μg of salmon sperm DNA, 50 ng pBCPB+2 μg of salmon sperm DNA, 2 μg of DInt and 50 ng salmon sperm DNA, or 2 μg pDInt and 50 ng pBCPB+ was added to an eppendorf tube. 100 μl Opti-Mem was added to each tube, followed by 12.3 μl Fugene6. After a 15-30 minute incubation, the mixture was added to a 60 mm dish of S2 cells at ~80% confluency. At 24 hours, 50 μl DNase was added to destroy unintegrated DNA and 1% of culture volume of $CuSO_4$ was added to induce the integrase. At 72 hours, the DNA was harvested for Hirt extractions (Hirt, 1967 J. Mol.

Biol. 26, 365-369). The Hirt protocol was adapted for *Drosophila* cells as described (Smith and Calos, 1995 Chromosoma 103:597-605).

Pseudo site identification: The attB-containing plasmid pDrBB2 was created as follows. The hygromycin gene driven by the copia promoter was removed from pMK33. The hygromycin gene was removed from pBBl (Thyagarajan, et al, 2000) and replaced with the copia-hygromycin cassette. To create the plasmid DInt-hyg, the hygromycin gene was removed from the plasmid DInt. The plasmid pDrBB2 was cotransfected with pDlnt into S2 cells. The integrase was induced at 24 hours by the addition of $CuSO_4$. Cells were selected with 125 µg/mL hygromycin for ~6 weeks, at which time the cells were harvested and the genomic DNA was recovered with the Qiagen Blood and Cell Culture Maxi kit.

Whole fly experiments: The plasmid pYellowP was created by removing attP from pTAattP (Groth et al., 2000 Proc. Natl. Acad. Sci. USA 97, 5995-6000) by SpeI digestion, blunting it, and cloning it into pCarY (gift of B. Baker, Stanford University), which had been linearized by SmaI digestion. The resulting plasmid, pYellowP contains a P-element that includes the yellow gene and the φC31 attP. The plasmid pWhiteB was created by removing the attB from pTAattB by SalI digestion, and cloning it into pUAST (gift of R. Nusse, Stanford Universityi), which had been linearized with BamHI. The resulting plasmid, pWhiteB, contains the white+ gene and the φC31 attB.

Results In order to test whether the φC31 integrase functioned in *Drosophila* cells, a plasmid was constructed which expresses the integrase gene under the control of the metallothionein promoter. This plasmid was contransfected with the assay plasmid pBCPB+into *Drosophila* S2 cells. Integrase was induced with $CuSO_4$ at 24 hours, and the cells were harvested at 72 hours. The low molecular weight DNA was harvested by Hirt extraction and transformed into bacteria to assay for recombination. The plasmid pBCPB+contains the lacZ gene flanked by the φC31 attachment sites. If a recombination event occurred in the *Drosophila* cells, the resulting plasmid would result in a white colony on plates containing X-Gal. If no recombination event occured, lacZ is expressed and the plasmid results in a blue colony.

The frequency of recombination was calculated by counting the white colonies and dividing by the total number of colonies and multiplying by 100. The experiment was repeated in triplicate and included a no DNA transfection, an Int only, a pBCPB+only, and three plates transfected with Int and assay plasmid. In order to ensure that recombination occurred in the *Drosophila* and not in the bacteria, the two plasmids were transformed into bacteria. All white colonies that resulted from a control transfection or transformation were analyzed by PCR for the recombination junction, and none had the expected band. Twenty-one white colonies from the Int+assay plasmid transfections were analyzed by PCR, and 18 had the expected product. Transfections with pDInt and pBCPB+resulted in an average of 48% white colonies. The results are shown in Table 5:

| Transfection | N | Total colonies | % white |
| --- | --- | --- | --- |
| no DNA | 3 | no colonies | — |
| pDInt only | 3 | no colonies | — |
| pBCPB+ only | 3 | 1000 | 1.7% ± 2.5% |
| pDInt + pBCPB+ | 9 | 8418 | 47.8% ± 11.7% |

Once it was established that the integrase functioned at a high level in the *Drosophila* environment, experiments were conducted to determine whether the *Drosophila* genome contained native pseudo attP sequences that could support φC31 integrase-mediated integration. In order to recover only integration events and not unintegrated plasmid, a PCR rescue technique was utilized. The genomic DNA was digested with two enzymes, for example HindIII and EcoRI, that cut on either side of the attB in pDrBB2. The digested DNA was then ligated overnight under dilute conditions (20 ng/µl). The small pieces of DNA that would result from unintegrated plasmid are not able to ligate to themselves due to incompatible ends. However, if an integration event occurred, the plasmid might have integrated near an EcoRI site. If an EcoRI site is found in the genome before a HindIII site, then the EcoRI sites could ligate to each other forming a minicircle.

The ligations were then subjected to nested PCR across the ligation junction. Bands of different sizes were gel isolated and Topo cloned using the Topo cloning kit (Invitrogen). Resulting clones were sequenced and analyzed with the BLAST program. Sequences that were identified as *Drosophila* sequences were subjected to further analysis. Oligonucleotides were designed to the *Drosophila* genome flanking the crossover region. AttL and attR junctions were then amplified by PCR from the selected genomic DNA, Topo cloned, and sequenced. Perfect crossovers were found at several genomic sequences. Three pseudo attP sites from the *Drosophila* genome were discovered.

Whole fly experiments: Experiments were conducted to discover whether φC31 integrase functioned in vivo in *Drosophila*. First, embryos were coinjected with 150 ng/µL pBCPB+ and either 600 ng/µL pDInt DNA or 800 ng/µL φC31 integrase mRNA. At 24 hours, the embryos were harvested, heated to 95°, incubated with Qiagen protease, and crushed. The DNA was then amplified by PCR for the recombination junction. Both groups were positive for recombination by PCR. The rest of the DNA was ethanol precipitated and transformed into *E. coli*. The integrase plasmid group showed a recombination frequency of 87.5% (7 whites, 1 blue). The integrase RNA group had a 100% recombination frequency (132 whites, 0 blues).

In order to determine whether the integrase can mediate integration into the *Drosophila* chromosome, 8 attP fly lines were created by coinjecting pYellowP and a P-element transposase-expressing plasmid into *Drosophila* embryos. Embryos from the lines are injected with integrase RNA and pWhiteB. The resulting flies are crossed to white-eyed flies, and the resulting red-eyed flies represent integration events. The flies are then further characterized by PCR and sequence analysis to demonstrate site-specific integration events.

The integrase is subjected to directed evolution to recognize the desired target sequence (Sclimenti et al., 2001) in the *Drosophila* genome at high efficiency. The DNA or mRNA corresponding to the evolved integrase is injected into embryos to direct site-specific integration into the target sequence in *Drosophila* genome, resulting in transgenic flies having the specific desired integration event.

Example 18

Stable Genetic Correction of Inherited Human Skin Disease

Materials and Methods

RDEB patients and cell growth Type VII collagen-deficient RDEB patients, as defined by clinical, immunohistological, ultrastructural and genetic criteria, were selected from the National Epidermolysis Bullosa Registry site at Stanford University. All patients studied had confirmed mutations in COL7A1 and an absence of Type VII collagen protein in skin, as defined by immunochemistry and immunoblotting of skin cell extracts. Normal control keratinocytes were obtained from unrelated individuals unaffected by EB. Cells were isolated and grown in culture in 50% serum-free medium (GIBCO/BRL) and 50% medium154 (Cascade Biologics).

Vectors and gene transfer The 250 base pair phiC31 attB sequence was inserted as a BglII fragment into the BglII sites of the backbone vector pcDNA3.1/zeo creating the plasmid pcDNAattB. IRES and blastocidin resistance sequences were removed from pWZL Blast vector as a blunted SnabI-NheI fragment which was inserted into the EQoRV/XbaI sites of pcDNAattB, creating the plasmid pcDNAattB-IB. Subsequently, the COL7A1 cDNA and LacZ genes were cloned as an EcoRI, HindII/EcoRI and EcoRI (blunt)/BamHI fragments into the EcoRI, HindIII/EcoRI, and HindIII (blunt)/BamHI sites, respectively, of pcDNAattb-IB, creating the transfer plasmids, pCOL7A1-attB and pLacZ-attB. Primary keratinocytes from RDEB patients deficient in collagen VII, were transfected with pCMVInt and either pCOL7A1-attB and pLacZ-attB using a modified polybrene shock. 3 Days later cells were subjected to 10 days of blasticidin selection (4ug/ml). Efficiency of gene transfer was verified by immunofluorescence microscopy and immunoblot analysis.

Plasmid rescue sequence analysis of integrants at pseudo attP sites After 10 days selection, keratinocyte colonies were trypsinized and subcloned at limiting dilution to obtain highly proliferative holoclone progenitors. Genomic DNA was extracted and linearized with HindIII which cuts once in the transfer plasmid. Digests were ligated with T4 ligase then extracted with phenol:chloroform and ethanol precipitated, with a fraction electroporated into competent DH10B *Escherichia Coli* cells. Bacteria were plated on Luria-Bertani agar containing 50ug Zeozin/ml and 100ug of ampicillin/ml to select for two of the resistance genes contained by COL7A-attB. Plasmid DNA was prepared from single colonies and subjected to restriction mapping and DNA sequencing to confirm genomic integration as described.

Animal Studies RDEB patient and normal control skin was regenerated using early passage keratinocytes on CB. 17 scid/scid mice using porcine dermal substrate to avoid immune cross-reactivity of antibodies to Type VII collagen as described. At 4, 8 and 12 weeks postgrafting, human skin tissue was excised and analyzed.

Analysis of Protein Expression and Tissue Ultrastructure Antibodies to human Type VII collagen, including rabbit antisera (Calbiochem) and the monoclonal antibody NP185 (gift of Lynn Y. Sakai) were used to verified expression of full-length Type VII collagen on immunoblot analysis. Keratinocyte extracts were prepared and 20 µg of extract protein electrophoresed on a 6% polyacrylamide gel. Blots were incubated simultaneously with BRG1, an internal control for protein concentration, extract quality and transfer efficiency. For immunohistochemistry, skin cryosections were fixed and immunostained with the rabbit antibodies to human Type VII collagen followed by a fluorescein labeled secondary antibody (Jackson Immunoresearch). Sections were also analyzed by electron microscopy and immunogold electron microscopy to assess human anchoring fibril formation and ultrastructure.

Results

Stable gene delivery to primary human epidermal cells using the phiC31 integrase We studied the capacity of the phiC31 integrase to stably introduce genes into a primary human cell type that represents a clinically relevant target for ex vivo gene therapy, epidermal keratinocytes. To do this, we generated transfer plasmid vectors encoding CMV promoter-driven COL 7A I cDNA and LacZ marker control that contained the phiC31 attB targeting sequence. Primary human epidermal keratinocytes were transfected with the pLacZ transfer vector with and without co-transfection with a phiC31 integrase expression plasmid. Both populations displayed a similar percentage of X-gal[+] cells 2 days after transfection (45.6+/−0.8% and 44.5+/−1.4%, respectively). After growth without selection for 14 days after transfection, however, the population co-transfected with the integrase expression vector displayed 33.4+/−2.3 fold more X-gal[+] cells, with a total of 15+/−3.1% of cells X-gal[+]. Therefore, the phiC31 integrase enhances the sustainability of gene delivery to primary human epidermal cells in vitro.

Restoration of Type VII collagen protein expression in epidermal progenitors Delivery of the Type VII collagen cDNA in RDEB has been hindered by its large size. Because phiC31 integrase-based gene delivery functions in a less size-constrained manner than other approaches to stable gene integration, we tested its ability to achieve stable COL7A1 gene expression in primary RDEB keratinocytes. To do this, we used primary epidermal cells from 4 unrelated patients with RDEB characterized by mutant COL7A1 alleles and absent Type VII collagen protein expression in skin; similar results in our studies were obtained in each patient in all cases. Primary RDEB cells were transfected with pCOL7A1 and pLacZ transfer plasmids with and without co-transfection with phiC31 integrase-encoding plasmid. To enrich the percentage of corrected cells in the bulk population, cells were exposed to short-term drug selection for 10 days. 14 days post-transfection, RDEB cells receiving both integrase and pCOL7A1 plasmids displayed restored expression of full-length Type VII collagen protein; expression was undetectable in control RDEB cells. At this timepoint, >99% of cells in RDEB[+] bulk populations demonstrated normalized cell morphology and expression of Type VII collagen protein by immunohistochemistry. Targeting the long-lived progenitors of high proliferative capacity that are capable of long-term self-renewal within such bulk populations is a pre-requisite of durable corrective epidermal gene delivery in this tissue. To study this, we subcloned cells at limiting dilution to isolate progenitor holoclone cells of high proliferative capacity and analyzed integration status. 98% of holoclones displayed stable gene integration, with 33% (3/9) of these integrating at a single previously characterized human genomic attP site A on chromosome 8. Thus, phiC31 integrase-based gene transfer stably integrates delivered genes into the genomes of epidermal progenitors.

Type VII collagen protein expression in RDEB patient skin tissue in vivo We next tested if phiC31 integrase-based COL7A1 gene transfer to epidermal progenitors could support correction of the major tissue disease features of RDEB. After 10 days selection in vitro, pCOL7A1 transfected cells were used to regenerate human skin tissue on immune deficient mice. This approach generates human tissue that faithfully shares the structural, functional and gene expression characteristics of the human donor, including recapitulation of abnormalities in a range of genodermatoses. Control transfected RDEB skin displayed histologic evidence of blistering and entirely lacked Type VII collagen expression characteristic of RDEB diseased donor skin. Skin regenerated from pCOL7A1 transfected RDEB cells from the same patients, however, displayed normal histology without dermal-epidermal separation. Furthermore, expression of Type VII collagen protein was correctly polarized to the cutaneous basement membrane zone in a fashion indistinguishable from normal controls. Consistent with confirmed targeting of epidermal holoclone progenitor cells, this normalized expression persisted for the full duration of the experiment. This time period spans multiple epidermal turnover cycles whose 3 to 4 week cycle was previously defined for regenerated human skin. Therefore, phiC31 integrase-based gene transfer to epidermal progenitors supports durable normalization of tissue histology and Type VII collagen protein expression in vivo.

Restoration of anchoring fibrils in vivo The ultrastructural consequences of COL7A1 ablation in mice and humans include an absence of anchoring fibrils in the epidermal basement membrane zone. To determine if anchoring fibrils were produced by expressed Type VII collagen in regenerated RDEB patient skin, we performed electron microscopy. While control transfected RDEB skin tissue failed to demonstrate detectable human anchoring fibrils, these structures were restored in pCOL7A1-expressing RDEB skin. Immunoelectron microscopy using species-specific antibodies to human Type VII collagen confirmed their human origin. These findings confirm restoration of the major ultrastructural abnormality characterizing RDEB.

Our findings indicate that nonviral gene transfer using the PHIC31 integrase supports corrective gene delivery in human tissue from a severely affected inherited skin disease via stable integration into progenitor cell genomes.

Example 19

Integrative Repair of a Defective CFTR Gene

Cystic fibrosis affects approximately 30,000 American and the most common fatal genetic disorder in the US. The gene for the disease was cloned in 1989, providing the raw material for gene therapy (Riordan et al., 1989 Science 245, 1066-1073). The defective gene is called CFTR, for cystic fibrosis transmembrane conductance regulator.

In this example, the CFTR gene is placed on a plasmid carrying a φC31 attB sequence and co-introduced with the φC31 integrase to mediate genomic integration of the CFTR-attB plasmid. The cDNA for CFTR is placed under control of a cellular promoter such as that for ubiquitin C, which gives relatively stable expression (Gill et al., 2001 Gene Therapy 8, 1539-1546). Expression is enhanced and prolonged after site-specific integration, and effectively treats the symptoms of cystic fibrosis.

A further strategy involves correction of the mutation involved in the disease, rather than simply addition of a surrogate correct copy. An advantage of correction is that the native CFTR promoter will be used to control expression of the gene, so that the correct expression pattern will be obtained.

A common mutation present in cystic fibrosis patients is the ΔF508 mutation in exon 9 of the CFTR gene (Collins, 1992 Science 256, 774-779). Integrative repair of the gene is brought about by targeting a correct copy of exon 9 to the defective gene. This targeting is accomplished by evolving an integrase to recognize a pseudo attP site present in an intron upstream of exon 9, for example in the intron immediately upstream of exon 9. Targeting integration to an intron rather than an exon ensures that small mutations that may be created at the integration site will not disturb the coding sequence. The attB plasmid contains the sequence downstream of the pseudo attP site, including the correct exon 9 and the correct remainder of the gene, in either the genomic or cDNA version.

The result of this integrative repair strategy is a CFTR gene in which the mutant version has been effectively disrupted and repaired by the addition of correct coding sequence. Because the disease is autosomal recessive, patients have two mutant chromosomes carrying the ΔF508 mutation. An active evolved integrase has the capacity to correct one or both copies of the mutant gene in target cells. Correction of one copy suffices to correct the disease phenotype, and correction of both copies is even more effective.

This strategy can be applied equally well to repair other genetic defects, even if they involve large-scale deletions or other rearrangements, by targeting a non-coding sequence such as an intron upstream of the disease lesion and introducing the correct downstream portion of the gene. The remaining defective portion of the gene will be severed from its control sequences and is not expressed. Transcriptional terminator sequences present on the correcting attB vector prevent read-through into the remnant defective portion of the gene. The corrected version of the disease gene is expressed in patient cells, and it may be expressed under correct native cellular tissue-specific control.

Example 20

Integrative Activation of the Gamma Globin Gene to Treat Sickle Cell Anemia

Sickle cell disease is one of the commonest genetic diseases worldwide but no effective gene therapy has been developed.

Effective treatment of sickle cell anemia can be provided using site-specific integration technology (Thyagarajan et al., 2001 Molecular and Cellular Biology 21, 3926-3934), that can bring about long-term expression through genomic integration of target genes into well-expressed chromosomal locations.

One strategy is to use the φC31 integrase to place a plasmid carrying attB and an expressed γ-globin or a mutant anti-sickling β-globin into a safe site in the genomes of hematopoietic stem cells of the patient, then introduce the corrected cells by bone marrow transplantation, after which they will re-populate the blood.

In another strategy, the native, inactive γ-globin gene, which is naturally anti-sickling, is activated in blood cells by using an altered, site-specific integrase to integrate an active promoter upstream of the γ-globin gene. This integration is carried out by searching the sequence upstream of the γ-globin gene for pseudo attP sites. An integrase is then evolved, for example by using methods that have been described (Sclimenti et al., 2001 Nucleic Acids Research 29, 5044-5051.), that has high specificity for the pseudo attP site upstream of the γ-globin gene.

This integrase is used to integrate a plasmid carrying attB adjacent to a promoter active in red blood cells, such as the β-globin promoter, upstream of the γ-globin gene. Hematopoietic stem cells from the patient are electroporated with the attB-promoter and evolved integrase plasmids, resulting in efficient integration of the β-globin promoter upstream of the γ-globin gene and its resultant activation. The modified hematopoietic stem cells are reintroduced into the patient by bone marrow transplantation and lead to production of red blood cells in which γ-globin is expressed in concert with γ-globin, correcting the sickling defect.

This gene activation strategy can also be employed in other gene therapy strategies in which activation of a native gene leads to correction of the disease phenotype.

Example 21

Therapeutic Modification of Stem Cells to Correct Genetic Diseases

If a patient has a homozygous mutation that knocks out function of a critical gene, then nuclei from the patient's cells can be transferred to enucleated oocytes or blastocysts from a donor, creating a line of embryonic stem (ES) cells genetically matched to the patient. A gene therapy method can then be applied to correct the ES cells in culture. The corrected ES cells would be caused to differentiate into the desired tissue by appropriate culture conditions, then the corrected cells would be engrafted on the patient, effecting a treatment of the disease.

In a recent landmark study (Rideout III et al., 2002 Cell. 109:17-27), created a Rag2$^{-/-}$ line of mouse ES cells by transplanting nuclei from immune-deficient Rag2$^{-/-}$ mice into enucleated oocytes and culturing the blastocyts. They then corrected one copy of the Rag2 gene by using homologous recombination. The repaired ES cells were differentiated into hematopoietic precursors, and these cells were engrafted into mutant mice. Partial correction of the immune deficiency was detectable within 3-4 weeks as these precursor cells proliferated and some immune system function was restored (Rideout III et al., 2002).

A step in this protocol is the use of homologous recombination to correct the genetic defect in the patient-derived ES cells. Because of the low frequency of homologous recombination, substantial time in tissue culture is required to execute genetic repair.

An alternative procedure involves use of a site-specific integrase such as the φC31 integrase (Groth et al., 2000 Proc. Natl. Acad. Sci. USA 97, 5995-6000; Thyagarajan et al., 2001 Molecular and Cellular Biology 21, 3926-3934) to perform genetic correction in the nuclear transfer-derived ES cells. In this case, the protocol is as follows. To correct the immune deficiency in patients with severe combined immune deficiency due to homozygous mutations at the human RAG2 gene, nuclei from somatic patient cells are transferred to enucleated donor nuclei or blastocysts and early embryo cells are cultured to produce an ES cell line. These patient-derived ES cells are transfected with integrase (as DNA, mRNA, or protein) and a plasmid carrying a correct copy of the RAG2 gene and an attB site.

The integrase is subjected to directed evolution (Sclimenti et al., 2001 Nucleic Acids Research 29, 5044-5051) so that it recognizes a preferred position in the genome, such as a safe location where strong, stable gene expression is obtained. Alternatively, the integrase can directly repair the affected gene by targetting integration into an intron upstream of the mutational lesion and integrating a corrected downstream portion of the gene. The integrase efficiently integrates a functional RAG2 gene into the ES cell genome at a specific position. A highly efficient integrase has the potential to correct both copies of the chromosomes carrying the RAG2 mutations.

The corrected patient-derived ES cells are differentiated in vitro by using the correct culture conditions that produce hematopoietic stem cells (Wiles and Keller, 1991 Development 111, 259-267). These cells are engrafted into the patient and lead to restoration of immune function.

This protocol and others similar to it can be used to correct other genetic diseases involving the hematopoietic lineage and also diseases involving other tissues that can be derived from ES cells. The ability to efficiently correct ES cells by using a site-specific integrase facilitates the genetic correction step of the protocol.

Example 22

Expression of Aprotinin in Tobacco Chloroplasts

Constructs for the Expression of Aprotinin in Chloroplasts
A DNA construct is prepared to direct the expression of the pharmaceutical protein aprotinin in the chloroplast. The nucleic acid sequence encoding for aprotinin is cloned into a plastid expression construct to control the expression of aprotinin from the T7 gene 10 leader promoter which is induced by a nuclearly expressed, plastid targeted T7 Polymerase, as described in as described in U.S. Pat. No. 5,576,198. Thus, pPROTININ contains an attV site, a nucleic acid encoding spectinomycin resistance and, as operably linked the T7 promoter, a nucleotide encoding for aprotinin and the psbA 3' transcription termination sequence. Tobacco plants have previously been transformed with a vector expressing a modified integrase that is targeted to the chloroplast with a chloroplast transit peptide.

Plastid transformation Tobacco plastids are transformed by particle gun delivery of microprojectiles as described by Svab and Maliga (Proc. Natl. Acad. Sci. (1993) 90:913-917). Dark green, round leaves are cut, preferably from the middle of the shoots, from 3-6 week old *Nicotiana tabacum* cv. Havana which have been maintained in vitro on hormone free MS medium (Murashige and Skoog, (1962) Physiol Plant. 15, 473-497) supplemented with B5 vitamins in Phytatrays or sundae cups with a 16 hour photoperiod at 24° C. Each cut leaf is then placed adaxial side up on sterile filter paper over tobacco shoot regeneration medium (TS0 medium: MS salts, 1 mg/l N$^6$-benzyladenine, 0.1 mg/l 1-naphthaleneacetic acid, 1 mg/l thiamine, 100 mg/l inositol, 7 g/l agar pH 5.8 and 30 g/l sucrose). Leaves are preferably placed in the center of the plate with as much contact with the medium as possible. The plates are preferably prepared immediately prior to use, but may be prepared up to a day before transformation by particle bombardment by wrapping in plastic bags and storing at 24° C. overnight.

Tungsten or gold particles are sterilized for use as microcarriers in bombardment experiments. Particles (50 mg) are sterilized with 1 ml of 100% ethanol, and stored at −20° C. or −80° C. Immediately prior to use, particles are sedimented by centrifugation, washed with 2 to 3 washes of 1 ml sterile deionised distilled water, vortexed and centrifuged between each wash. Washed particles are resuspended in 500 ul 50% glycerol.

Sterilized particles are coated with DNA for transformation. Twenty-five micoliter aliquots of sterilized particles are added to a 1.5 ml microfuge tube, and 5 ug of DNA of interest is added and mixed by tapping. Thirty-five microliters of a freshly prepared solution of 1.8 M CaCl$_2$ and 30 mM spermidine is added to the particle/DNA mixture, mixed gently, and incubated at room temperature for 20 minutes. The coated particles are sedimented by centrifuging briefly. The particles are washed twice by adding 200 ul 170% ethanol, mixing gently, and centifuging briefly. The coated particles are resuspended in 50 ul of 100% ethanol and mixed gently. Five to ten microliters of coated particles are used for each bombardment. Transformation by particle bombardment is carried out using the PDS 1000 Helium gun (Bio Rad, Richmond, Calif.) using a modified protocol described by the manufacturer. Plates containing the leaf samples are placed on the second shelf from the bottom of the vacuum chamber and bombarded using the 1100 p.s.i. rupture disk. After bombardment, petri plates containing the leaf samples are wrapped in plastic bags and incubated at 24° C. for 48 hours.

After incubation, bombarded leaves are cut into approximately 0.5 cm$^2$ pieces and placed abaxial side up on TSO medium supplemented with 500 ug/ml spectinomycin.

After 3 to 4 weeks on the selection medium, small, green spectinomycin resistant shoots will appear on the leaf tissue. These shoots will continue to grow on spectinomycin containing medium and are referred to as primary putative transformants.

When the primary putative transformants have developed 2 to 3 leaves, 2 small pieces (approximately 0.5 cm²) are cut from each leaf and used for either selection or for a second round of shoot regeneration. One piece is placed abaxial side up on plates containing TSO medium supplemented with 500 ug/ml spectinomycin, and the other piece is placed abaxial side up on TSO medium supplemented with 500 ug/ml each of spectinomycin and streptomycin. Positive transformants are identified as the shoots which form green callus on the TSO medium containing spectinomycin and streptomycin.

After 3 to 4 weeks, the tissue placed on TSO medium containing only spectinomycin, which has been identified as positive on the TSO medium with spectinomycin and streptomycin, will develop green shoots. Two to four shoots of each positive transformant are selected and transferred to TSO medium supplemented with 500 ug/ml spectinomycin for generation of roots. Southern analysis is performed on 2 shoots to confirm homoplasmy as described below. Shoots from homoplasmic events are transferred to the greenhouse for seed production, while transformants which are not homoplasmic are sent through a second round or regeneration on TSO medium with 500 ug/ml spectinomycin to attain homoplasmy.

Western Analysis of Aprotinin Expression in Chloroplasts Transformants are screened using PCR using a pair of PCR primers designed against the aprotinin gene. Homoplasmic tobacco lines expressing spectinomycin resistance are used to determine the expression of the aprotinin protein. Western blot analysis is performed on tobacco lines containing the pAPROTININ construct. Total protein extractions and western blot procedures are performed with a primary antibody raised against aprotinin.

Example 23

Expression of a Gene Providing Insect Resistance in Maize

Vector preparation for expression of *Bacillus thuringiensis* endotoxin Of particular importance in maintaining yield from corn plants and contributing significantly to controlling the cost of growing a corn crop is the protection of the corn against attack by insect pests. In the USA the major insect pests of corn include a variety of Lepidoptera pests such as the European corn borer, cutworms and earworms as well as Coleoptera species such as *Diabrotica* spp. The protection of corn against insect attack is expensive to the grower and requires the use of toxic chemical insecticides applied in a timely manner. Since traditional methods of breeding and selection have not allowed for the development of new lines of corn that are substantially resistant to major insect pests, the introduction and inheritance of insect resistance genes or sequences in corn plants in accord with the present invention would reduce costs to the grower, reduce the use of toxic chemical insecticides and provide for more effective control of insect pests.

Essential components of the present invention are the introduction of the insect resistance gene into the corn cell, mitotic replication of the gene so that the gene is incorporated into whole corn plants and is ultimately inherited by subsequent offspring of the plant via the processes of mitotic and meiotic division.

*Bacillus thuringiensis* (or "Bt") bacteria include nearly 20 known subspecies *of* bacteria which produce endotoxin polypeptides that are toxic when ingested by a wide variety of insect species. The biology and molecular biology of the endotoxin proteins (Bt proteins) and corresponding genes (Bt genes) has been reviewed by H. R. Whitely et al., Ann. Rev. Microbiol., 40, 549 (1986) and by H. Hofte et al., Microbiol. Rev., 53, 242 (1989). Genes coding for a variety of Bt proteins have been cloned and sequenced. Research has demonstrated that a segment of the Bt polypeptide is essential for toxicity to a variety of Lepidoptera pests and is contained within approximately the first 50% of the Bt polypeptide molecule. Consequently, a truncated Bt polypeptide coded by a truncated Bt gene will in many cases retain its toxicity towards a number of Lepidoptera insect pests. The HD73 and HD1 Bt polypeptides have been shown to be toxic to the larvae of the important Lepidoptera insect pests of corn plants in the USA such as the European corn borer, cutworms and earworms. The genes coding for the HD1 and HD73 Bt polypeptides have been cloned and sequenced by M. Geiser et al., Gene, 48, 109 (1986) and M. J. Adang et al., Gene, 36, 289 (1985), respectively, and can be cloned from HD1 and HD73 strains obtained from culture collections (e.g. *Bacillus* Genetic Stock Center, Columbus, Ohio or USDA Bt stock collection Peoria, Ill.) using standard protocols. The HD73 peptide is cloned into a integration vector that contains a hygromycin resistance gene for selection of transgenic plants. A separate vector is prepared for expression of a modified integrase, which is co-bombarded with the HD73 plasmid.

DNA Delivery AB12 callus is prepared for bombardment as follows. Five clumps of callus, each approximately 50 mg in wet weight are arranged in a cross pattern in the center of a sterile 60×15 mm petri plate (Falcon 1007). Plates are stored in a closed container with moist paper towels, throughout the bombardment process. Twelve plates are prepared.

Plasmids are coated onto M-10 tungsten particles (Biolistics) exactly as described by Klein et al. (Bio/Technol., 6, 559-563 (1988) except that, (i) twice the recommended quantity of DNA is used, (ii) the DNA precipitation onto the particles is performed at 0° C., and (iii) the tubes containing the DNA-coated tungsten particles are stored on ice throughout the bombardment process. All of the tubes contain 25 ul of 50 mg/ml M-10 tungsten in water, 25 ul of 2.5 M CaCl, and 10 ul of 100 mM spermidine along with a total of 5 ul of 1 mg/ml plasmid DNA. When both plasmids are used, each is present in an amount of 2.5 ul. All tubes are incubated on ice for 10 min., the particles are pelleted by centrifugation in an Eppendorf centrifuge at room temperature for 5 seconds, 25 ul of the supernatant is discarded. The tubes are stored on ice throughout the bombardment process. Each preparation is used for no more than 5 bombardments. Macroprojectiles and stopping plates are obtained from Biolistics, Inc. (Ithaca, N.Y.). They are sterilized as described by the supplier. The microprojectile bombardment instrument is obtained from Biolistics, Inc.

The sample plate tray is placed 5 cm below the bottom of the stopping plate tray of the microprojectile instrument, with the stopping plate in the slot nearest to the barrel. Plates of callus tissue are prepared as described above and centered on the sample plate tray and the petri dish lid removed. A 7×7 cm square rigid wire mesh with 3×3 mm mesh and made of galvanized steel is placed over the open dish in order to retain the tissue during the bombardment. Tungsten/DNA preparations are sonicated as described by Biolistics, Inc. and 2.5 ul of the suspensions are pipetted onto the top of the macroprojectiles for each bombardment. The instrument is operated as described by the manufacturer. The bombardments are performed.

Selection of Transformants and Recovery of Plant and Seed

Hygromycin B (Calbiochem) is incorporated into the medium prior to pouring plates by addition of the appropriate volume of filter-sterilized 100 mg/ml hygromycin B dissolved in water, when the medium had cooled to 45° C. Immediately after all samples had been bombarded, callus from all of the plates bombarded with pHYGI1/pBII221 is transferred onto F medium containing 15 mg/l hygromycin B (ten pieces of callus per plate). These are referred to as round 1 selection plates. After 14 days of selection, tissue appeared essentially identical on both selective and nonselective media. All callus from seven plates of the pHYGI1/pBII221 are transferred from round 1 selection plates to round 2 selection plates that contained 60 mg/l hygromycin. The round 2 selection plates each contain ten 30 mg pieces of callus per plate. After 21 days on the round 2 selection plates, all of the material is transferred to round 3 selection plates containing 60 mg/l hygromycin. After 79 days post-bombardment, the round 3 sets of selection plates are checked for viable sectors of callus. Proliferating callus is transferred to F medium without hygromycin. After 19 days on F medium without hygromycin, proliferatige callus is transferred to F-medium containing 60 mg/l hygromycin. Proliferatige callus is found to be capable of sustained growth through multiple subcultures in the presence of 60 mg/l hygromycin.

Portions of proliferatige callus are transferred directly from plates containing 60 mg/l hygromycin to RM5 medium which consists of MS basal salts (Murashige et al. 1962) supplemented with thiamine-HCl 0.5 mg/l, 2,4-D 0.75 mg/l, sucrose 50 g/l, asparagine 150 mg/l, and Gelrite 2.5 g/l (Kelco Inc., San Diego). After 14 days on RM5 medium, the majority of the proliferating callus and unselected control callus is transferred to R5 medium (RM5 medium, except that 2,4-D is omitted). The plates are cultured in the dark for 7 days at 26° C. and transferred to a light regime of 14 hrs light and 10 hrs dark for 14 days at 26° C. At this point, plantlets are transferred to one quart canning jars (Ball) containing 100 ml of R5 medium. Plants are transferred from jars to vermiculite for 7 or 8 days before transplanting them into soil and growing them to maturity.

Controlled pollinations of mature plants are conducted by standard techniques with inbred Zea mays lines MBS501 (Mike Brayton Seeds), FR4326 (Illinois Foundation Research) and the proprietary inbred line LM1112. Seed is harvested 45 days post-pollination and allowed to dry further for 1-2-weeks. Such methods of corn transformation, and regeneration are well known in the art e.g. U.S. Pat. Nos. 6,331,665, 6,160,208.

Analysis of the transgenic plants R1 plants are tested for the presence of the HPT and Bt endotoxin sequences by PCR analysis. Expression of the HPT gene is determined with an enzymatic assay for HPT activity. The transgenic corn plants produced herein plants are infested with European Corn Borer larvae to determine an insect resistance phenotype. Transgenic plants are expected to be at least partially resistant to infection by the European Corn Borer larvae.

Example 24

Activation of Endogenous Gene Expression

Vector preparation for activation of endogenous CBF in *Arabidopsis* Plant productivity is greatly affected by environmental stresses such as drought, salt loading, and freezing. It has been reported that overexpression of the cDNA encoding DREB 1A in transgenic plants results in improved tolerance to drought, salt loading, and freezing. However, use of the strong constitutive 35S cauliflower mosaic virus (CaMV) promoter to drive expression of DREB 1A results in severe growth retardation under normal growing conditions. In this example, a method is provided whereby exogenous DREB1A is activated using an exogenous stress inducible rd29A promoter (Kasuka et al Nat Biotechnol. 1999 17:287-291). It is predicted that this will give rise to minimal effects on plant growth while providing an even greater tolerance to stress conditions than expression of the gene from the CaMV promoter.

In this vector, the rd29A promoter is placed adjacent to an attV site in the vector and the integrase is evolved to recognize a site in the 500 base pairs of sequence immediately 5' adjacent to the ATG start codon of the DREB1A gene. The vector is a Ti vector based on the plant transformation vector pPZP100 (Hajdukiewicz Plant Mol. Biol. 1994 25:989-94). A separate vector expressing the modified integrase is prepared. The constructs are introduced into Agrobacterium tumefaciens by electroporation. The *Arabidopsis* plants selected for transformation are grown under continuous illumination in 9 cm pots at approximately 2500 lux and 22° C. for 6 weeks. *Agrobacterium* cultures are mixed and the plants are transformed by the vacuum infiltration method, as is known in the art. Transgenic $T_o$ seedlings are germinated on plates containing MS media with 50 ug/ml kanamycin and transgenic seedlings are selected. That the seedlings are transgenic is confirmed by PCR of the kanamycin resistance gene. Transgenic seedlings are transferred and grown in 9 cm pots filled with a 1:1 mixture of perlite and vermiculite. They are grown under continuous illumination of approximately 2500 lux at 22° C. Separate samples of the 3-week-old plants are exposed to freezing and drought stresses. Freezing stress is conducted by exposing the plants to −6° C. temperatures for 2 days, then returning to 22° C. for 5 days. Drought stress is conducted by withholding water for 2 weeks. High-salt stress are created by soaking plants that are grown on agar plates and gently pulled out of the growing medium in 600 mM NaCl solution for 2 h. The plants are then transferred to pots under normal growing conditions for 3 weeks. Plants containing the exogenous DNA are predicted to have better resistance to freezing and drought stresses.

Example 25

Inactivation of Endogenous Gene Function

Many plants contain proteins that are undesirable in regard to human use of the plant. For example, the castor plant *Ricinus communis* (L.) contains genes that encode the toxic protein ricin. The presence of ricin in the meal of the castor beans make the unprocessed meal unsuitable for applications such as feeding animals or other uses of plant proteins. Similarly, the presence of lectins in peanuts poses a health risk to many humans. The presence of lectins in the latex of rubber trees renders the latex gloves made from the rubber a health risk for many people who frequently wear latex gloves. Thus, it would be desirable to produce modified plants in which the genes encoding these or other undesirable plant proteins were inactivated. In many cases it has not been possible to accomplish this goal by breeding or by the application of mutagenic treatments followed by mutant screening. The invention described herein can be used to inactivate any plant gene, including the examples described here.

As noted in the foregoing examples, it is possible to modify the phiC31 integrase so that it will catalyze recombination between an attV site and a site near to or within any gene of interest. The former examples also illustrate that it is possible to introduce DNA into plants by a variety of methods such as biolistic methods or *agrobacterium*-mediated transformation. Thus, these methods can be combined to inactivate any deleterious gene in any plant. In brief the steps involved in accomplishing this are as follows:

A gene encoding the undesirable protein is cloned into a bacterial plasmid.

A modified phiC31 integrase is evolved so that the modified integrase will catalyze integration of a native or modified attV site into the gene of interest.

The modified integrase is cloned into a plasmid so that the gene is under transcriptional control of a suitable promoter and polyadenylation sequence so that it will be expressed in the plant of interest. The plasmid also contains the attV site that was used in the evolution of the modified integrase or, in some cases, the integrase and the attV site may be on separate plasmids. The plasmid containing the attV site also contains a marker gene that facilitates identification of plant cells in which the plasmid has become stably integrated. Suitable markers may include genes encoding beta-glucuronidase, fluorescent proteins, antibiotic resistance genes, herbicide resistance genes or genes that allow growth of plant cells under conditions that would not normally support growth.

The plasmid or plasmids containing the modified integrase and the att site are introduced into cells of the target plant and stable transformants are selected or identified. Tissues derived from stably transformed cells are then screened to identify events in which the plasmid containing the att site has integrated into the target gene. This screening can be readily accomplished by the polymerase chain reaction using oligonucleotide primers homologous to the integrating plasmid and the target gene. The same screen can also be accomplished by other methods such as southern blotting.

Upon identification of stable transformants in which the target gene has been inactivated, fertile plants are produced and self fertilized to produce progeny with homozygous gene inactivations. In some cases, such as where a diploid plant is vegetatively propagated, it will generally be necessary to screen for stable transformants in which both copies of the target gene have been inactivated by insertion of the integrating plasmid. Such stable transformants can then be vegetatively propagated and will be homozygous for the gene inactivation. In some cases it may be possible to apply the same method to plants with higher levels of ploidy than diploidy, and by screening large numbers of stable transformation events, to identify individuals in which all copies of the target gene have been inactivated.

Example 26

Improved Method of Plant Transformation

In brief the steps involved in accomplishing this are as follows:

A gene that is to be introduced into the plant is cloned into a bacterial plasmid containing an attV site. The plasmid will also typically contain a gene encoding a protein (a selectable marker) that confers a selectable phenotype on a transformed plant such as the ability to grow under conditions that will not support the growth of the nontransformed plants. Such conditions include growth in the presence of herbicides or antibiotics or growth on any chemical compound that is normally inhibitory to the growth of the non-transformed plant. Alternatively, instead of a selectable marker, the plasmid may contain a gene encoding a protein that leads to the formation of a readily recognizable change in the color or some other property of the transformed plant (i.e., a visible marker). Such proteins include fluorescent proteins such as the green fluorescent proteins from jellyfish, or proteins that encode enzymes that catalyze changes in the color of chemical compounds such as 5-bromo-4-chloro-3-indoyl-B-D-glucuronide or proteins such as beta-glucuronidase that alter the subcellular accumulation of fluorescent compounds such as Imagene Green. The plasmid may also contain a native or evolved integrase gene that contains a promoter and polyadenylation sequence that permits expression of the integrase gene in the plant and translation of a functional integrase protein. In some cases the integrase will have been previously modified so that it recognizes a preferred target sequence in the plant genome. Examples of suitable promoter and polyadenylation sequences include the cauliflower mosaic virus 35S promoter and the nopaline synthase polyadenylation sequence from the *Agrobacterium tumefaciens* Ti plasmid. As al alternative to placing the integrase on the same plasmid as the att site, the integrase may be on another plasmid that is simultaneously introduced into the target cells. This has the potential advantage that the plasmid containing the integrase gene may not be present in the stably transformed progeny cells.

In one implementation of the invention, the plasmid is introduced into cells of the apical meristem of seedlings, or the developing micro or megagametophytes, by physical methods such as particle bombardment or agitation with silicon carbide whiskers. The presence of stably transformed cells can be visualized by the development of progeny cells that express a visible marker. In many cases, the transformed cells will give rise to cell lineages that form the reproductive structures of the plant. Seeds resulting from the development of a mega- or microgametophyte from a cell lineage that has been stably transformed will be stably transformed. Such seeds can be identified by scoring the seedlings resulting from such seeds for the presence of the visible or selectable marker. Because of the high frequency with which the integrase catalyzes integration of DNA into the nuclear genome of the recipient, this method represents a significant improvement over methods that rely on physical introduction of DNA that does not contain the phiC32 integrase.

In another implementation of the invention the plasmid is introduced into gametophytic cells by first encapsulating the plasmid DNA in an anionic detergent preparation that is known to facilitate uptake of DNA into cells. The encapsulated DNA is then applied to the styles of receptive flowers which are then pollinated. Interaction of developing pollen tubes with the encapsulated DNA results in uptake of DNA into developing pollen tubes and integration of the plasmid into the nuclear genome of one or more pollen nuclei. The plants that result from fertilization of ovules with transformed pollen will be stably transformed.

In another implementation of the invention, the plasmid is introduced into pollen grains, developing pollen tubes, ovules or meristematic cells by microinjection. Because of the high efficient of the integrase, progeny cells of the injected cell will be stably transformed. Stably transformed plants resulting from growth and development of the transformed cells can be identified as described above.

Example 27

Removal of Ectopic DNA Following Transformation

Because of concern about the possible effects of certain genes that are introduced into plants during the transformation process, it may be desirable to remove part of the DNA that is introduced during transformation. This may be accomplished as follows.

The region of DNA that is introduced during the primary transformation process (the "transforming DNA") can be divided into two regions that we refer to here as A and B. Region A is intended to remain in the transformed plant permanently. Region B is intended to be lost from the transformed plant under specified conditions. Region B is defined as any region of DNA on the DNA construct that is used for transformation that is flanked by attV and attG sites, wherein the attV and attg sites are system sites for a system recombinase. Region B will typically also contain e.g. a native or modified recombinase that acts on the attV and attg sites used in the constructs. However, the recombianse may also be present on region A. The recombinase is placed under transcriptional control of a promoter as described below and contains a plant polyadenylation sequence.

Transgenic plants are produced that contain the transforming DNA. A wide range of methods are available to accomplish this result and the invention described herein is applicable to all such methods. Upon recovery of stably transformed tissues or plants the DNA in region B is excised by causing or expression of the integrase gene present on the transforming DNA. The region of DNA containing excised fragment B will not be replicated by the plant DNA replication machinery and will, therefore, not be transmitted to progeny cells. Expression of the integrase may be caused in a variety of ways. In one implementation, the integrase may be under transcriptional control of a chemically inducible promoter such as the dexamethasone-inducible promoter (Aoyama T, Chua N H (1997) A glucocorticoid-mediated transcriptional induction system in transgenic plants. PLANT JOURNAL 11, 605-612), phytohormones, elicitors, safeners, alcohol and so on. In another implementation expression may be caused by placing the integrase gene under transcriptional control of a developmentally regulated promoter such as a promoter that is induced by floral induction. In yet other implementations, expression of the integrase gene may be caused by the use of any of a wide variety of promoters that are induced by environmental treatments such as heat shock, cold shock, heavy metals, and so on.

It is evident from the above results and discussion that the subject invention provides an important new means for integrating a nucleic acid into a target cell genome. Specifically, the subject invention provides a system for integrating a nucleic acid in a site specific manner into the genome of a target cell, where the target cell may be a eukaryotic cell. As such, the subject methods and systems find use in a variety of different applications, including research, agricultural, therapeutic and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of site-specifically integrating a polynucleotide sequence of interest into the genome of an isolated cell, said method comprising:

introducing into the isolated cell (i) a circular targeting construct comprising a bacterial genomic recombination site (attB) and the polynucleotide sequence of interest, and (ii) a φC31 integrase or an expression cassette encoding the same, wherein the φC31 integrase comprises the amino acid sequence of SEQ ID NO:132, wherein the genome of the isolated eucaryotic cell comprises a pseudo-phage genomic recombination site (pseudo-attP) comprising a nucleic acid sequence of SEQ ID NO:102 and is native to the genome of the cell; and maintaining the isolated cell under conditions that allow recombination between the attB and the pseudo attP, wherein the recombination is mediated by the φC31 integrase and the recombination results in site-specific integration of the polynucleotide sequence of interest in the genome of the isolated cell.

2. The method of claim 1, wherein said polynucleotide sequence of interest is present in an expression cassette.

3. The method of claim 2, wherein said polynucleotide sequence of interest is a therapeutic gene.

4. The method of claim 2, wherein said polynucleotide sequence of interest comprises a eukaryotic coding sequence.

5. The method of claim 2, wherein said polynucleotide sequence of interest encodes a polypeptide.

6. The method of claim 2, wherein said polynucleotide sequence of interest encodes an RNA molecule.

7. The method of claim 1, wherein said cell is a mammalian cell.

8. The method of claim 7, wherein said mammalian cell is a human cell.

9. The method of claim 1, wherein said method comprises introducing an expression cassette encoding said φC31 integrase.

10. The method of claim 1, wherein said method comprises introducing said circular targeting construct concurrently with said φC31 integrase or an expression cassette encoding the same.

* * * * *

UNITED STATES PATENT AND TRADEMARK OFFICE
CERTIFICATE OF CORRECTION

PATENT NO. : 8,420,395 B2
APPLICATION NO. : 11/003941
DATED : April 16, 2013
INVENTOR(S) : Michele Pamela Calos It is certified that error appears in the above-identified patent and that said Letters Patent is hereby corrected as shown below:

In the Specification

In column 1, line 21, under the GOVERNMENT RIGHTS section, please replace lines 23-26 with the following:

--This invention was made with Government support under contracts DK058187, HG002571, and HL068112 awarded by the National Institutes of Health. The Government has certain rights in this invention.--

Signed and Sealed this
Twenty-fifth Day of June, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,420,395 B2 | Page 1 of 1 |
| APPLICATION NO. | : 11/003941 | |
| DATED | : April 16, 2013 | |
| INVENTOR(S) | : Calos | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this
Thirtieth Day of September, 2014

Michelle K. Lee
*Deputy Director of the United States Patent and Trademark Office*

SEQUENCE LISTING

```
<160> NUMBER OF SEQ ID NOS: 216

<210> SEQ ID NO 1
<211> LENGTH: 34
<212> TYPE: PRT
<213> ORGANISM: Bacteriophage Phi-C31

<400> SEQUENCE: 1

Asp Lys Gly Cys Ser Ala Val Gly Lys Tyr Gly Trp Gly Cys Met Ser
1               5                   10                  15

Thr Thr Ser Lys Ser His Tyr Ser Val Cys Ser Arg Asn Val Asn Asn
            20                  25                  30

His Asx

<210> SEQ ID NO 2
<211> LENGTH: 16
<212> TYPE: DNA
<213> ORGANISM: Bacteriophage Phi-C31

<400> SEQUENCE: 2
gtgccagggc gtgccc                                                    16

<210> SEQ ID NO 3
<211> LENGTH: 15
<212> TYPE: DNA
<213> ORGANISM: Bacteriophage Phi-C31

<400> SEQUENCE: 3
ggctccccgg gcgcg                                                     15

<210> SEQ ID NO 4
<211> LENGTH: 16
<212> TYPE: DNA
<213> ORGANISM: Bacteriophage Phi-C31
```

-continued

```
<400> SEQUENCE: 4
gtgccacggc gtcccc                                                   16

<210> SEQ ID NO 5
<211> LENGTH: 15
<212> TYPE: DNA
<213> ORGANISM: Bacteriophage Phi-C31

<400> SEQUENCE: 5
ggctcaccgt cgacg                                                    15

<210> SEQ ID NO 6
<211> LENGTH: 16
<212> TYPE: DNA
<213> ORGANISM: Bacteriophage Phi-C31

<400> SEQUENCE: 6
gtgccacgtc aagccc                                                   16

<210> SEQ ID NO 7
<211> LENGTH: 15
<212> TYPE: DNA
<213> ORGANISM: Bacteriophage Phi-C31

<400> SEQUENCE: 7
tgctcaccgg gcgcg                                                    15

<210> SEQ ID NO 8
<211> LENGTH: 16
<212> TYPE: DNA
<213> ORGANISM: Bacteriophage Phi-C31

<400> SEQUENCE: 8
gtgccacgtc aagccc                                                   16

<210> SEQ ID NO 9
<211> LENGTH: 15
<212> TYPE: DNA
<213> ORGANISM: Bacteriophage Phi-C31

<400> SEQUENCE: 9
tgctcaccgg gcgcg                                                    15

<210> SEQ ID NO 10
<211> LENGTH: 16
<212> TYPE: DNA
<213> ORGANISM: Bacteriophage Phi-C31

<400> SEQUENCE: 10
gtgccagggc gtggcc                                                   16

<210> SEQ ID NO 11
<211> LENGTH: 15
<212> TYPE: DNA
<213> ORGANISM: Bacteriophage Phi-C31

<400> SEQUENCE: 11
ggctgcccga gatcg                                                    15

<210> SEQ ID NO 12
<211> LENGTH: 16
<212> TYPE: DNA
<213> ORGANISM: Bacteriophage Phi-C31
```

-continued

<400> SEQUENCE: 12
gtgccagggc gtgccc                    16

<210> SEQ ID NO 13
<211> LENGTH: 15
<212> TYPE: DNA
<213> ORGANISM: Bacteriophage Phi-C31

<400> SEQUENCE: 13 tcccccoggg agcga                     15

<210> SEQ ID NO 14
<211> LENGTH: 16
<212> TYPE: DNA
<213> ORGANISM: Bacteriophage Phi-C31

<400> SEQUENCE: 14
atgccagggc gtgccg                    16

<210> SEQ ID NO 15
<211> LENGTH: 15
<212> TYPE: DNA
<213> ORGANISM: Bacteriophage Phi-C31

<400> SEQUENCE: 15
gcccccctag cgaca                     15

<210> SEQ ID NO 16
<211> LENGTH: 16
<212> TYPE: DNA
<213> ORGANISM: Bacteriophage Phi-C31

<400> SEQUENCE: 16
gttccagggc gatgcc                    16

<210> SEQ ID NO 17
<211> LENGTH: 15
<212> TYPE: DNA
<213> ORGANISM: Bacteriophage Phi-C31

<400> SEQUENCE: 17
agctccccgt ccgcg                     15

<210> SEQ ID NO 18
<211> LENGTH: 16
<212> TYPE: DNA
<213> ORGANISM: Bacteriophage Phi-C31

<400> SEQUENCE: 18
gagccagtgc gtcccc                    16

<210> SEQ ID NO 19
<211> LENGTH: 15
<212> TYPE: DNA
<213> ORGANISM: Bacteriophage Phi-C31

<400> SEQUENCE: 19
ggctccccgg acgca                     15

<210> SEQ ID NO 20
<211> LENGTH: 16
<212> TYPE: DNA
<213> ORGANISM: Bacteriophage Phi-C31

```
<400> SEQUENCE: 20
gtgccagggc gtgccg                                                    16

<210> SEQ ID NO 21
<211> LENGTH: 15
<212> TYPE: DNA
<213> ORGANISM: Bacteriophage Phi-C31

<400> SEQUENCE: 21
ggccccccgg gcgct                                                     15

<210> SEQ ID NO 22
<211> LENGTH: 16
<212> TYPE: DNA
<213> ORGANISM: Bacteriophage Phi-C31

<400> SEQUENCE: 22
gtgccagggc gtgccc                                                    16

<210> SEQ ID NO 23
<211> LENGTH: 15
<212> TYPE: DNA
<213> ORGANISM: Bacteriophage Phi-C31

<400> SEQUENCE: 23
ggatccccgg gcccc                                                     15

<210> SEQ ID NO 24
<211> LENGTH: 17
<212> TYPE: DNA
<213> ORGANISM: Bacteriophage Phi-C31

<400> SEQUENCE: 24
ctgccagggc gtgcacc                                                   17

<210> SEQ ID NO 25
<211> LENGTH: 15
<212> TYPE: DNA
<213> ORGANISM: Bacteriophage Phi-C31

<400> SEQUENCE: 25
ggctccccgg gtact                                                     15

<210> SEQ ID NO 26
<211> LENGTH: 16
<212> TYPE: DNA
<213> ORGANISM: Bacteriophage Phi-C31

<400> SEQUENCE: 26
gggacagggg gtgccc                                                    16

<210> SEQ ID NO 27
<211> LENGTH: 15
<212> TYPE: DNA
<213> ORGANISM: Bacteriophage Phi-C31

<400> SEQUENCE: 27
ggatccccga gcgcg                                                     15

<210> SEQ ID NO 28
<211> LENGTH: 16
<212> TYPE: DNA
<213> ORGANISM: Bacteriophage Phi-C31
```

<400> SEQUENCE: 28
gtgcgagggc gtgccc                                           16

<210> SEQ ID NO 29
<211> LENGTH: 15
<212> TYPE: DNA
<213> ORGANISM: Bacteriophage Phi-C31

<400> SEQUENCE: 29
ggtacgccct accat                                            15

<210> SEQ ID NO 30
<211> LENGTH: 16
<212> TYPE: DNA
<213> ORGANISM: Bacteriophage Phi-C31

<400> SEQUENCE: 30
gagtcagggc ctgccc                                           16

<210> SEQ ID NO 31
<211> LENGTH: 15
<212> TYPE: DNA
<213> ORGANISM: Bacteriophage Phi-C31

<400> SEQUENCE: 31
ggctctccgg gcgtg                                            15

<210> SEQ ID NO 32
<211> LENGTH: 16
<212> TYPE: DNA
<213> ORGANISM: Bacteriophage Phi-C31

<400> SEQUENCE: 32
gtgccagggc gtgccc                                           16

<210> SEQ ID NO 33
<211> LENGTH: 15
<212> TYPE: DNA
<213> ORGANISM: Bacteriophage Phi-C31

<400> SEQUENCE: 33
ggctcccccc gcctc                                            15

<210> SEQ ID NO 34
<211> LENGTH: 16
<212> TYPE: DNA
<213> ORGANISM: Bacteriophage Phi-C31

<400> SEQUENCE: 34
gagccagggc gtgccc                                           16

<210> SEQ ID NO 35
<211> LENGTH: 15
<212> TYPE: DNA
<213> ORGANISM: Bacteriophage Phi-C31

<400> SEQUENCE: 35
ggctccccga gcgcc                                            15

<210> SEQ ID NO 36
<211> LENGTH: 16
<212> TYPE: DNA
<213> ORGANISM: Bacteriophage Phi-C31

```
<400> SEQUENCE: 36
gtacctgggc gtgccc                                                   16

<210> SEQ ID NO 37
<211> LENGTH: 15
<212> TYPE: DNA
<213> ORGANISM: Bacteriophage Phi-C31

<400> SEQUENCE: 37
gactcaccgg gcgtg                                                    15

<210> SEQ ID NO 38
<211> LENGTH: 15
<212> TYPE: DNA
<213> ORGANISM: Bacteriophage Phi-C31

<400> SEQUENCE: 38
gactcaccgg gcgtg                                                    15

<210> SEQ ID NO 39
<211> LENGTH: 16
<212> TYPE: DNA
<213> ORGANISM: Bacteriophage Phi-C31

<400> SEQUENCE: 39
gtgccagggc gatccc                                                   16

<210> SEQ ID NO 40
<211> LENGTH: 15
<212> TYPE: DNA
<213> ORGANISM: Bacteriophage Phi-C31

<400> SEQUENCE: 40
ggctccccgg ccgtg                                                    15

<210> SEQ ID NO 41
<211> LENGTH: 16
<212> TYPE: DNA
<213> ORGANISM: Bacteriophage Phi-C31

<400> SEQUENCE: 41
gtgccaaggc gtgacc                                                   16

<210> SEQ ID NO 42
<211> LENGTH: 15
<212> TYPE: DNA
<213> ORGANISM: Bacteriophage Phi-C31

<400> SEQUENCE: 42
ggctccccgg gcgct                                                    15

<210> SEQ ID NO 43
<211> LENGTH: 16
<212> TYPE: DNA
<213> ORGANISM: Bacteriophage Phi-C31

<400> SEQUENCE: 43
atgccagggc gtgcca                                                   16

<210> SEQ ID NO 44
<211> LENGTH: 15
<212> TYPE: DNA
<213> ORGANISM: Bacteriophage Phi-C31
```

```
<400> SEQUENCE: 44
ggatccccag gcgcc                                                      15

<210> SEQ ID NO 45
<211> LENGTH: 16
<212> TYPE: DNA
<213> ORGANISM: Bacteriophage Phi-C31

<400> SEQUENCE: 45
gtgccagggc gtgccc                                                     16

<210> SEQ ID NO 46
<211> LENGTH: 15
<212> TYPE: DNA
<213> ORGANISM: Bacteriophage Phi-C31

<400> SEQUENCE: 46
ggctccccag cagcg                                                      15

<210> SEQ ID NO 47
<211> LENGTH: 16
<212> TYPE: DNA
<213> ORGANISM: Bacteriophage Phi-C31

<400> SEQUENCE: 47
gtgccacggc gtgccc                                                     16

<210> SEQ ID NO 48
<211> LENGTH: 15
<212> TYPE: DNA
<213> ORGANISM: Bacteriophage Phi-C31

<400> SEQUENCE: 48 ggcccccag gccca                                                       15

<210> SEQ ID NO 49
<211> LENGTH: 16
<212> TYPE: DNA
<213> ORGANISM: Bacteriophage Phi-C31

<400> SEQUENCE: 49 gtgcagggt gtgtcc                                                      16

<210> SEQ ID NO 50
<211> LENGTH: 15
<212> TYPE: DNA
<213> ORGANISM: Bacteriophage Phi-C31

<400> SEQUENCE: 50
ggcccgccgg gatcg                                                      15

<210> SEQ ID NO 51
<211> LENGTH: 16
<212> TYPE: DNA
<213> ORGANISM: Bacteriophage Phi-C31

<400> SEQUENCE: 51
gagccagggc gtgcca                                                     16

<210> SEQ ID NO 52
<211> LENGTH: 15
<212> TYPE: DNA
<213> ORGANISM: Bacteriophage Phi-C31
```

-continued

```
<400> SEQUENCE: 52
ggctccccga gcgcc                                                          15

<210> SEQ ID NO 53
<211> LENGTH: 16
<212> TYPE: DNA
<213> ORGANISM: Bacteriophage Phi-C31

<400> SEQUENCE: 53
gtgccagggc gtgcac                                                         16

<210> SEQ ID NO 54
<211> LENGTH: 15
<212> TYPE: DNA
<213> ORGANISM: Bacteriophage Phi-C31

<400> SEQUENCE: 54
ggctccccgg aaacc                                                          15

<210> SEQ ID NO 55
<211> LENGTH: 16
<212> TYPE: DNA
<213> ORGANISM: Bacteriophage Phi-C31

<400> SEQUENCE: 55
atgccagggc gtgccc                                                         16

<210> SEQ ID NO 56
<211> LENGTH: 15
<212> TYPE: DNA
<213> ORGANISM: Bacteriophage Phi-C31

<400> SEQUENCE: 56
ggctgcccgg gtgcg                                                          15

<210> SEQ ID NO 57
<211> LENGTH: 16
<212> TYPE: DNA
<213> ORGANISM: Bacteriophage Phi-C31

<400> SEQUENCE: 57
gtcccagggg atgcct                                                         16

<210> SEQ ID NO 58
<211> LENGTH: 15
<212> TYPE: DNA
<213> ORGANISM: Bacteriophage Phi-C31

<400> SEQUENCE: 58
ggctccctgg gcgcg                                                          15

<210> SEQ ID NO 59
<211> LENGTH: 16
<212> TYPE: DNA
<213> ORGANISM: Bacteriophage Phi-C31

<400> SEQUENCE: 59
gtgccggggc gtgccc                                                         16

<210> SEQ ID NO 60
<211> LENGTH: 15
<212> TYPE: DNA
<213> ORGANISM: Bacteriophage Phi-C31
```

```
<400> SEQUENCE: 60
ggctccccat gatcg                                                     15

<210> SEQ ID NO 61
<211> LENGTH: 16
<212> TYPE: DNA
<213> ORGANISM: Bacteriophage Phi-C31

<400> SEQUENCE: 61
gtgccaggca gtgccc                                                    16

<210> SEQ ID NO 62
<211> LENGTH: 15
<212> TYPE: DNA
<213> ORGANISM: Bacteriophage Phi-C31

<400> SEQUENCE: 62
ggctccccag gcgcg                                                     15

<210> SEQ ID NO 63
<211> LENGTH: 16
<212> TYPE: DNA
<213> ORGANISM: Bacteriophage Phi-C31

<400> SEQUENCE: 63
gtgacaaggc gggcgc                                                    16

<210> SEQ ID NO 64
<211> LENGTH: 15
<212> TYPE: DNA
<213> ORGANISM: Bacteriophage Phi-C31

<400> SEQUENCE: 64
ggctaccctc gcgcg                                                     15

<210> SEQ ID NO 65
<211> LENGTH: 16
<212> TYPE: DNA
<213> ORGANISM: Bacteriophage Phi-C31

<400> SEQUENCE: 65
gtgccagggc aagccc                                                    16

<210> SEQ ID NO 66
<211> LENGTH: 15
<212> TYPE: DNA
<213> ORGANISM: Bacteriophage Phi-C31

<400> SEQUENCE: 66
gtctctccgg gcgct                                                     15

<210> SEQ ID NO 67
<211> LENGTH: 16
<212> TYPE: DNA
<213> ORGANISM: Bacteriophage Phi-C31

<400> SEQUENCE: 67
gtggcagggc gtgccc                                                    16

<210> SEQ ID NO 68
<211> LENGTH: 15
<212> TYPE: DNA
<213> ORGANISM: Bacteriophage Phi-C31
```

-continued

```
<400> SEQUENCE: 68
ggttccccgg gcgag                                                    15

<210> SEQ ID NO 69
<211> LENGTH: 16
<212> TYPE: DNA
<213> ORGANISM: Bacteriophage Phi-C31

<400> SEQUENCE: 69
gtgccagggc cacccc                                                   16

<210> SEQ ID NO 70
<211> LENGTH: 15
<212> TYPE: DNA
<213> ORGANISM: Bacteriophage Phi-C31

<400> SEQUENCE: 70
ggctccccgg gcgcg                                                    15

<210> SEQ ID NO 71
<211> LENGTH: 16
<212> TYPE: DNA
<213> ORGANISM: Bacteriophage Phi-C31

<400> SEQUENCE: 71
gtgccagggc gtacca                                                   16

<210> SEQ ID NO 72
<211> LENGTH: 15
<212> TYPE: DNA
<213> ORGANISM: Bacteriophage Phi-C31

<400> SEQUENCE: 72
ggctccctgg gcgca                                                    15

<210> SEQ ID NO 73
<211> LENGTH: 16
<212> TYPE: DNA
<213> ORGANISM: Bacteriophage Phi-C31

<400> SEQUENCE: 73
ttgccagggc gtgcac                                                   16

<210> SEQ ID NO 74
<211> LENGTH: 15
<212> TYPE: DNA
<213> ORGANISM: Bacteriophage Phi-C31

<400> SEQUENCE: 74
tcttcggcgt gtgag                                                    15

<210> SEQ ID NO 75
<211> LENGTH: 16
<212> TYPE: DNA
<213> ORGANISM: Bacteriophage Phi-C31

<400> SEQUENCE: 75
atgccagggc gtctcc                                                   16

<210> SEQ ID NO 76
<211> LENGTH: 15
<212> TYPE: DNA
<213> ORGANISM: Bacteriophage Phi-C31
```

-continued

```
<400> SEQUENCE: 76
ggctcacccc gctcc                                                    15

<210> SEQ ID NO 77
<211> LENGTH: 16
<212> TYPE: DNA
<213> ORGANISM: Bacteriophage Phi-C31

<400> SEQUENCE: 77
gtgccagggc gtgccc                                                   16

<210> SEQ ID NO 78
<211> LENGTH: 15
<212> TYPE: DNA
<213> ORGANISM: Bacteriophage Phi-C31

<400> SEQUENCE: 78
ggcttcccgg ggggg                                                    15

<210> SEQ ID NO 79
<211> LENGTH: 16
<212> TYPE: DNA
<213> ORGANISM: Bacteriophage Phi-C31

<400> SEQUENCE: 79
gtgccagggt gtgccc                                                   16

<210> SEQ ID NO 80
<211> LENGTH: 15
<212> TYPE: DNA
<213> ORGANISM: Bacteriophage Phi-C31

<400> SEQUENCE: 80
ggctccccga gggag                                                    15

<210> SEQ ID NO 81
<211> LENGTH: 16
<212> TYPE: DNA
<213> ORGANISM: Bacteriophage Phi-C31

<400> SEQUENCE: 81
atgccagagc cagccc                                                   16

<210> SEQ ID NO 82
<211> LENGTH: 15
<212> TYPE: DNA
<213> ORGANISM: Bacteriophage Phi-C31

<400> SEQUENCE: 82
ggatccccgg gcgcg                                                    15

<210> SEQ ID NO 83
<211> LENGTH: 16
<212> TYPE: DNA
<213> ORGANISM: Bacteriophage Phi-C31

<400> SEQUENCE: 83
gtgccaaggc gtgccc                                                   16

<210> SEQ ID NO 84
<211> LENGTH: 15
<212> TYPE: DNA
<213> ORGANISM: Bacteriophage Phi-C31
```

-continued

```
<400> SEQUENCE: 84
ggctcccaag gcgtg                                                    15

<210> SEQ ID NO 85
<211> LENGTH: 16
<212> TYPE: DNA
<213> ORGANISM: Bacteriophage Phi-C31

<400> SEQUENCE: 85
atgccatgga gagacc                                                   16

<210> SEQ ID NO 86
<211> LENGTH: 15
<212> TYPE: DNA
<213> ORGANISM: Bacteriophage Phi-C31

<400> SEQUENCE: 86
ggcaccccgg gcgcc                                                    15

<210> SEQ ID NO 87
<211> LENGTH: 16
<212> TYPE: DNA
<213> ORGANISM: Bacteriophage Phi-C31

<400> SEQUENCE: 87
atgccagggt gtgccc                                                   16

<210> SEQ ID NO 88
<211> LENGTH: 15
<212> TYPE: DNA
<213> ORGANISM: Bacteriophage Phi-C31

<400> SEQUENCE: 88
ggctcccccg tcgct                                                    15

<210> SEQ ID NO 89
<211> LENGTH: 28
<212> TYPE: DNA
<213> ORGANISM: Bacteriophage Phi-C31

<400> SEQUENCE: 89
actggggtaa cctttgagtt ctctcagt                                      28

<210> SEQ ID NO 90
<211> LENGTH: 28
<212> TYPE: DNA
<213> ORGANISM: Bacteriophage Phi-C31

<400> SEQUENCE: 90
acttgggttt cccttggtgt ccccatgg                                      28

<210> SEQ ID NO 91
<211> LENGTH: 28
<212> TYPE: DNA
<213> ORGANISM: Bacteriophage Phi-C31

<400> SEQUENCE: 91
ccctcggaac ctctagggaa accccagg                                      28

<210> SEQ ID NO 92
<211> LENGTH: 28
<212> TYPE: DNA
<213> ORGANISM: Bacteriophage Phi-C31
```

<400> SEQUENCE: 92
cacaggatat ttgtaggact cccactgg                                      28

<210> SEQ ID NO 93
<211> LENGTH: 28
<212> TYPE: DNA
<213> ORGANISM: Bacteriophage Phi-C31

<400> SEQUENCE: 93
gacgggagag ctggagacag caccctgg                                      28

<210> SEQ ID NO 94
<211> LENGTH: 28
<212> TYPE: DNA
<213> ORGANISM: Bacteriophage Phi-C31

<400> SEQUENCE: 94
ccaaaggaag tctttcccta aacccagg                                      28

<210> SEQ ID NO 95
<211> LENGTH: 28
<212> TYPE: DNA
<213> ORGANISM: Bacteriophage Phi-C31

<400> SEQUENCE: 95
ccagggttag gcttaaagtg aacccaat                                      28

<210> SEQ ID NO 96
<211> LENGTH: 28
<212> TYPE: DNA
<213> ORGANISM: Bacteriophage Phi-C31

<400> SEQUENCE: 96
ccatagtaaa ctatacgcct attcaggg                                      28

<210> SEQ ID NO 97
<211> LENGTH: 28
<212> TYPE: DNA
<213> ORGANISM: Bacteriophage Phi-C31

<400> SEQUENCE: 97
acagtgaaaa ccttctagtt aaccatgg                                      28

<210> SEQ ID NO 98
<211> LENGTH: 28
<212> TYPE: DNA
<213> ORGANISM: Bacteriophage Phi-C31

<400> SEQUENCE: 98
cctcatttaa tctataggtt ctccttgt                                      28

<210> SEQ ID NO 99
<211> LENGTH: 28
<212> TYPE: DNA
<213> ORGANISM: Bacteriophage Phi-C31

<400> SEQUENCE: 99
ccatggtgaa gctaaagctg aatcttgg                                      28

<210> SEQ ID NO 100
<211> LENGTH: 28
<212> TYPE: DNA
<213> ORGANISM: Bacteriophage Phi-C31

```
<400> SEQUENCE: 100
ccctggagct tctaaaagat caccctga                                            28

<210> SEQ ID NO 101
<211> LENGTH: 28
<212> TYPE: DNA
<213> ORGANISM: Bacteriophage Phi-C31

<400> SEQUENCE: 101
ccagggaaaa gcttcagtct ctccctgg                                            28

<210> SEQ ID NO 102
<211> LENGTH: 28
<212> TYPE: DNA
<213> ORGANISM: Bacteriophage Phi-C31
<220> FEATURE:
<221> NAME/KEY: misc_feature
<222> LOCATION: 2, 6, 9, 13, 23, 24, 27
<223> OTHER INFORMATION: n = A,T,C or G
<220> FEATURE:
<221> NAME/KEY: misc_feature
<222> LOCATION: 2, 6, 9, 13, 23, 24, 27
<223> OTHER INFORMATION: n = A,T,C or G

<400> SEQUENCE: 102
ancganttnt ttnatgacag atnnaant                                            28

<210> SEQ ID NO 103
<211> LENGTH: 26
<212> TYPE: DNA
<213> ORGANISM: Bacteriophage Phi-C31
<220> FEATURE:
<221> NAME/KEY: misc_feature
<222> LOCATION: 2, 3, 4, 6, 7, 8, 9, 10, 12, 15, 16, 17, 18, 19, 20, 21,
      23, 24, 25
<223> OTHER INFORMATION: n = A,T,C or G
<220> FEATURE:
<221> NAME/KEY: misc_feature
<222> LOCATION: 2, 3, 4, 6, 7, 8, 9, 10, 12, 15, 16, 17, 18, 19, 20, 21,
      23, 24, 25
<223> OTHER INFORMATION: n = A,T,C or G

<400> SEQUENCE: 103
cnnngnnnnn cnttnnnnnn ncnnng                                              26

<210> SEQ ID NO 104
<211> LENGTH: 26
<212> TYPE: DNA
<213> ORGANISM: Bacteriophage Phi-C31
<220> FEATURE:
<221> NAME/KEY: misc_feature
<222> LOCATION: 2, 3, 6, 8, 9, 12, 13, 15, 16, 17, 18, 19, 21, 23, 24,
      25
<223> OTHER INFORMATION: n = A,T,C or G
<220> FEATURE:
<221> NAME/KEY: misc_feature
<222> LOCATION: 2, 3, 6, 8, 9, 12, 13, 15, 16, 17, 18, 19, 21, 23, 24,
      25
<223> OTHER INFORMATION: n = A,T,C or G

<400> SEQUENCE: 104
cnnggntnnc cnntnnnnnc ncnnng                                              26

<210> SEQ ID NO 105
<211> LENGTH: 14
<212> TYPE: DNA
<213> ORGANISM: Human
```

```
<220> FEATURE:
<221> NAME/KEY: misc_feature
<222> LOCATION: 11
<223> OTHER INFORMATION: n = A,T,C or G
<220> FEATURE:
<221> NAME/KEY: misc_feature
<222> LOCATION: 11
<223> OTHER INFORMATION: n = A,T,C or G

<400> SEQUENCE: 105
yyyyyyyyyy nyag                                                       14

<210> SEQ ID NO 106
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 106
cgcgtggtgc ttgcttagcg ctagcgcatg c                                    31

<210> SEQ ID NO 107
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 107
cgcgtgacgt caaaaccggt gcggccgcga attccggtcc gaaacctagg aaactgcagg     60
gcgcgccaaa gc                                                         72

<210> SEQ ID NO 108
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 108
taagctttgg cgcgccctgc agtttcctag gtttcggacc ggaattcgcg gccgcaccgg     60
ttttgacgtc a                                                          71

<210> SEQ ID NO 109
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 109
ggggtttaaa cggg                                                       14

<210> SEQ ID NO 110
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 110
cccgtttaaa cccc                                                       14
```

```
<210> SEQ ID NO 111
<211> LENGTH: 72
<212> TYPE: DNA
<213> ORGANISM: Phage T5

<400> SEQUENCE: 111
ctcataaaaa atttatttgc tttcaggaaa attttctgt ataatagatt cataaatttg      60
agagaggagt ta                                                         72

<210> SEQ ID NO 112
<211> LENGTH: 80
<212> TYPE: DNA
<213> ORGANISM: Phage T5

<400> SEQUENCE: 112
ccggtaactc ctctctcaaa tttatgaatc tattatacag aaaaattttc ctgaaagcaa     60
ataaattttt tatgagacgt                                                 80

<210> SEQ ID NO 113
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 113
gtccgtggat tgttcagaa cgctcggttg ccgccgggcg ttttttattg gc              52

<210> SEQ ID NO 114
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 114
ctaggccaat aaaaaacgcc cggcggcaac cgagcgttct gaacaaatcc acg            53

<210> SEQ ID NO 115
<211> LENGTH: 59
<212> TYPE: DNA
<213> ORGANISM: Bacteriophage Phi-C31

<400> SEQUENCE: 115
ggagtagtgc cccaactggg gtaacctttg agttctctca gttggggcg tagggtcgc       59

<210> SEQ ID NO 116
<211> LENGTH: 53
<212> TYPE: DNA
<213> ORGANISM: Bacteriophage Phi-C31

<400> SEQUENCE: 116
cgcgcctgcg ggtgccaggg cgtgcccttg ggctccccgg gcgcgtactc cgg            53

<210> SEQ ID NO 117
<211> LENGTH: 53
<212> TYPE: DNA
<213> ORGANISM: Bacteriophage Phi-C31

<400> SEQUENCE: 117
cgcgccggag tacgcgcccg gggagcccaa gggcacgccc tggcacccgc agg            53
```

```
<210> SEQ ID NO 118
<211> LENGTH: 20
<212> TYPE: DNA
<213> ORGANISM: Human

<400> SEQUENCE: 118
cgttgggacc cgtttccgtg                                                    20

<210> SEQ ID NO 119
<211> LENGTH: 20
<212> TYPE: DNA
<213> ORGANISM: Human

<400> SEQUENCE: 119
agagacgagg agaggggagc                                                    20

<210> SEQ ID NO 120
<211> LENGTH: 475
<212> TYPE: DNA
<213> ORGANISM: Human

<400> SEQUENCE: 120
atttgtagaa ctattatggg acttaaaggg gatatgggag gccacagttg agatgccttc        60
caatcagagg cttggtgaga ttccaagagg tggtttcaaa tacagcaata agtacttggg       120
tttcccttgg tgtccccatg gagattttaa gccatgacgc aatgtttaaa tcagagtggt       180
atttttatga cttaagcggg taaatatgca attggaaaat attcagggaa gggtgatttg       240
gtccagaaga gtgggggcat ccagagtaca gtgggtgaaa tggatcggac tttttggaag       300
agagccttgt gctggacagg atggtccagt attgtcaaca caagtttctc atgcttcact       360
ctccttccta gcaacaggaa gacggaaatg aggccatgga aaaataaaag accctgaaag       420
actccagaca ataccctgatc caccctacca ttcaccctgt atagccagaa gactt          475

<210> SEQ ID NO 121
<211> LENGTH: 20
<212> TYPE: DNA
<213> ORGANISM: Human

<400> SEQUENCE: 121
atttgtagaa ctattatggg                                                    20

<210> SEQ ID NO 122
<211> LENGTH: 20
<212> TYPE: DNA
<213> ORGANISM: Human

<400> SEQUENCE: 122
aagtcttctg gctatacagg                                                    20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
gtcacgctcg agagatctga                                                    20

<210> SEQ ID NO 124
<211> LENGTH: 19
<212> TYPE: DNA
<213> ORGANISM: Artificial Sequence
```

```
<220> FEATURE:
<223> OTHER INFORMATION: Synthetic oligonucleotide

<400> SEQUENCE: 124
ctagtcagat ctctcgagc                                                  19

<210> SEQ ID NO 125
<211> LENGTH: 1842
<212> TYPE: DNA
<213> ORGANISM: Bacteriophage Phi-C31

<400> SEQUENCE: 125
atgacacaag gggttgtgac cggggtggac acgtacgcgg gtgcttacga ccgtcagtcg      60
cgcgagcgcg aaaattcgag cgcagcaagc ccagcgacac agcgtagcgc caacgaagac     120
aaggcggccg accttcagcg cgaagtcgag cgcgacgggg gccggttcag gttcgtcggg     180
catttcagcg aagcgccggg cacgtcggcg ttcgggacgg cggagcgccc ggagttcgaa     240
cgcatcctga acgaatgccg cgccgggcgg ctcaacatga tcattgtcta tgacgtgtcg     300
cgcttctcgc gcctgaaggt catggacgcg attccgattg tctcggaatt gctcgccctg     360
ggcgtgacga ttgtttccac tcaggaaggc gtcttccggc agggaaacgt catggacctg     420
attcacctga ttatgcggct cgacgcgtcg cacaaagaat cttcgctgaa gtcggcgaag     480
attctcgaca cgaagaacct tcagcgcgaa ttgggcgggt acgtcggcgg aaggcgcct      540 tacggcttcg agcttgtttc ggagacgaag gagatcacgc gcaacggccg aatggtcaat     600
gtcgtcatca acaagcttgc gcactcgacc actcccctta ccggaccctt cgagttcgag     660
cccgacgtaa tccggtggtg gtggcgtgag atcaagacgc acaaacacct tcccttcaag     720
ccgggcagtc aagccgccat tcacccgggc agcatcacgg ggctttgtaa gcgcatggac     780
gctgacgccg tgccgacccg gggcgagacg attgggaaga agaccgcttc aagcgcctgg     840
gacccggcaa ccgttatgcg aatccttcgg gacccgcgta ttgcgggctt cgccgctgag     900
gtgatctaca agaagaagcc ggacggcacg ccgaccacga agattgaggg ttaccgcatt     960
cagcgcgacc cgatcacgct ccggccggtc gagcttgatt gcggaccgat catcgagccc    1020
gctgagtggt atgagcttca ggcgtggttg gacggcaggg ggcgcggcaa ggggctttcc    1080 cggggggcaag ccattctgtc cgccatggac aagctgtact gcgagtgtgg cgccgtcatg    1140
acttcgaagc gcggggaaga atcgatcaag gactcttacc gctgccgtcg ccggaaggtg    1200
gtcgacccgt ccgcacctgg gcagcacgaa ggcacgtgca acgtcagcat ggcggcactc    1260
gacaagttcg ttgcgaacg catcttcaac aagatcaggc acgccgaagg cgacgaagag    1320
acgttggcgc ttctgtggga agccgcccga cgcttcggca agctcactga ggcgcctgag    1380
aagagcggcg aacgggcgaa ccttgttgcg gagcgcgccg acgccctgaa cgcccttgaa    1440
gagctgtacg aagaccgcgc ggcaggcgcg tacgacggac ccgttggcag gaagcacttc    1500
cggaagcaac aggcagcgct gacgctccgg cagcaagggg cggaagagcg gcttgccgaa    1560
cttgaagccg ccgaagcccc gaagcttccc cttgaccaat ggttccccga agacgccgac    1620
gctgacccga ccggccctaa gtcgtggtgg gggcgcgcgt cagtagacga caagcgcgtg    1680 ttcgtcggc tcttcgtaga caagatcgtt gtcacgaagt cgactacggg caggggcag     1740 ggaacgccca tcgagaagcg cgcttcgatc acgtggcgca agccgccgac cgacgacgac    1800
gaagacgacg cccaggacgg cacggaagac gtagcggcgt ag                      1842
```

```
<210> SEQ ID NO 126
<211> LENGTH: 22
<212> TYPE: DNA
<213> ORGANISM: Bacteriophage Phi-C31

<400> SEQUENCE: 126
ctaaagggaa caaaagctgg ag                                              22

<210> SEQ ID NO 127
<211> LENGTH: 22
<212> TYPE: DNA
<213> ORGANISM: Bacteriophage Phi-C31

<400> SEQUENCE: 127
tgatatgggg caaatggtgg tc                                              22

<210> SEQ ID NO 128
<211> LENGTH: 613
<212> TYPE: PRT
<213> ORGANISM: Bacteriophage Phi-C31

<400> SEQUENCE: 128
```

Met Thr Gln Gly Val Val Thr Gly Val Asp Thr Tyr Ala Gly Ala Tyr
 1               5                  10                  15

Asp Arg Gln Ser Arg Glu Arg Glu Asn Ser Ser Ala Ala Ser Pro Ala
            20                  25                  30

Thr Gln Arg Ser Ala Asn Glu Asp Lys Ala Ala Asp Leu Gln Arg Glu
        35                  40                  45

Val Glu Arg Asp Gly Gly Arg Phe Arg Phe Val Gly His Phe Ser Glu
    50                  55                  60

Ala Pro Gly Thr Ser Ala Phe Gly Thr Ala Glu Arg Pro Glu Phe Glu
65                  70                  75                  80

Arg Ile Leu Asn Glu Cys Arg Ala Gly Arg Leu Asn Met Ile Ile Val
                85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

```
Leu Arg Asp Pro Arg Ile Ala Gly Phe Ala Ala Glu Val Ile Tyr Lys
290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
        355                 360                 365

Met Asp Lys Leu Tyr Cys Glu Cys Gly Ala Val Met Thr Ser Lys Arg
370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
            420                 425                 430

Arg His Ala Glu Gly Asp Glu Glu Thr Leu Ala Leu Leu Trp Glu Ala
        435                 440                 445

Ala Arg Arg Phe Gly Lys Leu Thr Glu Ala Pro Glu Lys Ser Gly Glu
450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Glu Ala Pro Lys
        515                 520                 525

Leu Pro Leu Asp Gln Trp Phe Pro Glu Asp Ala Asp Ala Asp Pro Thr
530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Glu Asp Ala Gln Asp Gly Thr
        595                 600                 605

Glu Asp Val Ala Ala
    610

<210> SEQ ID NO 129
<211> LENGTH: 613
<212> TYPE: PRT
<213> ORGANISM: Bacteriophage Phi-C31

<400> SEQUENCE: 129

Met Thr Gln Gly Val Val Thr Gly Val Asp Thr Tyr Ala Gly Ala Tyr
1               5                   10                  15

Asp Arg Gln Ser Arg Glu Arg Glu Asn Ser Ser Ala Ala Ser Pro Ala
            20                  25                  30

Thr Gln Arg Ser Ala Asn Glu Asp Lys Ala Ala Asp Leu Gln Arg Glu
        35                  40                  45
```

```
Val Glu Arg Asp Gly Gly Arg Phe Arg Phe Val Gly His Phe Ser Glu
     50                  55                  60
Ala Pro Gly Thr Ser Ala Phe Gly Thr Ala Glu Arg Pro Glu Phe Glu
 65                  70                  75                  80
Arg Ile Leu Asn Glu Cys Arg Ala Gly Arg Leu Asn Met Ile Ile Val
                 85                  90                  95
Tyr Asp Val Ser Arg Phe Ser Arg Leu Lys Val Met Asp Ala Ile Pro
            100                 105                 110
Ile Val Ser Glu Leu Leu Ala Leu Gly Val Thr Ile Val Ser Thr Gln
        115                 120                 125
Glu Gly Val Phe Arg Gln Gly Asn Val Met Asp Leu Ile His Leu Ile
    130                 135                 140
Met Arg Leu Asp Ala Ser His Lys Glu Ser Ser Leu Lys Ser Ala Lys
145                 150                 155                 160
Ile Leu Asp Thr Lys Asn Leu Gln Arg Glu Leu Gly Gly Tyr Val Gly
                165                 170                 175
Gly Lys Ala Pro Tyr Gly Phe Glu Leu Val Ser Glu Thr Lys Glu Ile
            180                 185                 190
Thr Arg Asn Gly Arg Met Val Asn Val Val Ile Asn Lys Leu Ala His
        195                 200                 205
Ser Thr Thr Pro Leu Thr Gly Pro Phe Glu Phe Glu Pro Asp Val Ile
    210                 215                 220
Arg Trp Trp Arg Glu Ile Lys Thr His Lys His Leu Pro Phe Lys
225                 230                 235                 240
Pro Gly Ser Gln Ala Ala Ile His Pro Gly Ser Ile Thr Gly Leu Cys
                245                 250                 255
Lys Arg Met Asp Ala Asp Ala Val Pro Thr Arg Gly Glu Thr Ile Gly
            260                 265                 270
Lys Lys Thr Ala Ser Ser Ala Trp Asp Pro Ala Thr Val Met Arg Ile
        275                 280                 285
Leu Arg Asp Pro Arg Ile Ala Gly Phe Ala Ala Glu Val Ile Tyr Lys
    290                 295                 300
Lys Lys Pro Asp Gly Thr Pro Thr Thr Lys Ile Glu Gly Tyr Arg Ile
305                 310                 315                 320
Gln Arg Asp Pro Ile Thr Leu Arg Pro Val Glu Leu Asp Cys Gly Pro
                325                 330                 335
Ile Ile Glu Pro Ala Glu Trp Tyr Glu Leu Gln Ala Trp Leu Asp Gly
            340                 345                 350
Arg Gly Arg Gly Lys Gly Leu Ser Arg Gly Gln Ala Ile Leu Ser Ala
        355                 360                 365
Met Asp Lys Leu Tyr Cys Glu Cys Gly Ala Val Met Thr Ser Lys Arg
    370                 375                 380
Gly Glu Glu Ser Ile Lys Asp Ser Tyr Arg Cys Arg Arg Arg Lys Val
385                 390                 395                 400
Val Asp Pro Ser Ala Pro Gly Gln His Glu Gly Thr Cys Asn Val Ser
                405                 410                 415
Met Ala Ala Leu Asp Lys Phe Val Ala Glu Arg Ile Phe Asn Lys Ile
            420                 425                 430
Arg His Ala Glu Gly Asp Glu Glu Thr Leu Ala Leu Leu Trp Glu Ala
        435                 440                 445
Ala Arg Arg Phe Gly Lys Leu Thr Glu Ala Pro Glu Lys Ser Gly Glu
    450                 455                 460
Arg Ala Asn Leu Val Ala Glu Arg Ala Asp Ala Leu Asn Ala Leu Glu
465                 470                 475                 480
```

```
Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
        515                 520                 525

Leu Pro Leu Asp Gln Trp Phe Pro Glu Asp Ala Asp Ala Asp Pro Thr
    530                 535                 540

Gly Pro Lys Ser Trp Trp Gly Arg Ala Ser Val Asp Lys Arg Met
545                 550                 555                 560

Phe Val Gly Leu Phe Val Asp Lys Ile Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Glu Asp Ala Gln Asp Gly Thr
                595                 600                 605

Gln Asp Val Ala Ala
    610

<210> SEQ ID NO 130
<211> LENGTH: 613
<212> TYPE: PRT
<213> ORGANISM: Bacteriophage Phi-C31

<400> SEQUENCE: 130

Met Thr Gln Gly Val Val Thr Gly Val Asp Thr Tyr Ala Gly Ala Tyr
 1               5                  10                  15

Asp Arg Gln Ser Arg Glu Arg Glu Asn Ser Ser Ala Ala Ser Pro Ala
                20                  25                  30

Thr Gln Arg Ser Ala Asn Glu Asp Lys Ala Ala Asp Leu Gln Arg Glu
            35                  40                  45

Val Glu Arg Asp Gly Gly Arg Phe Arg Phe Val Gly His Phe Ser Glu
        50                  55                  60

Ala Pro Gly Thr Ser Ala Phe Gly Thr Ala Glu Arg Pro Glu Phe Glu
65                  70                  75                  80

Arg Ile Leu Asn Glu Cys Arg Ala Gly Arg Leu Asn Met Ile Ile Val
                85                  90                  95

Tyr Asp Val Ser Arg Phe Ser Arg Leu Lys Val Met Asp Ala Ile Pro
                100                 105                 110

Ile Val Ser Glu Leu Leu Ala Leu Gly Val Thr Ile Val Ser Thr Gln
            115                 120                 125

Glu Gly Val Phe Arg Gln Gly Asn Val Met Asp Leu Ile His Leu Ile
        130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
                180                 185                 190

Thr Arg Asn Gly Arg Met Val Asn Val Val Ile Asn Lys Leu Ala His
            195                 200                 205

Ser Thr Thr Pro Leu Thr Gly Pro Phe Glu Phe Glu Pro Asp Val Ile
        210                 215                 220

Arg Trp Trp Trp Arg Glu Ile Lys Thr His Lys His Leu Pro Phe Lys
225                 230                 235                 240
```

```
Pro Gly Ser Gln Ala Thr Ile His Pro Gly Ser Ile Thr Gly Leu Cys
            245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
            275                 280                 285

Leu Arg Asp Pro Arg Ile Ala Gly Phe Ala Ala Glu Val Ile Tyr Lys
            290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
            325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
            355                 360                 365

Met Gly Lys Leu Tyr Cys Glu Cys Gly Ala Val Met Thr Ser Lys Arg
            370                 375                 380

Gly Glu Glu Ser Ile Lys Asp Ser Tyr Arg Cys Arg Arg Arg Lys Val
385                 390                 395                 400

Val Asp Pro Ser Ala Pro Gly Gln His Glu Gly Thr Cys Asn Val Ser
            405                 410                 415

Met Ala Ala Leu Asp Lys Phe Val Ala Glu Arg Ile Phe Asn Lys Ile
            420                 425                 430

Arg His Ala Glu Gly Asp Glu Glu Thr Leu Ala Leu Leu Trp Glu Ala
            435                 440                 445

Ala Arg Arg Phe Gly Lys Leu Thr Glu Ala Pro Glu Lys Ser Gly Glu
            450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
            485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
            515                 520                 525

Leu Pro Leu Asp Gln Trp Phe Pro Glu Asp Ala Asp Ala Asp Pro Thr
            530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Val Thr Lys Ser Thr Thr
            565                 570                 575

Gly Arg Gly Gln Gly Thr Pro Ile Glu Lys Arg Ala Ser Ile Thr Trp
            580                 585                 590

Ala Lys Pro Pro Thr Asp Asp Asp Glu Asp Asp Ala Gln Asp Gly Thr
            595                 600                 605

Glu Asp Val Ala Ala
    610

<210> SEQ ID NO 131
<211> LENGTH: 610
<212> TYPE: PRT
<213> ORGANISM: Bacteriophage Phi-C31
```

<400> SEQUENCE: 131

| | | | | | | | | | | | | | | |
|---|---|---|---|---|---|---|---|---|---|---|---|---|---|---|
| Met | Thr | Gln | Gly | Val | Val | Thr | Gly | Val | Asp | Thr | Tyr | Ala | Gly | Ala | Tyr |
| 1 | | | | 5 | | | | | 10 | | | | | 15 | |

| Asp | Arg | Gln | Ser | Arg | Glu | Arg | Glu | Asn | Ser | Ala | Ala | Ser | Pro | Ala |
|---|---|---|---|---|---|---|---|---|---|---|---|---|---|---|
| | | | 20 | | | | | 25 | | | | | 30 | |

| Thr | Gln | Arg | Ser | Ala | Asn | Glu | Asp | Lys | Ala | Ala | Asp | Leu | Gln | Arg | Glu |
|---|---|---|---|---|---|---|---|---|---|---|---|---|---|---|---|
| | | | | 35 | | | | | 40 | | | | | 45 | |

| Val | Glu | Arg | Asp | Gly | Gly | Arg | Phe | Arg | Phe | Val | Gly | His | Phe | Ser | Glu |
|---|---|---|---|---|---|---|---|---|---|---|---|---|---|---|---|
| | 50 | | | | | 55 | | | | | 60 | | | | |

| Ala | Pro | Gly | Thr | Ser | Ala | Phe | Gly | Thr | Ala | Glu | Arg | Pro | Glu | Phe | Glu |
|---|---|---|---|---|---|---|---|---|---|---|---|---|---|---|---|
| 65 | | | | | 70 | | | | | 75 | | | | | 80 |

| Arg | Ile | Leu | Asn | Glu | Cys | Arg | Ala | Gly | Arg | Leu | Asn | Met | Ile | Ile | Val |
|---|---|---|---|---|---|---|---|---|---|---|---|---|---|---|---|
| | | | | 85 | | | | | 90 | | | | | 95 | |

| Tyr | Asp | Val | Ser | Arg | Phe | Ser | Arg | Leu | Lys | Val | Met | Asp | Ala | Ile | Pro |
|---|---|---|---|---|---|---|---|---|---|---|---|---|---|---|---|
| | | | 100 | | | | | 105 | | | | | 110 | | |

| Ile | Val | Ser | Glu | Leu | Leu | Ala | Leu | Gly | Val | Thr | Ile | Val | Ser | Thr | Gln |
|---|---|---|---|---|---|---|---|---|---|---|---|---|---|---|---|
| | | 115 | | | | | 120 | | | | | 125 | | | |

| Glu | Gly | Val | Phe | Arg | Gln | Gly | Asn | Val | Met | Asp | Leu | Ile | His | Leu | Ile |
|---|---|---|---|---|---|---|---|---|---|---|---|---|---|---|---|
| | 130 | | | | | 135 | | | | | 140 | | | | |

| Met | Arg | Leu | Asp | Ala | Ser | His | Lys | Glu | Ser | Ser | Leu | Lys | Ser | Ala | Lys |
|---|---|---|---|---|---|---|---|---|---|---|---|---|---|---|---|
| 145 | | | | | 150 | | | | | 155 | | | | | 160 |

| Ile | Leu | Asp | Thr | Lys | Asn | Leu | Gln | Arg | Glu | Leu | Gly | Gly | Tyr | Val | Gly |
|---|---|---|---|---|---|---|---|---|---|---|---|---|---|---|---|
| | | | | 165 | | | | | 170 | | | | | 175 | |

| Gly | Lys | Ala | Pro | Tyr | Gly | Phe | Glu | Leu | Val | Ser | Glu | Thr | Lys | Glu | Ile |
|---|---|---|---|---|---|---|---|---|---|---|---|---|---|---|---|
| | | | 180 | | | | | 185 | | | | | 190 | | |

| Thr | Arg | Asn | Gly | Arg | Met | Val | Asn | Val | Val | Ile | Asn | Lys | Leu | Ala | His |
|---|---|---|---|---|---|---|---|---|---|---|---|---|---|---|---|
| | | 195 | | | | | 200 | | | | | 205 | | | |

| Ser | Thr | Thr | Pro | Leu | Thr | Gly | Pro | Phe | Glu | Phe | Glu | Pro | Asp | Val | Ile |
|---|---|---|---|---|---|---|---|---|---|---|---|---|---|---|---|
| | 210 | | | | | 215 | | | | | 220 | | | | |

| Arg | Trp | Trp | Arg | Glu | Ile | Lys | Thr | His | Lys | His | Leu | Pro | Phe | Lys |
|---|---|---|---|---|---|---|---|---|---|---|---|---|---|---|
| 225 | | | | | 230 | | | | | 235 | | | | | 240 |

| Pro | Gly | Ser | Gln | Ala | Ala | Ile | His | Pro | Gly | Ser | Ile | Thr | Gly | Leu | Cys |
|---|---|---|---|---|---|---|---|---|---|---|---|---|---|---|---|
| | | | | 245 | | | | | 250 | | | | | 255 | |

| Lys | Arg | Met | Asp | Ala | Asp | Ala | Val | Pro | Thr | Arg | Gly | Glu | Thr | Ile | Gly |
|---|---|---|---|---|---|---|---|---|---|---|---|---|---|---|---|
| | | | 260 | | | | | 265 | | | | | 270 | | |

| Lys | Lys | Thr | Ala | Ser | Ser | Ala | Trp | Asp | Pro | Ala | Thr | Val | Met | Arg | Ile |
|---|---|---|---|---|---|---|---|---|---|---|---|---|---|---|---|
| | | 275 | | | | | 280 | | | | | 285 | | | |

| Leu | Arg | Asp | Pro | Arg | Ile | Ala | Gly | Phe | Ala | Ala | Glu | Val | Ile | Tyr | Lys |
|---|---|---|---|---|---|---|---|---|---|---|---|---|---|---|---|
| | 290 | | | | | 295 | | | | | 300 | | | | |

| Lys | Lys | Pro | Asp | Gly | Thr | Pro | Thr | Thr | Lys | Ile | Glu | Gly | Tyr | Arg | Ile |
|---|---|---|---|---|---|---|---|---|---|---|---|---|---|---|---|
| 305 | | | | | 310 | | | | | 315 | | | | | 320 |

| Gln | Arg | Asp | Pro | Ile | Thr | Leu | Arg | Pro | Val | Glu | Leu | Asp | Cys | Gly | Pro |
|---|---|---|---|---|---|---|---|---|---|---|---|---|---|---|---|
| | | | | 325 | | | | | 330 | | | | | 335 | |

| Ile | Ile | Glu | Pro | Ala | Glu | Trp | Tyr | Glu | Leu | Gln | Ala | Trp | Leu | Asp | Gly |
|---|---|---|---|---|---|---|---|---|---|---|---|---|---|---|---|
| | | | 340 | | | | | 345 | | | | | 350 | | |

| Arg | Gly | Arg | Gly | Lys | Gly | Leu | Ser | Arg | Gly | Gln | Ala | Ile | Leu | Ser | Ala |
|---|---|---|---|---|---|---|---|---|---|---|---|---|---|---|---|
| | | 355 | | | | | 360 | | | | | 365 | | | |

| Met | Asp | Lys | Leu | Tyr | Cys | Glu | Cys | Gly | Ala | Ile | Met | Thr | Ser | Lys | Arg |
|---|---|---|---|---|---|---|---|---|---|---|---|---|---|---|---|
| | 370 | | | | | 375 | | | | | 380 | | | | |

| Gly | Glu | Glu | Ser | Ile | Lys | Asp | Ser | Tyr | Arg | Cys | Arg | Arg | Lys | Val |
|---|---|---|---|---|---|---|---|---|---|---|---|---|---|---|
| 385 | | | | | 390 | | | | | 395 | | | | | 400 |

| Val | Asp | Pro | Ser | Ala | Pro | Gly | Gln | His | Glu | Gly | Thr | Cys | Asn | Val | Ser |
|---|---|---|---|---|---|---|---|---|---|---|---|---|---|---|---|
| | | | | 405 | | | | | 410 | | | | | 415 | |

```
Met Ala Ala Leu Asp Lys Phe Val Ala Glu Arg Ile Phe Asn Lys Ile
            420                 425                 430

Arg His Ala Glu Gly Asp Glu Thr Leu Ala Leu Leu Trp Glu Ala
        435                 440                 445

Ala Arg Arg Phe Gly Lys Leu Thr Glu Ala Pro Glu Lys Ser Gly Glu
450                 455                 460

Arg Ala Asn Leu Val Ala Glu Arg Ala Asp Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
            515                 520                 525

Leu Pro Leu Asp Gln Trp Phe Pro Glu Asp Ala Asp Ala Asp Pro Thr
    530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Thr Lys Ser Thr Thr
                565                 570                 575

Gly Arg Gly Gln Gly Thr Pro Ile Glu Lys Arg Ala Ser Ile Thr Trp
                580                 585                 590

Ala Lys Pro Pro Thr Asp Asp Glu Asp Asp Ala Arg Thr Ala Arg
            595                 600                 605

Lys Thr
    610

<210> SEQ ID NO 132
<211> LENGTH: 613
<212> TYPE: PRT
<213> ORGANISM: Bacteriophage Phi-C31
<220> FEATURE:
<221> NAME/KEY: VARIANT
<222> LOCATION: 246
<223> OTHER INFORMATION: Xaa = No Consensus
<220> FEATURE:
<221> NAME/KEY: VARIANT
<222> LOCATION: 370
<223> OTHER INFORMATION: Xaa = No Consensus
<220> FEATURE:
<221> NAME/KEY: VARIANT
<222> LOCATION: 379
<223> OTHER INFORMATION: Xaa = No Consensus
<220> FEATURE:
<221> NAME/KEY: VARIANT
<222> LOCATION: 560
<223> OTHER INFORMATION: Xaa = No Consensus
<220> FEATURE:
<221> NAME/KEY: VARIANT
<222> LOCATION: (605)...(613)
<223> OTHER INFORMATION: Xaa = No Consensus
<220> FEATURE:
<221> NAME/KEY: VARIANT
<222> LOCATION: 246, 370, 379, 560, 605, 606, 607, 608, 609, 610, 611,
      612, 613
<223> OTHER INFORMATION: Xaa = Any Amino Acid

<400> SEQUENCE: 132

Met Thr Gln Gly Val Val Thr Gly Val Asp Thr Tyr Ala Gly Ala Tyr
1               5                   10                  15

Asp Arg Gln Ser Arg Glu Arg Glu Asn Ser Ser Ala Ala Ser Pro Ala
                20                  25                  30

Thr Gln Arg Ser Ala Asn Glu Asp Lys Ala Ala Asp Leu Gln Arg Glu
            35                  40                  45
```

-continued

```
Val Glu Arg Asp Gly Gly Arg Phe Arg Phe Val Gly His Phe Ser Glu
 50                  55                  60

Ala Pro Gly Thr Ser Ala Phe Gly Thr Ala Glu Arg Pro Glu Phe Glu
 65                  70                  75                  80

Arg Ile Leu Asn Glu Cys Arg Ala Gly Arg Leu Asn Met Ile Ile Val
                 85                  90                  95

Tyr Asp Val Ser Arg Phe Ser Arg Leu Lys Val Met Asp Ala Ile Pro
                100                 105                 110

Ile Val Ser Glu Leu Leu Ala Leu Gly Val Thr Ile Val Ser Thr Gln
            115                 120                 125

Glu Gly Val Phe Arg Gln Gly Asn Val Met Asp Leu Ile His Leu Ile
        130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Xaa Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
    290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala
        355                 360                 365

Met Xaa Lys Leu Tyr Cys Glu Cys Gly Ala Xaa Met Thr Ser Lys Arg
    370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
            420                 425                 430

Arg His Ala Glu Gly Asp Glu Glu Thr Leu Ala Leu Leu Trp Glu Ala
        435                 440                 445

Ala Arg Arg Phe Gly Lys Leu Thr Glu Ala Pro Glu Lys Ser Gly Glu
    450                 455                 460

Arg Ala Asn Leu Val Ala Glu Ala Asp Ala Leu Asn Ala Leu Glu
465                 470                 475                 480
```

```
Glu Leu Tyr Glu Asp Arg Ala Ala Gly Ala Tyr Asp Gly Pro Val Gly
            485                 490                 495

Arg Lys His Phe Arg Lys Gln Gln Ala Ala Leu Thr Leu Arg Gln Gln
        500                 505                 510

Gly Ala Glu Glu Arg Leu Ala Glu Leu Glu Ala Ala Glu Ala Pro Lys
        515                 520                 525

Leu Pro Leu Asp Gln Trp Phe Pro Glu Asp Ala Asp Ala Asp Pro Thr
    530                 535                 540

Gly Pro Lys Ser Trp Trp Gly Arg Ala Ser Val Asp Lys Arg Xaa
545                 550                 555                 560

Phe Val Gly Leu Phe Val Asp Lys Ile Val Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Asp Glu Asp Asp Ala Xaa Xaa Xaa Xaa
        595                 600                 605

Xaa Xaa Xaa Xaa Xaa
        610

<210> SEQ ID NO 133
<211> LENGTH: 1842
<212> TYPE: DNA
<213> ORGANISM: Bacteriophage Phi-C31

<400> SEQUENCE: 133
atgacacaag gggttgtgac cggggtggac acgtacgcgg gtgcttacga ccgtcagtcg      60
cgcgagcgcg aaaattcgag cgcagcaagc ccagcgacac agcgtagcgc caacgaagac     120
aaggcggccg accttcagcg cgaagtcgag cgcgacgggg gccggttcag gttcgtcggg     180
catttcagcg aagcgccggg cacgtcggcg ttcgggacgg cggagcgccc ggagttcgaa     240
cgcatcctga cgaatgccgc cgccgggcgg ctcaacatga tcattgtcta tgacgtgtcg     300
cgcttctcgc gcctgaaggt catggacgcg attccgattg tctcggaatt gctcgccctg     360
ggcgtgacga ttgttttccac tcaggaaggc gtcttccggc agggaaacgt catggacctg     420
attcacctga ttatgcggct cgacgcgtcg cacaaagaat cttcgctgaa gtcggcgaag     480
attctcgaca cgaagaacct tcagcgcgaa ttgggcgggt acgtcggcgg gaaggcgcct     540
tacggcttcg agcttgtttc ggagacgaag gagatcacgc gcaacggccg aatggtcaat     600
gtcgtcatca acaagcttgc gcactcgacc actcccctta ccggacccct tcgagttcgag     660 cccgacgtaa tccggtggtg gtggcgtgag atcaagacgc acaaacacct tcccttcaag     720
ccgggcagtc aagccgccat tcacccgggc agcatcacgg gctttgtaa gcgcatggac     780 gctgacgccg tgccgacccg gggcgagacg attgggaaga gaccgcttc aagcgcctgg     840 gacccggcaa ccgttatgcg aatccttcgg gacccgcgta tcgcgggctt cgccgctgag     900
gtgatctaca agaagaagcc ggacggcacg ccgaccacga agattgaggg ttaccgcatt     960
cagcgcgacc cgatcacgct ccggccggtc gagcttgatt gcggaccgat catcgagccc    1020
gctgagtggt atgagcttca ggcgtggttg acggcagggg ggcgcggcaa ggggcttttcc    1080 cgggggcaag ccattctgtc cgccatggaa aagctgtact gcgagtgtgg cgccgtcatg    1140
acttcgaagc gcggggaaga atcgatcaag gactcttacc gctgccgtcg ccggaaggtg    1200
gtcgacccgt ccgcacctgg gcagcacgaa ggcacgtgca acgtcagcat ggcggcactc    1260
gacaagttcg ttgcggaacg catcttcaac aagatcaggc acgccgaagg cgacgaagag    1320
acgttggcgc ttctgtggga agccgcccga cgcttcggca agctcactga ggcgcctgag    1380
```

```
aagagcggcg aacgggcgaa ccttgttgcg gagcgcgccg acgccctgaa cgcccttgaa   1440
gagctgtacg aagaccgcgc ggcaggcgcg tacgacggac ccgttggcag gaagcacttc   1500
cggaagcaac aggcagcgct gacgctccgg cagcaagggg cggaagagcg gcttgccgaa   1560
cttgaagccg ccgaagcccc gaagcttccc cttgaccaat ggttcccgga agacgccgac   1620
gctgacccga ccggccctaa gtcgtggtgg gggcgcgcgt cagtagacga caagcgcatg   1680
ttcgtcgggc tcttcgtaga caagatcgtt gtcacgaagt cgactacggg caggggcag    1740 ggaacgccca tcgagaagcg cgcttcgatc acgtgggcga agccgccgac cgacgacgac   1800
gaagacgacg cccaggacgg cacgcaagac gtagcggcgt ag                      1842
```

<210> SEQ ID NO 134
<211> LENGTH: 1839
<212> TYPE: DNA
<213> ORGANISM: Bacteriophage Phi-C31

<400> SEQUENCE: 134

```
atgacacaag gggttgtgac cggggtggac acgtacgcgg gtgcttacga ccgtcagtcg     60
cgcgagcgcg aaaattcgag cgcagcaagc ccagcgacac agcgtagcgc caacgaagac    120
aaggcggccg accttcagcg cgaagtcgag cgcgacgggg gccggttcag attcgtcggg    180
catttcagcg aagcgccggg cacgtcggcg ttcgggacgg cggagcgccc ggagttcgaa    240
cgcatcctga cgaatgccgc cgccgggcgg ctcaacatga tcattgtcta tgacgtgtcg    300
cgcttctcgc gcctgaaggt catggacgcg attccgattg tctcggaatt gctcgccctg    360
ggcgtgacga ttgtttccac tcaggaaggc gtcttccggc agggaaacgt catggacctg    420
attcacctga ttatgcggct cgacgcgtcg cacaaagaat cttcgctgaa gtcggcgaag    480
attctcgaca cgaagaacct tcagcgcgaa ttgggcgggt acgtcggcgg gaaggcgcct    540
tacggcttcg agcttgtttc ggagacgaag gagatcacgc gcaacggccg aatggtcaat    600
gtcgtcatca acaagcttgc gcactcgacc actcccctta ccggaccctt cgagttcgag    660
cccgacgtaa tccggtggtg gtggcgtgag atcaagacgc acaaacacct tccccttcaag    720 ccgggcagtc aagccaccat tcacccgggc agcatcacgg gctttgtaa gcgcatggac    780 gctgacgccg tgccgacccg gggcgagacg attgggaaga agaccgcttc aagcgcctgg    840
gacccggcaa ccgttatgcg aatccttcgg gacccgcgta ttgcgggctt cgccgctgag    900
gtgatctaca agaagaagcc ggacggcacg ccgaccacga agattgaggg ttaccgcatt    960
cagcgcgacc cgatcacgct ccggccggtc gagcttgatt gcggaccgat catcgagccc   1020
gctgagtggt atgagcttca ggcgtggttg gacggcaggg ggcgcggcaa ggggctttcc   1080
cgggggcaag ccattctgtc cgccatgggc aagctgtact gcgagtgtgg cgccgtcatg   1140
acttcgaagc gcggggaaga atcgatcaag gactcttacc gctgccgtcg ccggaaggtg   1200
gtcgacccgt ccgcacctgg gcagcacgaa ggcacgtgca acgtcagcat ggcggcactc   1260
gacaagttcg ttgcggaacg catcttcaac aagatcagga cgccgaagg cgacgaagag   1320 acgttggcgc ttctgtggga agccgcccga cgcttcggca agctcactga ggcgcctgag   1380
aagagcggcg aacgggcgaa ccttgttgcg gagcgcgccg acgccctgaa cgcccttgaa   1440
gagctgtacg aagaccgcgc ggcaggcgcg tacgacggac ccgttggcag gaagcacttc   1500
cggaagcaac aggcagcgct gacgctccgg cagcaagggg cggaagagcg gcttgccgaa   1560
cttgaagccg ccgaagcccc gaagcttccc cttgaccaat ggttcccgga agacgccgac   1620
gctgacccga ccggccctaa gtcgtggtgg gggcgcgcgt cagtagacga caagcgcgtg   1680
```

```
ttcgtcgggc tcttcgtaga caagatcgtt gtcacgaagt cgactacggg caggggggcag   1740 ggaacgccca tcgagaagcg cgcttcgatc acgtgggcga agccgccaac cgacgacgac   1800
gaagacgacg cccaggacgg cacggaagac gtagcggcg                          1839
```

<210> SEQ ID NO 135
<211> LENGTH: 1834
<212> TYPE: DNA
<213> ORGANISM: Bacteriophage Phi-C31

<400> SEQUENCE: 135

```
atgacacaag gggttgtgac cggggtggac acgtacgcgg gtgcttacga ccgtcagtcg    60
cgcgagcgcg aaaattcgag cgcagcaagc ccagcgacac agcgtagcgc caacgaagac   120
aaggcggccg accttcagcg cgaagtcgag cgcgacgggg gccggttcag gttcgtcggg   180
catttcagcg aagcgccggg cacgtcggcg ttcgggacgg cggaacgccc ggagttcgaa   240
cgcatcctga cgaatgccgc gccgggcgg ctcaacatga tcattgtcta tgacgtgtcg   300
cgcttctcgc gcctgaaggt catggacgcg attccgattg tctcggaatt gctcgccctg   360
ggcgtgacga ttgtttccac tcaggaaggc gtcttccggc agggaaacgt catggacctg   420
attcacctga ttatgcggct cgacgcgtcg cacaaagaat cttcgctgaa gtcggcgaag   480
attctcgaca cgaagaacct tcagcgcgaa ctgggcgggt acgtcggcgg aaggcgcct   540 tacggcttcg agcttgtttc ggagacgaag gagatcacgc gcaacggccg aatggtcaat   600
gtcgtcatca acaagcttgc gcactcgacc actcccctta ccggacccctt cgagttcgag   660 cccgacgtaa tccggtggtg gtggcgtgag atcaagacgc acaaacacct tcccttcaag   720
ccgggcagtc aagccgccat tcacccgggc agcatcacgg ggcttgtaa gcgcatggac   780 gctgacgccg tgccgacccg gggcgagacg attgggaaga agaccgcttc aagcgcctgg   840
gacccggcaa ccgttatgcg aatccttcgg gacccgcgta ttgcgggctt cgccgctgag   900
gtgatctaca agaagaagcc ggacggcacg ccgaccacga agattgaggg ttaccgcatt   960
cagcgcgacc cgatcacgct ccggccggtc gagcttgatt gcggaccgat catcgagccc  1020
gctgagtggt atgagcttca ggcgtggttg gacggcaggg ggcgcggcaa gggggcttcc  1080
cgggggcaag ccattctgtc cgccatggac aagctgtact gcgagtgtgg cgccatcatg  1140
acttcgaagc gcggggaaga atcgatcaag gactcttacc gctgccgtcg ccggaaggtg  1200
gtcgacccgt ccgcacctgg gcagcacgaa ggcacgtgca acgtcagcat ggcggcactc  1260
gacaagttcg ttgcggaacg catcttcaac aagatcaggc acgccgaagg cgacgaagag  1320
acgttggcgc ttctgtggga agccgcccga cgcttcggca agctcactga ggcgcctgag  1380
aagagcggcg aacgggcgaa ccttgttgcg gagcgcgccg acgccctgaa cgcccttgaa  1440
gagctgtacg aagaccgcgc ggcaggcgcg tacgacggac ccgttggcag gaagcacttc  1500
cggaagcagc aggcagcgct gacgctccgg cagcaagggg cggaagagcg gcttgccgaa  1560
cttgaagccg ccgaagcccc gaagcttccc cttgaccaat ggttcccccga agacgccgac  1620 gctgacccga ccggccctaa gtcgtggtgg gggcgcgcgt cagtagacga caagcgcgtg  1680
ttcgtcgggc tcttcgtaga caagattgtt gtcacgaagt cgactacggg caggggggcag  1740 ggaacgccca tcgagaagcg cgcttcgatc acgtgggcga agccgccgac cgacgacgac  1800
gaagacgacg cccaggacgg cacggaagac gtag                               1834
```

```
<210> SEQ ID NO 136
<211> LENGTH: 279
<212> TYPE: DNA
<213> ORGANISM: Bacteriophage Phi-C31

<400> SEQUENCE: 136
cgatgtaggt cacggtctcg aagccgcggt gcgggtgcca gggcgtgccc ttgggctccc    60
cgggcgcgta ctccacctca cccatctggt ccatcatgat gaacgggtcg aggtggcggt   120
agttgatccc ggcgaacgcg cggcgcaccg ggaagccctc gccctcgaaa ccgctgggcg   180
cggtggtcac ggtgagcacg ggacgtcgca cggcgtcggc gggtgcggat acgcggggca   240
gcgtcagcgg gttctcgacg gtcacggcgg gcatgtcga                          279

<210> SEQ ID NO 137
<211> LENGTH: 26
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 2, 3, 4, 6, 7, 8, 9, 10, 12, 15, 16, 17, 18, 19, 20, 21,
      23, 24, 25
<223> OTHER INFORMATION: n = A,T,C or G

<400> SEQUENCE: 137
cnnngnnnnn cnttnnnnnn ncnnng                                         26

<210> SEQ ID NO 138
<211> LENGTH: 26
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 2, 3, 6, 8, 9, 12, 13, 15, 16, 17, 18, 19, 21, 23, 24,
      25
<223> OTHER INFORMATION: n = A,T,C or G

<400> SEQUENCE: 138
cnnggntnnc cnntnnnnnc ncnnng                                         26

<210> SEQ ID NO 139
<211> LENGTH: 40
<212> TYPE: DNA
<213> ORGANISM: Human

<400> SEQUENCE: 139
cctttgccag agacaatctt tggtgttcta aggaaaaggc                           40

<210> SEQ ID NO 140
<211> LENGTH: 40
<212> TYPE: DNA
<213> ORGANISM: Human

<400> SEQUENCE: 140
ctgccatgtt ggagatccat catctctccc ttcaatttgt                           40

<210> SEQ ID NO 141
<211> LENGTH: 21
<212> TYPE: DNA
<213> ORGANISM: Human

<400> SEQUENCE: 141
gataccaggt tctgagctgc c                                              21
```

```
<210> SEQ ID NO 142
<211> LENGTH: 21
<212> TYPE: DNA
<213> ORGANISM: Human

<400> SEQUENCE: 142
aagtccgatc catttcaccc a                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 143
gttttcccag tcacgacgtt g                                              21

<210> SEQ ID NO 144
<211> LENGTH: 21
<212> TYPE: DNA
<213> ORGANISM: Human

<400> SEQUENCE: 144
cttccaatca gaggcttggt g                                              21

<210> SEQ ID NO 145
<211> LENGTH: 20
<212> TYPE: DNA
<213> ORGANISM: Human

<400> SEQUENCE: 145
atttgtagaa ctattatggg                                                20

<210> SEQ ID NO 146
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 146
gttttcccag tcacgacgtt g                                              21

<210> SEQ ID NO 147
<211> LENGTH: 21
<212> TYPE: DNA
<213> ORGANISM: Human

<400> SEQUENCE: 147
gataccaggt tctgagctgc c                                              21

<210> SEQ ID NO 148
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 148
gttttcccag tcacgacgtt g                                              21

<210> SEQ ID NO 149
<211> LENGTH: 21
<212> TYPE: DNA
<213> ORGANISM: Human
```

```
<400> SEQUENCE: 149
gataccaggt tctgagctgc c                                          21

<210> SEQ ID NO 150
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 150
gatggcccac tacgtgaacc                                            20

<210> SEQ ID NO 151
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 151
cactttatgc ttccggctcg ta                                         22

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 152
ggcgagaaag gaagggaaga                                            20

<210> SEQ ID NO 153
<211> LENGTH: 32
<212> TYPE: DNA
<213> ORGANISM: Bacteriophage TP901

<400> SEQUENCE: 153
tgatgttact gctgataatg tagatatcat at                              32

<210> SEQ ID NO 154
<211> LENGTH: 25
<212> TYPE: DNA
<213> ORGANISM: Bacteriophage TP901

<400> SEQUENCE: 154
attaaaattc acggaagaaa gcttt                                      25

<210> SEQ ID NO 155
<211> LENGTH: 38
<212> TYPE: DNA
<213> ORGANISM: Bacteriophage TP901

<400> SEQUENCE: 155
cgagttttta tttcgtttat ttcaatcaag gtaaatgc                        38

<210> SEQ ID NO 156
<211> LENGTH: 20
<212> TYPE: DNA
<213> ORGANISM: Bacteriophage Phi-C31

<400> SEQUENCE: 156
ggcttcacgt tttcccaggt                                            20
```

-continued

<210> SEQ ID NO 157
<211> LENGTH: 20
<212> TYPE: DNA
<213> ORGANISM: Bacteriophage Phi-C31

<400> SEQUENCE: 157
ccagatgggt gaggtggagt                                                    20

<210> SEQ ID NO 158
<211> LENGTH: 24
<212> TYPE: DNA
<213> ORGANISM: Bacteriophage Phi-C31

<400> SEQUENCE: 158
ctggggtaac ctttgggctc cccg                                               24

<210> SEQ ID NO 159
<211> LENGTH: 20
<212> TYPE: DNA
<213> ORGANISM: Phage R4

<400> SEQUENCE: 159
tctcatgcat agaaggcccg                                                    20

<210> SEQ ID NO 160
<211> LENGTH: 19
<212> TYPE: DNA
<213> ORGANISM: Phage R4

<400> SEQUENCE: 160
ggctacacgg agcaggacc                                                     19

<210> SEQ ID NO 161
<211> LENGTH: 32
<212> TYPE: DNA
<213> ORGANISM: Phage R4

<400> SEQUENCE: 161
cgataccact tgaagcagtg gtagaagggc ac                                      32

<210> SEQ ID NO 162
<211> LENGTH: 21
<212> TYPE: DNA
<213> ORGANISM: Human

<400> SEQUENCE: 162
gggtcgctgc ataaactgtt g                                                  21

<210> SEQ ID NO 163
<211> LENGTH: 21
<212> TYPE: DNA
<213> ORGANISM: Human

<400> SEQUENCE: 163
aaattccaca cgtgacctcg t                                                  21

<210> SEQ ID NO 164
<211> LENGTH: 25
<212> TYPE: DNA
<213> ORGANISM: Human

<400> SEQUENCE: 164
atgcctggtg ctttgcgact tgtca                                              25

```
<210> SEQ ID NO 165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 165
ctcggagggc gaagaatctc                                                    20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
gcagctattt acccgcagga                                                    20

<210> SEQ ID NO 167
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 167
tcagcttcga tgtaggaggg cgtgg                                              25

<210> SEQ ID NO 168
<211> LENGTH: 21
<212> TYPE: DNA
<213> ORGANISM: Human

<400> SEQUENCE: 168
agagacaagg tcttgccatg t                                                  21

<210> SEQ ID NO 169
<211> LENGTH: 21
<212> TYPE: DNA
<213> ORGANISM: Human

<400> SEQUENCE: 169
aggctgcatt gctgagttct t                                                  21

<210> SEQ ID NO 170
<211> LENGTH: 40
<212> TYPE: DNA
<213> ORGANISM: Human

<400> SEQUENCE: 170
catttgacag atgaggacat tgagggctca aggacgaggc                              40

<210> SEQ ID NO 171
<211> LENGTH: 40
<212> TYPE: DNA
<213> ORGANISM: Human

<400> SEQUENCE: 171
tcctgctctg ggaatctcac tcatctggct cagggtttcc                              40

<210> SEQ ID NO 172
<211> LENGTH: 22
<212> TYPE: DNA
<213> ORGANISM: Bacteriophage Phi-C31
```

```
<400> SEQUENCE: 172
gtcgacatgc ccgccgtgac cg                                              22

<210> SEQ ID NO 173
<211> LENGTH: 20
<212> TYPE: DNA
<213> ORGANISM: Bacteriophage Phi-C31

<400> SEQUENCE: 173
tcaactaccg ccacctcgac                                                 20

<210> SEQ ID NO 174
<211> LENGTH: 40
<212> TYPE: DNA
<213> ORGANISM: Chinese hamster

<400> SEQUENCE: 174
tgaaaaaccc taaggtattc tagggagaa actgtcttcc                            40

<210> SEQ ID NO 175
<211> LENGTH: 40
<212> TYPE: DNA
<213> ORGANISM: Chinese hamster

<400> SEQUENCE: 175
gagtcttagc tgaggtcatc cttgtggatt cctaggagtt                           40

<210> SEQ ID NO 176
<211> LENGTH: 40
<212> TYPE: DNA
<213> ORGANISM: Chinese hamster

<400> SEQUENCE: 176
ttactttccc tgtggttacc ctgggtcagc cataccacat                           40

<210> SEQ ID NO 177
<211> LENGTH: 40
<212> TYPE: DNA
<213> ORGANISM: Chinese hamster

<400> SEQUENCE: 177
ttgtagggcc ccagcaaaac cttgtccagg cggatttcct                           40

<210> SEQ ID NO 178
<211> LENGTH: 37
<212> TYPE: DNA
<213> ORGANISM: Bacteriophage Phi-C31

<400> SEQUENCE: 178
ccccaactgg ggtaaccttt gagttctctc agttggg                              37

<210> SEQ ID NO 179
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 179
atgtaggtca cggtctcgaa gc                                              22
```

```
<210> SEQ ID NO 180
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 180
cctactcaga caatgcgatg c                                    21

<210> SEQ ID NO 181
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 181
cgaagccgcg gtgcg                                           15

<210> SEQ ID NO 182
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 182
ggaggggcaa acaacagat                                       19

<210> SEQ ID NO 183
<211> LENGTH: 20
<212> TYPE: DNA
<213> ORGANISM: Mouse

<400> SEQUENCE: 183
gtggcacatt ccttaatccc                                      20

<210> SEQ ID NO 184
<211> LENGTH: 20
<212> TYPE: DNA
<213> ORGANISM: Mouse

<400> SEQUENCE: 184
tgaggaggag ccttagcaac                                      20

<210> SEQ ID NO 185
<211> LENGTH: 20
<212> TYPE: DNA
<213> ORGANISM: Mouse

<400> SEQUENCE: 185
tgagtctgcc ttgagcctta                                      20

<210> SEQ ID NO 186
<211> LENGTH: 20
<212> TYPE: DNA
<213> ORGANISM: Mouse

<400> SEQUENCE: 186
caaagggcct gacctagagt                                      20

<210> SEQ ID NO 187
<211> LENGTH: 19
<212> TYPE: DNA
<213> ORGANISM: Artificial Sequence
```

```
<220> FEATURE:
<223> OTHER INFORMATION: Synthetic oligonucleotide

<400> SEQUENCE: 187
caatacgcaa accgcctct                                                 19

<210> SEQ ID NO 188
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 188
cggtgcgggt gcca                                                      14

<210> SEQ ID NO 189
<211> LENGTH: 29
<212> TYPE: DNA
<213> ORGANISM: Mouse

<400> SEQUENCE: 189
aagcctttaa taaaatgaag caaaagttc                                      29

<210> SEQ ID NO 190
<211> LENGTH: 34
<212> TYPE: DNA
<213> ORGANISM: Mouse

<400> SEQUENCE: 190
tgttttagtt ttgcaccttc ccatttattc acag                                34

<210> SEQ ID NO 191
<211> LENGTH: 21
<212> TYPE: DNA
<213> ORGANISM: Mouse

<400> SEQUENCE: 191
agagcacagc agaggtgacc a                                              21

<210> SEQ ID NO 192
<211> LENGTH: 28
<212> TYPE: DNA
<213> ORGANISM: Mouse

<400> SEQUENCE: 192
tcttgttttg cttcctgtcc atcaaggg                                       28

<210> SEQ ID NO 193
<211> LENGTH: 24
<212> TYPE: DNA
<213> ORGANISM: Mouse

<400> SEQUENCE: 193
caacaaccag gacagcgtcc caca                                           24

<210> SEQ ID NO 194
<211> LENGTH: 22
<212> TYPE: DNA
<213> ORGANISM: Mouse

<400> SEQUENCE: 194
caaacttctg ccactcgaac ct                                             22
```

```
<210> SEQ ID NO 195
<211> LENGTH: 20
<212> TYPE: DNA
<213> ORGANISM: Mouse

<400> SEQUENCE: 195
tggtttctga tggcaatgga                                              20

<210> SEQ ID NO 196
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 196
tgatgccgct ggcgattcag g                                            21

<210> SEQ ID NO 197
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 197
cgcaaggcga caaggtg                                                 17

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 198
ccatcacaaa cggcatgatg                                              20

<210> SEQ ID NO 199
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 199
cgactagtca tatggacacg tacgcgggtg ct                                32

<210> SEQ ID NO 200
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 200
agccggatcc gggtgtctcg cta                                          23

<210> SEQ ID NO 201
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 201
gatcgcgcca aaaaaaaaa aaaaaaaaa aaaaaaaac cg                        42
```

```
<210> SEQ ID NO 202
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 202
gatccggttt tttttttttt tttttttttt tttttttggc gc            42

<210> SEQ ID NO 203
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 203
atgtaggtca cggtctcgaa gc                                  22

<210> SEQ ID NO 204
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 204
tggcggccgc tctagaacta                                     20

<210> SEQ ID NO 205
<211> LENGTH: 15
<212> TYPE: DNA
<213> ORGANISM: Mouse

<400> SEQUENCE: 205
cgaagccgcg gtgcg                                          15

<210> SEQ ID NO 206
<211> LENGTH: 20
<212> TYPE: DNA
<213> ORGANISM: Mouse

<400> SEQUENCE: 206
gtaaatgtta ttgcggctct                                     20

<210> SEQ ID NO 207
<211> LENGTH: 20
<212> TYPE: DNA
<213> ORGANISM: Mouse

<400> SEQUENCE: 207
tgaggaggag ccttagcaac                                     20

<210> SEQ ID NO 208
<211> LENGTH: 20
<212> TYPE: DNA
<213> ORGANISM: Mouse

<400> SEQUENCE: 208
tgaggaggag ccttagcaac                                     20

<210> SEQ ID NO 209
<211> LENGTH: 14
<212> TYPE: DNA
<213> ORGANISM: Artificial Sequence
```

-continued

```
<220> FEATURE:
<223> OTHER INFORMATION: Synthetic construct
<220> FEATURE:
<221> NAME/KEY: misc_feature
<222> LOCATION: 11
<223> OTHER INFORMATION: n = A,T,C or G

<400> SEQUENCE: 209
yyyyyyyyyy nyag                                                        14

<210> SEQ ID NO 210
<211> LENGTH: 613
<212> TYPE: PRT
<213> ORGANISM: Bacteriophage Phi-C31
<220> FEATURE:
<221> NAME/KEY: VARIANT
<222> LOCATION: 611
<223> OTHER INFORMATION: Xaa = STOP
<220> FEATURE:
<221> NAME/KEY: VARIANT
<222> LOCATION: (1)...(613)
<223> OTHER INFORMATION: Xaa = Any Amino Acid
<223> OTHER INFORMATION: Xaa = Any Amino Acid

<400> SEQUENCE: 210

Met Ile Gln Gly Val Val Thr Gly Val Asp Thr Tyr Ala Gly Ala Tyr
  1               5                  10                  15

Asp Arg Gln Ser Arg Glu Arg Glu Asn Ser Ser Ala Ala Ser Pro Ala
             20                  25                  30

Thr Gln Arg Ser Ala Asn Glu Asp Lys Ala Ala Asp Leu Gln Arg Glu
         35                  40                  45

Val Glu Arg Asp Gly Gly Arg Phe Arg Phe Val Gly His Phe Ser Glu
     50                  55                  60

Ala Pro Gly Thr Ser Ala Phe Gly Thr Ala Glu Arg Pro Glu Phe Glu
 65                  70                  75                  80

Arg Ile Leu Asn Glu Cys Arg Ala Gly Arg Leu Asn Met Ile Ile Val
                 85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Pro Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270
```

```
Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
        290                 295                 300

Lys Lys Pro Asp Gly Thr Ser Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
                340                 345                 350

Arg Arg Arg Gly Lys Gly Leu Ser Arg Gly Gln Ala Ile Leu Ser Ala
            355                 360                 365

Met Asp Lys Leu Tyr Cys Glu Cys Gly Ala Val Met Thr Ser Lys Arg
370                 375                 380

Gly Glu Glu Ser Ile Lys Asp Ser Tyr Arg Cys Arg Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Val Glu Arg Ile Phe Asn Lys Ile
                420                 425                 430

Arg His Ala Glu Gly Asp Glu Glu Thr Leu Ala Leu Leu Trp Glu Ala
            435                 440                 445

Ala Arg Arg Phe Gly Lys Leu Thr Glu Ala Pro Glu Lys Ser Gly Glu
        450                 455                 460

Arg Ala Asn Leu Val Ala Glu Arg Ala Asn Ala Leu Asn Ala Leu Glu
465                 470                 475                 480

Glu Pro Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
                500                 505                 510

Gly Ala Glu Glu Arg Leu Ala Glu Leu Glu Ala Ala Glu Ala Pro Lys
            515                 520                 525

Leu Pro Leu Asp Gln Trp Phe Pro Glu Asp Ala Asp Ala Asp Pro Thr
530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Asp Glu Asp Asp Ala Arg Thr Ala Arg
        595                 600                 605

Lys Thr Xaa Arg Arg
        610

<210> SEQ ID NO 211
<211> LENGTH: 1841
<212> TYPE: DNA
<213> ORGANISM: Bacteriophage Phi-C31

<400> SEQUENCE: 211
atgatacaag gggttgtgac cggggtggac acgtacgcgg gtgcttacga ccgtcagtcg    60
cgcgagcgcg aaaattcgag cgcagcaagc ccagcgacac agcgtagcgc caacgaagac   120
aaggcggccg accttcagcg cgaagtcgag cgcgacgggg gccggttcag gttcgtcggg   180
```

```
catttcagcg aagcgccggg cacgtcggcg ttcgggacgg cggagcgccc ggagttcgaa      240
cgcatcctga cgaatgccg cgccgggcgg ctcaacatga tcattgtcta tgacgtgtcg      300
cgcttctcgc gcctgaaggt catggacgcg attccgattg tctcggaatt gctcgccctg      360
ggcgtgacga ttgtttccac tcaggaaggc gtcttccggc cgggaaacgt catggacctg      420
attcacctga ttatgcggct cgacgcgtcg cacaaagaat cttcgctgaa gtcggcgaag      480
attctcgaca cgaagaacct tcagcgcgaa ttgggcgggt acgtcggcgg gaaggcgcct      540
tacggcttcg agcttgtttc ggagacgaag gagatcacgc gcaacggccg aatggtcaat      600
gtcgtcatca acaagcttgc gcactcgacc actcccctta ccggacccct cgagttcgag      660
cccgacgtaa tccggtggtg gtggcgtgag atcaagacgc acaaacacct tcccttcaag      720
ccgggcagtc aagccgccat tcacccgggc agcatcacgg gctttgtaa gcgcatggac      780 gctgacgccg tgccgacccg gggcgagacg attgggaaga gaccgcttc aagcgcctgg      840 gacccggcaa ccgttatgcg aatccttcgg gacccgcgta ttgcgggctt cgccgctgag      900
gtgatctaca agaagaagcc ggacggcacg tcgaccacga agattgaggg ttaccgcatt      960
cagcgcgacc cgatcacgct ccggccggtc gagcttgatt gcggaccgat catcgagccc     1020
gctgagtggt atgagcttca ggcgtggttg gacggcagga ggcgcggcaa ggggctttcc     1080
cgggggcaag ccattctgtc cgccatggac aagctgtact gcgagtgtgg cgccgtcatg     1140
acttcgaagc gcggggaaga atcgatcaag gactcttacc gctgccgtcg ccggaaggtg     1200
gtcgacccgt ccgcacctgg gcagcacgaa ggcacgtgca acgtcagcat ggcggcactc     1260
gacaagttcg ttgtggaacg catcttcaac aagatcaggc acgccgaagg cgacgaagag     1320
acgttggcgc ttctgtggga agccgcccga cgcttcggca agctcactga ggcgcctgag     1380
aagagcggcg aacgggcgaa ccttgttgcg gagcgcgcca acgccctgaa cgcccttgaa     1440
gagccgtacg aagaccgcgc ggcaggcgcg tacgacggac ccgttggcag gaagcacttc     1500
cggaagcaac aggcagcgct gacgctccgg cagcaagggg cagaagagcg gcttgccgaa     1560
cttgaagccg ccgaagcccc gaagcttccc cttgaccaat ggttccccga agacgccgac     1620
gctgacccga ccggccctaa gtcgtggtgg gggcgcgcgt cagtagacga caagcgcgtg     1680
ttcgtcgggc tcttcgtaga caagattgtt gtcacgaagt cgactacggg caggggcag      1740 ggaacgccca tcgagaagcg cgcttcgatc acgtgggcga agccgccaac cgacgacgac     1800
gaagacgacg ccaggacggc acggaagacg tagcggcgca g                        1841
```

<210> SEQ ID NO 212
<211> LENGTH: 610
<212> TYPE: PRT
<213> ORGANISM: Bacteriophage Phi-C31

<400> SEQUENCE: 212

```
Met Thr Gln Gly Val Val Thr Gly Val Asp Thr Tyr Ala Gly Ala Tyr
  1               5                  10                  15

Asp Arg Gln Ser Arg Glu Arg Glu Asn Ser Ser Ala Ala Ser Pro Ala
             20                  25                  30

Thr Gln Arg Ser Ala Asn Glu Asp Lys Ala Ala Asp Leu Gln Arg Glu
         35                  40                  45

Val Glu Arg Asp Gly Gly Arg Phe Arg Phe Val Gly His Phe Ser Glu
     50                  55                  60

Ala Pro Gly Thr Ser Ala Phe Gly Thr Ala Glu Arg Pro Glu Phe Glu
 65                  70                  75                  80
```

-continued

```
Arg Ile Leu Asn Glu Cys Arg Ala Arg Arg Leu Asn Met Ile Ile Val
            85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
            115                 120                 125

Glu Gly Val Phe Arg Pro Gly Asn Val Met Asp Leu Ile His Leu Ile
            130                 135                 140

Met Arg Leu Asp Ala Ser His Lys Glu Ser Ser Leu Lys Ser Ala Arg
145                 150                 155                 160

Ile Leu Asp Thr Lys Asn Leu Gln Arg Glu Leu Gly Gly Tyr Val Gly
            165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
            195                 200                 205

Ser Thr Thr Pro Leu Thr Gly Pro Phe Glu Phe Glu Pro Asp Val Ile
            210                 215                 220

Arg Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
            245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
            275                 280                 285

Leu Arg Asp Pro Arg Ile Ala Gly Phe Ala Ala Glu Val Ile Tyr Lys
            290                 295                 300

Lys Lys Pro Asp Gly Thr Pro Thr Thr Lys Val Glu Gly Tyr Arg Ile
305                 310                 315                 320

Gln Arg Asp Pro Ile Thr Leu Arg Pro Val Glu Leu Asp Cys Gly Pro
            325                 330                 335

Ile Ile Glu Pro Ala Glu Trp Tyr Glu Leu Gln Ala Trp Leu Asp Gly
            340                 345                 350

Arg Arg Arg Gly Lys Gly Leu Ser Arg Gly Gln Ala Ile Leu Ser Ala
            355                 360                 365

Met Asp Lys Leu Tyr Cys Glu Cys Gly Ala Val Met Thr Ser Lys Arg
            370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
            405                 410                 415

Met Ala Ala Leu Asp Lys Phe Val Ala Glu Arg Ile Phe Asn Lys Ile
            420                 425                 430

Arg His Ala Glu Gly Asp Glu Thr Leu Ala Leu Leu Trp Glu Ala
            435                 440                 445

Ala Arg Arg Phe Gly Lys Leu Thr Glu Ala Pro Glu Lys Ser Gly Glu
            450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
            485                 490                 495

Arg Lys His Phe Arg Lys Gln Gln Ala Ala Leu Thr Leu Arg Gln Gln
            500                 505                 510
```

```
Gly Ala Val Glu Arg Leu Ala Glu Leu Glu Ala Ala Glu Ala Pro Lys
        515                 520                 525
Leu Pro Leu Asp Gln Trp Phe Pro Glu Asp Ala Ala Asp Pro Thr
    530                 535                 540
Gly Pro Lys Ser Trp Trp Gly Arg Ala Ser Val Asp Asp Lys Arg Val
545                 550                 555                 560
Phe Val Gly Leu Phe Val Asp Lys Ile Val Thr Lys Ser Thr Thr
                565                 570                 575
Gly Arg Gly Gln Gly Thr Pro Ile Glu Lys Arg Ala Ser Ile Thr Trp
                580                 585                 590
Arg Ser Arg Gln Pro Thr Thr Thr Lys Thr Thr Pro Arg Thr Ala Arg
                595                 600                 605
Lys Thr
    610

<210> SEQ ID NO 213
<211> LENGTH: 1841
<212> TYPE: DNA
<213> ORGANISM: Bacteriophage Phi-C31

<400> SEQUENCE: 213
atgacacaag gggttgtgac cggggtggac acgtacgcgg gtgcttacga ccgtcagtcg      60
cgcgagcgcg aaaattcgag cgcagcaagc ccagcgacac agcgtagcgc aacgaagac     120
aaggcggccg accttcagcg cgaagtcgag cgcgacgggg gccggttcag gttcgtcggg     180
catttcagcg aagcaccggg cacgtcggcg ttcgggacgg cggagcgccc ggagttcgaa     240
cgcatcctga cgaatgccg cgccaggcgg ctcaacatga tcattgtcta tgacgtgtcg     300
cgcttctcgc gcctgaaggt catggacgcg attccgattg tctcggaatt gctcgccctg     360
ggcgtgacga ttgttccac tcaggaaggc gtcttccggc cgggaaacgt catggacctg     420
attcacctga ttatgcggct cgacgcgtcg cacaaagaat cttcgctgaa gtcggcgagg     480
attctcgaca cgaagaacct tcagcgcgaa ttgggcgggt acgtcggcgg aaggcgcct     540
tacggcttcg agcttgtttc ggagacgaag gagatcacgc gcaacggccg aatggtcaat     600
gtcgtcatca acaagcttgc gcactcgacc actcccctta ccggacccct tcgagttcgag     660
cccgacgtaa tccggtggtg gtggcgtgag atcaagacgc acaaacacct tcccttcaag     720
ccgggcagtc aagccgccat tcacccgggc agcatcacgg ggctttgtaa gcgcatggac     780
gctgacgccg tgccgacccg gggcgagacg attgggaaga gaccgcttc aagcgcctgg     840
gacccggcaa ccgttatgcg aatccttcgg gacccgcgta ttgcgggctt cgccgctgag     900
gtgatctaca gaagaagcc ggacggcacg ccgaccacga aggttgaggg ttaccgcatt     960
cagcgcgacc cgatcacgct ccggccggtc gagcttgatt gcggaccgat catcgagccc    1020
gctgagtggt atgagcttca ggcgtggttg acggcagga ggcgcggcaa gggcttttcc    1080
cgggggcaag ccattctgtc cgccatggac aagctgtact gcgagtgtgg cgccgtcatg    1140
acttcgaagc gcggggagga atcgatcaag gactcttacc gctgccgtcg ccggaaggtg    1200
gtcgacccgt ccgcacctgg gcagcacgaa ggcacgtgca acgtcagcat ggcggcactc    1260
gacaagttcg ttgcggaacg catcttcaac aagatcaggc acgccgaagg cgacgaagag    1320
acgttggcgc ttctgtggga agccgcccga cgcttcggca agctcactga ggcgcctgag    1380
aagagcggcg aacgggcgaa ccttgttgcg gagcgcgccg acgccctgaa cgcccttgaa    1440
gagctgtacg aagaccgcgc ggcaggcgcg tacgacggac ccgttggcag gaagcacttc    1500
cggaagcaac aggcagcgct gacgctccgg cagcaagggg cggtagagcg gcttgccgaa    1560
```

```
cttgaagccg ccgaagcccc gaagcttccc cttgaccaat ggttccccga agacgccgac    1620
gctgacccga ccggccctaa gtcgtggtgg gggcgcgcgt cagtagacga caagcgcgtg    1680
ttcgtcgggc tcttcgtaga caagatcgtt gtcacgaagt cgactacggg caggggggcag   1740 ggaacgccca tcgagaagcg cgcttcgatc acgtggcgaa gccgccaacc gacgacgacg    1800
aagacgacgc ccaggacggc acggaagacg tagcggcgta g                        1841

<210> SEQ ID NO 214
<211> LENGTH: 218
<212> TYPE: DNA
<213> ORGANISM: Bacteriophage Phi-C31

<400> SEQUENCE: 214
ccggtactga cggacacacc gaagccccgg cggcaaccct cagcggatgc cccggggctt      60
cacgttttcc caggtcagaa gcggttttcg ggagtagtgc cccaactggg gtaacctttg     120
agttctctca gttgggggcg tagggtcgcc gacatgacac aaggggttgt gaccggggtg     180
gacacgtacg cgggtgctta cgaccgtcag tcgcggcc                             218

<210> SEQ ID NO 215
<211> LENGTH: 295
<212> TYPE: DNA
<213> ORGANISM: Bacteriophage R4

<400> SEQUENCE: 215
cgtggggacg ccgtacaggg acgtgcacct ctcccgctgc accgcctcca gcgtcgccgc      60
cggctcgaag gacggggccg ggatgacgat gcaggcggcg tgggaggtgg cgcccaagtt     120
gcccatgacc atgccgaagc agtggtagaa gggcaccggc agacacaccc ggtcctgctc     180
cgtgtagccg accgtgcggc ccacccagta gccgttgttg aggatgttgt ggtgggagag     240
cgtggcgccc ttggggaagc cggtggtgcc ggaggtgtac tggatgttga ccggg          295

<210> SEQ ID NO 216
<211> LENGTH: 64
<212> TYPE: DNA
<213> ORGANISM: Bacteriophage R4

<400> SEQUENCE: 216
gcatgttccc caaagcgata ccacttgaag cagtggtact gcttgtgggt acactctgcg      60
ggtg                                                                   64
```